US008158360B2

(12) United States Patent
Heise et al.

(10) Patent No.: US 8,158,360 B2
(45) Date of Patent: Apr. 17, 2012

(54) EFFECTS OF INHIBITORS OF FGFR3 ON GENE TRANSCRIPTION

(75) Inventors: Carla Heise, Benicia, CA (US); Esther Masih-Khan, Ontario (CA); Edward Moler, Walnut Creek, CA (US); Michael Rowe, Oakland, CA (US); Keith Stewart, Scottsdale, AZ (US); Suzanne Trudel, Ontario (CA)

(73) Assignee: Novartis AG, Basel (CH)

( * ) Notice: Subject to any disclaimer, the term of this patent is extended or adjusted under 35 U.S.C. 154(b) by 533 days.

(21) Appl. No.: 12/096,222

(22) PCT Filed: Dec. 7, 2006

(86) PCT No.: PCT/US2006/061766
§ 371 (c)(1),
(2), (4) Date: Jun. 19, 2008

(87) PCT Pub. No.: WO2007/067968
PCT Pub. Date: Jun. 14, 2007

(65) Prior Publication Data
US 2009/0048266 A1    Feb. 19, 2009

Related U.S. Application Data

(60) Provisional application No. 60/748,944, filed on Dec. 8, 2005.

(51) Int. Cl.
*C12Q 1/68*    (2006.01)
*G01N 33/53*    (2006.01)

(52) U.S. Cl. ...................................... 435/6.14; 435/7.1
(58) Field of Classification Search .................. None
See application file for complete search history.

(56) References Cited

OTHER PUBLICATIONS

Masih-Kham E. et al: "Macrophage inflammatory protein (MIP)-lalpha (CCL3) is a downstream target of FGFR3 and RAS signaling in multiple myeloma", Blood, vol. 106, No. 11, Part 1, Nov. 2005, pp. 76A-77A, & 47th Annual meeting of the American-Society-of-Hematology; Atlanta, GA, USA; Dec. 10-13, 2005 ISSN: 0006-4971 abstract.

Paterson J.L. et al.: "Preclinical studies of fibroblast growth factor receptor 3 as a therapeutic target in multiple myeloma", British Journal of Haematoloy, vol. 124, No. 5, Mar. 2004, pp. 595-603, XP002429018, ISSN: 0007-1048, abstract; figures 1-8.

Grand E.K. et al.: "Targeting FGFR3 in multiple myeloma: inhibition of t(4;14)-positive cells by SU5402 and PD173074", Leukemia (Basingstoke), vol. 18, No. 5, May 2004, pp. 962-966, XP00249019, ISSN: 0887-6924.

Trudel S. et al.: "CHIR-258, a novel, multitargeted tyrosine kinase inhibitor for the potential treatment of t(4;14) multiple myeloma", Blood Apr. 1, 2005, vol. 105, No. 7, pp. 2941-2948, XP002429020, ISSN: 0006-4971.

Keegan K. et al.: "Isolation of an additional member of the fibroblast growth factor receptor family, FGFR-3", Proceedings of the national Academy of Sciences of USA, National Academy of Science, Washington, DC, US, vol. 88, Feb. 1991, pp. 1095-1099, XP002071229, ISSN: 0027=-8424.

Claudio J.O., et al.: "A molecular compendium of genes expressed in multiple myeloma", Blood, W.B. Saunders Company, Orlando, FL, US, vol. 100, No. 6, Sep. 15, 2002, pp. 2175-2186, XP008038999, USSN: 0006-4971, abstract.

Chang H. et al.: "immunohistochemistry accurately predicts FGFR3 aberrant expression and t(4;14) in multiple myeloma", Blood, vol. 106, No. 1, Jul. 2005, pp. 353-355, 345, XP002429021, ISSN: 0006-4971.

Lee, S.H. et al. "In vivo Target Modulation and Biological Activity of CHIR-258, a Multitargeted Growth Factor Receptor Kinase Inhibitor, in Colon Cancer Models", Clinical Cancer Research, 2005. vol. 11, No. 10 (May), pp. 3633-3641.

Lopes De Menezes, D.E. et al. "CHIR-258: A Potent Inhibitor of FLT3 Kinase in Experimental Tumor Xenograft Models of Human Acute Myelogenous Leukemia", Clincal Cancer Research. 2005, vol. 11, No. 14 (Jul.), pp. 5281-5291.

Serveiev P. V., "Brief Course in Molecular Pharmacology", Ministry of Health of the Russian Soviet Federative Socialist Republic No. 1 Pirogov $2^{nd}$ Moscow Medical Institute, p. 10, 1975.

Kholodov L.E. et al., Clinical Pharmacokinetics Textbook, Moscow "Meditsina" [Medicine], pp. 83-98, 134-138, 160, 378-380, 1985.

*Primary Examiner* — James Martinell
(74) *Attorney, Agent, or Firm* — Cozette M McAvoy

(57) ABSTRACT

Methods of utilizing biomarkers to identify patients for treatment or to monitor response to treatment are taught herein. Alterations in levels of gene expression of the biomarkers, particularly in response to FGFR3 inhibition, are measured and identifications or adjustments may be made accordingly.

34 Claims, No Drawings

EFFECTS OF INHIBITORS OF FGFR3 ON GENE TRANSCRIPTION

This application claims benefit of U.S. Provisional Application No. 60/748,944, filed Dec. 8, 2005, which in its entirety is herein incorporated by reference.

BACKGROUND OF THE INVENTION

The present invention relates generally to the field of pharmacogenomics and in particular to the use of biomarkers for identifying patients suitable for treatment as well as to methods of following their response to methods of treatment.

An effort to understand an individual patient's response or disease progression is the topic of present day research. Indeed, the field of pharmacogenomics or pharmacogenetics utilizes genomic data, pharmacology, and medicine, and often relies on advanced research tools to correlate genetic variability to one or more of predisposition to a disease and/or its progression, as well as therapeutic response to a drug or therapeutic regimen. Typically, multiple genes are analyzed simultaneously in a large-scale, genome-wide approach.

Proliferative cell disorders such as cancers usually develop through the accumulation of a series of mutations in the patient's DNA within a subpopulation of cells. These mutations may confer a survival advantage on the cells that causes them to grow and spread in an uncontrolled manner that is deleterious to the surrounding tissues. The particular set of mutations may be unique to an individual patient's tumor. Cancers of the same tissue or organ in different individuals may have originated from different sets of mutations, though certain mutations may be prevalent among particular cancer types. The characteristic set of mutations will determine how the cancer cells behave, and in particular, their likelihood of response to a given therapeutic regimen.

One may characterize the genetic alterations in a tumor by using advanced research tools that measure the genetic sequence of the tumor's DNA, or the RNA or proteins that are the expression of the altered DNA. It is a goal of current research to identify characteristics of an individual's tumor that are predictive of the likelihood of that tumor's response to various therapeutic treatments. Thus, one or more genes would be identified where presence of particular genetic mutations in the DNA, or their levels of expression, either as RNA transcripts or as proteins, or a combination of these factors, would be predictive of the likelihood that a particular treatment would affect the tumor in a manner that would be beneficial to the patient.

One main purpose is to determine which variations in individuals or subpopulations, associated with their genetics or the genetic characteristics of their disease, factor into drug efficacy and to create suitable tests, including diagnostic tests. Drugs that are tailored for patients with a particular genetic sequence, or for diseases characterized by particular genetic alterations, may thus be produced. The tests may also be used to guide treatment decisions, such as which drug or drug combination is mostly likely to be beneficial to the patient, and what dosing and schedule is most appropriate. Diagnostic tests and genetic profiling will help avoid the expense and the potentially detrimental trial-and-error approach to the suitability of a particular treatment regimen or a particular dosage level.

While the era of customized drugs may be coming, methods that utilize genetic information to identify specific individuals or subgroups for a particular type of treatment or optimization of a treatment may be immediately put to use today.

An individual's response to a particular treatment or predisposition to disease and the correlation to a particular gene of interest has been documented. It is now believed that cancer chemotherapy is limited by the predisposition of specific populations to drug toxicity or poor drug response. For a review of the use of germline polymorphisms in clinical oncology, see Lenz, H.-J. (2004) J. Clin. Oncol. 22(13):2519-2521. For a review of pharmacogenetic and pharmacogenomics in therapeutic antibody development for the treatment of cancer, see Yan and Beckman (2005) Biotechniques 39:565-568.

Results from numerous studies suggest several genes may play a major role in the principal pathways of cancer progression and recurrence, and that the corresponding germ-line polymorphisms may lead to significant differences at transcriptional and/or translational levels. Polymorphism has been linked to cancer susceptibility (oncogenes, tumor suppressor genes, and genes of enzymes involved in metabolic pathways) of individuals. In patients younger than 35 years, several markers for increased cancer risk have been identified. Cytochrome P4501A1 and gluthathione S-transferase M1 genotypes influence the risk of developing prostate cancer in younger patients. Similarly, mutations in the tumor suppressor gene, p53, are associated with brain tumors in young adults.

This approach may be extended to mutations that are specific to cancer cells, and not otherwise found in the patient's genome. For instance, it has been demonstrated clinically in patients with gastrointestinal stromal tumors (GIST) treated with the drug Gleevec (imatinib mesylate; Novartis) that particular activating mutations in the genes KIT and PDGFA are linked to higher response rates to the drug, see *J Clin Oncol.* 2003 Dec. 1; 21(23):4342-9.

By measuring changes in gene expression of cancer cell lines induced by treatment with a particular therapeutic agent, one may characterize the cells' response to that agent. This approach provides insight into the mechanism of the drug, including what biological processes or pathways it impacts. Such information can help guide the treatment of patients, by providing expectations as to which genes will change in response to treatment. An assay of those genes from a sample collected from a patient post-treatment could then be used to determine whether the drug was having the intended effect, and by extension, whether the dose or schedule should be altered, or the regimen discontinued. This approach would improve efficacy by ensuring that patients receive the most appropriate treatment.

SUMMARY OF THE INVENTION

One embodiment of the invention relates to a method of identifying a patient for treatment. The method may optionally include an administration of an FGFR3 inhibitor to the patient prior to measurement of gene expression on a sample obtained from the patient. The gene expression analysis is intended to detect the presence and/or alteration in level of expression of biomarkers disclosed herein. Notable detection or alteration in the levels compared to baseline levels is indicative of the candidacy of the patient for treatment.

Another embodiment of the invention comprises a method of monitoring response of a patient to treatment. The method may include the step of administration of an FGFR3 inhibitor to the patient prior to measurement of gene expression on a sample obtained from the patient. Alternatively, monitoring may be conducted on a sample obtained from a patient who has previously been treated so that an administration step by one practicing the method of monitoring response is not required. Detection of an alteration in the level of expression of at least one biomarker compared to baseline is indicative of a favorable response of the patient to the treatment.

Another aspect of the invention is a method of utilizing a biomarker in treatment of a patient. An FGFR3 inhibitor may be administered and gene expression level of one or more biomarkers tested. Thereafter, the same or a different inhibitor may be administered in the treatment.

Yet another aspect of the invention is a method of treatment for multiple myeloma. The method utilizes an agent that alters the level of expression of one or more of the identified biomarkers.

A method of adjusting a dosage amount of an inhibitor of FGFR3 for treatment of a cell proliferative disorder in a patient is also taught herein. The method comprises administering an initial amount of the inhibitor of FGFR3 to the patient, monitoring gene expression on a sample from the patient for at least one of the identified biomarkers and adjusting the dosage amount for subsequent administration to the patient, depending on the level of expression of the biomarker or biomarkers that has occurred upon administration of the initial amount.

A further embodiment of the invention is a method of utilizing a biomarker to identify an FGFR3 inhibitory compound for potential treatment or further development.

DETAILED DESCRIPTION OF THE PREFERRED EMBODIMENTS

The invention is an example of translational medicine at work, wherein patients may be treated selectively based on their particular genetic profile.

Definitions and Techniques

The practice of the present invention will employ, unless otherwise indicated, conventional techniques of immunology, molecular biology, microbiology, cell biology and recombinant DNA, which are within the skill of the art. See e.g., Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL and ANIMAL CELL CULTURE (R. I. Freshney, ed. (1987)).

As used herein, certain terms have the following defined meanings.

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for guanine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

A "gene" refers to a polynucleotide containing at least one open reading frame (ORF) that is capable of encoding a particular polypeptide or protein after being transcribed and translated. A polynucleotide sequence may be used to identify larger fragments or full-length coding sequences of the gene with which they are associated. Methods of isolating larger fragment sequences are known to those of skill in the art.

A "gene product" or alternatively a "gene expression product" refers to the amino acid (e.g., peptide or polypeptide) generated when a gene is transcribed and translated.

The term "polypeptide" is used interchangeably with the term "protein" and in its broadest sense refers to a compound of two or more subunit amino acids, amino acid analogs, or peptidomimetics. The subunits may be linked by peptide bonds. In another embodiment, the subunit may be linked by other bonds, e.g., ester, ether, etc.

As used herein the term "amino acid" refers to either natural and/or unnatural or synthetic amino acids, and both the D and L optical isomers, amino acid analogs, and peptidomimetics.

A peptide of three or more amino acids is commonly called an oligopeptide if the peptide chain is short. If the peptide chain is long, the peptide is commonly called a polypeptide or a protein.

As used herein, the term "comprising" is intended to mean that the methods include the recited elements, but do not exclude others. "Consisting essentially of" when used to define compositions and methods, shall mean excluding other elements of any essential significance to the combination. Thus, for example, a composition consisting essentially of elements as listed would not exclude trace contaminants from the isolation and purification method and pharmaceutically acceptable carriers, such as phosphate buffered saline, preservatives and the like. "Consisting of" shall mean excluding more than trace elements of other ingredients and substantial method steps of this invention. Embodiments defined by each of these transition terms are within the scope of this invention.

The term "isolated" means separated from constituents, cellular and otherwise, in which the polynucleotide, peptide, polypeptide, protein, antibody or fragment(s) thereof, are normally associated within nature. In one aspect of this invention, an isolated polynucleotide is separated from the 3' and 5' contiguous nucleotides with which it is normally associated within its native or natural environment, e.g., on the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated", "separated" or "diluted" polynucleotide, peptide, polypeptide, protein, antibody or fragment(s) thereof, is distinguishable from its naturally occurring counterpart in that the concentration or number of molecules per volume is greater in a "concentrated" version or less than in a "separated" version than that of its naturally occurring counterpart. A polynucleotide, peptide, polypeptide, protein, antibody, or fragment(s) thereof, which differs from the naturally occurring counterpart in its primary sequence or, for example, by its glycosylation pattern, need not be present in its isolated form since it is distinguishable from its naturally occurring counterpart by its primary sequence or, alternatively, by another characteristic such as glycosylation pattern. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reactior" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in "PCR: A PRACTICAL APPROACH" (M. MacPherson et al, IRL Press at Oxford University Press (1991)). All processes of producing replicate copies of a polynucleotide, such as PCR or gene cloning, are collectively referred to herein as "replication." A primer can also be used as a probe in hybridization reactions, such as Southern or Northern blot analyses. Sambrook et al., supra.

As used herein, "expression" refers to the process by which polynucleotides are transcribed into mRNA and/or the process by which the transcribed mRNA is subsequently translated into peptides, polypeptides or proteins. If the polynucleotide is derived from genomic DNA, expression may include splicing of the mRNA in a eukaryotic cell. "Differentially expressed" as applied to a gene, refers to the differential production of the mRNA transcribed and/or translated from the gene or the protein product encoded by the gene. A differentially expressed gene may be overexpressed or underexpressed as compared to the expression level of a normal or control cell. However, as used herein overpression generally is at least 1.25 fold or, alternatively, at least 1.5 fold or, alternatively, at least 2 fold expression, or alternatively, at least 4 fold expression over that detected in a normal or healthy counterpart cell or tissue. The term "differentially expressed" also refers to nucleotide sequences in a cell or tissue which are expressed where silent in a control cell or not expressed where expressed in a control cell.

A high expression level of the gene may occur because of over expression of the gene or an increase in gene copy number. The gene may also be translated into more protein because of deregulation of a negative regulator.

A "gene expression profile" refers to a pattern of expression of a set of genes that recurs in multiple samples and reflects a property shared by those samples, such as tissue type, response to a particular treatment, or activation of a particular biological process or pathway in the cells. Furthermore, a gene expression profile differentiates between samples that share that common property and those that do not with better accuracy than would likely be achieved by assigning the samples to the two groups at random. A gene expression profile may be used to predict whether samples of unknown status share that common property or not. Some variation between the levels of the individual genes of the set and the typical profile is to be expected, but the overall similarity of the expression levels to the typical profile is such that it is statistically unlikely that the similarity would be observed by chance in samples not sharing the common property that the expression profile reflects.

An expression "database" denotes a set of stored data that represent a collection of sequences, which in turn represent a collection of biological reference materials.

The term "cDNAs" refers to complementary DNA, i.e. mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Exemplary vectors for libraries include bacteriophage (also known as "phage"), viruses that infect bacteria, for example, lambda phage. The library can then be probed for the specific cDNA (and thus mRNA) of interest.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels, microarrays, and chips. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany), or polydimethylacrylamide resin (obtained from Milligen/Bioscarch, California).

A polynucleotide also can be attached to a solid support for use in high throughput screening assays. PCT WO 97/10365, for example, discloses the construction of high density oligonucleotide chips. See also, U.S. Pat. Nos. 5,405,783; 5,412, 087; and 5,445,934. Using this method, the probes are synthesized on a derivatized glass surface to form chip arrays. Photoprotected nucleoside phosphoramidites are coupled to the glass surface, selectively deprotected by photolysis through a photo litho graphic mask and reacted with a second protected nucleoside phosphoramidite. The coupling/deprotection process is repeated until the desired probe is complete.

As an example, transcriptional activity may be assessed by measuring levels of messenger RNA using a gene chip such as the Affymetrix HG-U133-Plus-2 GeneChips. High-throughput, real-time quanititation of RNA (of hundreds of genes simultaneously) thus becomes possible in a reproducible system.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff 60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: www.ncbi.nlm.nih.gov/cgi-bin/BLAST.

The term "cell proliferative disorders" shall include dysregulation of normal physiological function characterized by abnormal cell growth and/or division or loss of function. Examples of "cell proliferative disorders" includes but is not limited to hyperplasia, neoplasia, metaplasia, and various autoimmune disorders, e.g., those characterized by the dysregulation of T cell apoptosis.

Hyperplasia is a form of controlled cell proliferation involving an increase in cell number in a tissue or organ, without significant alteration in structure or function. Metaplasia is a form of controlled cell growth in which one type of fully differentiated cell substitutes for another type of differentiated cell. Metaplasia can occur in epithelial or connective tissue cells. Atypical metaplasia involves a somewhat disorderly metaplastic epithelium.

As used herein, the terms "neoplastic cells," "neoplastic disease," "neoplasia," "tumor," "tumor cells," "cancer," and "cancer cells," (used interchangeably) refer to cells which exhibit relatively autonomous growth, so that they exhibit an aberrant growth phenotype characterized by a significant loss of control of cell proliferation (i.e., dc-regulated cell division). Neoplastic cells can be malignant or benign. A metastatic cell or tissue means that the cell can invade and destroy neighboring body structures.

"Suppressing" tumor growth indicates a growth state that is curtailed when compared to growth without contact with educated, antigen-specific immune effector cells. Tumor cell growth can be assessed by any means known in the art, including, but not limited to, measuring tumor size, determining whether tumor cells are proliferating using a $^3$H-thymidine incorporation assay or counting tumor cells. "Suppressing" tumor cell growth means any or all of the following states: slowing, delaying and stopping tumor growth, as well as tumor shrinkage.

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents.

The compositions also can include stabilizers and preservatives and any of the above noted carriers with the additional provisio that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998).

An "effective amount" is an amount sufficient to effect beneficial or desired results. An effective amount can be administered in one or more administrations, applications or dosages.

A "subject," "individual" or "patient" is used interchangeably herein, which refers to a vertebrate, preferably a mammal, more preferably a human. Mammals include, but are not limited to, murines, simians, humans, farm animals, sport animals, and pets.

"FGFR3" is the acronym for fibroblast growth factor receptor 3. The fibroblast growth factors are a family of polypeptide growth factors involved in a variety of activities, including mitogenesis, angiogenesis, and wound healing. They contain an extracellular domain with either 2 or 3 immunoglobulin (Ig)-like domains, a transmembrane domain, and a cytoplasmic tyrosine kinase domain. FGFR3 was cloned by Keegan et al., PNAS, 88:1095-1099 (1991). Inhibition of activated FGFR3 in t(4; 14) multiple myeloma patients is thought to lead to apoptosis. Trudel, et al., *Blood*, 105(7): 2941-2948 (2005); Grand, et al., *Leukemia*, 18:962-966 (2004).

An "inhibitor" of FGFR3 as used herein binds or blocks or diminishes the effect of the FGFR3. Examples include, but are not limited to CHIR-258 and related compounds, SU-5402, PD-173074, and siRNA.

A "biomarker" is a distinctive indicator or specific feature or characteristic of a biological process or event. As used herein, a biomarker is a gene. A biomarker may be especially useful for measuring the progress of a disease or the response to a given treatment. In addition to assessing prognosis, in some instances, it may be used to diagnose an illness or screen for patients within a category, such as those most likely to respond to a certain type of treatment. A biomarker may also be useful in guiding the development or administration of an agent for treatment of a disease.

As noted above, the invention provides methods of identifying patients suitable for treatment and methods of monitoring response in patients receiving treatment. Also provided are methods of treatment and methods of adjusting dosage amounts by utilizing the biomarkers disclosed herein. Methods of identifying the appropriate inhibitory compound are also within the scope of the invention.

The present invention also provides a screen for various agents and methods that may supplement or replace the anti-FGFR3 therapy known in the art. In one aspect, the agent, alone or in combination with another agent or therapy method, is provided to the patient. After administration, a sample from the patient is screened for expression of one or more biomarkers identified herein and then compared to a pre-determined baseline.

Kits containing an FGFR3 inhibitor and instructions necessary to perform a method of the invention also are within the scope of the invention.

Further details regarding the practice of the invention are discussed below.

Biomarkers

Panels of genes have now been identified, whose expression correlates with the inhibition of FGFR3. The presence or absence of gene expression or the level or amount of gene expression of one or more of the biomarkers identified herein may be used to guide treatment decisions and measure responsiveness of the patient to a given type of treatment. For example, detection of the presence or lack thereof of gene expression or alteration of the level of gene expression compared to a predetermined baseline of one or more of the biomarkers identified in Tables I-V provides information regarding whether a patient may be a suitable candidate for treatment by CHIR-258 or another FGFR3 inhibitor.

It should be noted that any or all of the following biomarkers may be of particular interest: CCL3, LOC150271, CD48, DUSP4, ITGB7, DUSP6, ANXA9, CR2, AL531683, ZNF589, AW274468, FRMD3, LTB, and WDR42A.

As is apparent to one of skill in the art, gene expression can be measured by detecting the presence or absence, or presence and/or absolute or relative quantity of a gene expression product (e.g., RNA, mRNA, or the protein or polypeptide transcript) or the alteration in gene copy number. In some embodiments, altered expression is likely the result of an increase in copy number. In alternative embodiment, altered expression is likely the result of the loss of function of another gene such as a tumor suppressor or other negative regulator. In yet a further embodiment, expression is altered by the "turning on" of an enhancer. Accordingly, the specific method used to detect altered expression, as compared to the control or baseline, may be different and dependent on the particular biomarker selected. In yet further embodiments, the method requires analysis of gene expression of one or more predetermined biomarkers by more than one method, e.g., by use of immunohistochemical and molecular techniques such as a gene chip or array.

Tables

Tables I through V are presented below and constitute an integral part of this disclosure.

Table I is a list of biomarkers whose expression is indicative of activity related to FGFR3 inhibition.

Table II is a preferred subset of Table I according to one aspect of the invention, listing biomarkers generally having a higher level of alteration of gene expression compared to baseline in response to FGFR3 inhibition.

Table III is more preferred subset of Table I according to one aspect of the invention, listing biomarkers generally having the highest level of alteration of gene expression compared to baseline in response to FGFR3 inhibition.

Table IV is a preferred subset of Table I according to a second aspect of the invention, listing biomarkers generally exhibiting the strongest correlation of gene expression in response to FGFR3 inhibition by the preferred compound, CHIR-258.

Table V is a more preferred subset of Table I according to a second aspect of the invention, listing biomarkers generally exhibiting the strongest correlation of gene expression in response to FGFR3 inhibition by the preferred compound, CHIR-258, in preference to either SU-5402 or PD-173074.

In each of Tables I through V, the biomarkers are shown with Entrez Gene ID Number (referring to the National Cancer Institute database identifier), Gene Symbol, and Gene Description.

TABLE I

| | ENTREZ GENE ID | GENE SYMBOL | GENE DESCRIPTION |
|---|---|---|---|
| 1. | 6348 | CCL3 | chemokine (C-C motif) ligand 3 |
| 2. | 200734 | SPRED2 | sprouty-related, EVH1 domain containing 2 |
| 3. | 117854 | TRIM6 | tripartite motif-containing 6 |
| 4. | 1846 | DUSP4 | dual specificity phosphatase 4 |
| 5. | 894 | CCND2 | cyclin D2 |
| 6. | 6241 | RRM2 | ribonucleotide reductase M2 polypeptide |
| 7. | 4821 | NKX2-2 | NK2 transcription factor related, locus 2 (*Drosophila*) |
| 8. | 3037 | HAS2 | hyaluronan synthase 2 |
| 9. | 990 | CDC6 | CDC6 cell division cycle 6 homolog (*S. cerevisiae*) |
| 10. | 57405 | SPBC25 | spindle pole body component 25 homolog (*S. cerevisiae*) |
| 11. | 934 | CD24 | CD24 antigen (small cell lung carcinoma cluster 4 antigen) |
| 12. | 55165 | C10orf3 | chromosome 10 open reading frame 3 |
| 13. | 55388 | MCM10 | MCM10 minichromosome maintenance deficient 10 (*S. cerevisiae*) |
| 14. | 79019 | C22orf18 | chromosome 22 open reading frame 18 |
| 15. | 9768 | KIAA0101 | KIAA0101 |
| 16. | 51659 | Pfs2 | DNA replication complex GINS protein PSF2 |
| 17. | 4605 | MYBL2 | v-myb myeloblastosis viral oncogene homolog (avian)-like 2 |
| 18. | 161742 | SPRED1 | sprouty-related, EVH1 domain containing 1 |
| 19. | 4175 | MCM6 | MCM6 minichromosome maintenance deficient 6 (MIS5 homolog, *S. pombe*) (*S. cerevisiae*) |
| 20. | 11130 | ZWINT | ZW10 interactor |
| 21. | 26298 | EHF | ets homologous factor |
| 22. | 7117 | TMSL3 | thymosin-like 3 |
| 23. | 890 | CCNA2 | cyclin A2 |
| 24. | 79075 | DCC1 | defective in sister chromatid cohesion homolog 1 (*S. cerevisiae*) |
| 25. | 83879 | CDCA7 | cell division cycle associated 7 |
| 26. | 22873 | DZIP1 | DAZ interacting protein 1 |
| 27. | 51514 | DTL | denticleless homolog (*Drosophila*) |
| 28. | 55789 | DEPDC1B | DEP domain containing 1B |
| 29. | 55355 | DKFZp762E1312 | hypothetical protein DKFZp762E1312 |
| 30. | 10052 | GJA7 | gap junction protein, alpha 7, 45 kDa (connexin 45) |
| 31. | 146909 | LOC146909 | hypothetical protein LOC146909 |
| 32. | 113130 | CDCA5 | cell division cycle associated 5 |
| 33. | 1017 | CDK2 | cyclin-dependent kinase 2 |
| 34. | 4176 | MCM7 | MCM7 minichromosome maintenance deficient 7 (*S. cerevisiae*) |
| 35. | 81610 | C20orf129 | chromosome 20 open reading frame 129 |
| 36. | 9833 | MELK | maternal embryonic leucine zipper kinase |
| 37. | 29128 | UHRF1 | ubiquitin-like, containing PHD and RING finger domains, 1 |
| 38. | 4171 | MCM2 | MCM2 minichromosome maintenance deficient 2, mitotin (*S. cerevisiae*) |
| 39. | 79801 | SHCBP1 | SHC SH2-domain binding protein 1 |
| 40. | 28231 | SLCO4A1 | solute carrier organic anion transporter family, member 4A1 |
| 41. | 113115 | FAM54A | family with sequence similarity 54, member A |
| 42. | 22974 | TPX2 | TPX2, microtubule-associated protein homolog (*Xenopus laevis*) |
| 43. | 9232 | PTTG1 | pituitary tumor-transforming 1 |
| 44. | 137392 | LOC137392 | similar to CG6405 gene product |
| 45. | 195828 | ZNF367 | zinc finger protein 367 |
| 46. | 4288 | MKI67 | antigen identified by monoclonal antibody Ki-67 |
| 47. | 701 | BUB1B | BUB1 budding uninhibited by benzimidazoles 1 homolog beta (yeast) |
| 48. | 9928 | KIF14 | kinesin family member 14 |
| 49. | 3832 | KIF11 | kinesin family member 11 |
| 50. | 11065 | UBE2C | ubiquitin-conjugating enzyme E2C |
| 51. | 9837 | PSF1 | DNA replication complex GINS protein PSF1 |
| 52. | 387103 | C6orf173 | chromosome 6 open reading frame 173 |
| 53. | 1870 | E2F2 | E2F transcription factor 2 |
| 54. | 79733 | E2F8 | E2F transcription factor 8 |
| 55. | 991 | CDC20 | CDC20 cell division cycle 20 homolog (*S. cerevisiae*) |
| 56. | 3014 | H2AFX | H2A histone family, member X |
| 57. | 10112 | KIF20A | kinesin family member 20A |
| 58. | 993 | CDC25A | cell division cycle 25A |
| 59. | 24137 | KIF4A | kinesin family member 4A |
| 60. | 80144 | FRAS1 | Fraser syndrome 1 |
| 61. | 55010 | FLJ20641 | hypothetical protein FLJ20641 |
| 62. | 9319 | TRIP13 | thyroid hormone receptor interactor 13 |
| 63. | 9355 | LHX2 | LIM homeobox 2 |
| 64. | 7153 | TOP2A | topoisomerase (DNA) II alpha 170 kDa |
| 65. | 4174 | MCM5 | MCM5 minichromosome maintenance deficient 5, cell division cycle 46 (*S. cerevisiae*) |
| 66. | 55215 | FLJ10719 | hypothetical protein FLJ10719 |

TABLE I-continued

| | ENTREZ GENE ID | GENE SYMBOL | GENE DESCRIPTION |
|---|---|---|---|
| 67. | 11013 | TMSL8 | thymosin-like 8 |
| 68. | 5983 | RFC3 | replication factor C (activator 1) 3, 38 kDa |
| 69. | 1063 | CENPF | centromere protein F, 350/400ka (mitosin) |
| 70. | 3683 | ITGAL | integrin, alpha L (antigen CD11A (p180), lymphocyte function-associated antigen 1; alpha polypeptide) |
| 71. | 2237 | FEN1 | flap structure-specific endonuclease 1 |
| 72. | 27338 | UBE2S | ubiquitin-conjugating enzyme E2S |
| 73. | 4001 | LMNB1 | lamin B1 |
| 74. | 29089 | UBE2T | ubiquitin-conjugating enzyme E2T (putative) |
| 75. | 55839 | BM039 | uncharacterized bone marrow protein BM039 |
| 76. | 2115 | ETV1 | ets variant gene 1 |
| 77. | 440279 | UNC13C | unc-13 homolog C (*C. elegans*) |
| 78. | 962 | CD48 | CD48 antigen (B-cell membrane protein) |
| 79. | 54910 | SEMA4C | sema domain, immunoglobulin domain (Ig), transmembrane domain (TM) and short cytoplasmic domain, (semaphorin) 4C |
| 80. | 1902 | EDG2 | endothelial differentiation, lysophosphatidic acid G-protein-coupled receptor, 2 |
| 81. | 64946 | CENPH | centromere protein H |
| 82. | 157570 | ESCO2 | establishment of cohesion 1 homolog 2 (*S. cerevisiae*) |
| 83. | 389835 | FAM72A | family with sequence similarity 72, member A |
| 84. | 144455 | E2F7 | E2F transcription factor 7 |
| 85. | 51512 | GTSE1 | G-2 and S-phase expressed 1 |
| 86. | 7298 | TYMS | thymidylate synthetase |
| 87. | 7374 | UNG | uracil-DNA glycosylase |
| 88. | 5578 | PRKCA | protein kinase C, alpha |
| 89. | 672 | BRCA1 | breast cancer 1, early onset |
| 90. | 84952 | CGNL1 | cingulin-like 1 |
| 91. | 10252 | SPRY1 | sprouty homolog 1, antagonist of FGF signaling (*Drosophila*) |
| 92. | 79682 | MLF1IP | MLF1 interacting protein |
| 93. | 8851 | CDK5R1 | cyclin-dependent kinase 5, regulatory subunit 1 (p35) |
| 94. | 10635 | RAD51AP1 | RAD51 associated protein 1 |
| 95. | 22998 | KIAA1102 | KIAA1102 protein |
| 96. | 148203 | LOC148203 | hypothetical protein LOC148203 |
| 97. | 7465 | WEE1 | WEE1 homolog (*S. pombe*) |
| 98. | 83540 | CDCA1 | cell division cycle associated 1 |
| 99. | 3070 | HELLS | helicase, lymphoid-specific |
| 100. | 891 | CCNB1 | cyclin B1 |
| 101. | 6790 | STK6 | serine/threonine kinase 6 |
| 102. | 56992 | KIF15 | kinesin family member 15 |
| 103. | 7112 | TMPO | thymopoietin |
| 104. | 63901 | FLJ22794 | FLJ22794 protein |
| 105. | 9493 | KIF23 | kinesin family member 23 |
| 106. | 9133 | CCNB2 | cyclin B2 |
| 107. | 4173 | MCM4 | MCM4 minichromosome maintenance deficient 4 (*S. cerevisiae*) |
| 108. | 7083 | TK1 | thymidine kinase 1, soluble |
| 109. | 983 | CDC2 | cell division cycle 2, G1 to S and G2 to M |
| 110. | 11339 | OIP5 | Opa interacting protein 5 |
| 111. | 51203 | NUSAP1 | nucleolar and spindle associated protein 1 |
| 112. | 5111 | PCNA | proliferating cell nuclear antigen |
| 113. | 11004 | KIF2C | kinesin family member 2C |
| 114. | 54443 | ANLN | anillin, actin binding protein (scraps homolog, *Drosophila*) |
| 115. | 83461 | CDCA3 | cell division cycle associated 3 |
| 116. | 4085 | MAD2L1 | MAD2 mitotic arrest deficient-like 1 (yeast) |
| 117. | 9201 | DCAMKL1 | doublecortin and CaM kinase-like 1 |
| 118. | 1111 | CHEK1 | CHK1 checkpoint homolog (*S. pombe*) |
| 119. | 9055 | PRC1 | protein regulator of cytokinesis 1 |
| 120. | 7804 | LRP8 | low density lipoprotein receptor-related protein 8, apolipoprotein e receptor |
| 121. | 4915 | NTRK2 | neurotrophic tyrosine kinase, receptor, type 2 |
| 122. | 28951 | TRIB2 | tribbles homolog 2 (*Drosophila*) |
| 123. | 4281 | MID1 | midline 1 (Opitz/BBB syndrome) |
| 124. | 3148 | HMGB2 | high-mobility group box 2 |
| 125. | 3161 | HMMR | hyaluronan-mediated motility receptor (RHAMM) |
| 126. | 10276 | NET1 | neuroepithelial cell transforming gene 1 |
| 127. | 29028 | ATAD2 | ATPase family, AAA domain containing 2 |
| 128. | 1062 | CENPE | centromere protein E, 312 kDa |
| 129. | 1491 | CTH | cystathionase (cystathionine gamma-lyase) |
| 130. | 10615 | SPAG5 | sperm associated antigen 5 |
| 131. | 64581 | CLEC7A | C-type lectin domain family 7, member A |
| 132. | 10592 | SMC2L1 | SMC2 structural maintenance of chromosomes 2-like 1 (yeast) |
| 133. | 332 | BIRC5 | baculoviral IAP repeat-containing 5 (survivin) |

TABLE I-continued

| | ENTREZ GENE ID | GENE SYMBOL | GENE DESCRIPTION |
|---|---|---|---|
| 134. | 4172 | MCM3 | MCM3 minichromosome maintenance deficient 3 (*S. cerevisiae*) |
| 135. | 64105 | FKSG14 | leucine zipper protein FKSG14 |
| 136. | 64151 | HCAP-G | chromosome condensation protein G |
| 137. | 1163 | CKS1B | CDC28 protein kinase regulatory subunit 1B |
| 138. | 122769 | PPIL5 | peptidylprolyl isomerase (cyclophilin)-like 5 |
| 139. | 3398 | ID2 | inhibitor of DNA binding 2, dominant negative helix-loop-helix protein |
| 140. | 22822 | PHLDA1 | pleckstrin homology-like domain, family A, member 1 |
| 141. | 1718 | DHCR24 | 24-dehydrocholesterol reductase |
| 142. | 145482 | ZADH1 | zinc binding alcohol dehydrogenase, domain containing 1 |
| 143. | 1847 | DUSP5 | dual specificity phosphatase 5 |
| 144. | 26271 | FBXO5 | F-box protein 5 |
| 145. | 9212 | AURKB | aurora kinase B |
| 146. | 29968 | PSAT1 | phosphoserine aminotransferase 1 |
| 147. | 26147 | PHF19 | PHD finger protein 19 |
| 148. | 55635 | DEPDC1 | DEP domain containing 1 |
| 149. | 10403 | KNTC2 | kinetochore associated 2 |
| 150. | 64081 | MAWBP | MAWD binding protein |
| 151. | 84858 | ZNF503 | zinc finger protein 503 |
| 152. | 55723 | ASF1B | ASF1 anti-silencing function 1 homolog B (*S. cerevisiae*) |
| 153. | 7272 | TTK | TTK protein kinase |
| 154. | 9535 | GMFG | glia maturation factor, gamma |
| 155. | 1058 | CENPA | centromere protein A, 17 kDa |
| 156. | 84515 | MCM8 | MCM8 minichromosome maintenance deficient 8 (*S. cerevisiae*) |
| 157. | 54069 | C21orf45 | chromosome 21 open reading frame 45 |
| 158. | 5984 | RFC4 | replication factor C (activator 1) 4, 37 kDa |
| 159. | 389831 | LOC389831 | hypothetical gene supported by AL713796 |
| 160. | 157313 | CDCA2 | cell division cycle associated 2 |
| 161. | 29127 | RACGAP1 | Rac GTPase activating protein 1 |
| 162. | 55872 | PBK | PDZ binding kinase |
| 163. | 4678 | NASP | nuclear autoantigenic sperm protein (histone-binding) |
| 164. | 7171 | TPM4 | tropomyosin 4 |
| 165. | 7443 | VRK1 | vaccinia related kinase 1 |
| 166. | 699 | BUB1 | BUB1 budding uninhibited by benzimidazoles 1 homolog (yeast) |
| 167. | 3925 | STMN1 | stathmin 1/oncoprotein 18 |
| 168. | 865 | CBFB | core-binding factor, beta subunit |
| 169. | 399664 | RKHD1 | ring finger and KH domain containing 1 |
| 170. | 11168 | PSIP1 | PC4 and SFRS1 interacting protein 1 |
| 171. | 84057 | GAJ | GAJ protein |
| 172. | 57082 | CASC5 | cancer susceptibility candidate 5 |
| 173. | 23286 | KIBRA | KIBRA protein |
| 174. | 285513 | LOC285513 | hypothetical protein LOC285513 |
| 175. | 259266 | ASPM | asp (abnormal spindle)-like, microcephaly associated (*Drosophila*) |
| 176. | 150468 | FLJ40629 | hypothetical protein FLJ40629 |
| 177. | 6659 | SOX4 | SRY (sex determining region Y)-box 4 |
| 178. | 51053 | GMNN | geminin, DNA replication inhibitor |
| 179. | 3159 | HMGA1 | high mobility group AT-hook 1 |
| 180. | 81620 | CDT1 | DNA replication factor |
| 181. | 11332 | BACH | brain acyl-CoA hydrolase |
| 182. | 4751 | NEK2 | NIMA (never in mitosis gene a)-related kinase 2 |
| 183. | 1033 | CDKN3 | cyclin-dependent kinase inhibitor 3 (CDK2-associated dual specificity phosphatase) |
| 184. | 8864 | PER2 | period homolog 2 (*Drosophila*) |
| 185. | 3418 | IDH2 | isocitrate dehydrogenase 2 (NADP+), mitochondrial |
| 186. | 63979 | FIGNL1 | fidgetin-like 1 |
| 187. | 55646 | LYAR | hypothetical protein FLJ20425 |
| 188. | 91614 | LOC91614 | novel 58.3 KDA protein |
| 189. | 8630 | HSD17B6 | hydroxysteroid (17-beta) dehydrogenase 6 |
| 190. | 1038 | CDR1 | cerebellar degeneration-related protein 1, 34 kDa |
| 191. | 6941 | TCF19 | transcription factor 19 (SC1) |
| 192. | 256435 | ST6GALNAC3 | ST6 (alpha-N-acetyl-neuraminyl-2,3-beta-galactosyl-1,3)-N-acetylgalactosaminide alpha-2,6-sialyltransferase 3 |
| 193. | 54892 | LUZP5 | leucine zipper protein 5 |
| 194. | 4603 | MYBL1 | v-myb myeloblastosis viral oncogene homolog (avian)-like 1 |
| 195. | 1719 | DHFR | dihydrofolate reductase |
| 196. | 170954 | KIAA1949 | KIAA1949 |
| 197. | 7903 | ST8SIA4 | ST8 alpha-N-acetyl-neuraminide alpha-2,8-sialyltransferase 4 |
| 198. | 9787 | DLG7 | discs, large homolog 7 (*Drosophila*) |
| 199. | 56935 | FN5 | FN5 protein |

TABLE I-continued

| | ENTREZ GENE ID | GENE SYMBOL | GENE DESCRIPTION |
|---|---|---|---|
| 200. | 3015 | H2AFZ | H2A histone family, member Z |
| 201. | 10189 | THOC4 | THO complex 4 |
| 202. | 494143 | LOC494143 | similar to RIKEN cDNA 2510006C20 gene |
| 203. | 6240 | RRM1 | ribonucleotide reductase M1 polypeptide |
| 204. | 1894 | ECT2 | epithelial cell transforming sequence 2 oncogene |
| 205. | 7913 | DEK | DEK oncogene (DNA binding) |
| 206. | 2146 | EZH2 | enhancer of zeste homolog 2 (*Drosophila*) |
| 207. | 55055 | FLJ10036 | Zwilch |
| 208. | 11073 | TOPBP1 | topoisomerase (DNA) II binding protein 1 |
| 209. | 55502 | HES6 | hairy and enhancer of split 6 (*Drosophila*) |
| 210. | 55247 | NEIL3 | nei endonuclease VIII-like 3 (*E. coli*) |
| 211. | 54885 | FLJ20298 | FLJ20298 protein |
| 212. | 83641 | C10orf45 | chromosome 10 open reading frame 45 |
| 213. | 64919 | BCL11B | B-cell CLL/lymphoma 11B (zinc finger protein) |
| 214. | 26095 | PTPN20 | protein tyrosine phosphatase, non-receptor type 20 |
| 215. | 23590 | TPRT | trans-prenyltransferase |
| 216. | 387882 | LOC387882 | hypothetical protein |
| 217. | 51232 | CRIM1 | cysteine-rich motor neuron 1 |
| 218. | 801 | CALM1 | calmodulin 1 (phosphorylase kinase, delta) |
| 219. | 55964 | SEPT3 | septin 3 |
| 220. | 493861 | EID3 | E1A-like inhibitor of differentiation 3 |
| 221. | 29980 | DONSON | downstream neighbor of SON |
| 222. | 147138 | EVER2 | epidermodysplasia verruciformis 2 |
| 223. | 80150 | ASRGL1 | asparaginase like 1 |
| 224. | 5985 | RFC5 | replication factor C (activator 1) 5, 36.5 kDa |
| 225. | 51155 | HN1 | hematological and neurological expressed 1 |
| 226. | 7004 | TEAD4 | TEA domain family member 4 |
| 227. | 4325 | MMP16 | matrix metalloproteinase 16 (membrane-inserted) |
| 228. | 203068 | TUBB | tubulin, beta polypeptide |
| 229. | 4602 | MYB | v-myb myeloblastosis viral oncogene homolog (avian) |
| 230. | 55706 | TMEM48 | transmembrane protein 48 |
| 231. | 348235 | FAM33A | family with sequence similarity 33, member A |
| 232. | 8871 | SYNJ2 | synaptojanin 2 |
| 233. | 81563 | C1orf21 | chromosome 1 open reading frame 21 |
| 234. | 51192 | CKLF | chemokine-like factor |
| 235. | 2326 | FMO1 | flavin containing monooxygenase 1 |
| 236. | 91057 | NY-REN-41 | NY-REN-41 antigen |
| 237. | 10376 | K-ALPHA-1 | tubulin, alpha, ubiquitous |
| 238. | 23234 | DNAJC9 | DnaJ (Hsp40) homolog, subfamily C, member 9 |
| 239. | 5982 | RFC2 | replication factor C (activator 1) 2, 40 kDa |
| 240. | 51063 | FAM26B | family with sequence similarity 26, member B |
| 241. | 9953 | HS3ST3B1 | heparan sulfate (glucosamine) 3-O-sulfotransferase 3B1 |
| 242. | 79723 | SUV39H2 | suppressor of variegation 3-9 homolog 2 (*Drosophila*) |
| 243. | 79596 | C13orf7 | chromosome 13 open reading frame 7 |
| 244. | 23165 | NUP205 | nucleoporin 205 kDa |
| 245. | 9530 | BAG4 | BCL2-associated athanogene 4 |
| 246. | 3146 | HMGB1 | high-mobility group box 1 |
| 247. | 445815 | PALM2-AKAP2 | PALM2-AKAP2 protein |
| 248. | 5557 | PRIM1 | primase, polypeptide 1, 49 kDa |
| 249. | 2983 | GUCY1B3 | guanylate cyclase 1, soluble, beta 3 |
| 250. | 51776 | ZAK | sterile alpha motif and leucine zipper containing kinase AZK |
| 251. | 10926 | ASK | activator of S phase kinase |
| 252. | 8833 | GMPS | guanine monphosphate synthetase |
| 253. | 84930 | MASTL | microtubule associated serine/threonine kinase-like |
| 254. | 90417 | C15orf23 | chromosome 15 open reading frame 23 |
| 255. | 8530 | CST7 | cystatin F (leukocystatin) |
| 256. | 9532 | BAG2 | BCL2-associated athanogene 2 |
| 257. | 23310 | hCAP-D3 | KIAA0056 protein |
| 258. | 283991 | MGC29814 | hypothetical protein MGC29814 |
| 259. | 91607 | FLJ34922 | hypothetical protein FLJ34922 |
| 260. | 7398 | USP1 | ubiquitin specific protease 1 |
| 261. | 2669 | GEM | GTP binding protein overexpressed in skeletal muscle |
| 262. | 151246 | SGOL2 | shugoshin-like 2 (*S. pombe*) |
| 263. | 23421 | ITGB3BP | integrin beta 3 binding protein (beta3-endonexin) |
| 264. | 84969 | C20orf100 | chromosome 20 open reading frame 100 |
| 265. | 201725 | LOC201725 | hypothetical protein LOC201725 |
| 266. | 5361 | PLXNA1 | plexin A1 |
| 267. | 3708 | ITPR1 | inositol 1,4,5-triphosphate receptor, type 1 |
| 268. | 55740 | ENAH | enabled homolog (*Drosophila*) |
| 269. | 126731 | C1orf96 | chromosome 1 open reading frame 96 |
| 270. | 57037 | ANKMY2 | ankyrin repeat and MYND domain containing 2 |

TABLE I-continued

| | ENTREZ GENE ID | GENE SYMBOL | GENE DESCRIPTION |
|---|---|---|---|
| 271. | 23331 | KIAA1043 | KIAA1043 protein |
| 272. | 3930 | LBR | lamin B receptor |
| 273. | 3838 | KPNA2 | karyopherin alpha 2 (RAG cohort 1, importin alpha 1) |
| 274. | 1230 | CCR1 | chemokine (C-C motif) receptor 1 |
| 275. | 2200 | FBN1 | fibrillin 1 (Marfan syndrome) |
| 276. | 6867 | TACC1 | transforming, acidic coiled-coil containing protein 1 |
| 277. | 27115 | PDE7B | phosphodiesterase 7B |
| 278. | 11151 | CORO1A | coronin, actin binding protein, 1A |
| 279. | 6385 | SDC4 | syndecan 4 (amphiglycan, ryudocan) |
| 280. | 3182 | HNRPAB | heterogeneous nuclear ribonucleoprotein A/B |
| 281. | 5757 | PTMA | prothymosin, alpha (gene sequence 28) |
| 282. | 83990 | BRIP1 | BRCA1 interacting protein C-terminal helicase 1 |
| 283. | 9830 | TRIM14 | tripartite motif-containing 14 |
| 284. | 57761 | TRIB3 | tribbles homolog 3 (*Drosophila*) |
| 285. | 2026 | ENO2 | enolase 2 (gamma, neuronal) |
| 286. | 8727 | CTNNAL1 | catenin (cadherin-associated protein), alpha-like 1 |
| 287. | 5880 | RAC2 | ras-related C3 botulinum toxin substrate 2 (rho family, small GTP bindin protein Rac2) |
| 288. | 864 | RUNX3 | runt-related transcription factor 3 |
| 289. | 10950 | BTG3 | BTG family, member 3 |
| 290. | 81539 | SLC38A1 | solute carrier family 38, member 1 |
| 291. | 26051 | PPP1R16B | protein phosphatase 1, regulatory (inhibitor) subunit 16B |
| 292. | 5793 | PTPRG | protein tyrosine phosphatase, receptor type, G |
| 293. | 2767 | GNA11 | guanine nucleotide binding protein (G protein), alpha 11 (Gq class) |
| 294. | 55013 | FLJ20647 | hypothetical protein FLJ20647 |
| 295. | 4885 | NPTX2 | neuronal pentraxin II |
| 296. | 79710 | MORC4 | MORC family CW-type zinc finger 4 |
| 297. | 490 | ATP2B1 | ATPase, Ca++ transporting, plasma membrane 1 |
| 298. | 2956 | MSH6 | mutS homolog 6 (*E. coli*) |
| 299. | 6611 | SMS | spermine synthase |
| 300. | 6627 | SNRPA1 | small nuclear ribonucleoprotein polypeptide A[1] |
| 301. | 1434 | CSE1L | CSE1 chromosome segregation 1-like (yeast) |
| 302. | 7371 | UCK2 | uridine-cytidine kinase 2 |
| 303. | 7277 | TUBA1 | tubulin, alpha 1 (testis specific) |
| 304. | 1786 | DNMT1 | DNA (cytosine-5-)-methyltransferase 1 |
| 305. | 54801 | FAM29A | family with sequence similarity 29, member A |
| 306. | 54908 | FLJ20364 | hypothetical protein FLJ20364 |
| 307. | 119467 | MGC32871 | hypothetical protein MGC32871 |
| 308. | 90390 | THRAP6 | thyroid hormone receptor associated protein 6 |
| 309. | 60468 | BACH2 | BTB and CNC homology 1, basic leucine zipper transcription factor 2 |
| 310. | 6510 | SLC1A5 | solute carrier family 1 (neutral amino acid transporter), member 5 |
| 311. | 6628 | SNRPB | small nuclear ribonucleoprotein polypeptides B and B1 |
| 312. | 205 | AK3L1 | adenylate kinase 3-like 1 |
| 313. | 116832 | RPL39L | ribosomal protein L39-like |
| 314. | 79902 | PCNT1 | pericentrin 1 |
| 315. | 54962 | FLJ20516 | timeless-interacting protein |
| 316. | 23279 | NUP160 | nucleoporin 160 kDa |
| 317. | 23046 | KIF21B | kinesin family member 21B |
| 318. | 2288 | FKBP4 | FK506 binding protein 4, 59 kDa |
| 319. | 5698 | PSMB9 | proteasome (prosome, macropain) subunit, beta type, 9 (large multifunctional protease 2) |
| 320. | 10160 | FARP1 | FERM, RhoGEF (ARHGEF) and pleckstrin domain protein 1 (chondrocyte-derived) |
| 321. | 8502 | PKP4 | plakophilin 4 |
| 322. | 10675 | CSPG5 | chondroitin sulfate proteoglycan 5 (neuroglycan C) |
| 323. | 29899 | GPSM2 | G-protein signalling modulator 2 (AGS3-like, *C. elegans*) |
| 324. | 10602 | CDC42EP3 | CDC42 effector protein (Rho GTPase binding) 3 |
| 325. | 8243 | SMC1L1 | SMC1 structural maintenance of chromosomes 1-like 1 (yeast) |
| 326. | 6347 | CCL2 | chemokine (C-C motif) ligand 2 |
| 327. | 5932 | RBBP8 | retinoblastoma binding protein 8 |
| 328. | 6877 | TAF5 | TAF5 RNA polymerase II, TATA box binding protein (TBP)-associated factor, 100 kDa |
| 329. | 10801 | SEPT9 | septin 9 |
| 330. | 55536 | CDCA7L | cell division cycle associated 7-like |
| 331. | 11340 | EXOSC8 | exosome component 8 |
| 332. | 5873 | RAB27A | RAB27A, member RAS oncogene family |
| 333. | 53354 | PANK1 | pantothenate kinase 1 |
| 334. | 2534 | FYN | FYN oncogene related to SRC, FGR, YES |
| 335. | 55166 | C6orf139 | chromosome 6 open reading frame 139 |

TABLE I-continued

| | ENTREZ GENE ID | GENE SYMBOL | GENE DESCRIPTION |
|---|---|---|---|
| 336. | 27346 | MAC30 | hypothetical protein MAC30 |
| 337. | 79037 | MGC2463 | hypothetical protein MGC2463 |
| 338. | 116496 | C1orf24 | chromosome 1 open reading frame 24 |
| 339. | 84314 | MGC10744 | hypothetical protein MGC10744 |
| 340. | 23531 | MMD | monocyte to macrophage differentiation-associated |
| 341. | 6558 | SLC12A2 | solute carrier family 12 (sodium/potassium/chloride transporters), member 2 |
| 342. | 64282 | PAPD5 | PAP associated domain containing 5 |
| 343. | 55636 | CHD7 | chromodomain helicase DNA binding protein 7 |
| 344. | 55026 | FLJ20716 | hypothetical protein FLJ20716 |
| 345. | 22929 | SEPHS1 | selenophosphate synthetase 1 |
| 346. | 10541 | ANP32B | acidic (leucine-rich) nuclear phosphoprotein 32 family, member B |
| 347. | 79621 | FLJ11712 | hypothetical protein FLJ11712 |
| 348. | 6432 | SFRS7 | splicing factor, arginine/serine-rich 7, 35 kDa |
| 349. | 5214 | PFKP | phosphofructokinase, platelet |
| 350. | 26031 | OSBPL3 | oxysterol binding protein-like 3 |
| 351. | 1102 | RCBTB2 | regulator or chromosome condensation (RCC1) and BTB (POZ) domain containing protein 2 |
| 352. | 6929 | TCF3 | transcription factor 3 (E2A immunoglobulin enhancer binding factors E12/E47) |
| 353. | 6632 | SNRPD1 | small nuclear ribonucleoprotein D1 polypeptide 16 kDa |
| 354. | 2047 | EPHB1 | EPH receptor B1 |
| 355. | 5168 | ENPP2 | ectonucleotide pyrophosphatase/phosphodiesterase 2 (autotaxin) |
| 356. | 55257 | C20orf20 | chromosome 20 open reading frame 20 |
| 357. | 81611 | ANP32E | acidic (leucine-rich) nuclear phosphoprotein 32 family, member E |
| 358. | 23246 | BOP1 | block of proliferation 1 |
| 359. | 23526 | HA-1 | minor histocompatibility antigen HA-1 |
| 360. | 84250 | ANKRD32 | ankyrin repeat domain 32 |
| 361. | 6999 | TDO2 | tryptophan 2,3-dioxygenase |
| 362. | 8317 | CDC7 | CDC7 cell division cycle 7 (S. cerevisiae) |
| 363. | 55752 | SEPT11 | spetin 11 |
| 364. | 39 | ACAT2 | acetyl-Coenzyme A acetyltransferase 2 (acetoacetyl Coenzyme A thiolase) |
| 365. | 54830 | FLJ20130 | hypothetical protein FLJ20130 |
| 366. | 83732 | RIOK1 | RIO kinase 1 (yeast) |
| 367. | 10808 | HSPH1 | heat shock 105 kDa/110 kDa protein 1 |
| 368. | 489 | ATP2A3 | ATPase, Ca++ transporting, ubiquitous |
| 369. | 3251 | HPRT1 | hypoxanthine phosphoribosyltransferase 1 (Lesch-Nyhan syndrome) |
| 370. | 10051 | SMC4L1 | SMC4 structural maintenance of chromosomes 4-like 1 (yeast) |
| 371. | 55816 | DOK5 | docking protein 5 |
| 372. | 3676 | ITGA4 | intergin, alpha 4 (antigen CD49D, alpha 4 subunit of VLA-4 receptor) |
| 373. | 8819 | SAP30 | sin3-associated polypeptide, 30 kDa |
| 374. | 4436 | MSH2 | mutS homolog 2, colon cancer, nonpolyposis type 1 (E. coli) |
| 375. | 10212 | DDX39 | DEAD (Asp-Glu-Ala-Asp) box polypeptide 39 |
| 376. | 5889 | RAD51C | RAD51 homolog C (S. cerevisiae) |
| 377. | 134111 | FLJ25076 | similar to CG4502-PA |
| 378. | 51377 | UCHL5 | ubiquitin carboxyl-terminal hydrolase L5 |
| 379. | 6657 | SOX2 | SRY (sex determining region Y)-box 2 |
| 380. | 241 | ALOX5AP | arachidonate 5-lipoxygenase-activating protein |
| 381. | 79888 | FLJ12443 | hypothetical protein FLJ12443 |
| 382. | 1368 | CPM | carboxypeptidase M |
| 383. | 397 | ARHGDIB | Rho GDP dissociation inhibitor (GDI) beta |
| 384. | 3336 | HSPE1 | heat shock 10 kDa protein 1 (chaperonin 10) |
| 385. | 2104 | ESRRG | estrogen-related receptor gamma |
| 386. | 2171 | FABP5 | fatty acid binding protein 5 (psoriasis-associated) |
| 387. | 6574 | SLC20A1 | solute carrier family 20 (phosphate transporter), member 1 |
| 388. | 2743 | GLRB | glycine receptor, beta |
| 389. | 1019 | CDK4 | cyclin-dependent kinase 4 |
| 390. | 9295 | SFRS11 | splicing factor, arginine/serine-rich 11 |
| 391. | 56952 | PRTFDC1 | phosphoribosyl transferase domain containing 1 |
| 392. | 6472 | SHMT2 | serine hydroxymethyltransferase 2 (mitochondrial) |
| 393. | 23512 | SUZ12 | suppressor of zeste 12 homolog (Drosophila) |
| 394. | 586 | BCAT1 | branched chain aminotransferase 1, cytosolic |
| 395. | 8836 | GGH | gamma-glutamyl hydrolase (conjugase, folylpolygammaglutamyl hydrolase) |
| 396. | 10383 | TUBB2 | tubulin, beta, 2 |
| 397. | 54101 | RIPK4 | receptor-interacting serine-threonine kinase 4 |

TABLE I-continued

| | ENTREZ GENE ID | GENE SYMBOL | GENE DESCRIPTION |
|---|---|---|---|
| 398. | 130271 | PLEKHH2 | pleckstrin homology domain containing, family H (with MyTH4 domain) member 2 |
| 399. | 129401 | NUP35 | nucleoporin 35 kDa |
| 400. | 10128 | LRPPRC | leucine-rich PPR-motif containing |
| 401. | 51703 | ACSL5 | acyl-CoA synthetase long-chain family member 5 |
| 402. | 9448 | MAP4K4 | mitogen-activated protein kinase kinase kinase kinase 4 |
| 403. | 79017 | C7orf24 | chromosome 7 open reading frame 24 |
| 404. | 262 | AMD1 | adenosylmethionine decarboxylase 1 |
| 405. | 960 | CD44 | CD44 antigen (homing function and Indian blood group system) |
| 406. | 81930 | KIF18A | kinesin family member 18A |
| 407. | 64116 | SLC39A8 | solute carrier family 39 (zinc transporter), member 8 |
| 408. | 26586 | CKAP2 | cytoskeleton associated protein 2 |
| 409. | 51144 | HSD17B12 | hydroxysteroid (17-beta) dehydrogenase 12 |
| 410. | 51002 | CGI-121 | CGI-121 protein |
| 411. | 9126 | CSPG6 | chondroitin sulfate proteoglycan 6 (bamacan) |
| 412. | 79154 | MGC4172 | short-chain dehydrogenase/reductase |
| 413. | 11096 | ADAMTS5 | a disintegrin-like and metalloprotease (reprolysin type) with thrombospondin type 1 mofit, 5 (aggrecanase-2) |
| 414. | 84803 | MGC11324 | hypothetical protein MGC11324 |
| 415. | 4082 | MARCKS | myristoylated alanine-rich protein kinase C substrate |
| 416. | 4086 | SMAD1 | SMAD, mothers against DPP homolog 1 (*Drosophila*) |
| 417. | 9446 | GSTO1 | glutathione S-transferase omega 1 |
| 418. | 23636 | NUP62 | nucleoporin 62 kDa |
| 419. | 81839 | VANGL1 | vang-like 1 (van gogh, Drosophila) |
| 420. | 3149 | HMGB3 | high-mobility group box 3 |
| 421. | 79023 | NUP37 | nucleoporin 37 kDa |
| 422. | 10606 | PAICS | phosphoribosylaminoimidazole carboxylase, phosphoribosylaminoimidazole succinocarboxamide synthetase |
| 423. | 10492 | SYNCRIP | synaptotagmin binding, cytoplasmic RNA interacting protein |
| 424. | 3320 | HSPCA | heat shock 90 kDa protein 1, alpha |
| 425. | 6119 | RPA3 | replication protein A3, 14 kDa |
| 426. | 55352 | HSA272196 | hypothetical protein, clone 2746033 |
| 427. | 9759 | HDAC4 | histone deacetylase 4 |
| 428. | 5725 | PTBP1 | polypyrimidine tract binding protein 1 |
| 429. | 2119 | ETV5 | ets variant gene 5 (ets-related molecule) |
| 430. | 10019 | LNK | lymphocyte adaptor protein |
| 431. | 9734 | HDAC9 | histone deacetylase 9 |
| 432. | 5885 | RAD21 | RAD21 homolog (*S. pombe*) |
| 433. | 79930 | DOK3 | docking protein 3 |
| 434. | 22837 | COBLL1 | COBL-like 1 |
| 435. | 339448 | LOC339448 | hypothetical protein LOC339448 |
| 436. | 11051 | NUDT21 | nudix (nucleoside diphosphate linked moiety X)-type motif 21 |
| 437. | 9735 | KNTC1 | kinetochore associated 1 |
| 438. | 4148 | MATN3 | matrilin 3 |
| 439. | 4200 | ME2 | malic enzyme 2, NAD(+)-dependent, mitochondrial |
| 440. | 26084 | SGEF | Src homology 3 domain-containing guanine nucleotide exchange factor |
| 441. | 27101 | CACYBP | calcyclin binding protein |
| 442. | 23012 | STK38L | serine/threonine kinase 38 like |
| 443. | 54566 | EPB41L4B | erythrocyte membrane protein band 4.1 like 4B |
| 444. | 6566 | SLC16A1 | solute carrier family 16 (monocarboxylic acid transporters), member 1 |
| 445. | 54947 | FLJ20481 | hypothetical protein FLJ20481 |
| 446. | 255488 | IBRDC2 | IBR domain containing 2 |
| 447. | 2289 | FKBP5 | FK506 binding protein 5 |
| 448. | 5036 | PA2G4 | proliferation-associated 2G4, 38 kDa |
| 449. | 4869 | NPM1 | nucleophosmin (nucleolar phosphoprotein B23, numatrin) |
| 450. | 10384 | BTN3A3 | butyrophilin, subfamily 3, member A3 |
| 451. | 10785 | WDR4 | WD repeat domain 4 |
| 452. | 3099 | HK2 | hexokinase 2 |
| 453. | 56121 | PCDHB15 | protocadherin beta 15 |
| 454. | 10155 | TRIM28 | tripartite motif-containing 28 |
| 455. | 6340 | SCNN1G | sodium channel, nonvoltage-gated 1, gamma |
| 456. | 25804 | LSM4 | LSM4 homolog, U6 small nuclear RNA associated (*S. cerevisiae*) |
| 457. | 3939 | LDHA | lactate dehydrogenase A |
| 458. | 57552 | AADACL1 | arylacetamide deacetylase-like 1 |
| 459. | 9184 | BUB3 | BUB3 budding uninhibited by benzimidazoles 3 |

TABLE I-continued

| | ENTREZ GENE ID | GENE SYMBOL | GENE DESCRIPTION |
|---|---|---|---|
| | | | homolog (yeast) |
| 460. | 657 | BMPR1A | bone morphogenetic protein receptor, type IA |
| 461. | 5631 | PRPS1 | phosphoribosyl pyrophosphate synthetase 1 |
| 462. | 204 | AK2 | adenylate kinase 2 |
| 463. | 55270 | NUDT15 | nudix (nucleoside diphosphate linked moiety X)-type motif 15 |
| 464. | 10265 | IRX5 | iroquois homeobox protein 5 |
| 465. | 4640 | MYO1A | myosin IA |
| 466. | 79180 | EFHD2 | EF hand domain family, member D2 |
| 467. | 4076 | M11S1 | membrane component, chromosome 11, surface marker 1 |
| 468. | 55276 | PGM2 | phosphoglucomutase 2 |
| 469. | 83857 | ARG99 | ARG99 protein |
| 470. | 116448 | OLIG1 | oligodendrocyte transcription factor 1 |
| 471. | 5696 | PSMB8 | proteasome (prosome, macropain) subunit, beta type, 8 (large multifunctional protease 7) |
| 472. | 1407 | CRY1 | cryptochrome 1 (photolyase-like) |
| 473. | 11177 | BAZ1A | bromodomain adjacent to zinc finger domain, 1A |
| 474. | 51015 | ISOC1 | isochorismatase domain containing 1 |
| 475. | 1789 | DNMT3B | DNA (cytosine-5-)-methyltransferase 3 beta |
| 476. | 22948 | CCT5 | chaperonin containing TCP1, subunit 5 (epsilon) |
| 477. | 158563 | LOC158563 | hypothetical protein LOC158563 |
| 478. | 89891 | WDR34 | WD repeat domain 34 |
| 479. | 119 | ADD2 | adducin 2 (beta) |
| 480. | 5358 | PLS3 | plastin 3 (T isoform) |
| 481. | 7086 | TKT | transketolase (Wernicke-Korsakoff syndrome) |
| 482. | 51174 | TUBD1 | tubulin, delta 1 |
| 483. | 23255 | KIAA0802 | KIAA0802 |
| 484. | 54149 | C21orf91 | chromosome 21 open reading frame 91 |
| 485. | 2271 | FH | fumarate hydratase |
| 486. | 55076 | TMEM45A | transmembrane protein 45A |
| 487. | 10436 | C2F | C2f protein |
| 488. | 8553 | BHLHB2 | basic helix-loop-helix domain containing, class B, 2 |
| 489. | 10409 | BASP1 | brain abundant, membrane attached signal protein 1 |
| 490. | 22856 | CHSY1 | carbohydrate (chondroitin) synthase 1 |
| 491. | 84451 | KIAA1804 | mixed lineage kinase 4 |
| 492. | 3150 | HMGN1 | high-mobility group nucleosome binding domain 1 |
| 493. | 961 | CD47 | CD47 antigen (Rh-related antigen, integrin-associated signal transducer) |
| 494. | 79038 | ZFYVE21 | zinc finger, FYVE domain containing 21 |
| 495. | 7291 | TWIST1 | twist homolog 1 (acrocephalosyndactyly 3; Saethre-Chotzen syndrome) (Drosohila) |
| 496. | 9738 | CP110 | CP110 protein |
| 497. | 10625 | IVNS1ABP | influenza virus NS1A binding protein |
| 498. | 9368 | SLC9A3R1 | solute carrier family 9 (sodium/hydrogen exchanger), isoform 3 regulator 1 |
| 499. | 3613 | IMPA2 | inositol(myo)-1(or 4)-monophosphatase 2 |
| 500. | 8514 | KCNAB2 | potassium voltage-gated channel, shaker-related subfamily, beta member 2 |
| 501. | 4957 | ODF2 | outer dense fiber of sperm tails 2 |
| 502. | 4673 | NAP1L1 | nucleosome assembly protein 1-like 1 |
| 503. | 26018 | LRIG1 | leucine-rich repeats and immunoglobulin-like domains 1 |
| 504. | 3033 | HADHSC | L-3-hydroxyacyl-Coenzyme A dehydrogenase, short chain |
| 505. | 139886 | LOC139886 | hypothetical protein LOC139886 |
| 506. | 10360 | NPM3 | nucleophosmin/nucleoplasmin, 3 |
| 507. | 200894 | ARL2L1 | ADP-ribosylation factor-like 2-like 1 |
| 508. | 8364 | HIST1H4C | histone 1, H4c |
| 509. | 378708 | APITD1 | apoptosis-inducing, TAF9-like domain 1 |
| 510. | 169270 | ZNF596 | zinc finger protein 596 |
| 511. | 6917 | TCEA1 | transcription elongation factor A (SII), 1 |
| 512. | 7091 | TLE4 | transducin-like enhancer of split 4 (E(sp1) homolog, *Drosophila*) |
| 513. | 3725 | JUN | v-jun sarcoma virus 17 oncogene homolog (avian) |
| 514. | 1736 | DKC1 | dyskeratosis congenita 1, dyskerin |
| 515. | 8566 | PDXK | pyridoxal (pyridoxine, vitamin B6) kinase |
| 516. | 51176 | LEF1 | lymphoid enhancer-binding factor 1 |
| 517. | 87 | ACTN1 | actinin, alpha 1 |
| 518. | 10838 | ZNF275 | zinc finger protein 275 |
| 519. | 54517 | FLJ20485 | hypothetical protein FLJ20485 |
| 520. | 5150 | PDE7A | phosphodiesterase 7A |
| 521. | 384 | ARG2 | arginase, type II |
| 522. | 27316 | RBMX | RNA binding motif protein, X-linked |
| 523. | 389206 | CCDC4 | coiled-coil domain containing 4 |
| 524. | 51312 | SLC25A37 | solute carrier family 25, member 37 |

TABLE I-continued

| | ENTREZ GENE ID | GENE SYMBOL | GENE DESCRIPTION |
|---|---|---|---|
| 525. | 9112 | MTA1 | metastasis associated 1 |
| 526. | 6711 | SPTBN1 | spectrin, beta, non-erythrocytic 1 |
| 527. | 10129 | 13CDNA73 | hypothetical protein CG003 |
| 528. | 80014 | BOMB | BH3-only member B protein |
| 529. | 27131 | SNX5 | sorting nexin 5 |
| 530. | 23089 | PEG10 | paternally expressed 10 |
| 531. | 5270 | SERPINE2 | serine (or cysteine) proteinase inhibitor, clade E (nexin, plasminogen activator inhibitor type 1), member 2 |
| 532. | 6764 | ST5 | suppression of tumorigenicity 5 |
| 533. | 7791 | ZYX | zyxin |
| 534. | 22995 | Cep152 | KIAA0912 protein |
| 535. | 4137 | MAPT | microtubule-associated protein tau |
| 536. | 5411 | PNN | pinin, desmosome associated protein |
| 537. | 3087 | HHEX | hematopoietically expressed homeobox |
| 538. | 23171 | GPD1L | glycerol-3-phosphate dehydrogenase 1-like |
| 539. | 56905 | DKFZP434H132 | DKFZP434H132 protein |
| 540. | 3189 | HNRPH3 | heterogeneous nuclear ribonucleoprotein H3 (2H9) |
| 541. | 9099 | USP2 | ubiquitin specific protease 2 |
| 542. | 10098 | TSPAN5 | tetraspanin 5 |
| 543. | 401505 | C9orf105 | chromosome 9 open reading frame 105 |
| 544. | 51444 | RNF138 | ring finger protein 138 |
| 545. | 11118 | BTN3A2 | butyrophilin, subfamily 3, member A2 |
| 546. | 8089 | YEATS4 | YEATS domain containing 4 |
| 547. | 84108 | PCGF6 | polycomb group ring finger 6 |
| 548. | 7514 | XPO1 | exportin 1 (CRM1 homolog, yeast) |
| 549. | 9818 | NUPL1 | nucleoporin like 1 |
| 550. | 10923 | PC4 | activated RNA polymerase II transcription cofactor 4 |
| 551. | 6526 | SLC5A3 | solute carrier family 5 (inositol transporters), member 3 |
| 552. | 26010 | DNAPTP6 | DNA polymerase-transactivated protein 6 |
| 553. | 5307 | PITX1 | paired-like homeodomain transcription factor 1 |
| 554. | 2643 | GCH1 | GTP cyclohydrolase 1 (dopa-responsive dystonia) |
| 555. | 1503 | CTPS | CTP synthase |
| 556. | 5777 | PTPN6 | protein tyrosine phosphatase, non-receptor type 6 |
| 557. | 23122 | CLASP2 | cytoplasmic linker associated protein 2 |
| 558. | 5588 | PRKCQ | protein kinase C, theta |
| 559. | 64770 | CCDC14 | coiled-coil domain containing 14 |
| 560. | 6426 | SFRS1 | splicing factor, arginine/serine-rich 1 (splicing factor 2, alternate splicing factor) |
| 561. | 81831 | NETO2 | neuropilin (NRP) and tolloid (TLL)-like 2 |
| 562. | 56888 | KCMF1 | potassium channel modulatory factor 1 |
| 563. | 9221 | NOLC1 | nucleolar and coiled-body phosphoprotein 1 |
| 564. | 79366 | NSBP1 | nucleosomal binding protein 1 |
| 565. | 51729 | WBP11 | WW domain binding protein 11 |
| 566. | 84444 | DOT1L | DOT1-like, histone H3 methyltransferase (*S. cerevisiae*) |
| 567. | 80218 | MAK3 | Mak3 homolog (*S. cerevisiae*) |
| 568. | 84319 | MGC4308 | hypothetical protein MGC4308 |
| 569. | 112479 | MGC16943 | similar to RIKEN cDNA 4933424N09 gene |
| 570. | 64396 | GMCL1L | germ cell-less homolog 1 (*Drosophila*)-like |
| 571. | 5905 | RANGAP1 | Ran GTPase activating protein 1 |
| 572. | 2177 | FANCD2 | Fanconi anemia, complementation group D2 |
| 573. | 55632 | KIAA1333 | KIAA1333 |
| 574. | 3695 | ITGB7 | integrin, beta 7 |
| 575. | 9793 | CKAP5 | cytoskeleton associated protein 5 |
| 576. | 5318 | PKP2 | plakophilin 2 |
| 577. | 6652 | SORD | sorbitol dehydrogenase |
| 578. | 80709 | AKNA | AT-hook transcription factor |
| 579. | 55120 | FANCL | Fanconi anemia, complementation group L |
| 580. | 92667 | C20orf72 | chromosome 20 open reading frame 72 |
| 581. | 3654 | IRAK1 | interleukin-1 receptor-associated kinase 1 |
| 582. | 55975 | KLHL7 | kelch-like 7 (*Drosophila*) |
| 583. | 6397 | SEC14L1 | SEC14-like 1 (*S. cerevisiae*) |
| 584. | 29117 | BRD7 | bromodomain containing 7 |
| 585. | 6732 | SRPK1 | SFRS protein kinase 1 |
| 586. | 401081 | FLJ22763 | hypothetical gene supported by AK026416 |
| 587. | 8520 | HAT1 | histone acetyltransferase 1 |
| 588. | 3119 | HLA-DQB1 | major histocompatibility complex, class II, DQ beta 1 |
| 589. | 7283 | TUBG1 | tubulin, gamma 1 |
| 590. | 4809 | NHP2L1 | NHP2 non-histone chromosome protein 2-like 1 (*S. cerevisiae*) |
| 591. | 2778 | GNAS | GNAS complex locus |
| 592. | 5359 | PLSCR1 | phospholipid scramblase 1 |
| 593. | 196294 | FLJ25059 | hypothetical protein FLJ25059 |
| 594. | 3181 | HNRPA2B1 | heterogeneous nuclear ribonucleoprotein A2/B1 |
| 595. | 1794 | DOCK2 | dedicator of cytokinesis 2 |
| 596. | 55148 | C14orf130 | chromosome 14 open reading frame 130 |

TABLE I-continued

| | ENTREZ GENE ID | GENE SYMBOL | GENE DESCRIPTION |
|---|---|---|---|
| 597. | 25924 | MYRIP | myosin VIIA and Rab interacting protein |
| 598. | 7533 | YWHAH | tyrosine 3-monooxygenase/tryptophan 5-monooxygenase activation protein, eta polypeptide |
| 599. | 64968 | MRPS6 | mitochondrial ribosomal protein S6 |
| 600. | 4830 | NME1 | non-metastatic cells 1, protein (NM23A) expressed in |
| 601. | 165055 | FLJ32745 | hypothetical protein FLJ32745 |
| 602. | 151827 | LRRC34 | leucine rich repeat containing 34 |
| 603. | 93081 | LOC93081 | hypothetical protein BC015148 |
| 604. | 196527 | TMEM16F | transmembrane protein 16F |
| 605. | 1827 | DSCR1 | Down syndrome critical region gene 1 |
| 606. | 203562 | TMEM31 | transmembrane protein 31 |
| 607. | 11335 | CBX3 | chromobox homolog 3 (HP1 gamma homolog, *Drosophila*) |
| 608. | 3662 | IRF4 | interferon regulatory factor 4 |
| 609. | 8624 | DSCR2 | Down syndrome critical region gene 2 |
| 610. | 4092 | SMAD7 | SMAD, mothers against DPP homolog 7 (*Drosophila*) |
| 611. | 6934 | TCF7L2 | transcription factor 7-like 2 (T-cell specific, HMG-box) |
| 612. | 26112 | DKFZP434C171 | DKFZP434C171 protein |
| 613. | 3329 | HSPD1 | heat shock 60 kDa protein 1 (chaperonin) |
| 614. | 5577 | PRKAR2B | protein kinase, cAMP-dependent, regulatory, type II, beta |
| 615. | 3202 | HOXA5 | homeo box A5 |
| 616. | 79442 | LRRC2 | leucine rich repeat containing 2 |
| 617. | 9631 | NUP155 | nucleoporin 155 kDa |
| 618. | 55366 | LGR4 | leucine-rich repeat-containing G protein-coupled receptor 4 |
| 619. | 23350 | SR140 | U2-associated SR140 protein |
| 620. | 6434 | SFRS10 | splicing factor, arginine/serine-rich 10 (transformer 2 homolog, *Drosophila*) |
| 621. | 7975 | MAFK | v-maf musculoaponeurotic fibrosarcoma oncogene homolog K (avian) |
| 622. | 3187 | HNRPH1 | heterogeneous nuclear ribonucleoprotein H1 (H) |
| 623. | 94239 | H2AFV | H2A histone family, member V |
| 624. | 54913 | RPP25 | ribonuclease P 25 kDa subunit |
| 625. | 9521 | EEF1E1 | eukaryotic translation elongation factor 1 epsilon 1 |
| 626. | 5471 | PPAT | phosphoribosyl pyrophosphate amidotransferase |
| 627. | 340252 | ZNF680 | zinc finger protein 680 |
| 628. | 1021 | CDK6 | cyclin-dependent kinase 6 |
| 629. | 10560 | SLC19A2 | solute carrier family 19 (thiamine transporter), member 2 |
| 630. | 4201 | MEA1 | male-enhanced antigen 1 |
| 631. | 440145 | LOC440145 | similar to RIKEN cDNA 2410129H14 |
| 632. | 3843 | RANBP5 | RAN binding protein 5 |
| 633. | 3298 | HSF2 | heat shock transcription factor 2 |
| 634. | 387914 | TMEM46 | transmembrane protein 46 |
| 635. | 27347 | STK39 | serine threonine kinase 39 (STE20/SPS1 homolog, yeast) |
| 636. | 6256 | RXRA | retinoid X receptor, alpha |
| 637. | 6637 | SNRPG | small nuclear ribonucleoprotein polypeptide G |
| 638. | 22800 | RRAS2 | related RAS viral (r-ras) oncogene homolog 2 |
| 639. | 91694 | FLJ23749 | hypothetical protein FLJ23749 |
| 640. | 22823 | MTF2 | metal response element binding transcription factor 2 |
| 641. | 51184 | MGC14560 | protein x 0004 |
| 642. | 10856 | RUVBL2 | RuvB-like 2 (*E. coli*) |
| 643. | 7188 | TRAF5 | TNF receptor-associated factor 5 |
| 644. | 5272 | SERPINB9 | serine (or cysteine) proteinase inhibitor, clade B (ovalbumin), member 9 |
| 645. | 11169 | WDHD1 | WD repeat and HMG-box DNA binding protein 1 |
| 646. | 5606 | MAP2K3 | mitogen-activated protein kinase kinase 3 |
| 647. | 4783 | NFIL3 | nuclear factor, interleukin 3 regulated |
| 648. | 51691 | LSM8 | LSM8 homolog, U6 small nuclear RNA associated (*S. cerevisiae*) |
| 649. | 1528 | CYB5 | cytochrome b-5 |
| 650. | 79899 | FLJ14213 | hypothetical protein FLJ14213 |
| 651. | 7334 | UBE2N | ubiquitin-conjugating enzyme E2N (UBC13 homolog, yeast) |
| 652. | 2730 | GCLM | glutamate-cysteine ligase, modifier subunit |
| 653. | 23157 | SEPT6 | septin 6 |
| 654. | 56155 | TEX14 | testis expressed sequence 14 |
| 655. | 23658 | LSM5 | LSM5 homolog, U6 small nuclear RNA associated (*S. cerevisiae*) |
| 656. | 1400 | CRMP1 | collapsin response mediator protein 1 |

TABLE I-continued

| | ENTREZ GENE ID | GENE SYMBOL | GENE DESCRIPTION |
|---|---|---|---|
| 657. | 5684 | PSMA3 | proteasome (prosome, macropain) subunit, alpha type, 3 |
| 658. | 6713 | SQLE | squalene epoxidase |
| 659. | 84955 | NUDCD1 | NudC domain containing 1 |
| 660. | 64318 | C10orf117 | chromosome 10 open reading frame 117 |
| 661. | 10196 | HRMT1L3 | HMT1 hnRNP methyltransferase-like 3 (*S. cerevisiae*) |
| 662. | 29841 | GRHL1 | grainyhead-like 1 (*Drosophila*) |
| 663. | 10055 | SAE1 | SUMO-1 activating enzyme subunit 1 |
| 664. | 9214 | FAIM3 | Fas apoptotic inhibitory molecule 3 |
| 665. | 57406 | ABHD6 | abhydrolase domain containing 6 |
| 666. | 25914 | RTTN | rotatin |
| 667. | 23244 | SCC-112 | SCC-112 protein |
| 668. | 3183 | HNRPC | heterogeneous nuclear ribonucleoprotein C (C1/C2) |
| 669. | 55117 | SLC6A15 | solute carrier family 6, member 15 |
| 670. | 6950 | TCP1 | t-complex 1 |
| 671. | 4660 | PPP1R12B | protein phosphatase 1, regulatory (inhibitor) subunit 12B |
| 672. | 134429 | STARD4 | START domain containing 4, sterol regulated |
| 673. | 157503 | LOC157503 | hypothetical protein LOC157503 |
| 674. | 253832 | ZDHHC20 | zinc finger, DHHC-type containing 20 |
| 675. | 375061 | MGC15887 | hypothetical gene supported by BC009447 |
| 676. | 84986 | ARHGAP19 | Rho GTPase activating protein 19 |
| 677. | 8407 | TAGLN2 | transgelin 2 |
| 678. | 285704 | RGMB | RGM domain family, member B |
| 679. | 5050 | PAFAH1B3 | platelet-activating factor acetylhydrolase, isoform Ib, gamma subunit 29 kDa |
| 680. | 4208 | MEF2C | MADS box transcription enhancer factor 2, polypeptide C (myocyte enhancer factor 2C) |
| 681. | 55614 | C20orf23 | chromosome 20 open reading frame 23 |
| 682. | 388796 | LOC388796 | hypothetical LOC388796 |
| 683. | 85463 | ZC3H12C | zinc finger CCCH-type containing 12C |
| 684. | 51465 | UBE2J1 | ubiquitin-conjugating enzyme E2, J1 (UBC6 homolog, yeast) |
| 685. | 9994 | CASP8AP2 | CASP8 associated protein 2 |
| 686. | 26135 | PAI-RBP1 | PAI-1 mRNA binding protein |
| 687. | 5634 | PRPS2 | phosphoribosyl pyrophosphate synthetase 2 |
| 688. | 286319 | TUSC1 | tumor suppressor candidate 1 |
| 689. | 6470 | SHMT1 | serine hydroxymethyltransferase 1 (soluble) |
| 690. | 9397 | NMT2 | N-myristoyltransferase 2 |
| 691. | 10762 | NUP50 | nucleoporin 50 kDa |
| 692. | 201161 | PRR6 | proline rich 6 |
| 693. | 5019 | OXCT1 | 3-oxoacid CoA transferase 1 |
| 694. | 159 | ADSS | adenylosuccinate synthase |
| 695. | 23587 | DERP6 | S-phase 2 protein |
| 696. | 10151 | HNRPA3P1 | heterogeneous nuclear ribonucleoprotein A3 pseudogene 1 |
| 697. | 8564 | KMO | kynurenine 3-monooxygenase (kynurenine 3-hydroxylase) |
| 698. | 1349 | COX7B | cytochrome c oxidase subunit VIIb |
| 699. | 283824 | LOC283824 | hypothetical protein LOC283824 |
| 700. | 1123 | CHN1 | chimerin (chimaerin) 1 |
| 701. | 57522 | SRGAP1 | SLIT-ROBO Rho GTPase activating protein 1 |
| 702. | 253782 | LASS6 | LAG1 longevity assurance homolog 6 (*S. cerevisiae*) |
| 703. | 57685 | KIAA1573 | KIAA1573 protein |
| 704. | 79695 | GALNT12 | UDP-N-acetyl-alpha-D-galactosamine:polypeptide N-acetylgalactosaminyltransferase 12 (GalNAc-T12) |
| 705. | 90861 | C16orf34 | chromosome 16 open reading frame 34 |
| 706. | 26207 | PITPNC1 | phosphatidylinositol transfer protein, cytoplasmic 1 |
| 707. | 1164 | CKS2 | CDC28 protein kinase regulatory subunit 2 |
| 708. | 396 | ARHGDIA | Rho GDP dissociation inhibitor (GDI) alpha |
| 709. | 57530 | CGN | cingulin |
| 710. | 1633 | DCK | deoxycytidine kinase |
| 711. | 9208 | LRRFIP1 | leucine rich repeat (in FLII) interacting protein 1 |
| 712. | 6453 | ITSN1 | intersectin 1 (SH3 domain protein) |
| 713. | 24147 | FJX1 | four jointed box 1 (*Drosophila*) |
| 714. | 9882 | TBC1D4 | TBC1 domain family, member 4 |
| 715. | 169200 | DKFZp762C1112 | hypothetical protein DKFZp762C1112 |
| 716. | 9331 | B4GALT6 | UDP-Gal:betaGlcNAc beta 1,4-galactosyltransferease, polypeptide 6 |
| 717. | 55183 | RIF1 | RAP1 interacting factor homolog (yeast) |
| 718. | 221362 | LOC221362 | hypothetical protein LOC221362 |
| 719. | 8458 | TTF2 | transcription termination factor, RNA polymerase II |
| 720. | 1047 | CLGN | calmegin |
| 721. | 56919 | DHX33 | DEAH (Asp-Glu-Ala-His) box polypeptide 33 |
| 722. | 93949 | CXorf10 | chromosome X open reading frame 10 |

TABLE I-continued

| | ENTREZ GENE ID | GENE SYMBOL | GENE DESCRIPTION |
|---|---|---|---|
| 723. | 5569 | PKIA | protein kinase (cAMP-dependent, catalytic) inhibitor alpha |
| 724. | 6891 | TAP2 | transporter 2, ATP-binding cassette, sub-family B (MDR/TAP) |
| 725. | 1960 | EGR3 | early growth response 3 |
| 726. | 11252 | PACSIN2 | protein kinase C and casein kinase substrate in neurons 2 |
| 727. | 51762 | RAB8B | RAB8B, member RAS oncogene family |
| 728. | 81575 | DKFZP434F0318 | hypothetical protein DKFZp434F0318 |
| 729. | 56906 | THAP10 | THAP domain containing 10 |
| 730. | 55110 | FLJ10292 | mago-nashi homolog |
| 731. | 5267 | SERPINA4 | serine (or cysteine) proteinase inhibitor, clade A (alpha-1 antiproteinase, antitrypsin), member 4 |
| 732. | 1844 | DUSP2 | dual specificity phosphatase 2 |
| 733. | 9612 | NCOR2 | nuclear receptor co-repressor 2 |
| 734. | 3276 | HRMT1L2 | HMT1 hnRNP methyltransferase-like 2 (*S. cerevisiae*) |
| 735. | 257415 | MGC40405 | hypothetical protein MGC40405 |
| 736. | 79720 | FLJ12750 | hypothetical protein FLJ12750 |
| 737. | 160897 | ITR | intimal thickness-related receptor |
| 738. | 4522 | MTHFD1 | methylenetetrahydrofolate dehydrogenase (NADP+ dependent) 1, methenyltetrahydrofolate cyclohydrolase, formyltetrahydrofolate synthetase |
| 739. | 4668 | NAGA | N-acetylgalactosaminidase, alpha- |
| 740. | 84890 | C10orf22 | chromosome 10 open reading frame 22 |
| 741. | 5198 | PFAS | phosphoribosylformylglycinamidine synthase (FGAR amidotransferase) |
| 742. | 55544 | RNPC1 | RNA-binding region (RNP1, RRM) containing 1 |
| 743. | 2618 | GART | phosphoribosylglycinamide formyltransferase, phoshoribosylglycinamide synthetase, phosphoribosylaminoimidazole synthetase |
| 744. | 9261 | MAPKAPK2 | mitogen-activated protein kinase-activated protein kinase 2 |
| 745. | 285761 | DCBLD1 | discoidin, CUB and LCCL domain containing 1 |
| 746. | 23225 | NUP210 | nucleoporin 210 kDa |
| 747. | 9792 | SERTAD2 | SERTA domain containing 2 |
| 748. | 56938 | ARNTL2 | aryl hydrocarbon receptor nuclear translocator-like 2 |
| 749. | 23254 | KIAA1026 | kazrin |
| 750. | 4628 | MYH10 | myosin, heavy polypeptide 10, non-muscle |
| 751. | 23176 | SEPT8 | septin 8 |
| 752. | 1432 | MAPK14 | mitogen-activated protein kinase 14 |
| 753. | 84549 | RBM13 | RNA binding motif protein 13 |
| 754. | 84133 | ZNRF3 | zinc and ring finger 3 |
| 755. | 6502 | SKP2 | S-phase kinase-associated protein 2 (p45) |
| 756. | 59274 | MESDC1 | mesoderm development candidate 1 |
| 757. | 51496 | HSPC129 | hypothetical protein HSPC129 |
| 758. | 55151 | TMEM38B | transmembrane protein 38B |
| 759. | 57609 | KIAA1463 | KIAA1463 protein |
| 760. | 1039 | CDR2 | cerebellar degeneration-related protein 2, 62 kDa |
| 761. | 143098 | MPP7 | membrane protein, palmitoylated 7 (MAGUK p55 subfamily member 7) |
| 762. | 130589 | GALM | galactose mutarotase (aldose 1-epimerase) |
| 763. | 3937 | LCP2 | lymphocyte cytosolic protein 2 (SH2 domain containing leukocyte protein of 76 kDa) |
| 764. | 5420 | PODXL | podocalyxin-like |
| 765. | 6509 | SLC1A4 | solute carrier family 1 (glutamate/neutral amino acid transporter), member 4 |
| 766. | 64397 | ZFP106 | zinc finger protein 106 homolog (mouse) |
| 767. | 4860 | NP | nucleoside phosphorylase |
| 768. | 3535 | IGL@ | immunoglobulin lambda locus |
| 769. | 1396 | CRIP1 | cysteine-rich protein 1 (intestinal) |
| 770. | 1660 | DHX9 | DEAH (Asp-Glu-Ala-His) box polypeptide 9 |
| 771. | 4291 | MLF1 | myeloid leukemia factor 1 |
| 772. | 26973 | CHORDC1 | cysteine and histidine-rich domain (CHORD)-containing, zinc binding protein 1 |
| 773. | 81037 | CRR9 | cisplatin resistance related protein CRR9p |
| 774. | 10574 | CCT7 | chaperonin containing TCP1, subunit 7 (eta) |
| 775. | 79892 | C10orf119 | chromosome 10 open reading frame 119 |
| 776. | 9972 | NUP153 | nucleoporin 153 kDa |
| 777. | 10459 | MAD2L2 | MAD2 mitotic arrest deficient-like 2 (yeast) |
| 778. | 483 | ATP1B3 | ATPase, Na+/K+ transporting, beta 3 polypeptide |
| 779. | 7552 | ZNF6 | zinc finger protein 6 (CMPX1) |
| 780. | 8165 | AKAP1 | A kinase (PRKA) anchor protein 1 |
| 781. | 29097 | CNIH4 | cornichon homolog 4 (*Drosophila*) |
| 782. | 11198 | SUPT16H | suppressor of Ty 16 homolog (*S. cerevisiae*) |
| 783. | 2184 | FAH | fumarylacetoacetate hydrolase (fumarylacetoacetase) |

TABLE I-continued

| | ENTREZ GENE ID | GENE SYMBOL | GENE DESCRIPTION |
|---|---|---|---|
| 784. | 7037 | TFRC | transferrin receptor (p90, CD71) |
| 785. | 6461 | SHB | Src homology 2 domain containing adaptor protein B |
| 786. | 509 | ATP5C1 | ATP synthase, H+ transporting, mitochondrial F1 complex, gamma polypeptide 1 |
| 787. | 5591 | PRKDC | protein kinase, DNA-activated, catalytic polypeptide |
| 788. | 10682 | EBP | emopamil binding protein (sterol isomerase) |
| 789. | 9188 | DDX21 | DEAD (Asp-Glu-Ala-Asp) box polypeptide 21 |
| 790. | 3837 | KPNB1 | karyopherin (importin) beta 1 |
| 791. | 3191 | HNRPL | heterogeneous nuclear ribonucleoprotein L |
| 792. | 10236 | HNRPR | heterogeneous nuclear ribonucleoprotein R |
| 793. | 6907 | TBL1X | transducin (beta)-like 1X-linked |
| 794. | 56172 | ANKH | ankylosis, progressive homolog (mouse) |
| 795. | 23367 | LARP1 | La ribonucleoprotein domain family, member 1 |
| 796. | 5778 | PTPN7 | protein tyrosine phosphatase, non-receptor type 7 |
| 797. | 100 | ADA | adenosine deaminase |
| 798. | 2821 | GPI | glucose phosphate isomerase |
| 799. | 9697 | TRAM2 | translocation associated membrane protein 2 |
| 800. | 54927 | CHCHD3 | coiled-coil-helix-coiled-coil-helix domain containing 3 |
| 801. | 58478 | MASA | E-1 enzyme |
| 802. | 6322 | SCML1 | sex comb on midleg-like 1 (*Drosophila*) |
| 803. | 292 | SLC25A5 | solute carrier family 25 (mitochondrial carrier; adenine nucleotide translocator), member 5 |
| 804. | 10857 | PGRMC1 | progesterone receptor membrane component 1 |
| 805. | 55342 | STRBP | spermatid perinuclear RNA binding protein |
| 806. | 7150 | TOP1 | topoisomerase (DNA) I |
| 807. | 874 | GBR3 | carbonyl reductase 3 |
| 808. | 51096 | WDR50 | WD repeat domain 50 |
| 809. | 253558 | LYCAT | lysocardiolipin acyltransferase |
| 810. | 79053 | ALG8 | asparagine-linked glycosylation 8 homolog (yeast, alpha-1,3-glucosyltransferase) |
| 811. | 84300 | C6orf125 | chromosome 6 open reading frame 125 |
| 812. | 8975 | USP13 | ubiquitin specific protease 13 (isopeptidase T-3) |
| 813. | 220988 | HNRPA3 | heterogeneous nuclear ribonucleoprotein A3 |
| 814. | 5315 | PKM2 | pyruvate kinase, muscle |
| 815. | 7411 | VBP1 | von Hippel-Lindau binding protein 1 |
| 816. | 1665 | DHX15 | DEAH (Asp-Glu-Ala-His) box polypeptide 15 |
| 817. | 10963 | STIP1 | stress-induced-phosphoprotein 1 (Hsp70/Hsp90-organizing protein) |
| 818. | 253461 | ZBTB38 | zinc finger and BTB domain containing 38 |
| 819. | 29080 | HSPC128 | HSPC128 protein |
| 820. | 84275 | MGC4399 | mitochondrial carrier protein |
| 821. | 1622 | DBI | diazepam binding inhibitor (GABA receptor modulator, acyl-Coenzyme A binding protein) |
| 822. | 4953 | ODC1 | ornithine decarboxylase 1 |
| 823. | 2029 | ENSA | endosulfine alpha |
| 824. | 6404 | SELPLG | selectin P ligand |
| 825. | 81034 | MFTC | mitochondrial folate transporter/carrier |
| 826. | 81542 | TXNDC | thioredoxin domain containing |
| 827. | 25816 | TNFAIP8 | tumor necrosis factor, alpha-induced protein 8 |
| 828. | 51582 | AZIN1 | antizyme inhibitor 1 |
| 829. | 27436 | EML4 | echinoderm microtubule associated protein like 4 |
| 830. | 55720 | FLJ10534 | hypothetical protein FLJ10534 |
| 831. | 7295 | TXN | thioredoxin |
| 832. | 10539 | TXNL2 | thioredoxin-like 2 |
| 833. | 86 | ACTL6A | actin-like 6A |
| 834. | 6731 | SRP72 | signal recognition particle 72 kDa |
| 835. | 23314 | SATB2 | SATB family member 2 |
| 836. | 2273 | FHL1 | four and a half LIM domains 1 |
| 837. | 3422 | IDI1 | isopentenyl-diphosphate delta isomerase |
| 838. | 10935 | PRDX3 | peroxiredoxin 3 |
| 839. | 2958 | GTF2A2 | general transcription factor IIA, 2, 12 kDa |
| 840. | 4144 | MAT2A | methionine adenosyltransferase II, alpha |
| 841. | 1964 | EIF1AX | eukaryotic translation initiation factor 1A, X-linked |
| 842. | 60 | ACTB | actin, beta |
| 843. | 11191 | PTENP1 | phosphatase and tensin homolog (mutated in multiple advanced cancers 1), pseudogene 1 |
| 844. | 90843 | TCEAL8 | transcription elongation factor A (SII)-like 8 |
| 845. | 57181 | SLC39A10 | solute carrier family 39 (zinc transporter), member 10 |
| 846. | 11147 | HHLA3 | HERV-H LTR-associating 3 |
| 847. | 10553 | HTATIP2 | HIV-1 Tat interactive protein 2, 30 kDa |
| 848. | 3338 | DNAJC4 | DnaJ (Hsp40) homolog, subfamily C, member 4 |
| 849. | 84888 | SPPL2A | signal peptide peptidase-like 2A |
| 850. | 1955 | EGFL5 | EGF-like-domain, multiple 5 |
| 851. | 329 | BIRC2 | baculoviral IAP repeat-containing 2 |
| 852. | 29927 | SEC61A1 | Sec61 alpha 1 subunit (*S. cerevisiae*) |

TABLE I-continued

| | ENTREZ GENE ID | GENE SYMBOL | GENE DESCRIPTION |
|---|---|---|---|
| 853. | 9559 | VPS26 | vacuolar protein sorting 26 (yeast) |
| 854. | 23270 | TSPYL4 | TSPY-like 4 |
| 855. | 6309 | SC5DL | sterol-C5-desaturase (ERG3 delta-5-desaturase homolog, fungal)-like |
| 856. | 10397 | NDRG1 | N-myc downstream regulated gene 1 |
| 857. | 27032 | ATP2C1 | ATPase, Ca++ transporting, type 2C, member 1 |
| 858. | 11112 | HIBADH | 3-hydroxyisobutyrate dehydrogenase |
| 859. | 1476 | CSTB | cystatin B (stefin B) |
| 860. | 9620 | CELSR1 | cadherin, EGF LAG seven-pass G-type receptor 1 (flamingo homolog, Drosophila) |
| 861. | 56650 | C3orf4 | chromosome 3 open reading frame 4 |
| 862. | 29922 | NME7 | non-metastatic cells 7, protein expressed in (nucleoside-diphosphate kinase) |
| 863. | 8887 | TAX1BP1 | Tax1 (human T-cell leukemia virus type I) binding protein 1 |
| 864. | 5445 | PON2 | paraoxonase 2 |
| 865. | 81889 | FAHD1 | fumarylacetoacetate hydrolase domain containing 1 |
| 866. | 694 | BTG1 | B-cell translocation gene 1, anti-proliferative |
| 867. | 29058 | C20orf30 | chromosome 20 open reading frame 30 |
| 868. | 2752 | GLUL | glutamate-ammonia ligase (glutamine synthase) |
| 869. | 79717 | FLJ11838 | hypothetical protein FLJ11838 |
| 870. | 170622 | COMMD6 | COMM domain containing 6 |
| 871. | 5792 | PTPRF | protein tyrosine phosphatase, receptor type, F |
| 872. | 64393 | WIG1 | p53 target zinc finger protein |
| 873. | 549 | AUH | AU RNA binding protein/enoyl-Coenzyme A hydratase |
| 874. | 51282 | SCAND1 | SCAN domain containing 1 |
| 875. | 79027 | ZNF655 | zinc finger protein 655 |
| 876. | 6451 | SH3BGRL | SH3 domain binding glutamic acid-rich protein like |
| 877. | 1347 | COX7A2 | cytochrome c oxidase subunit VIIa polypeptide 2 (liver) |
| 878. | 550643 | LOC550643 | hypothetical protein LOC550643 |
| 879. | 6926 | TBX3 | T-box 3 (ulnar mammary syndrome) |
| 880. | 51614 | SDBCAG84 | serologically defined breast cancer antigen 84 |
| 881. | 9520 | NPEPPS | aminopeptidase puromycin sensitive |
| 882. | 51065 | RPS27L | ribosomal protein S27-like |
| 883. | 10116 | FEM1B | fem-1 homolog b (C. elegans) |
| 884. | 10521 | DDX17 | DEAD (Asp-Glu-Ala-Asp) box polypeptide 17 |
| 885. | 81557 | MAGED4 | melanoma antigen family D, 4 |
| 886. | 10133 | OPTN | optineurin |
| 887. | 54504 | CPVL | carboxypeptidase, vitellogenic-like |
| 888. | 64082 | C13orf10 | chromosome 13 open reading frame 10 |
| 889. | 401115 | LOC401115 | hypothetical gene supported by BC038466; BC062790 |
| 890. | 6892 | TAPBP | TAP binding protein (tapasin) |
| 891. | 8087 | FXR1 | fragile X mental retardation, autosomal homolog 1 |
| 892. | 7905 | C5orf18 | chromosome 5 open reading frame 18 |
| 893. | 3916 | LAMP1 | lysosomal-associated membrane protein 1 |
| 894. | 22982 | KIAA0934 | KIAA0934 |
| 895. | 55615 | PRR5 | proline rich protein 5 |
| 896. | 5651 | PRSS7 | protease, serine, 7 (enterokinase) |
| 897. | 10449 | ACAA2 | acetyl-Coenzyme A acyltransferase 2 (mitochondrial 3-oxoacyl-Coenzyme A thiolase) |
| 898. | 8934 | RAB7L1 | RAB7, member RAS oncogene family-like 1 |
| 899. | 10114 | HIPK3 | homeodomain interacting protein kinase 3 |
| 900. | 57560 | WDR56 | WD repeat domain 56 |
| 901. | 51205 | ACP6 | acid phosphatase 6, lysophosphatidic |
| 902. | 6238 | RRBP1 | ribosome binding protein 1 homolog 180 kDa (dog) |
| 903. | 151011 | SEPT10 | septin 10 |
| 904. | 22920 | KIFAP3 | kinesin-associated protein 3 |
| 905. | 3958 | LGALS3 | lectin, galactoside-binding, soluble, 3 (galectin 3) |
| 906. | 84186 | ZCCHC7 | zinc finger, CCHC domain containing 7 |
| 907. | 9452 | ITM2A | integral membrane protein 2A |
| 908. | 10159 | ATP6AP2 | ATPase, H+ transporting, lysosomal accessory protein 2 |
| 909. | 23641 | LDOC1 | leucine zipper, down-regulated in cancer 1 |
| 910. | 967 | CD63 | CD63 antigen (melanoma 1 antigen) |
| 911. | 2517 | FUCA1 | fucosidase, alpha-L-1, tissue |
| 912. | 23219 | FBXO28 | F-box protein 28 |
| 913. | 79982 | DNAJB14 | DnaJ (Hsp40) homolog, subfamily B, member 14 |
| 914. | 7328 | UBE2H | ubiquitin-conjugating enzyme E2H (UBC8 homolog, yeast) |
| 915. | 23355 | KIAA0804 | KIAA0804 |
| 916. | 257103 | C21orf86 | chromosome 21 open reading frame 86 |
| 917. | 6307 | SC4MOL | sterol-C4-methyl oxidase-like |
| 918. | 23376 | KIAA0776 | KIAA0776 |

TABLE I-continued

| | ENTREZ GENE ID | GENE SYMBOL | GENE DESCRIPTION |
|---|---|---|---|
| 919. | 57700 | KIAA1600 | KIAA1600 |
| 920. | 85461 | TANC | TPR domain, ankyrin-repeat and coiled-coil-containing |
| 921. | 4247 | MGAT2 | mannosyl (alpha-1,6-)-glycoprotein beta-1,2-N-acetylglucosaminyltransferase |
| 922. | 3383 | ICAM1 | intercellular adhesion molecule 1 (CD54), human rhinovirus receptor |
| 923. | 493812 | HCG11 | HLA complex group 11 |
| 924. | 5921 | RASA1 | RAS p21 protein activator (GTPase activating protein) 1 |
| 925. | 23563 | CHST5 | carbohydrate (N-acetylglucosamine 6-O) sulfotransferase 5 |
| 926. | 51100 | SH3GLB1 | SH3-domain GRB2-like endophilin B1 |
| 927. | 339988 | LOC339988 | hypothetical protein LOC339988 |
| 928. | 79080 | MGC2574 | hypothetical protein MGC2574 |
| 929. | 55761 | TTC17 | tetratricopeptide repeat domain 17 |
| 930. | 144871 | LOC144871 | hypothetical protein LOC144871 |
| 931. | 4194 | MDM4 | Mdm4, transformed 3T3 cell double minute 4, p53 binding protein (mouse) |
| 932. | 51030 | FAM18B | family with sequence similarity 18, member B |
| 933. | 1650 | DDOST | dolichyl-diphosphooligosaccharide-protein glycosyltransferase |
| 934. | 147463 | ANKRD29 | ankyrin repeat domain 29 |
| 935. | 3757 | KCNH2 | potassium voltage-gated channel, subfamily H (eag-related), member 2 |
| 936. | 116442 | RAB39B | RAB39B, member RAS oncogene family |
| 937. | 10972 | TMP21 | transmembrane trafficking protein |
| 938. | 57798 | GATAD1 | GATA zinc finger domain containing 1 |
| 939. | 1314 | COPA | coatomer protein complex, subunit alpha |
| 940. | 2581 | GALC | galactosylceramidase (Krabbe disease) |
| 941. | 91452 | ACBD5 | acyl-Coenzyme A binding domain containing 5 |
| 942. | 8879 | SGPL1 | sphingosine-1-phosphate lyase 1 |
| 943. | 4897 | NRCAM | neuronal cell adhesion molecule |
| 944. | 23209 | MLC1 | megalencephalic leukoencephalopathy with subcortical cysts 1 |
| 945. | 440270 | LOC440270 | golgin-67 |
| 946. | 5034 | P4HB | procollagen-proline, 2-oxoglutarate 4-dioxygenase (proline 4-hydroxylase), beta polypeptide (protein disulfide isomerase-associated 1) |
| 947. | 148646 | FLJ32096 | hypothetical protein FLJ32096 |
| 948. | 399917 | LOC399917 | similar to polymerase |
| 949. | 7096 | TLR1 | toll-like receptor 1 |
| 950. | 80853 | KIAA1718 | KIAA1718 protein |
| 951. | 378938 | MALAT1 | metastasis associated lung adenocarcinoma transcript 1 (non-coding RNA) |
| 952. | 1266 | CNN3 | calponin 3, acidic |
| 953. | 58486 | LOC58486 | transposon-derived Buster1 transposase-like protein gene |
| 954. | 1040 | CDS1 | CDP-diacylglycerol synthase (phosphatidate cytidylyltransferase) 1 |
| 955. | 9895 | KIAA0329 | KIAA0329 |
| 956. | 1509 | CTSD | cathepsin D (lysosomal aspartyl protease) |
| 957. | 26115 | DKFZP564D166 | putative ankyrin-repeat containing protein |
| 958. | 57162 | PELI1 | pellino homolog 1 (*Drosophila*) |
| 959. | 57599 | WDR48 | WD repeat domain 48 |
| 960. | 285464 | FLJ34443 | hypothetical protein FLJ34443 |
| 961. | 55857 | C20orf19 | chromosome 20 open reading frame 19 |
| 962. | 339456 | LOC339456 | hypothetical protein LOC339456 |
| 963. | 51569 | UFM1 | ubiquitin-fold modifier 1 |
| 964. | 582 | BBS1 | Bardet-Biedl syndrome 1 |
| 965. | 4637 | MYL6 | myosin, light polypeptide 6, alkali, smooth muscle and non-muscle |
| 966. | 1186 | CLCN7 | chloride channel 7 |
| 967. | 3490 | IGFBP7 | insulin-like growth factor binding protein 7 |
| 968. | 5095 | PCCA | propionyl Coenzyme A carboxylase, alpha polypeptide |
| 969. | 10966 | RAB40B | RAB40B, member RAS oncogene family |
| 970. | 285362 | SUMF1 | sulfatase modifying factor 1 |
| 971. | 56122 | PCDHB14 | protocadherin beta 14 |
| 972. | 57534 | MIB1 | mindbomb homolog 1 (*Drosophila*) |
| 973. | 56951 | C5orf15 | chromosome 5 open reading frame 15 |
| 974. | 113177 | C19orf36 | chromosome 19 open reading frame 36 |
| 975. | 10379 | ISGF3G | interferon-stimulated transcription factor 3, gamma 48 kDa |
| 976. | 64224 | FLJ22313 | hypothetical protein FLJ22313 |
| 977. | 65084 | FLJ22104 | hypothetical protein FLJ22104 |

TABLE I-continued

| | ENTREZ GENE ID | GENE SYMBOL | GENE DESCRIPTION |
|---|---|---|---|
| 978. | 10537 | UBD | ubiquitin D |
| 979. | 8548 | BLZF1 | basic leucine zipper nuclear factor 1 (JEM-1) |
| 980. | 284214 | LOC284214 | hypothetical protein LOC284214 |
| 981. | 8334 | HIST1H2AC | histone 1, H2ac |
| 982. | 80210 | FLJ12584 | melanoma/melanocyte specific protein KU-MEL-1 |
| 983. | 1182 | CLCN3 | chloride channel 3 |
| 984. | 26751 | SH3YL1 | SH3 domain containing, Ysc84-like 1 (*S. cerevisiae*) |
| 985. | 114327 | EFHC1 | EF-hand domain (C-terminal) containing 1 |
| 986. | 7351 | UCP2 | uncoupling protein 2 (mitochondrial, proton carrier) |
| 987. | 10724 | MGEA5 | meningioma expressed antigen 5 (hyaluronidase) |
| 988. | 9652 | KIAA0372 | KIAA0372 |
| 989. | 200958 | MUC20 | mucin 20 |
| 990. | 161527 | LOC161527 | hypothetical protein LOC161527 |
| 991. | 10314 | LANCL1 | LanC lantibiotic synthetase component C-like 1 (bacterial) |
| 992. | 2923 | PDIA3 | protein disulfide isomerase family A, member 3 |
| 993. | 84247 | LDOC1L | leucine zipper, down-regulated in cancer 1-like |
| 994. | 3006 | HIST1H1C | histone1, H1c |
| 995. | 9562 | MINPP1 | multiple inositol polyphosphate histidine phosphatase, 1 |
| 996. | 115024 | MGC20781 | hypothetical protein MGC20781 |
| 997. | 65982 | FLJ12895 | hypothetical protein FLJ12895 |
| 998. | 5268 | SERPINB5 | serine (or cysteine) proteinase inhibitor, clade B (ovalbumin), member 5 |
| 999. | 94240 | EPSTI1 | epithelial stromal interaction 1 (breast) |
| 1000. | 2621 | GAS6 | growth arrest-specific 6 |
| 1001. | 401024 | FLJ44048 | FLJ44048 protein |
| 1002. | 57142 | RTN4 | reticulon 4 |
| 1003. | 50854 | C6orf48 | chromosome 6 open reading frame 48 |
| 1004. | 317649 | EIF4E3 | eukaryotic translation initiation factor 4E member 3 |
| 1005. | 4179 | MCP | membrane cofactor protein (CD46, trophoblast-lymphocyte cross-reactive antigen) |
| 1006. | 54884 | RetSat | all-trans-13,14-dihydroretinol saturase |
| 1007. | 10154 | PLXNC1 | plexin C1 |
| 1008. | 2630 | GBAP | glucosidase, beta; acid, pseudogene |
| 1009. | 7077 | TIMP2 | tissue inhibitor of metalloproteinase 2 |
| 1010. | 23741 | CRI1 | CREBBP/EP300 inhibitor 1 |
| 1011. | 949 | SCARB1 | scavenger receptor class B, member 1 |
| 1012. | 1519 | CTSO | cathepsin O |
| 1013. | 51136 | LOC51136 | PTD016 protein |
| 1014. | 3428 | IFI16 | interferon, gamma-inducible protein 16 |
| 1015. | 9516 | LITAF | lipopolysaccharide-induced TNF factor |
| 1016. | 3123 | HLA-DRB1 | major histocompatibility complex, class II, DR beta 1 |
| 1017. | 1389 | CREBL2 | cAMP responsive element binding protein-like 2 |
| 1018. | 5027 | P2RX7 | purinergic receptor P2X, ligand-gated ion channel, 7 |
| 1019. | 6782 | STCH | stress 70 protein chaperone, microsome-associated, 60 kDa |
| 1020. | 5645 | PRSS2 | protease, serine, 2 (trypsin 2) |
| 1021. | 84282 | RNF135 | ring finger protein 135 |
| 1022. | 9852 | EPM2AIP1 | EPM2A (laforin) interacting protein 1 |
| 1023. | 84333 | PCGF5 | polycomb group ring finger 5 |
| 1024. | 23475 | QPRT | quinolinate phosphoribosyltransferase (nicotinate-nucleotide pyrophosphorylase (carboxylating)) |
| 1025. | 11142 | PKIG | protein kinase (cAMP-dependent, catalytic) inhibitor gamma |
| 1026. | 54832 | VPS13C | vacuolar protein sorting 13C (yeast) |
| 1027. | 1486 | CTBS | chitobiase, di-N-acetyl- |
| 1028. | 4601 | MXI1 | MAX interactor 1 |
| 1029. | 1365 | CLDN3 | claudin 3 |
| 1030. | 81622 | UNC93B1 | unc-93 homolog B1 (*C. elegans*) |
| 1031. | 54664 | FLJ11273 | hypothetical protein FLJ11273 |
| 1032. | 9993 | DGCR2 | DiGeorge syndrome critical region gene 2 |
| 1033. | 57179 | KIAA1191 | KIAA1191 protein |
| 1034. | 55958 | KLHL9 | kelch-like 9 (*Drosophila*) |
| 1035. | 81671 | TMEM49 | transmembrane protein 49 |
| 1036. | 9666 | DZIP3 | zinc finger DAZ interacting protein 3 |
| 1037. | 10509 | SEMA4B | sema domain, immunoglobulin domain (Ig), transmembrane domain (TM) and short cytoplasmic domain, semaphorin 4B |
| 1038. | 3782 | KCNN3 | potassium intermediate/small conductance calcium-activated channel, subfamily N, member 3 |
| 1039. | 4644 | MYO5A | myosin VA (heavy polypeptide 12, myoxin) |
| 1040. | 55179 | FAIM | Fas apoptotic inhibitory molecule |
| 1041. | 9687 | GREB1 | GREB1 protein |
| 1042. | 25861 | DFNB31 | deafness, autosomal recessive 31 |

TABLE I-continued

| | ENTREZ GENE ID | GENE SYMBOL | GENE DESCRIPTION |
|---|---|---|---|
| 1043. | 9197 | SLC33A1 | solute carrier family 33 (acetyl-CoA transporter), member 1 |
| 1044. | 10549 | PRDX4 | peroxiredoxin 4 |
| 1045. | 27090 | ST6GALNAC4 | ST6 (alpha-N-acetyl-neuraminyl-2,3-beta-galactosyl-1,3)-N-acetylgalactosaminide alpha-2,6-sialyltransferase 4 |
| 1046. | 3988 | LIPA | lipase A, lysosomal acid, cholesterol esterase (Wolman disease) |
| 1047. | 10577 | NPC2 | Niemann-Pick disease, type C2 |
| 1048. | 441951 | HSUP1 | similar to RPE-spondin |
| 1049. | 26275 | HIBCH | 3-hydroxyisobutyryl-Coenzyme A hydrolase |
| 1050. | 401397 | LOC401397 | hypothetical LOC401397 |
| 1051. | 81555 | YIPF5 | Yip1 domain family, member 5 |
| 1052. | 19 | ABCA1 | ATP-binding cassette, sub-family A (ABC1), member 1 |
| 1053. | 2896 | GRN | granulin |
| 1054. | 1312 | COMT | catechol-O-methyltransferase |
| 1055. | 127018 | LYPLAL1 | lysophospholipase-like 1 |
| 1056. | 5911 | RAP2A | RAP2A, member of RAS oncogene family |
| 1057. | 3017 | HIST1H2BD | histone 1, H2bd |
| 1058. | 9139 | CBFA2T2 | core-binding factor, runt domain, alpha subunit 2; translocated to, 2 |
| 1059. | 50848 | F11R | F11 receptor |
| 1060. | 3728 | JUP | junction plakoglobin |
| 1061. | 8615 | VDP | vesicle docking protein p115 |
| 1062. | 79090 | MGC2650 | hypothetical protein MGC2650 |
| 1063. | 51303 | FKBP11 | FK506 binding protein 11, 19 kDa |
| 1064. | 64747 | MFSD1 | major facilitator superfamily domain containing 1 |
| 1065. | 23471 | TRAM1 | translocation associated membrane protein 1 |
| 1066. | 1832 | DSP | desmoplakin |
| 1067. | 125144 | MGC40157 | hypothetical protein MGC40157 |
| 1068. | 10150 | MBNL2 | muscleblind-like 2 (*Drosophila*) |
| 1069. | 3082 | HGF | hepatocyte growth factor (hepapoietin A; scatter factor) |
| 1070. | 7750 | ZNF198 | zinc finger protein 198 |
| 1071. | 2908 | NR3C1 | nuclear receptor subfamily 3, group C, member 1 (glucocorticoid receptor) |
| 1072. | 25758 | G2 | G2 protein |
| 1073. | 10653 | SPINT2 | serine protease inhibitor, Kunitz type, 2 |
| 1074. | 116151 | C20orf108 | chromosome 20 open reading frame 108 |
| 1075. | 8933 | CXX1 | CAAX box 1 |
| 1076. | 475 | ATOX1 | ATX1 antioxidant protein 1 homolog (yeast) |
| 1077. | 23406 | COTL1 | coactosin-like 1 (Dictyostelium) |
| 1078. | 57561 | ARRDC3 | arrestin domain containing 3 |
| 1079. | 55205 | ZNF532 | zinc finger protein 532 |
| 1080. | 25796 | PGLS | 6-phosphogluconolactonase |
| 1081. | 283846 | DKFZp547E087 | PI-3-kinase-related kinase SMG-1-like |
| 1082. | 57185 | DJ462O23.2 | hypothetical protein dJ462O23.2 |
| 1083. | 54431 | DNAJC10 | DnaJ (Hsp40) homolog, subfamily C, member 10 |
| 1084. | 5800 | PTPRO | protein tyrosine phosphatase, receptor type, O |
| 1085. | 1465 | CSRP1 | cysteine and glycine-rich protein 1 |
| 1086. | 950 | SCARB2 | scavenger receptor class B, member 2 |
| 1087. | 51019 | CGI-116 | CGI-116 protein |
| 1088. | 5476 | PPGB | protective protein for beta-galactosidase (galactosialidosis) |
| 1089. | 54145 | H2BFS | H2B histone family, member S |
| 1090. | 65981 | C1QDC1 | C1q domain containing 1 |
| 1091. | 81502 | HM13 | histocompatibility (minor) 13 |
| 1092. | 3572 | IL6ST | interleukin 6 signal transducer (gp130, oncostatin M receptor) |
| 1093. | 1299 | COL9A3 | collagen, type IX, alpha 3 |
| 1094. | 1386 | ATF2 | activating transcription factor 2 |
| 1095. | 4134 | MAP4 | microtubule-associated protein 4 |
| 1096. | 3981 | LIG4 | ligase IV, DNA, ATP-dependent |
| 1097. | 57714 | KIAA1618 | KIAA1618 |
| 1098. | 80315 | CPEB4 | cytoplasmic polyadenylation element binding protein 4 |
| 1099. | 107 | ADCY1 | adenylate cyclase 1 (brain) |
| 1100. | 8804 | CREG1 | cellular repressor of E1A-stimulated genes 1 |
| 1101. | 84181 | CHD6 | chromodomain helicase DNA binding protein 6 |
| 1102. | 22871 | NLGN1 | neuroligin 1 |
| 1103. | 659 | BMPR2 | bone morphogenetic protein receptor, type II (serine/threonine kinase) |
| 1104. | 79158 | MGC4170 | MGC4170 protein |
| 1105. | 112399 | EGLN3 | egl nine homolog 3 (*C. elegans*) |
| 1106. | 10550 | ARL6IP5 | ADP-ribosylation-like factor 6 interacting protein 5 |
| 1107. | 55573 | H41 | hypothetical protein H41 |

TABLE I-continued

| | ENTREZ GENE ID | GENE SYMBOL | GENE DESCRIPTION |
|---|---|---|---|
| 1108. | 51706 | NQO3A2 | NAD(P)H:quinone oxidoreductase type 3, polypeptide A2 |
| 1109. | 79738 | FLJ23560 | hypothetical protein FLJ23560 |
| 1110. | 6672 | SP100 | nuclear antigen Sp100 |
| 1111. | 145173 | B3GTL | beta 3-glycosyltransferase-like |
| 1112. | 3275 | HRMT1L1 | HMT1 hnRNP methyltransferase-like 1 (*S. cerevisiae*) |
| 1113. | 54059 | C21orf57 | chromosome 21 open reading frame 57 |
| 1114. | 571 | BACH1 | BTB and CNC homology 1, basic leucine zipper transcription factor 1 |
| 1115. | 6990 | TCTE1L | t-complex-associated-testis-expressed 1-like |
| 1116. | 9341 | VAMP3 | vesicle-associated membrane protein 3 (cellubrevin) |
| 1117. | 2180 | ACSL1 | acyl-CoA synthetase long-chain family member 1 |
| 1118. | 2799 | GNS | glucosamine (N-acetyl)-6-sulfatase (Sanfilippo disease IIID) |
| 1119. | 9236 | CCPG1 | cell cycle progression 1 |
| 1120. | 51111 | SUV420H1 | suppressor of variegation 4-20 homolog 1 (*Drosophila*) |
| 1121. | 598 | BCL2L1 | BCL2-like 1 |
| 1122. | 57674 | C17orf27 | chromosome 17 open reading frame 27 |
| 1123. | 1488 | CTBP2 | C-terminal binding protein 2 |
| 1124. | 80267 | C1orf22 | chromosome 1 open reading frame 22 |
| 1125. | 90701 | SEC11L3 | SEC11-like 3 (*S. cerevisiae*) |
| 1126. | 84218 | TBC1D3 | TBC1 domain family, member 3 |
| 1127. | 7844 | RNF103 | ring finger protein 103 |
| 1128. | 8440 | NCK2 | NCK adaptor protein 2 |
| 1129. | 25934 | NIPSNAP3A | nipsnap homolog 3A (*C. elegans*) |
| 1130. | 3897 | L1CAM | L1 cell adhesion molecule |
| 1131. | 114915 | TIGA1 | TIGA1 |
| 1132. | 754 | PTTG1IP | pituitary tumor-transforming 1 interacting protein |
| 1133. | 10525 | HYOU1 | hypoxia up-regulated 1 |
| 1134. | 966 | CD59 | CD59 antigen p18-20 (antigen identified by monoclonal antibodies 16.3A5, EJ16, EJ30, EL32 and G344) |
| 1135. | 25976 | TIPARP | TCDD-inducible poly(ADP-ribose) polymerase |
| 1136. | 3714 | JAG2 | jagged 2 |
| 1137. | 8780 | RIOK3 | RIO kinase 3 (yeast) |
| 1138. | 55827 | IQWD1 | IQ motif and WD repeats 1 |
| 1139. | 55830 | GLT8D1 | glycosyltransferase 8 domain containing 1 |
| 1140. | 4779 | NFE2L1 | nuclear factor (erythroid-derived 2)-like 1 |
| 1141. | 7286 | TUFT1 | tuftelin 1 |
| 1142. | 1028 | CDKN1C | cyclin-dependent kinase inhibitor 1C (p57, Kip2) |
| 1143. | 60492 | MDS025 | hypothetical protein MDS025 |
| 1144. | 27319 | BHLHB5 | basic helix-loop-helix domain containing, class B, 5 |
| 1145. | 1958 | EGR1 | early growth response 1 |
| 1146. | 89796 | NAV1 | neuron navigator 1 |
| 1147. | 9240 | PNMA1 | paraneoplastic antigen MA1 |
| 1148. | 6773 | STAT2 | signal transducer and activator of transcription 2, 113 kDa |
| 1149. | 7494 | XBP1 | X-box binding protein 1 |
| 1150. | 11057 | ABHD2 | abhydrolase domain containing 2 |
| 1151. | 9451 | EIF2AK3 | eukaryotic translation initiation factor 2-alpha kinase 3 |
| 1152. | 8878 | SQSTM1 | sequestosome 1 |
| 1153. | 302 | ANXA2 | annexin A2 |
| 1154. | 2590 | GALNT2 | UDP-N-acetyl-alpha-D-galactosamine:polypeptide N-acetylgalactosaminyltransferase 2 (GalNAc-T2) |
| 1155. | 1200 | TPP1 | tripeptidyl peptidase I |
| 1156. | 5973 | RENBP | renin binding protein |
| 1157. | 7259 | TSPYL1 | TSPY-like 1 |
| 1158. | 112770 | C1orf85 | chromosome 1 open reading frame 85 |
| 1159. | 93953 | ACRC | acidic repeat containing |
| 1160. | 90634 | CG018 | hypothetical gene CG018 |
| 1161. | 1030 | CDKN2B | cyclin-dependent kinase inhibitor 2B (p15, inhibits CDK4) |
| 1162. | 158158 | RASEF | RAS and EF hand domain containing |
| 1163. | 2824 | GPM6B | glycoprotein M6B |
| 1164. | 9706 | ULK2 | unc-51-like kinase 2 (*C. elegans*) |
| 1165. | 92370 | ACPL2 | acid phosphatase-like 2 |
| 1166. | 1203 | CLN5 | ceroid-lipofuscinosis, neuronal 5 |
| 1167. | 8337 | HIST2H2AA | histone 2, H2aa |
| 1168. | 3998 | LMAN1 | lectin, mannose-binding, 1 |
| 1169. | 56675 | NRIP3 | nuclear receptor interacting protein 3 |
| 1170. | 4864 | NPC1 | Niemann-Pick disease, type C1 |
| 1171. | 3358 | HTR2C | 5-hydroxytryptamine (serotonin) receptor 2C |
| 1172. | 304 | ANXA2P2 | annexin A2 pseudogene 2 |
| 1173. | 81790 | RNF170 | ring finger protein 170 |
| 1174. | 2537 | G1P3 | interferon, alpha-inducible protein (clone IFI-6-16) |

TABLE I-continued

| | ENTREZ GENE ID | GENE SYMBOL | GENE DESCRIPTION |
|---|---|---|---|
| 1175. | 55251 | C20orf36 | chromosome 20 open reading frame 36 |
| 1176. | 27344 | PCSK1N | proprotein convertase subtilisin/kexin type 1 inhibitor |
| 1177. | 10057 | ABCC5 | ATP-binding cassette, sub-family C (CFTR/MRP), member 5 |
| 1178. | 81031 | SLC2A10 | solute carrier family 2 (facilitated glucose transporter), member 10 |
| 1179. | 467 | ATF3 | activating transcription factor 3 |
| 1180. | 94103 | ORMDL3 | ORM1-like 3 (*S. cerevisiae*) |
| 1181. | 375593 | TRIM50B | tripartite motif-containing 50B |
| 1182. | 23015 | GM88 | 88-kDa golgi protein |
| 1183. | 55818 | JMJD1A | jumonji domain containing 1A |
| 1184. | 5274 | SERPINI1 | serine (or cysteine) proteinase inhibitor, clade I (neuroserpin), member 1 |
| 1185. | 23336 | DMN | desmuslin |
| 1186. | 255631 | COL24A1 | collagen, type XXIV, alpha 1 |
| 1187. | 3995 | FADS3 | fatty acid desaturase 3 |
| 1188. | 5797 | PTPRM | protein tyrosine phosphatase, receptor type, M |
| 1189. | 55876 | GSDML | gasdermin-like |
| 1190. | 999 | CDH1 | cadherin 1, type 1, E-cadherin (epithelial) |
| 1191. | 84897 | TBRG1 | transforming growth factor beta regulator 1 |
| 1192. | 51363 | GALNAC4S-6ST | B cell RAG associated protein |
| 1193. | 9961 | MVP | major vault protein |
| 1194. | 2982 | GUCY1A3 | guanylate cyclase 1, soluble, alpha 3 |
| 1195. | 706 | BZRP | benzodiazapine receptor (peripheral) |
| 1196. | 144203 | OVOS2 | ovostatin 2 |
| 1197. | 8516 | ITGA8 | integrin, alpha 8 |
| 1198. | 2037 | EPB41L2 | erythrocyte membrane protein band 4.1-like 2 |
| 1199. | 1524 | CX3CR1 | chemokine (C—X3—C motif) receptor 1 |
| 1200. | 222166 | EIIs1 | hypothetical protein EIIs1 |
| 1201. | 339803 | LOC339803 | hypothetical protein LOC339803 |
| 1202. | 5360 | PLTP | phospholipid transfer protein |
| 1203. | 1612 | DAPK1 | death-associated protein kinase 1 |
| 1204. | 90161 | HS6ST2 | heparan sulfate 6-O-sulfotransferase 2 |
| 1205. | 115701 | ALPK2 | alpha-kinase 2 |
| 1206. | 50640 | IPLA2(GAMMA) | intracellular membrane-associated calcium-independent phospholipase A2 gamma |
| 1207. | 8473 | OGT | O-linked N-acetylglucosamine (GlcNAc) transferase (UDP-N-acetylglucosamine:polypeptide-N-acetylglucosaminyl transferase) |
| 1208. | 252839 | TMEM9 | transmembrane protein 9 |
| 1209. | 150759 | LOC150759 | hypothetical protein LOC150759 |
| 1210. | 401152 | LOC401152 | HCV F-transactivated protein 1 |
| 1211. | 64065 | PERP | PERP, TP53 apoptosis effector |
| 1212. | 114793 | FMNL2 | formin-like 2 |
| 1213. | 477 | ATP1A2 | ATPase, Na+/K+ transporting, alpha 2 (+) polypeptide |
| 1214. | 59338 | PLEKHA1 | pleckstrin homology domain containing, family A (phosphoinositide binding specific) member 1 |
| 1215. | 3727 | JUND | jun D proto-oncogene |
| 1216. | 85236 | HIST1H2BK | histone 1, H2bk |
| 1217. | 6513 | SLC2A1 | solute carrier family 2 (facilitated glucose transporter), member 1 |
| 1218. | 155038 | GIMAP8 | GTPase, IMAP family member 8 |
| 1219. | 3055 | HCK | hemopoietic cell kinase |
| 1220. | 6542 | SLC7A2 | solute carrier family 7 (cationic amino acid transporter, y+ system), member 2 |
| 1221. | 8996 | NOL3 | nucleolar protein 3 (apoptosis repressor with CARD domain) |
| 1222. | 9728 | KIAA0256 | KIAA0256 gene product |
| 1223. | 51237 | PACAP | proapoptotic caspase adaptor protein |
| 1224. | 8987 | GENX-3414 | genethonin 1 |
| 1225. | 132720 | FLJ39370 | hypothetical protein FLJ39370 |
| 1226. | 1601 | DAB2 | disabled homolog 2, mitogen-responsive phosphoprotein (*Drosophila*) |
| 1227. | 54741 | LEPROT | leptin receptor overlapping transcript |
| 1228. | 81631 | MAP1LC3B | microtubule-associated protein 1 light chain 3 beta |
| 1229. | 9473 | C1orf38 | chromosome 1 open reading frame 38 |
| 1230. | 94241 | TP53INP1 | tumor protein p53 inducible nuclear protein 1 |
| 1231. | 5816 | PVALB | parvalbumin |
| 1232. | 115294 | LOC115294 | similar to hypothetical protein FLJ10883 |
| 1233. | 23461 | ABCA5 | ATP-binding cassette, sub-family A (ABC1), member 5 |
| 1234. | 10370 | CITED2 | Cbp/p300-interacting transactivator, with Glu/Asp-rich carboxy-terminal domain, 2 |
| 1235. | 9604 | RNF14 | ring finger protein 14 |
| 1236. | 387263 | C6orf120 | chromosome 6 open reading frame 120 |

TABLE I-continued

| | ENTREZ GENE ID | GENE SYMBOL | GENE DESCRIPTION |
|---|---|---|---|
| 1237. | 9120 | SLC16A6 | solute carrier family 16 (monocarboxylic acid transporters), member 6 |
| 1238. | 3915 | LAMC1 | laminin, gamma 1 (formerly LAMB2) |
| 1239. | 23092 | ARHGAP26 | Rho GTPase activating protein 26 |
| 1240. | 64778 | FNDC3B | fibronectin type III domain containing 3B |
| 1241. | 10140 | TOB1 | transducer of ERBB2, 1 |
| 1242. | 23208 | SYT11 | synaptotagmin XI |
| 1243. | 57730 | KIAA1641 | KIAA1641 |
| 1244. | 120196 | MGC34830 | hypothetical protein MGC34830 |
| 1245. | 7832 | BTG2 | BTG family, member 2 |
| 1246. | 23259 | DDHD2 | DDHD domain containing 2 |
| 1247. | 84981 | MGC14376 | hypothetical protein MGC14376 |
| 1248. | 6448 | SGSH | N-sulfoglucosamine sulfohydrolase (sulfamidase) |
| 1249. | 9910 | RABGAP1L | RAB GTPase activating protein 1-like |
| 1250. | 1611 | DAP | death-associated protein |
| 1251. | 126823 | KARCA1 | kelch/ankyrin repeat containing cyclin A1 interacting protein |
| 1252. | 388403 | YPEL2 | yippee-like 2 (*Drosophila*) |
| 1253. | 6720 | SREBF1 | sterol regulatory element binding transcription factor 1 |
| 1254. | 58476 | TP53INP2 | tumor protein p53 inducible nuclear protein 2 |
| 1255. | 8605 | PLA2G4C | phospholipase A2, group IVC (cytosolic, calcium-independent) |
| 1256. | 3983 | ABLIM1 | actin binding LIM protein 1 |
| 1257. | 4189 | DNAJB9 | DnaJ (Hsp40) homolog, subfamily B, member 9 |
| 1258. | 1604 | DAF | decay accelerating factor for complement (CD55, Cromer blood group system) |
| 1259. | 29994 | BAZ2B | bromodomain adjacent to zinc finger domain, 2B |
| 1260. | 10156 | RASA4 | RAS p21 protein activator 4 |
| 1261. | 9123 | SLC16A3 | solute carrier family 16 (monocarboxylic acid transporters), member 3 |
| 1262. | 7846 | TUBA3 | tubulin, alpha 3 |
| 1263. | 3956 | LGALS1 | lectin, galactoside-binding, soluble, 1 (galectin 1) |
| 1264. | 1647 | GADD45A | growth arrest and DNA-damage-inducible, alpha |
| 1265. | 6609 | SMPD1 | sphingomyelin phosphodiesterase 1, acid lysosomal (acid sphingomyelinase) |
| 1266. | 56904 | SH3GLB2 | SH3-domain GRB2-like endophilin B2 |
| 1267. | 440081 | DDX12 | DEAD/H (Asp-Glu-Ala-Asp/His) box polypeptide 12 (CHL1-like helicase homolog, *S. cerevisiae*) |
| 1268. | 5163 | PDK1 | pyruvate dehydrogenase kinase, isoenzyme 1 |
| 1269. | 25840 | DKFZP586A0522 | DKFZP586A0522 protein |
| 1270. | 51566 | ARMCX3 | armadillo repeat containing, X-linked 3 |
| 1271. | 9388 | LIPG | lipase, endothelial |
| 1272. | 27250 | PDCD4 | programmed cell death 4 (neoplastic transformation inhibitor) |
| 1273. | 6302 | SAS | sarcoma amplified sequence |
| 1274. | 83937 | RASSF4 | Ras association (RalGDS/AF-6) domain family 4 |
| 1275. | 388677 | NOTCH2NL | Notch homolog 2 (*Drosophila*) N-terminal like |
| 1276. | 23646 | PLD3 | phospholipase D family, member 3 |
| 1277. | 23643 | LY96 | lymphocyte antigen 96 |
| 1278. | 9855 | FARP2 | FERM, RhoGEF and pleckstrin domain protein 2 |
| 1279. | 65018 | PINK1 | PTEN induced putative kinase 1 |
| 1280. | 57035 | C1orf63 | chromosome 1 open reading frame 63 |
| 1281. | 85352 | KIAA1644 | KIAA1644 protein |
| 1282. | 283131 | TncRNA | trophoblast-derived noncoding RNA |
| 1283. | 143888 | KDELC2 | KDEL (Lys-Asp-Glu-Leu) containing 2 |
| 1284. | 56204 | FLJ10980 | hypothetical protein FLJ10980 |
| 1285. | 23446 | CDW92 | CDW92 antigen |
| 1286. | 23766 | GABARAPL3 | GABA(A) receptors associated protein like 3 |
| 1287. | 1508 | CTSB | cathepsin B |
| 1288. | 4094 | MAF | v-maf musculoaponeurotic fibrosarcoma oncogene homolog (avian) |
| 1289. | 22932 | POMZP3 | POM (POM121 homolog, rat) and ZP3 fusion |
| 1290. | 56243 | KIAA1217 | KIAA1217 |
| 1291. | 1663 | DDX11 | DEAD/H (Asp-Glu-Ala-Asp/His) box polypeptide 11 (CHL1-like helicase homolog, *S. cerevisiae*) |
| 1292. | 1414 | CRYBB1 | crystallin, beta B1 |
| 1293. | 154091 | SLC2A12 | solute carrier family 2 (facilitated glucose transporter), member 12 |
| 1294. | 4121 | MAN1A1 | mannosidase, alpha, class 1A, member 1 |
| 1295. | 11178 | LZTS1 | leucine zipper, putative tumor suppressor 1 |
| 1296. | 10628 | TXNIP | thioredoxin interacting protein |
| 1297. | 83719 | YPEL3 | yippee-like 3 (*Drosophila*) |
| 1298. | 9863 | MAGI2 | membrane associated guanylate kinase, WW and PDZ domain containing 2 |
| 1299. | 5660 | PSAP | prosaposin (variant Gaucher disease and variant metachromatic leukodystrophy) |

TABLE I-continued

| | ENTREZ GENE ID | GENE SYMBOL | GENE DESCRIPTION |
|---|---|---|---|
| 1300. | 145788 | FLJ27352 | hypothetical LOC145788 |
| 1301. | 84513 | HTPAP | HTPAP protein |
| 1302. | 57612 | KIAA1466 | KIAA1466 gene |
| 1303. | 57515 | TDE2 | tumor differentially expressed 2 |
| 1304. | 29005 | PRO1073 | PRO1073 protein |
| 1305. | 51646 | YPEL5 | yippee-like 5 (*Drosophila*) |
| 1306. | 5269 | SERPINB6 | serine (or cysteine) proteinase inhibitor, clade B (ovalbumin), member 6 |
| 1307. | 30061 | SLC40A1 | solute carrier family 40 (iron-regulated transporter), member 1 |
| 1308. | 81030 | ZBP1 | Z-DNA binding protein 1 |
| 1309. | 347733 | RP11-506K6.1 | tubulin, beta polypeptide paralog |
| 1310. | 390 | RND3 | Rho family GTPase 3 |
| 1311. | 10765 | JARID1B | Jumonji, AT rich interactive domain 1B (RBP2-like) |
| 1312. | 9783 | RIMS3 | regulating synaptic membrane exocytosis 3 |
| 1313. | 27122 | DKK3 | dickkopf homolog 3 (*Xenopus laevis*) |
| 1314. | 151556 | GPR155 | G protein-coupled receptor 155 |
| 1315. | 8365 | HIST1H4H | histone 1, H4h |
| 1316. | 6480 | ST6GAL1 | ST6 beta-galactosamide alpha-2,6-sialyltranferase 1 |
| 1317. | 6591 | SNAI2 | snail homolog 2 (*Drosophila*) |
| 1318. | 54800 | DRE1 | DRE1 protein |
| 1319. | 3669 | ISG20 | interferon stimulated exonuclease gene 20 kDa |
| 1320. | 23710 | GABARAPL1 | GABA(A) receptor-associated protein like 1 |
| 1321. | 400172 | LOC400172 | similar to KIAA1641 protein; melanoma-associated antigen; CLL-associated antigen KW-1 |
| 1322. | 153222 | LOC153222 | adult retina protein |
| 1323. | 54981 | C9orf95 | chromosome 9 open reading frame 95 |
| 1324. | 5641 | LGMN | legumain |
| 1325. | 257019 | FRMD3 | FERM domain containing 3 |
| 1326. | 8357 | HIST1H3H | histone 1, H3h |
| 1327. | 55281 | FLJ11000 | hypothetical protein FLJ11000 |
| 1328. | 4050 | LTB | lymphotoxin beta (TNF superfamily, member 3) |
| 1329. | 203 | AK1 | adenylate kinase 1 |
| 1330. | 5920 | RARRES3 | retinoic acid receptor responder (tazarotene induced) 3 |
| 1331. | 284801 | LOC284801 | hypothetical protein LOC284801 |
| 1332. | 150271 | LOC150271 | hypothetical protein LOC150271 |

TABLE II

| | ENTREZ GENE ID | GENE SYMBOL | GENE DESCRIPTION |
|---|---|---|---|
| 1. | 6348 | CCL3 | chemokine (C-C motif) ligand 3 |
| 2. | 55388 | MCM10 | MCM10 minichromosome maintenance deficient 10 (*S. cerevisiae*) |
| 3. | 7117 | TMSL3 | thymosin-like 3 |
| 4. | 1017 | CDK2 | cyclin-dependent kinase 2 |
| 5. | 79019 | C22orf18 | chromosome 22 open reading frame 18 |
| 6. | 6241 | RRM2 | ribonucleotide reductase M2 polypeptide |
| 7. | 4605 | MYBL2 | v-myb myeloblastosis viral oncogene homolog (avian)-like 2 |
| 8. | 894 | CCND2 | cyclin D2 |
| 9. | 57405 | SPBC25 | spindle pole body component 25 homolog (*S. cerevisiae*) |
| 10. | 146909 | LOC146909 | hypothetical protein LOC146909 |
| 11. | 150271 | LOC150271 | hypothetical protein LOC150271 |
| 12. | 203 | AK1 | adenylate kinase 1 |
| 13. | 4050 | LTB | lymphotoxin beta (TNF superfamily, member 3) |
| 14. | 257019 | FRMD3 | FERM domain containing 3 |
| 15. | 8357 | HIST1H3H | histone 1, H3h |
| 16. | 23710 | GABARAPL1 | GABA(A) receptor-associated protein like 1 |
| 17. | 4171 | MCM2 | MCM2 minichromosome maintenance deficient 2, mitotin (*S. cerevisiae*) |
| 18. | 4176 | MCM7 | MCM7 minichromosome maintenance deficient 7 (*S. cerevisiae*) |
| 19. | 29089 | UBE2T | ubiquitin-conjugating enzyme E2T (putative) |
| 20. | 890 | CCNA2 | cyclin A2 |
| 21. | 51514 | DTL | denticleless homolog (*Drosophila*) |
| 22. | 440279 | UNC13C | unc-13 homolog C (*C. elegans*) |
| 23. | 11130 | ZWINT | ZW10 interactor |
| 24. | 9768 | KIAA0101 | KIAA0101 |
| 25. | 27338 | UBE2S | ubiquitin-conjugating enzyme E2S |
| 26. | 1846 | DUSP4 | dual specificity phosphatase 4 |

TABLE II-continued

| | ENTREZ GENE ID | GENE SYMBOL | GENE DESCRIPTION |
|---|---|---|---|
| 27. | 9833 | MELK | maternal embryonic leucine zipper kinase |
| 28. | 387103 | C6orf173 | chromosome 6 open reading frame 173 |
| 29. | 137392 | LOC137392 | similar to CG6405 gene product |
| 30. | 7374 | UNG | uracil-DNA glycosylase |
| 31. | 4915 | NTRK2 | neurotrophic tyrosine kinase, receptor, type 2 |
| 32. | 990 | CDC6 | CDC6 cell division cycle 6 homolog (*S. cerevisiae*) |
| 33. | 55165 | C10orf3 | chromosome 10 open reading frame 3 |
| 34. | 4001 | LMNB1 | lamin B1 |
| 35. | 51659 | Pfs2 | DNA replication complex GINS protein PSF2 |
| 36. | 11065 | UBE2C | ubiquitin-conjugating enzyme E2C |
| 37. | 4174 | MCM5 | MCM5 minichromosome maintenance deficient 5, cell division cycle 46 (*S. cerevisiae*) |
| 38. | 113130 | CDCA5 | cell division cycle associated 5 |
| 39. | 9535 | GMFG | glia maturation factor, gamma |
| 40. | 195828 | ZNF367 | zinc finger protein 367 |
| 41. | 55355 | DKFZp762E1312 | hypothetical protein DKFZp762E1312 |
| 42. | 9928 | KIF14 | kinesin family member 14 |
| 43. | 83879 | CDCA7 | cell division cycle associated 7 |
| 44. | 701 | BUB1B | BUB1 budding uninhibited by benzimidazoles 1 homolog beta (yeast) |
| 45. | 200734 | SPRED2 | sprouty-related, EVH1 domain containing 2 |
| 46. | 991 | CDC20 | CDC20 cell division cycle 20 homolog (*S. cerevisiae*) |
| 47. | 22974 | TPX2 | TPX2, microtubule-associated protein homolog (*Xenopus laevis*) |
| 48. | 3832 | KIF11 | kinesin family member 11 |
| 49. | 4288 | MKI67 | antigen identified by monoclonal antibody Ki-67 |
| 50. | 983 | CDC2 | cell division cycle 2, G1 to S and G2 to M |
| 51. | 28231 | SLCO4A1 | solute carrier organic anion transporter family, member 4A1 |
| 52. | 79801 | SHCBP1 | SHC SH2-domain binding protein 1 |
| 53. | 7804 | LRP8 | low density lipoprotein receptor-related protein 8, apolipoprotein e receptor |
| 54. | 7298 | TYMS | thymidylate synthetase |
| 55. | 7083 | TK1 | thymidine kinase 1, soluble |
| 56. | 26147 | PHF19 | PHD finger protein 19 |
| 57. | 55839 | BM039 | uncharacterized bone marrow protein BM039 |
| 58. | 9232 | PTTG1 | pituitary tumor-transforming 1 |
| 59. | 10592 | SMC2L1 | SMC2 structural maintenance of chromosomes 2-like 1 (yeast) |
| 60. | 3398 | ID2 | inhibitor of DNA binding 2, dominant negative helix-loop-helix protein |
| 61. | 4085 | MAD2L1 | MAD2 mitotic arrest deficient-like 1 (yeast) |
| 62. | 1063 | CENPF | centromere protein F, 350/400ka (mitosin) |
| 63. | 3418 | IDH2 | isocitrate dehydrogenase 2 (NADP+), mitochondrial |
| 64. | 1163 | CKS1B | CDC28 protein kinase regulatory subunit 1B |
| 65. | 55215 | FLJ10719 | hypothetical protein FLJ10719 |
| 66. | 29127 | RACGAP1 | Rac GTPase activating protein 1 |
| 67. | 7153 | TOP2A | topoisomerase (DNA) II alpha 170 kDa |
| 68. | 122769 | PPIL5 | peptidylprolyl isomerase (cyclophilin)-like 5 |
| 69. | 79682 | MLF1IP | MLF1 interacting protein |
| 70. | 6790 | STK6 | serine/threonine kinase 6 |
| 71. | 3925 | STMN1 | stathmin 1/oncoprotein 18 |
| 72. | 11004 | KIF2C | kinesin family member 2C |
| 73. | 10276 | NET1 | neuroepithelial cell transforming gene 1 |
| 74. | 3015 | H2AFZ | H2A histone family, member Z |
| 75. | 891 | CCNB1 | cyclin B1 |
| 76. | 389835 | FAM72A | family with sequence similarity 72, member A |
| 77. | 5111 | PCNA | proliferating cell nuclear antigen |
| 78. | 9837 | PSF1 | DNA replication complex GINS protein PSF1 |
| 79. | 3148 | HMGB2 | high-mobility group box 2 |
| 80. | 7112 | TMPO | thymopoietin |
| 81. | 63901 | FLJ22794 | FLJ22794 protein |
| 82. | 51203 | NUSAP1 | nucleolar and spindle associated protein 1 |
| 83. | 29128 | UHRF1 | ubiquitin-like, containing PHD and RING finger domains, 1 |
| 84. | 79075 | DCC1 | defective in sister chromatid cohesion homolog 1 (*S. cerevisiae*) |
| 85. | 9319 | TRIP13 | thyroid hormone receptor interactor 13 |
| 86. | 1033 | CDKN3 | cyclin-dependent kinase inhibitor 3 (CDK2-associated dual specificity phosphatase) |
| 87. | 10189 | THOC4 | THO complex 4 |
| 88. | 9133 | CCNB2 | cyclin B2 |
| 89. | 55010 | FLJ20641 | hypothetical protein FLJ20641 |
| 90. | 83540 | CDCA1 | cell division cycle associated 1 |
| 91. | 1870 | E2F2 | E2F transcription factor 2 |
| 92. | 962 | CD48 | CD48 antigen (B-cell membrane protein) |
| 93. | 55789 | DEPDC1B | DEP domain containing 1B |
| 94. | 170954 | KIAA1949 | KIAA1949 |

TABLE II-continued

| | ENTREZ GENE ID | GENE SYMBOL | GENE DESCRIPTION |
|---|---|---|---|
| 95. | 332 | BIRC5 | baculoviral IAP repeat-containing 5 (survivin) |
| 96. | 445815 | PALM2-AKAP2 | PALM2-AKAP2 protein |
| 97. | 865 | CBFB | core-binding factor, beta subunit |
| 98. | 7913 | DEK | DEK oncogene (DNA binding) |
| 99. | 5983 | RFC3 | replication factor C (activator 1) 3, 38 kDa |
| 100. | 84515 | MCM8 | MCM8 minichromosome maintenance deficient 8 (*S. cerevisiae*) |
| 101. | 51053 | GMNN | geminin, DNA replication inhibitor |
| 102. | 1111 | CHEK1 | CHK1 checkpoint homolog (*S. pombe*) |
| 103. | 7443 | VRK1 | vaccinia related kinase 1 |
| 104. | 10376 | K-ALPHA-1 | tubulin, alpha, ubiquitous |
| 105. | 3014 | H2AFX | H2A histone family, member X |
| 106. | 9055 | PRC1 | protein regulator of cytokinesis 1 |
| 107. | 2237 | FEN1 | flap structure-specific endonuclease 1 |
| 108. | 81563 | C1orf21 | chromosome 1 open reading frame 21 |
| 109. | 51192 | CKLF | chemokine-like factor |
| 110. | 1062 | CENPE | centromere protein E, 312 kDa |
| 111. | 11339 | OIP5 | Opa interacting protein 5 |
| 112. | 10615 | SPAG5 | sperm associated antigen 5 |
| 113. | 55646 | LYAR | hypothetical protein FLJ20425 |
| 114. | 55706 | TMEM48 | transmembrane protein 48 |
| 115. | 1058 | CENPA | centromere protein A, 17 kDa |
| 116. | 3070 | HELLS | helicase, lymphoid-specific |
| 117. | 4173 | MCM4 | MCM4 minichromosome maintenance deficient 4 (*S. cerevisiae*) |
| 118. | 23421 | ITGB3BP | integrin beta 3 binding protein (beta3-endonexin) |
| 119. | 9530 | BAG4 | BCL2-associated athanogene 4 |
| 120. | 801 | CALM1 | calmodulin 1 (phosphorylase kinase, delta) |
| 121. | 54069 | C21orf45 | chromosome 21 open reading frame 45 |
| 122. | 283991 | MGC29814 | hypothetical protein MGC29814 |
| 123. | 63979 | FIGNL1 | fidgetin-like 1 |
| 124. | 64105 | FKSG14 | leucine zipper protein FKSG14 |
| 125. | 4172 | MCM3 | MCM3 minichromosome maintenance deficient 3 (*S. cerevisiae*) |
| 126. | 24137 | KIF4A | kinesin family member 4A |
| 127. | 7398 | USP1 | ubiquitin specific protease 1 |
| 128. | 84930 | MASTL | microtubule associated serine/threonine kinase-like |
| 129. | 51512 | GTSE1 | G-2 and S-phase expressed 1 |
| 130. | 4678 | NASP | nuclear autoantigenic sperm protein (histone-binding) |
| 131. | 699 | BUB1 | BUB1 budding uninhibited by benzimidazoles 1 homolog (yeast) |
| 132. | 1719 | DHFR | dihydrofolate reductase |
| 133. | 494143 | LOC494143 | similar to RIKEN cDNA 2510006C20 gene |
| 134. | 55055 | FLJ10036 | Zwilch |
| 135. | 672 | BRCA1 | breast cancer 1, early onset |
| 136. | 64946 | CENPH | centromere protein H |
| 137. | 83461 | CDCA3 | cell division cycle associated 3 |
| 138. | 7465 | WEE1 | WEE1 homolog (*S. pombe*) |
| 139. | 5984 | RFC4 | replication factor C (activator 1) 4, 37 kDa |
| 140. | 64581 | CLEC7A | C-type lectin domain family 7, member A |
| 141. | 1230 | CCR1 | chemokine (C-C motif) receptor 1 |
| 142. | 4175 | MCM6 | MCM6 minichromosome maintenance deficient 6 (MIS5 homolog, *S. pombe*) (*S. cerevisiae*) |
| 143. | 55502 | HES6 | hairy and enhancer of split 6 (*Drosophila*) |
| 144. | 64151 | HCAP-G | chromosome condensation protein G |
| 145. | 11151 | CORO1A | coronin, actin binding protein, 1A |
| 146. | 203068 | TUBB | tubulin, beta polypeptide |
| 147. | 10926 | ASK | activator of S phase kinase |
| 148. | 11073 | TOPBP1 | topoisomerase (DNA) II binding protein 1 |
| 149. | 90417 | C15orf23 | chromosome 15 open reading frame 23 |
| 150. | 9493 | KIF23 | kinesin family member 23 |
| 151. | 387882 | LOC387882 | hypothetical protein |
| 152. | 23234 | DNAJC9 | DnaJ (Hsp40) homolog, subfamily C, member 9 |
| 153. | 2146 | EZH2 | enhancer of zeste homolog 2 (*Drosophila*) |
| 154. | 6627 | SNRPA1 | small nuclear ribonucleoprotein polypeptide A' |
| 155. | 5982 | RFC2 | replication factor C (activator 1) 2, 40 kDa |
| 156. | 51155 | HN1 | hematological and neurological expressed 1 |
| 157. | 10635 | RAD51AP1 | RAD51 associated protein 1 |
| 158. | 91057 | NY-REN-41 | NY-REN-41 antigen |
| 159. | 11168 | PSIP1 | PC4 and SFRS1 interacting protein 1 |
| 160. | 10403 | KNTC2 | kinetochore associated 2 |
| 161. | 4751 | NEK2 | NIMA (never in mitosis gene a)-related kinase 2 |
| 162. | 29028 | ATAD2 | ATPase family, AAA domain containing 2 |
| 163. | 26271 | FBXO5 | F-box protein 5 |
| 164. | 54892 | LUZP5 | leucine zipper protein 5 |

TABLE II-continued

| | ENTREZ GENE ID | GENE SYMBOL | GENE DESCRIPTION |
|---|---|---|---|
| 165. | 79723 | SUV39H2 | suppressor of variegation 3-9 homolog 2 (*Drosophila*) |
| 166. | 23590 | TPRT | trans-prenyltransferase |
| 167. | 2288 | FKBP4 | FK506 binding protein 4, 59 kDa |
| 168. | 23165 | NUP205 | nucleoporin 205 kDa |
| 169. | 6240 | RRM1 | ribonucleotide reductase M1 polypeptide |
| 170. | 81539 | SLC38A1 | solute carrier family 38, member 1 |
| 171. | 1894 | ECT2 | epithelial cell transforming sequence 2 oncogene |
| 172. | 55872 | PBK | PDZ binding kinase |
| 173. | 55635 | DEPDC1 | DEP domain containing 1 |
| 174. | 11013 | TMSL8 | thymosin-like 8 |
| 175. | 259266 | ASPM | asp (abnormal spindle)-like, microcephaly associated (*Drosophila*) |
| 176. | 10950 | BTG3 | BTG family, member 3 |
| 177. | 56992 | KIF15 | kinesin family member 15 |
| 178. | 29980 | DONSON | downstream neighbor of SON |
| 179. | 5757 | PTMA | prothymosin, alpha (gene sequence 28) |
| 180. | 5932 | RBBP8 | retinoblastoma binding protein 8 |
| 181. | 7903 | ST8SIA4 | ST8 alpha-N-acetyl-neuraminide alpha-2,8-sialyltransferase 4 |
| 182. | 348235 | FAM33A | family with sequence similarity 33, member A |
| 183. | 3182 | HNRPAB | heterogeneous nuclear ribonucleoprotein A/B |
| 184. | 3161 | HMMR | hyaluronan-mediated motility receptor (RHAMM) |
| 185. | 5985 | RFC5 | replication factor C (activator 1) 5, 36.5 kDa |
| 186. | 864 | RUNX3 | runt-related transcription factor 3 |
| 187. | 3930 | LBR | lamin B receptor |
| 188. | 1434 | CSE1L | CSE1 chromosome segregation 1-like (yeast) |
| 189. | 81610 | C20orf129 | chromosome 20 open reading frame 129 |
| 190. | 3146 | HMGB1 | high-mobility group box 1 |
| 191. | 55636 | CHD7 | chromodomain helicase DNA binding protein 7 |
| 192. | 54443 | ANLN | anillin, actin binding protein (scraps homolog, *Drosophila*) |
| 193. | 5698 | PSMB9 | proteasome (prosome, macropain) subunit, beta type, 9 (large multifunctional protease 2) |
| 194. | 7277 | TUBA1 | tubulin, alpha 1 (testis specific) |
| 195. | 64282 | PAPD5 | PAP associated domain containing 5 |
| 196. | 201725 | LOC201725 | hypothetical protein LOC201725 |
| 197. | 7171 | TPM4 | tropomyosin 4 |
| 198. | 3838 | KPNA2 | karyopherin alpha 2 (RAG cohort 1, importin alpha 1) |
| 199. | 116832 | RPL39L | ribosomal protein L39-like |
| 200. | 4602 | MYB | v-myb myeloblastosis viral oncogene homolog (avian) |
| 201. | 54962 | FLJ20516 | timeless-interacting protein |
| 202. | 10541 | ANP32B | acidic (leucine-rich) nuclear phosphoprotein 32 family, member B |
| 203. | 9787 | DLG7 | discs, large homolog 7 (*Drosophila*) |
| 204. | 147138 | EVER2 | epidermodysplasia verruciformis 2 |
| 205. | 157313 | CDCA2 | cell division cycle associated 2 |
| 206. | 11340 | EXOSC8 | exosome component 8 |
| 207. | 2956 | MSH6 | mutS homolog 6 (*E. coli*) |
| 208. | 151246 | SGOL2 | shugoshin-like 2 (*S. pombe*) |
| 209. | 27346 | MAC30 | hypothetical protein MAC30 |
| 210. | 5873 | RAB27A | RAB27A, member RAS oncogene family |
| 211. | 79596 | C13orf7 | chromosome 13 open reading frame 7 |
| 212. | 10051 | SMC4L1 | SMC4 structural maintenance of chromosomes 4-like 1 (yeast) |
| 213. | 3336 | HSPE1 | heat shock 10 kDa protein 1 (chaperonin 10) |
| 214. | 6432 | SFRS7 | splicing factor, arginine/serine-rich 7, 35 kDa |
| 215. | 8819 | SAP30 | sin3-associated polypeptide, 30 kDa |
| 216. | 54801 | FAM29A | family with sequence similarity 29, member A |
| 217. | 1123 | CHN1 | chimerin (chimaerin) 1 |
| 218. | 694 | BTG1 | B-cell translocation gene 1, anti-proliferative |
| 219. | 153222 | LOC153222 | adult retina protein |
| 220. | 3669 | ISG20 | interferon stimulated exonuclease gene 20 kDa |
| 221. | 151556 | GPR155 | G protein-coupled receptor 155 |
| 222. | 6591 | SNAI2 | snail homolog 2 (*Drosophila*) |
| 223. | 5920 | RARRES3 | retinoic acid receptor responder (tazarotene induced) 3 |
| 224. | 400172 | LOC400172 | similar to KIAA1641 protein; melanoma-associated antigen; CLL-associated antigen KW-1 |
| 225. | 55281 | FLJ11000 | hypothetical protein FLJ11000 |
| 226. | 9783 | RIMS3 | regulating synaptic membrane exocytosis 3 |
| 227. | 6480 | ST6GAL1 | ST6 beta-galactosamide alpha-2,6-sialyltranferase 1 |
| 228. | 390 | RND3 | Rho family GTPase 3 |
| 229. | 10765 | JARID1B | Jumonji, AT rich interactive domain 1B (RBP2-like) |

TABLE II-continued

| | ENTREZ GENE ID | GENE SYMBOL | GENE DESCRIPTION |
|---|---|---|---|
| 230. | 154091 | SLC2A12 | solute carrier family 2 (facilitated glucose transporter), member 12 |
| 231. | 54981 | C9orf95 | chromosome 9 open reading frame 95 |
| 232. | 1663 | DDX11 | DEAD/H (Asp-Glu-Ala-Asp/His) box polypeptide 11 (CHL1-like helicase homolog, *S. cerevisiae*) |
| 233. | 54800 | DRE1 | DRE1 protein |
| 234. | 57515 | TDE2 | tumor differentially expressed 2 |
| 235. | 83719 | YPEL3 | yippee-like 3 (*Drosophila*) |
| 236. | 5269 | SERPINB6 | serine (or cysteine) proteinase inhibitor, clade B (ovalbumin), member 6 |
| 237. | 30061 | SLC40A1 | solute carrier family 40 (iron-regulated transporter), member 1 |
| 238. | 5660 | PSAP | prosaposin (variant Gaucher disease and variant metachromatic leukodystrophy) |
| 239. | 51646 | YPEL5 | yippee-like 5 (*Drosophila*) |
| 240. | 145788 | FLJ27352 | hypothetical LOC145788 |
| 241. | 81030 | ZBP1 | Z-DNA binding protein 1 |
| 242. | 57035 | C1orf63 | chromosome 1 open reading frame 63 |
| 243. | 9863 | MAGI2 | membrane associated guanylate kinase, WW and PDZ domain containing 2 |
| 244. | 9855 | FARP2 | FERM, RhoGEF and pleckstrin domain protein 2 |
| 245. | 57612 | KIAA1466 | KIAA1466 gene |
| 246. | 56243 | KIAA1217 | KIAA1217 |
| 247. | 8365 | HIST1H4H | histone 1, H4h |
| 248. | 440081 | DDX12 | DEAD/H (Asp-Glu-Ala-Asp/His) box polypeptide 12 (CHL1-like helicase homolog, *S. cerevisiae*) |
| 249. | 83937 | RASSF4 | Ras association (RalGDS/AF-6) domain family 4 |
| 250. | 56204 | FLJ10980 | hypothetical protein FLJ10980 |
| 251. | 22932 | POMZP3 | POM (POM121 homolog, rat) and ZP3 fusion |
| 252. | 10628 | TXNIP | thioredoxin interacting protein |
| 253. | 6720 | SREBF1 | sterol regulatory element binding transcription factor 1 |
| 254. | 1508 | CTSB | cathepsin B |
| 255. | 84513 | HTPAP | HTPAP protein |
| 256. | 85352 | KIAA1644 | KIAA1644 protein |
| 257. | 9388 | LIPG | lipase, endothelial |
| 258. | 5163 | PDK1 | pyruvate dehydrogenase kinase, isoenzyme 1 |
| 259. | 23446 | CDW92 | CDW92 antigen |
| 260. | 10156 | RASA4 | RAS p21 protein activator 4 |
| 261. | 23766 | GABARAPL3 | GABA(A) receptors associated protein like 3 |
| 262. | 56904 | SH3GLB2 | SH3-domain GRB2-like endophilin B2 |
| 263. | 6609 | SMPD1 | sphingomyelin phosphodiesterase 1, acid lysosomal (acid sphingomyelinase) |
| 264. | 23259 | DDHD2 | DDHD domain containing 2 |
| 265. | 23092 | ARHGAP26 | Rho GTPase activating protein 26 |
| 266. | 27250 | PDCD4 | programmed cell death 4 (neoplastic transformation inhibitor) |
| 267. | 3983 | ABLIM1 | actin binding LIM protein 1 |
| 268. | 23461 | ABCA5 | ATP-binding cassette, sub-family A (ABC1), member 5 |
| 269. | 4094 | MAF | v-maf musculoaponeurotic fibrosarcoma oncogene homolog (avian) |
| 270. | 23646 | PLD3 | phospholipase D family, member 3 |
| 271. | 51566 | ARMCX3 | armadillo repeat containing, X-linked 3 |
| 272. | 58476 | TP53INP2 | tumor protein p53 inducible nuclear protein 2 |
| 273. | 29994 | BAZ2B | bromodomain adjacent to zinc finger domain, 2B |
| 274. | 283131 | TncRNA | trophoblast-derived noncoding RNA |
| 275. | 4189 | DNAJB9 | DnaJ (Hsp40) homolog, subfamily B, member 9 |
| 276. | 9123 | SLC16A3 | solute carrier family 16 (monocarboxylic acid transporters), member 3 |
| 277. | 8473 | OGT | O-linked N-acetylglucosamine (GlcNAc) transferase (UDP-N-acetylglucosamine:polypeptide-N-acetylglucosaminyl transferase) |
| 278. | 65018 | PINK1 | PTEN induced putative kinase 1 |
| 279. | 339448 | LOC339448 | hypothetical protein LOC339448 |
| 280. | 6513 | SLC2A1 | solute carrier family 2 (facilitated glucose transporter), member 1 |
| 281. | 3995 | FADS3 | fatty acid desaturase 3 |
| 282. | 155038 | GIMAP8 | GTPase, IMAP family member 8 |
| 283. | 90634 | CG018 | hypothetical gene CG018 |
| 284. | 55573 | H41 | hypothetical protein H41 |
| 285. | 9201 | DCAMKL1 | doublecortin and CaM kinase-like 1 |
| 286. | 388403 | YPEL2 | yippee-like 2 (*Drosophila*) |
| 287. | 255631 | COL24A1 | collagen, type XXIV, alpha 1 |
| 288. | 8440 | NCK2 | NCK adaptor protein 2 |
| 289. | 81790 | RNF170 | ring finger protein 170 |
| 290. | 9706 | ULK2 | unc-51-like kinase 2 (*C. elegans*) |

TABLE II-continued

| | ENTREZ GENE ID | GENE SYMBOL | GENE DESCRIPTION |
|---|---|---|---|
| 291. | 934 | CD24 | CD24 antigen (small cell lung carcinoma cluster 4 antigen) |
| 292. | 9532 | BAG2 | BCL2-associated athanogene 2 |
| 293. | 23331 | KIAA1043 | KIAA1043 protein |
| 294. | 10675 | CSPG5 | chondroitin sulfate proteoglycan 5 (neuroglycan C) |
| 295. | 1102 | RCBTB2 | regulator of chromosome condensation (RCC1) and BTB (POZ) domain containing protein 2 |
| 296. | 2119 | ETV5 | ets variant gene 5 (ets-related molecule) |
| 297. | 255488 | IBRDC2 | IBR domain containing 2 |
| 298. | 55076 | TMEM45A | transmembrane protein 45A |
| 299. | 8364 | HIST1H4C | histone 1, H4c |
| 300. | 3725 | JUN | v-jun sarcoma virus 17 oncogene homolog (avian) |
| 301. | 384 | ARG2 | arginase, type II |
| 302. | 10129 | 13CDNA73 | hypothetical protein CG003 |
| 303. | 1960 | EGR3 | early growth response 3 |
| 304. | 27122 | DKK3 | dickkopf homolog 3 (*Xenopus laevis*) |
| 305. | 11178 | LZTS1 | leucine zipper, putative tumor suppressor 1 |
| 306. | 143888 | KDELC2 | KDEL (Lys-Asp-Glu-Leu) containing 2 |
| 307. | 1601 | DAB2 | disabled homolog 2, mitogen-responsive phosphoprotein (*Drosophila*) |
| 308. | 6542 | SLC7A2 | solute carrier family 7 (cationic amino acid transporter, y+ system), member 2 |
| 309. | 477 | ATP1A2 | ATPase, Na+/K+ transporting, alpha 2 (+) polypeptide |
| 310. | 90161 | HS6ST2 | heparan sulfate 6-O-sulfotransferase 2 |
| 311. | 81031 | SLC2A10 | solute carrier family 2 (facilitated glucose transporter), member 10 |
| 312. | 56675 | NRIP3 | nuclear receptor interacting protein 3 |
| 313. | 1958 | EGR1 | early growth response 1 |
| 314. | 3714 | JAG2 | jagged 2 |
| 315. | 3897 | L1CAM | L1 cell adhesion molecule |
| 316. | 1488 | CTBP2 | C-terminal binding protein 2 |
| 317. | 145173 | B3GTL | beta 3-glycosyltransferase-like |
| 318. | 112399 | EGLN3 | egl nine homolog 3 (*C. elegans*) |
| 319. | 22871 | NLGN1 | neuroligin 1 |
| 320. | 8804 | CREG1 | cellular repressor of E1A-stimulated genes 1 |
| 321. | 401081 | FLJ22763 | hypothetical gene supported by AK026416 |
| 322. | 25924 | MYRIP | myosin VIIA and Rab interacting protein |
| 323. | 91694 | FLJ23749 | hypothetical protein FLJ23749 |
| 324. | 56155 | TEX14 | testis expressed sequence 14 |
| 325. | 1349 | COX7B | cytochrome c oxidase subunit VIIb |
| 326. | 3695 | ITGB7 | integrin, beta 7 |
| 327. | 1164 | CKS2 | CDC28 protein kinase regulatory subunit 2 |
| 328. | 56919 | DHX33 | DEAH (Asp-Glu-Ala-His) box polypeptide 33 |
| 329. | 3276 | HRMT1L2 | HMT1 hnRNP methyltransferase-like 2 (*S. cerevisiae*) |
| 330. | 116151 | C20orf108 | chromosome 20 open reading frame 108 |
| 331. | 25758 | G2 | G2 protein |
| 332. | 25861 | DFNB31 | deafness, autosomal recessive 31 |
| 333. | 9666 | DZIP3 | zinc finger DAZ interacting protein 3 |
| 334. | 1486 | CTBS | chitobiase, di-N-acetyl- |
| 335. | 3123 | HLA-DRB1 | major histocompatibility complex, class II, DR beta 1 |
| 336. | 317649 | EIF4E3 | eukaryotic translation initiation factor 4E member 3 |
| 337. | 50854 | C6orf48 | chromosome 6 open reading frame 48 |
| 338. | 401024 | FLJ44048 | FLJ44048 protein |
| 339. | 114327 | EFHC1 | EF-hand domain (C-terminal) containing 1 |
| 340. | 8334 | HIST1H2AC | histone 1, H2ac |
| 341. | 284214 | LOC284214 | hypothetical protein LOC284214 |
| 342. | 10379 | ISGF3G | interferon-stimulated transcription factor 3, gamma 48 kDa |
| 343. | 113177 | C19orf36 | chromosome 19 open reading frame 36 |
| 344. | 56951 | C5orf15 | chromosome 5 open reading frame 15 |
| 345. | 285362 | SUMF1 | sulfatase modifying factor 1 |
| 346. | 3490 | IGFBP7 | insulin-like growth factor binding protein 7 |
| 347. | 1186 | CLCN7 | chloride channel 7 |
| 348. | 582 | BBS1 | Bardet-Biedl syndrome 1 |
| 349. | 339456 | LOC339456 | hypothetical protein LOC339456 |
| 350. | 26115 | DKFZP564D166 | putative ankyrin-repeat containing protein |
| 351. | 9895 | KIAA0329 | KIAA0329 |
| 352. | 1040 | CDS1 | CDP-diacylglycerol synthase (phosphatidate cytidylyltransferase) 1 |
| 353. | 117854 | TRIM6 | tripartite motif-containing 6 |
| 354. | 3037 | HAS2 | hyaluronan synthase 2 |
| 355. | 4821 | NKX2-2 | NK2 transcription factor related, locus 2 (*Drosophila*) |
| 356. | 26298 | EHF | ets homologous factor |
| 357. | 22873 | DZIP1 | DAZ interacting protein 1 |
| 358. | 161742 | SPRED1 | sprouty-related, EVH1 domain containing 1 |
| 359. | 10052 | GJA7 | gap junction protein, alpha 7, 45 kDa (connexin 45) |

TABLE II-continued

| | ENTREZ GENE ID | GENE SYMBOL | GENE DESCRIPTION |
|---|---|---|---|
| 360. | 79733 | E2F8 | E2F transcription factor 8 |
| 361. | 10112 | KIF20A | kinesin family member 20A |
| 362. | 54910 | SEMA4C | sema domain, immunoglobulin domain (Ig), transmembrane domain (TM) and short cytoplasmic domain, (semaphorin) 4C |
| 363. | 993 | CDC25A | cell division cycle 25A |
| 364. | 3683 | ITGAL | integrin, alpha L (antigen CD11A (p180), lymphocyte function-associated antigen 1; alpha polypeptide) |
| 365. | 9355 | LHX2 | LIM homeobox 2 |
| 366. | 5578 | PRKCA | protein kinase C, alpha |
| 367. | 157570 | ESCO2 | establishment of cohesion 1 homolog 2 (*S. cerevisiae*) |
| 368. | 10252 | SPRY1 | sprouty homolog 1, antagonist of FGF signaling (*Drosophila*) |
| 369. | 22998 | KIAA1102 | KIAA1102 protein |
| 370. | 144455 | E2F7 | E2F transcription factor 7 |
| 371. | 2115 | ETV1 | ets variant gene 1 |
| 372. | 80144 | FRAS1 | Fraser syndrome 1 |
| 373. | 1902 | EDG2 | endothelial differentiation, lysophosphatidic acid G-protein-coupled receptor, 2 |
| 374. | 148203 | LOC148203 | hypothetical protein LOC148203 |
| 375. | 8851 | CDK5R1 | cyclin-dependent kinase 5, regulatory subunit 1 (p35) |
| 376. | 28951 | TRIB2 | tribbles homolog 2 (*Drosophila*) |
| 377. | 1491 | CTH | cystathionase (cystathionine gamma-lyase) |
| 378. | 4281 | MID1 | midline 1 (Opitz/BBB syndrome) |
| 379. | 145482 | ZADH1 | zinc binding alcohol dehydrogenase, domain containing 1 |
| 380. | 84858 | ZNF503 | zinc finger protein 503 |
| 381. | 55723 | ASF1B | ASF1 anti-silencing function 1 homolog B (*S. cerevisiae*) |
| 382. | 1718 | DHCR24 | 24-dehydrocholesterol reductase |
| 383. | 1847 | DUSP5 | dual specificity phosphatase 5 |
| 384. | 64081 | MAWBP | MAWD binding protein |
| 385. | 22822 | PHLDA1 | pleckstrin homology-like domain, family A, member 1 |
| 386. | 389831 | LOC389831 | hypothetical gene supported by AL713796 |
| 387. | 9212 | AURKB | aurora kinase B |
| 388. | 7272 | TTK | TTK protein kinase |
| 389. | 84952 | CGNL1 | cingulin-like 1 |
| 390. | 150468 | FLJ40629 | hypothetical protein FLJ40629 |
| 391. | 23286 | KIBRA | KIBRA protein |
| 392. | 29968 | PSAT1 | phosphoserine aminotransferase 1 |
| 393. | 8864 | PER2 | period homolog 2 (*Drosophila*) |
| 394. | 4603 | MYBL1 | v-myb myeloblastosis viral oncogene homolog (avian)-like 1 |
| 395. | 285513 | LOC285513 | hypothetical protein LOC285513 |
| 396. | 64919 | BCL11B | B-cell CLL/lymphoma 11B (zinc finger protein) |
| 397. | 83641 | C10orf45 | chromosome 10 open reading frame 45 |
| 398. | 6659 | SOX4 | SRY (sex determining region Y)-box 4 |
| 399. | 55964 | 3-Sep | septin 3 |
| 400. | 80150 | ASRGL1 | asparaginase like 1 |
| 401. | 8630 | HSD17B6 | hydroxysteroid (17-beta) dehydrogenase 6 |
| 402. | 7004 | TEAD4 | TEA domain family member 4 |
| 403. | 8871 | SYNJ2 | synaptojanin 2 |
| 404. | 56935 | FN5 | FN5 protein |
| 405. | 51232 | CRIM1 | cysteine-rich motor neuron 1 |
| 406. | 493861 | EID3 | E1A-like inhibitor of differentiation 3 |
| 407. | 2983 | GUCY1B3 | guanylate cyclase 1, soluble, beta 3 |
| 408. | 51776 | ZAK | sterile alpha motif and leucine zipper containing kinase AZK |
| 409. | 9953 | HS3ST3B1 | heparan sulfate (glucosamine) 3-O-sulfotransferase 3B1 |
| 410. | 23310 | hCAP-D3 | KIAA0056 protein |
| 411. | 2326 | FMO1 | flavin containing monooxygenase 1 |
| 412. | 51063 | FAM26B | family with sequence similarity 26, member B |
| 413. | 1038 | CDR1 | cerebellar degeneration-related protein 1, 34 kDa |
| 414. | 4325 | MMP16 | matrix metalloproteinase 16 (membrane-inserted) |
| 415. | 55247 | NEIL3 | nei endonuclease VIII-like 3 (*E. coli*) |
| 416. | 91607 | FLJ34922 | hypothetical protein FLJ34922 |
| 417. | 284801 | LOC284801 | hypothetical protein LOC284801 |
| 418. | 5641 | LGMN | legumain |
| 419. | 4121 | MAN1A1 | mannosidase, alpha, class 1A, member 1 |
| 420. | 1414 | CRYBB1 | crystallin, beta B1 |
| 421. | 8530 | CST7 | cystatin F (leukocystatin) |
| 422. | 2669 | GEM | GTP binding protein overexpressed in skeletal muscle |
| 423. | 126731 | C1orf96 | chromosome 1 open reading frame 96 |
| 424. | 26095 | PTPN20 | protein tyrosine phosphatase, non-receptor type 20 |

TABLE II-continued

| | ENTREZ GENE ID | GENE SYMBOL | GENE DESCRIPTION |
|---|---|---|---|
| 425. | 57037 | ANKMY2 | ankyrin repeat and MYND domain containing 2 |
| 426. | 3708 | ITPR1 | inositol 1,4,5-triphosphate receptor, type 1 |
| 427. | 55740 | ENAH | enabled homolog (Drosophila) |
| 428. | 57761 | TRIB3 | tribbles homolog 3 (Drosophila) |
| 429. | 6867 | TACC1 | transforming, acidic coiled-coil containing protein 1 |
| 430. | 27115 | PDE7B | phosphodiesterase 7B |
| 431. | 5361 | PLXNA1 | plexin A1 |
| 432. | 54908 | FLJ20364 | hypothetical protein FLJ20364 |
| 433. | 79710 | MORC4 | MORC family CW-type zinc finger 4 |
| 434. | 399664 | RKHD1 | ring finger and KH domain containing 1 |
| 435. | 90390 | THRAP6 | thyroid hormone receptor associated protein 6 |
| 436. | 2767 | GNA11 | guanine nucleotide binding protein (G protein), alpha 11 (Gq class) |
| 437. | 5793 | PTPRG | protein tyrosine phosphatase, receptor type, G |
| 438. | 6385 | SDC4 | syndecan 4 (amphiglycan, ryudocan) |
| 439. | 205 | AK3L1 | adenylate kinase 3-like 1 |
| 440. | 490 | ATP2B1 | ATPase, Ca++ transporting, plasma membrane 1 |
| 441. | 2026 | ENO2 | enolase 2 (gamma, neuronal) |
| 442. | 23046 | KIF21B | kinesin family member 21B |
| 443. | 60468 | BACH2 | BTB and CNC homology 1, basic leucine zipper transcription factor 2 |
| 444. | 55013 | FLJ20647 | hypothetical protein FLJ20647 |
| 445. | 256435 | ST6GALNAC3 | ST6 (alpha-N-acetyl-neuraminyl-2,3-beta-galactosyl-1,3)-N-acetylgalactosaminide alpha-2,6-sialyltransferase 3 |
| 446. | 6611 | SMS | spermine synthase |
| 447. | 79037 | MGC2463 | hypothetical protein MGC2463 |
| 448. | 23279 | NUP160 | nucleoporin 160 kDa |
| 449. | 10160 | FARP1 | FERM, RhoGEF (ARHGEF) and pleckstrin domain protein 1 (chondrocyte-derived) |
| 450. | 6877 | TAF5 | TAF5 RNA polymerase II, TATA box binding protein (TBP)-associated factor, 100 kDa |
| 451. | 2534 | FYN | FYN oncogene related to SRC, FGR, YES |
| 452. | 23531 | MMD | monocyte to macrophage differentiation-associated |
| 453. | 79621 | FLJ11712 | hypothetical protein FLJ11712 |
| 454. | 29899 | GPSM2 | G-protein signalling modulator 2 (AGS3-like, C. elegans) |
| 455. | 53354 | PANK1 | pantothenate kinase 1 |
| 456. | 2047 | EPHB1 | EPH receptor B1 |
| 457. | 6558 | SLC12A2 | solute carrier family 12 (sodium/potassium/chloride transporters), member 2 |
| 458. | 8502 | PKP4 | plakophilin 4 |
| 459. | 116496 | C1orf24 | chromosome 1 open reading frame 24 |
| 460. | 84314 | MGC10744 | hypothetical protein MGC10744 |
| 461. | 54830 | FLJ20130 | hypothetical protein FLJ20130 |
| 462. | 10602 | CDC42EP3 | CDC42 effector protein (Rho GTPase binding) 3 |
| 463. | 55257 | C20orf20 | chromosome 20 open reading frame 20 |
| 464. | 4885 | NPTX2 | neuronal pentraxin II |
| 465. | 8317 | CDC7 | CDC7 cell division cycle 7 (S. cerevisiae) |
| 466. | 55816 | DOK5 | docking protein 5 |
| 467. | 83732 | RIOK1 | RIO kinase 1 (yeast) |
| 468. | 489 | ATP2A3 | ATPase, Ca++ transporting, ubiquitous |
| 469. | 83990 | BRIP1 | BRCA1 interacting protein C-terminal helicase 1 |
| 470. | 9295 | SFRS11 | splicing factor, arginine/serine-rich 11 |
| 471. | 55166 | C6orf139 | chromosome 6 open reading frame 139 |
| 472. | 119467 | MGC32871 | hypothetical protein MGC32871 |
| 473. | 54101 | RIPK4 | receptor-interacting serine-threonine kinase 4 |
| 474. | 241 | ALOX5AP | arachidonate 5-lipoxygenase-activating protein |
| 475. | 2104 | ESRRG | estrogen-related receptor gamma |
| 476. | 6574 | SLC20A1 | solute carrier family 20 (phosphate transporter), member 1 |
| 477. | 960 | CD44 | CD44 antigen (homing function and Indian blood group system) |
| 478. | 26031 | OSBPL3 | oxysterol binding protein-like 3 |
| 479. | 23636 | NUP62 | nucleoporin 62 kDa |
| 480. | 9448 | MAP4K4 | mitogen-activated protein kinase kinase kinase kinase 4 |
| 481. | 26084 | SGEF | Src homology 3 domain-containing guanine nucleotide exchange factor |
| 482. | 9735 | KNTC1 | kinetochore associated 1 |
| 483. | 84803 | MGC11324 | hypothetical protein MGC11324 |
| 484. | 81839 | VANGL1 | vang-like 1 (van gogh, Drosophila) |
| 485. | 9734 | HDAC9 | histone deacetylase 9 |
| 486. | 51703 | ACSL5 | acyl-CoA synthetase long-chain family member 5 |
| 487. | 10155 | TRIM28 | tripartite motif-containing 28 |
| 488. | 54566 | EPB41L4B | erythrocyte membrane protein band 4.1 like 4B |
| 489. | 10019 | LNK | lymphocyte adaptor protein |

TABLE II-continued

| | ENTREZ GENE ID | GENE SYMBOL | GENE DESCRIPTION |
|---|---|---|---|
| 490. | 4082 | MARCKS | myristoylated alanine-rich protein kinase C substrate |
| 491. | 23012 | STK38L | serine/threonine kinase 38 like |
| 492. | 9759 | HDAC4 | histone deacetylase 4 |
| 493. | 657 | BMPR1A | bone morphogenetic protein receptor, type IA |
| 494. | 22837 | COBLL1 | COBL-like 1 |
| 495. | 79888 | FLJ12443 | hypothetical protein FLJ12443 |
| 496. | 79154 | MGC4172 | short-chain dehydrogenase/reductase |
| 497. | 4076 | M11S1 | membrane component, chromosome 11, surface marker 1 |
| 498. | 79930 | DOK3 | docking protein 3 |
| 499. | 4086 | SMAD1 | SMAD, mothers against DPP homolog 1 (Drosophila) |
| 500. | 79180 | EFHD2 | EF hand domain family, member D2 |
| 501. | 6340 | SCNN1G | sodium channel, nonvoltage-gated 1, gamma |
| 502. | 51015 | ISOC1 | isochorismatase domain containing 1 |
| 503. | 6999 | TDO2 | tryptophan 2,3-dioxygenase |
| 504. | 55276 | PGM2 | phosphoglucomutase 2 |
| 505. | 55270 | NUDT15 | nudix (nucleoside diphosphate linked moiety X)-type motif 15 |
| 506. | 51174 | TUBD1 | tubulin, delta 1 |
| 507. | 1789 | DNMT3B | DNA (cytosine-5-)-methyltransferase 3 beta |
| 508. | 84451 | KIAA1804 | mixed lineage kinase 4 |
| 509. | 5036 | PA2G4 | proliferation-associated 2G4, 38 kDa |
| 510. | 11177 | BAZ1A | bromodomain adjacent to zinc finger domain, 1A |
| 511. | 158563 | LOC158563 | hypothetical protein LOC158563 |
| 512. | 4957 | ODF2 | outer dense fiber of sperm tails 2 |
| 513. | 89891 | WDR34 | WD repeat domain 34 |
| 514. | 4640 | MYO1A | myosin IA |
| 515. | 26018 | LRIG1 | leucine-rich repeats and immunoglobulin-like domains 1 |
| 516. | 9738 | CP110 | CP110 protein |
| 517. | 378708 | APITD1 | apoptosis-inducing, TAF9-like domain 1 |
| 518. | 56952 | PRTFDC1 | phosphoribosyl transferase domain containing 1 |
| 519. | 3099 | HK2 | hexokinase 2 |
| 520. | 200894 | ARL2L1 | ADP-ribosylation factor-like 2-like 1 |
| 521. | 10625 | IVNS1ABP | influenza virus NS1A binding protein |
| 522. | 10436 | C2F | C2f protein |
| 523. | 79038 | ZFYVE21 | zinc finger, FYVE domain containing 21 |
| 524. | 7091 | TLE4 | transducin-like enhancer of split 4 (E(sp1) homolog, Drosophila) |
| 525. | 7291 | TWIST1 | twist homolog 1 (acrocephalosyndactyly 3; Saethre-Chotzen syndrome) (Drosophila) |
| 526. | 87 | ACTN1 | actinin, alpha 1 |
| 527. | 1736 | DKC1 | dyskeratosis congenita 1, dyskerin |
| 528. | 10265 | IRX5 | iroquois homeobox protein 5 |
| 529. | 8553 | BHLHB2 | basic helix-loop-helix domain containing, class B, 2 |
| 530. | 54947 | FLJ20481 | hypothetical protein FLJ20481 |
| 531. | 5150 | PDE7A | phosphodiesterase 7A |
| 532. | 83857 | ARG99 | ARG99 protein |
| 533. | 7791 | ZYX | zyxin |
| 534. | 27131 | SNX5 | sorting nexin 5 |
| 535. | 9112 | MTA1 | metastasis associated 1 |
| 536. | 80014 | BOMB | BH3-only member B protein |
| 537. | 139886 | LOC139886 | hypothetical protein LOC139886 |
| 538. | 3189 | HNRPH3 | heterogeneous nuclear ribonucleoprotein H3 (2H9) |
| 539. | 56905 | DKFZP434H132 | DKFZP434H132 protein |
| 540. | 10838 | ZNF275 | zinc finger protein 275 |
| 541. | 11118 | BTN3A2 | butyrophilin, subfamily 3, member A2 |
| 542. | 401505 | C9orf105 | chromosome 9 open reading frame 105 |
| 543. | 10384 | BTN3A3 | butyrophilin, subfamily 3, member A3 |
| 544. | 8566 | PDXK | pyridoxal (pyridoxine, vitamin B6) kinase |
| 545. | 10098 | TSPAN5 | tetraspanin 5 |
| 546. | 6526 | SLC5A3 | solute carrier family 5 (inositol transporters), member 3 |
| 547. | 6711 | SPTBN1 | spectrin, beta, non-erythrocytic 1 |
| 548. | 26010 | DNAPTP6 | DNA polymerase-transactivated protein 6 |
| 549. | 84108 | PCGF6 | polycomb group ring finger 6 |
| 550. | 51444 | RNF138 | ring finger protein 138 |
| 551. | 23089 | PEG10 | paternally expressed 10 |
| 552. | 22995 | Cep152 | KIAA0912 protein |
| 553. | 1503 | CTPS | CTP synthase |
| 554. | 6302 | SAS | sarcoma amplified sequence |
| 555. | 3956 | LGALS1 | lectin, galactoside-binding, soluble, 1 (galectin 1) |
| 556. | 126823 | KARCA1 | kelch/ankyrin repeat containing cyclin A1 interacting protein |

TABLE II-continued

| | ENTREZ GENE ID | GENE SYMBOL | GENE DESCRIPTION |
|---|---|---|---|
| 557. | 8605 | PLA2G4C | phospholipase A2, group IVC (cytosolic, calcium-independent) |
| 558. | 84981 | MGC14376 | hypothetical protein MGC14376 |
| 559. | 9120 | SLC16A6 | solute carrier family 16 (monocarboxylic acid transporters), member 6 |
| 560. | 5816 | PVALB | parvalbumin |
| 561. | 115294 | LOC115294 | similar to hypothetical protein FLJ10883 |
| 562. | 8996 | NOL3 | nucleolar protein 3 (apoptosis repressor with CARD domain) |
| 563. | 3055 | HCK | hemopoietic cell kinase |
| 564. | 339803 | LOC339803 | hypothetical protein LOC339803 |
| 565. | 252839 | TMEM9 | transmembrane protein 9 |
| 566. | 2982 | GUCY1A3 | guanylate cyclase 1, soluble, alpha 3 |
| 567. | 706 | BZRP | benzodiazapine receptor (peripheral) |
| 568. | 5797 | PTPRM | protein tyrosine phosphatase, receptor type, M |
| 569. | 9961 | MVP | major vault protein |
| 570. | 999 | CDH1 | cadherin 1, type 1, E-cadherin (epithelial) |
| 571. | 2537 | G1P3 | interferon, alpha-inducible protein (clone IFI-6-16) |
| 572. | 94103 | ORMDL3 | ORM1-like 3 (*S. cerevisiae*) |
| 573. | 8337 | HIST2H2AA | histone 2, H2aa |
| 574. | 10057 | ABCC5 | ATP-binding cassette, sub-family C (CFTR/MRP), member 5 |
| 575. | 5274 | SERPINI1 | serine (or cysteine) proteinase inhibitor, clade I (neuroserpin), member 1 |
| 576. | 3358 | HTR2C | 5-hydroxytryptamine (serotonin) receptor 2C |
| 577. | 158158 | RASEF | RAS and EF hand domain containing |
| 578. | 304 | ANXA2P2 | annexin A2 pseudogene 2 |
| 579. | 7259 | TSPYL1 | TSPY-like 1 |
| 580. | 8878 | SQSTM1 | sequestosome 1 |
| 581. | 7494 | XBP1 | X-box binding protein 1 |
| 582. | 302 | ANXA2 | annexin A2 |
| 583. | 4864 | NPC1 | Niemann-Pick disease, type C1 |
| 584. | 8780 | RIOK3 | RIO kinase 3 (yeast) |
| 585. | 27319 | BHLHB5 | basic helix-loop-helix domain containing, class B, 5 |
| 586. | 55827 | IQWD1 | IQ motif and WD repeats 1 |
| 587. | 966 | CD59 | CD59 antigen p18-20 (antigen identified by monoclonal antibodies 16.3A5, EJ16, EJ30, EL32 and G344) |
| 588. | 55830 | GLT8D1 | glycosyltransferase 8 domain containing 1 |
| 589. | 25934 | NIPSNAP3A | nipsnap homolog 3A (*C. elegans*) |
| 590. | 9451 | EIF2AK3 | eukaryotic translation initiation factor 2-alpha kinase 3 |
| 591. | 80267 | C1orf22 | chromosome 1 open reading frame 22 |
| 592. | 754 | PTTG1IP | pituitary tumor-transforming 1 interacting protein |
| 593. | 9236 | CCPG1 | cell cycle progression 1 |
| 594. | 6773 | STAT2 | signal transducer and activator of transcription 2, 113 kDa |
| 595. | 90701 | SEC11L3 | SEC11-like 3 (*S. cerevisiae*) |
| 596. | 2590 | GALNT2 | UDP-N-acetyl-alpha-D-galactosamine:polypeptide N-acetylgalactosaminyltransferase 2 (GalNac-T2) |
| 597. | 25976 | TIPARP | TCDD-inducible poly(ADP-ribose) polymerase |
| 598. | 57674 | C17orf27 | chromosome 17 open reading frame 27 |
| 599. | 7844 | RNF103 | ring finger protein 103 |
| 600. | 93953 | ACRC | acidic repeat containing |
| 601. | 6990 | TCTE1L | t-complex-associated-testis-expressed 1-like |
| 602. | 571 | BACH1 | BTB and CNC homology 1, basic leucine zipper transcription factor 1 |
| 603. | 6672 | SP100 | nuclear antigen Sp100 |
| 604. | 2799 | GNS | glucosamine (N-acetyl)-6-sulfatase (Sanfilippo disease IIID) |
| 605. | 10550 | ARL6IP5 | ADP-ribosylation-like factor 6 interacting protein 5 |
| 606. | 79738 | FLJ23560 | hypothetical protein FLJ23560 |
| 607. | 54059 | C21orf57 | chromosome 21 open reading frame 57 |
| 608. | 3275 | HRMT1L1 | HMT1 hnRNP methyltransferase-like 1 (*S. cerevisiae*) |
| 609. | 51706 | NQO3A2 | NAD(P)H:quinone oxidoreductase type 3, polypeptide A2 |
| 610. | 79158 | MGC4170 | MGC4170 protein |
| 611. | 80315 | CPEB4 | cytoplasmic polyadenylation element binding protein 4 |
| 612. | 3981 | LIG4 | ligase IV, DNA, ATP-dependent |
| 613. | 1299 | COL9A3 | collagen, type IX, alpha 3 |
| 614. | 3572 | IL6ST | interleukin 6 signal transducer (gp130, oncostatin M receptor) |
| 615. | 107 | ADCY1 | adenylate cyclase 1 (brain) |
| 616. | 84181 | CHD6 | chromodomain helicase DNA binding protein 6 |
| 617. | 54431 | DNAJC10 | DnaJ (Hsp40) homolog, subfamily C, member 10 |
| 618. | 283846 | DKFZp547E087 | PI-3-kinase-related kinase SMG-1-like |
| 619. | 25796 | PGLS | 6-phosphogluconolactonase |
| 620. | 5800 | PTPRO | protein tyrosine phosphatase, receptor type, O |

TABLE II-continued

| | ENTREZ GENE ID | GENE SYMBOL | GENE DESCRIPTION |
|---|---|---|---|
| 621. | 5476 | PPGB | protective protein for beta-galactosidase (galactosialidosis) |
| 622. | 54885 | FLJ20298 | FLJ20298 protein |
| 623. | 1368 | CPM | carboxypeptidase M |
| 624. | 586 | BCAT1 | branched chain aminotransferase 1, cytosolic |
| 625. | 130271 | PLEKHH2 | pleckstrin homology domain containing, family H (with MyTH4 domain) member 2 |
| 626. | 81930 | KIF18A | kinesin family member 18A |
| 627. | 11096 | ADAMTS5 | a disintegrin-like and metalloprotease (reprolysin type) with thrombospondin type 1 motif, 5 (aggrecanase-2) |
| 628. | 4148 | MATN3 | matrilin 3 |
| 629. | 56121 | PCDHB15 | protocadherin beta 15 |
| 630. | 57552 | AADACL1 | arylacetamide deacetylase-like 1 |
| 631. | 64396 | GMCL1L | germ cell-less homolog 1 (*Drosophila*)-like |
| 632. | 3119 | HLA-DQB1 | major histocompatibility complex, class II, DQ beta 1 |
| 633. | 1827 | DSCR1 | Down syndrome critical region gene 1 |
| 634. | 3202 | HOXA5 | homeo box A5 |
| 635. | 3298 | HSF2 | heat shock transcription factor 2 |
| 636. | 387914 | TMEM46 | transmembrane protein 46 |
| 637. | 11169 | WDHD1 | WD repeat and HMG-box DNA binding protein 1 |
| 638. | 79899 | FLJ14213 | hypothetical protein FLJ14213 |
| 639. | 1400 | CRMP1 | collapsin response mediator protein 1 |
| 640. | 55117 | SLC6A15 | solute carrier family 6, member 15 |
| 641. | 134429 | STARD4 | START domain containing 4, sterol regulated |
| 642. | 253832 | ZDHHC20 | zinc finger, DHHC-type containing 20 |
| 643. | 84986 | ARHGAP19 | Rho GTPase activating protein 19 |
| 644. | 5050 | PAFAH1B3 | platelet-activating factor acetylhydrolase, isoform Ib, gamma subunit 29 kDa |
| 645. | 4208 | MEF2C | MADS box transcription enhancer factor 2, polypeptide C (myocyte enhancer factor 2C) |
| 646. | 9994 | CASP8AP2 | CASP8 associated protein 2 |
| 647. | 5634 | PRPS2 | phosphoribosyl pyrophosphate synthetase 2 |
| 648. | 23587 | DERP6 | S-phase 2 protein |
| 649. | 57685 | KIAA1573 | KIAA1573 protein |
| 650. | 57530 | CGN | cingulin |
| 651. | 1633 | DCK | deoxycytidine kinase |
| 652. | 24147 | FJX1 | four jointed box 1 (*Drosophila*) |
| 653. | 9882 | TBC1D4 | TBC1 domain family, member 4 |
| 654. | 55183 | RIF1 | RAP1 interacting factor homolog (yeast) |
| 655. | 221362 | LOC221362 | hypothetical protein LOC221362 |
| 656. | 5569 | PKIA | protein kinase (cAMP-dependent, catalytic) inhibitor alpha |
| 657. | 6891 | TAP2 | transporter 2, ATP-binding cassette, sub-family B (MDR/TAP) |
| 658. | 11252 | PACSIN2 | protein kinase C and casein kinase substrate in neurons 2 |
| 659. | 81575 | DKFZP434F0318 | hypothetical protein DKFZp434F0318 |
| 660. | 56906 | THAP10 | THAP domain containing 10 |
| 661. | 55110 | FLJ10292 | mago-nashi homolog |
| 662. | 9612 | NCOR2 | nuclear receptor co-repressor 2 |
| 663. | 257415 | MGC40405 | hypothetical protein MGC40405 |
| 664. | 160897 | ITR | intimal thickness-related receptor |
| 665. | 4668 | NAGA | N-acetylgalactosaminidase, alpha- |
| 666. | 84890 | C10orf22 | chromosome 10 open reading frame 22 |
| 667. | 2618 | GART | phosphoribosylglycinamide formyltransferase, phosphoribosylglycinamide synthetase, phosphoribosylaminoimidazole synthetase |
| 668. | 80210 | FLJ12584 | melanoma/melanocyte specific protein KU-MEL-1 |
| 669. | 57534 | MIB1 | mindbomb homolog 1 (*Drosophila*) |
| 670. | 56122 | PCDHB14 | protocadherin beta 14 |
| 671. | 10966 | RAB40B | RAB40B, member RAS oncogene family |
| 672. | 5095 | PCCA | propionyl Coenzyme A carboxylase, alpha polypeptide |
| 673. | 55857 | C20orf19 | chromosome 20 open reading frame 19 |
| 674. | 285464 | FLJ34443 | hypothetical protein FLJ34443 |
| 675. | 1509 | CTSD | cathepsin D (lysosomal aspartyl protease) |
| 676. | 91614 | LOC91614 | novel 58.3 KDA protein |
| 677. | 2200 | FBN1 | fibrillin 1 (Marfan syndrome) |
| 678. | 6347 | CCL2 | chemokine (C-C motif) ligand 2 |
| 679. | 2743 | GLRB | glycine receptor, beta |
| 680. | 116448 | OLIG1 | oligodendrocyte transcription factor 1 |
| 681. | 3613 | IMPA2 | inositol(myo)-1(or 4)-monophosphatase 2 |
| 682. | 6764 | ST5 | suppression of tumorigenicity 5 |
| 683. | 4137 | MAPT | microtubule-associated protein tau |
| 684. | 9099 | USP2 | ubiquitin specific protease 2 |
| 685. | 5777 | PTPN6 | protein tyrosine phosphatase, non-receptor type 6 |

TABLE II-continued

| | ENTREZ GENE ID | GENE SYMBOL | GENE DESCRIPTION |
|---|---|---|---|
| 686. | 59338 | PLEKHA1 | pleckstrin homology domain containing, family A (phosphoinositide binding specific) member 1 |
| 687. | 1028 | CDKN1C | cyclin-dependent kinase inhibitor 1C (p57, Kip2) |
| 688. | 2177 | FANCD2 | Fanconi anemia, complementation group D2 |
| 689. | 165055 | FLJ32745 | hypothetical protein FLJ32745 |
| 690. | 151827 | LRRC34 | leucine rich repeat containing 34 |
| 691. | 203562 | TMEM31 | transmembrane protein 31 |
| 692. | 6934 | TCF7L2 | transcription factor 7-like 2 (T-cell specific, HMG-box) |
| 693. | 5577 | PRKAR2B | protein kinase, cAMP-dependent, regulatory, type II, beta |
| 694. | 79442 | LRRC2 | leucine rich repeat containing 2 |
| 695. | 55366 | LGR4 | leucine-rich repeat-containing G protein-coupled receptor 4 |
| 696. | 7975 | MAFK | v-maf musculoaponeurotic fibrosarcoma oncogene homolog K (avian) |
| 697. | 340252 | ZNF680 | zinc finger protein 680 |
| 698. | 22800 | RRAS2 | related RAS viral (r-ras) oncogene homolog 2 |
| 699. | 2730 | GCLM | glutamate-cysteine ligase, modifier subunit |
| 700. | 29841 | GRHL1 | grainyhead-like 1 (*Drosophila*) |
| 701. | 9214 | FAIM3 | Fas apoptotic inhibitory molecule 3 |
| 702. | 57406 | ABHD6 | abhydrolase domain containing 6 |
| 703. | 4660 | PPP1R12B | protein phosphatase 1, regulatory (inhibitor) subunit 12B |
| 704. | 157503 | LOC157503 | hypothetical protein LOC157503 |
| 705. | 285704 | RGMB | RGM domain family, member B |
| 706. | 55614 | C20orf23 | chromosome 20 open reading frame 23 |
| 707. | 85463 | ZC3H12C | zinc finger CCCH-type containing 12C |
| 708. | 6470 | SHMT1 | serine hydroxymethyltransferase 1 (soluble) |
| 709. | 9397 | NMT2 | N-myristoyltransferase 2 |
| 710. | 201161 | PRR6 | proline rich 6 |
| 711. | 8564 | KMO | kynurenine 3-monooxygenase (kynurenine 3-hydroxylase) |
| 712. | 283824 | LOC283824 | hypothetical protein LOC283824 |
| 713. | 57522 | SRGAP1 | SLIT-ROBO Rho GTPase activating protein 1 |
| 714. | 79695 | GALNT12 | UDP-N-acetyl-alpha-D-galactosamine:polypeptide N-acetylgalactosaminyltransferase 12 (GalNAc-T12) |
| 715. | 396 | ARHGDIA | Rho GDP dissociation inhibitor (GDI) alpha |
| 716. | 9208 | LRRFIP1 | leucine rich repeat (in FLII) interacting protein 1 |
| 717. | 6453 | ITSN1 | intersectin 1 (SH3 domain protein) |
| 718. | 169200 | DKFZp762C1112 | hypothetical protein DKFZp762C1112 |
| 719. | 9331 | B4GALT6 | UDP-Gal:betaGlcNAc beta 1,4-galactosyltransferase, polypeptide 6 |
| 720. | 8458 | TTF2 | transcription termination factor, RNA polymerase II |
| 721. | 1047 | CLGN | calmegin |
| 722. | 93949 | CXorf10 | chromosome X open reading frame 10 |
| 723. | 51762 | RAB8B | RAB8B, member RAS oncogene family |
| 724. | 5267 | SERPINA4 | serine (or cysteine) proteinase inhibitor, clade A (alpha-1 antiproteinase, antitrypsin), member 4 |
| 725. | 1844 | DUSP2 | dual specificity phosphatase 2 |
| 726. | 79720 | FLJ12750 | hypothetical protein FLJ12750 |
| 727. | 4522 | MTHFD1 | methylenetetrahydrofolate dehydrogenase (NADP+ dependent) 1, methenyltetrahydrofolate cyclohydrolase, formyltetrahydrofolate synthetase |
| 728. | 5198 | PFAS | phosphoribosylformylglycinamidine synthase (FGAR amidotransferase) |
| 729. | 55544 | RNPC1 | RNA-binding region (RNP1, RRM) containing 1 |
| 730. | 9261 | MAPKAPK2 | mitogen-activated protein kinase-activated protein kinase 2 |
| 731. | 285761 | DCBLD1 | discoidin, CUB and LCCL domain containing 1 |
| 732. | 161527 | LOC161527 | hypothetical protein LOC161527 |
| 733. | 8548 | BLZF1 | basic leucine zipper nuclear factor 1 (JEM-1) |
| 734. | 10537 | UBD | ubiquitin D |
| 735. | 64224 | FLJ22313 | hypothetical protein FLJ22313 |
| 736. | 4637 | MYL6 | myosin, light polypeptide 6, alkali, smooth muscle and non-muscle |
| 737. | 51569 | UFM1 | ubiquitin-fold modifier 1 |
| 738. | 57599 | WDR48 | WD repeat domain 48 |
| 739. | 57162 | PELI1 | pellino homolog 1 (*Drosophila*) |
| 740. | 58486 | LOC58486 | transposon-derived Buster1 transposase-like protein gene |
| 741. | 1266 | CNN3 | calponin 3, acidic |

TABLE III

| | ENTREZ GENE ID | GENE SYMBOL | GENE DESCRIPTION |
|---|---|---|---|
| 1. | 6348 | CCL3 | chemokine (C-C motif) ligand 3 |
| 2. | 55388 | MCM10 | MCM10 minichromosome maintenance deficient 10 (*S. cerevisiae*) |
| 3. | 7117 | TMSL3 | thymosin-like 3 |
| 4. | 1017 | CDK2 | cyclin-dependent kinase 2 |
| 5. | 79019 | C22orf18 | chromosome 22 open reading frame 18 |
| 6. | 6241 | RRM2 | ribonucleotide reductase M2 polypeptide |
| 7. | 4605 | MYBL2 | v-myb myeloblastosis viral oncogene homolog (avian)-like 2 |
| 8. | 894 | CCND2 | cyclin D2 |
| 9. | 57405 | SPBC25 | spindle pole body component 25 homolog (*S. cerevisiae*) |
| 10. | 146909 | LOC146909 | hypothetical protein LOC146909 |
| 11. | 150271 | LOC150271 | hypothetical protein LOC150271 |
| 12. | 203 | AK1 | adenylate kinase 1 |
| 13. | 4050 | LTB | lymphotoxin beta (TNF superfamily, member 3) |
| 14. | 257019 | FRMD3 | FERM domain containing 3 |
| 15. | 8357 | HIST1H3H | histone 1, H3h |
| 16. | 23710 | GABARAPL1 | GABA(A) receptor-associated protein like 1 |
| 17. | 9201 | DCAMKL1 | doublecortin and CaM kinase-like 1 |
| 18. | 934 | CD24 | CD24 antigen (small cell lung carcinoma cluster 4 antigen) |
| 19. | 9532 | BAG2 | BCL2-associated athanogene 2 |
| 20. | 23331 | KIAA1043 | KIAA1043 protein |
| 21. | 10675 | CSPG5 | chondroitin sulfate proteoglycan 5 (neuroglycan C) |
| 22. | 1102 | RCBTB2 | regulator of chromosome condensation (RCC1) and BTB (POZ) domain containing protein 2 |
| 23. | 2119 | ETV5 | ets variant gene 5 (ets-related molecule) |
| 24. | 255488 | IBRDC2 | IBR domain containing 2 |
| 25. | 55076 | TMEM45A | transmembrane protein 45A |
| 26. | 8364 | HIST1H4C | histone 1, H4c |
| 27. | 3725 | JUN | v-jun sarcoma virus 17 oncogene homolog (avian) |
| 28. | 384 | ARG2 | arginase, type II |
| 29. | 10129 | 13CDNA73 | hypothetical protein CG003 |
| 30. | 1960 | EGR3 | early growth response 3 |
| 31. | 27122 | DKK3 | dickkopf homolog 3 (*Xenopus laevis*) |
| 32. | 11178 | LZTS1 | leucine zipper, putative tumor suppressor 1 |
| 33. | 143888 | KDELC2 | KDEL (Lys-Asp-Glu-Leu) containing 2 |
| 34. | 1601 | DAB2 | disabled homolog 2, mitogen-responsive phosphoprotein (*Drosophila*) |
| 35. | 6542 | SLC7A2 | solute carrier family 7 (cationic amino acid transporter, y+ system), member 2 |
| 36. | 477 | ATP1A2 | ATPase, Na+/K+ transporting, alpha 2 (+) polypeptide |
| 37. | 90161 | HS6ST2 | heparan sulfate 6-O-sulfotransferase 2 |
| 38. | 81031 | SLC2A10 | solute carrier family 2 (facilitated glucose transporter), member 10 |
| 39. | 56675 | NRIP3 | nuclear receptor interacting protein 3 |
| 40. | 1958 | EGR1 | early growth response 1 |
| 41. | 3714 | JAG2 | jagged 2 |
| 42. | 3897 | L1CAM | L1 cell adhesion molecule |
| 43. | 1488 | CTBP2 | C-terminal binding protein 2 |
| 44. | 145173 | B3GTL | beta 3-glycosyltransferase-like |
| 45. | 112399 | EGLN3 | egl nine homolog 3 (*C. elegans*) |
| 46. | 22871 | NLGN1 | neuroligin 1 |
| 47. | 8804 | CREG1 | cellular repressor of E1A-stimulated genes 1 |
| 48. | 117854 | TRIM6 | tripartite motif-containing 6 |
| 49. | 3037 | HAS2 | hyaluronan synthase 2 |
| 50. | 4821 | NKX2-2 | NK2 transcription factor related, locus 2 (*Drosophila*) |
| 51. | 26298 | EHF | ets homologous factor |
| 52. | 22873 | DZIP1 | DAZ interacting protein 1 |
| 53. | 161742 | SPRED1 | sprouty-related, EVH1 domain containing 1 |
| 54. | 10052 | GJA7 | gap junction protein, alpha 7, 45 kDa (connexin 45) |
| 55. | 79733 | E2F8 | E2F transcription factor 8 |
| 56. | 10112 | KIF20A | kinesin family member 20A |
| 57. | 54910 | SEMA4C | sema domain, immunoglobulin domain (Ig), transmemebrane domain (TM) and short cytoplasmic domain, (semaphorin) 4C |
| 58. | 993 | CDC25A | cell division cycle 25A |
| 59. | 3683 | ITGAL | integrin, alpha L (antigen CD11A (p180), lymphocyte function-associated antigen 1; alpha polypeptide) |
| 60. | 9355 | LHX2 | LIM homeobox 2 |
| 61. | 5578 | PRKCA | protein kinase C, alpha |
| 62. | 157570 | ESCO2 | establishment of cohesion 1 homolog 2 (*S. cerevisiae*) |
| 63. | 10252 | SPRY1 | sprouty homolog 1, antagonist of FGF signaling (*Drosophila*) |

TABLE III-continued

| | ENTREZ GENE ID | GENE SYMBOL | GENE DESCRIPTION |
|---|---|---|---|
| 64. | 22998 | KIAA1102 | KIAA1102 protein |
| 65. | 144455 | E2F7 | E2F transcription factor 7 |
| 66. | 2115 | ETV1 | ets variant gene 1 |
| 67. | 80144 | FRAS1 | Fraser syndrome 1 |
| 68. | 1902 | EDG2 | endothelial differentiation, lysophosphatidic acid G-protein-coupled receptor, 2 |
| 69. | 148203 | LOC148203 | hypothetical protein LOC148203 |
| 70. | 8851 | CDK5R1 | cyclin-dependent kinase 5, regulatory subunit 1 (p35) |
| 71. | 28951 | TRIB2 | tribbles homolog 2 (Drosophila) |
| 72. | 1491 | CTH | cystathionase (cystathionine gamma-lyase) |
| 73. | 4281 | MID1 | midline 1 (Opitz/BBB syndrome) |
| 74. | 145482 | ZADH1 | zinc binding alcohol dehydrogenase, domain containing 1 |
| 75. | 84858 | ZNF503 | zinc finger protein 503 |
| 76. | 55723 | ASF1B | ASF1 anti-silencing function 1 homolog B (S. cerevisiae) |
| 77. | 1718 | DHCR24 | 24-dehydrocholesterol reductase |
| 78. | 1847 | DUSP5 | dual specificity phosphatase 5 |
| 79. | 64081 | MAWBP | MAWD binding protein |
| 80. | 22822 | PHLDA1 | pleckstrin homology-like domain, family A, member 1 |
| 81. | 389831 | LOC389831 | hypothetical gene supported by AL713796 |
| 82. | 9212 | AURKB | aurora kinase B |
| 83. | 7272 | TTK | TTK protein kinase |
| 84. | 84952 | CGNL1 | cingulin-like 1 |
| 85. | 150468 | FLJ40629 | hypothetical protein FLJ40629 |
| 86. | 23286 | KIBRA | KIBRA protein |
| 87. | 29968 | PSAT1 | phosphoserine aminotransferase 1 |
| 88. | 8864 | PER2 | period homolog 2 (Drosophila) |
| 89. | 4603 | MYBL1 | v-myb myeloblastosis viral oncogene homolog (avian)-like 1 |
| 90. | 285513 | LOC285513 | hypothetical protein LOC285513 |
| 91. | 64919 | BCL11B | B-cell CLL/lymphoma 11B (zinc finger protein) |
| 92. | 83641 | C10orf45 | chromosome 10 open reading frame 45 |
| 93. | 6659 | SOX4 | SRY (sex determining region Y)-box 4 |
| 94. | 55964 | 3-Sep | septin 3 |
| 95. | 80150 | ASRGL1 | asparaginase like 1 |
| 96. | 8630 | HSD17B6 | hydroxysteroid (17-beta) dehydrogenase 6 |
| 97. | 7004 | TEAD4 | TEA domain family member 4 |
| 98. | 8871 | SYNJ2 | synaptojanin 2 |
| 99. | 56935 | FN5 | FN5 protein |
| 100. | 51232 | CRIM1 | cysteine-rich motor neuron 1 |
| 101. | 493861 | EID3 | E1A-like inhibitor of differentiation 3 |
| 102. | 2983 | GUCY1B3 | guanylate cyclase 1, soluble, beta 3 |
| 103. | 51776 | ZAK | sterile alpha motif and leucine zipper containing kinase AZK |
| 104. | 9953 | HS3ST3B1 | heparan sulfate (glucosamine) 3-O-sulfotransferase 3B1 |
| 105. | 23310 | hCAP-D3 | KIAA0056 protein |
| 106. | 2326 | FMO1 | flavin containing monooxygenase 1 |
| 107. | 51063 | FAM26B | family with sequence similarity 26, member B |
| 108. | 1038 | CDR1 | cerebellar degeneration-related protein 1, 34 kDa |
| 109. | 4325 | MMP16 | matrix metalloproteinase 16 (membrane-inserted) |
| 110. | 55247 | NEIL3 | nei endonuclease VIII-like 3 (E. coli) |
| 111. | 91607 | FLJ34922 | hypothetical protein FLJ34922 |
| 112. | 284801 | LOC284801 | hypothetical protein LOC284801 |
| 113. | 5641 | LGMN | legumain |
| 114. | 4121 | MAN1A1 | mannosidase, alpha, class 1A, member 1 |
| 115. | 1414 | CRYBB1 | crystallin, beta B1 |
| 116. | 54885 | FLJ20298 | FLJ20298 protein |
| 117. | 1368 | CPM | carboxypeptidase M |
| 118. | 586 | BCAT1 | branched chain aminotransferase 1, cytosolic |
| 119. | 130271 | PLEKHH2 | pleckstrin homology domain containing, family H (with MyTH4 domain) member 2 |
| 120. | 81930 | KIF18A | kinesin family member 18A |
| 121. | 11096 | ADAMTS5 | a disintegrin-like and metalloprotease (reprolysin type) with thrombospondin type 1 motif, 5 (aggrecanase-2) |
| 122. | 4148 | MATN3 | matrilin 3 |
| 123. | 56121 | PCDHB15 | protocadherin beta 15 |
| 124. | 57552 | AADACL1 | arylacetamide deacetylase-like 1 |
| 125. | 91614 | LOC91614 | novel 58.3 KDA protein |
| 126. | 2200 | FBN1 | fibrillin 1 (Marfan syndrome) |
| 127. | 6347 | CCL2 | chemokine (C-C motif) ligand 2 |
| 128. | 2743 | GLRB | glycine receptor, beta |
| 129. | 116448 | OLIG1 | oligodendrocyte transcription factor 1 |
| 130. | 3613 | IMPA2 | inositol(myo)-1(or 4)-monophosphatase 2 |
| 131. | 6764 | ST5 | suppression of tumorigenicity 5 |

TABLE III-continued

|     | ENTREZ GENE ID | GENE SYMBOL | GENE DESCRIPTION |
| --- | --- | --- | --- |
| 132. | 4137 | MAPT | microtubule-associated protein tau |
| 133. | 9099 | USP2 | ubiquitin specific protease 2 |
| 134. | 5777 | PTPN6 | protein tyrosine phosphatase, non-receptor type 6 |
| 135. | 59338 | PLEKHA1 | pleckstrin homology domain containing, family A (phosphoinositide binding specific) member 1 |
| 136. | 1028 | CDKN1C | cyclin-dependent kinase inhibitor 1C (p57, Kip2) |

TABLE IV

|     | ENTREZ GENE ID | GENE SYMBOL | GENE DESCRIPTION |
| --- | --- | --- | --- |
| 1. | 6348 | CCL3 | chemokine (C-C motif) ligand 3 |
| 2. | 55388 | MCM10 | MCM10 minichromosome maintenance deficient 10 (*S. cerevisiae*) |
| 3. | 7117 | TMSL3 | thymosin-like 3 |
| 4. | 1017 | CDK2 | cyclin-dependent kinase 2 |
| 5. | 79019 | C22orf18 | chromosome 22 open reading frame 18 |
| 6. | 6241 | RRM2 | ribonucleotide reductase M2 polypeptide |
| 7. | 4605 | MYBL2 | v-myb myeloblastosis viral oncogene homolog (avian)-like 2 |
| 8. | 894 | CCND2 | cyclin D2 |
| 9. | 57405 | SPBC25 | spindle pole body component 25 homolog (*S. cerevisiae*) |
| 10. | 146909 | LOC146909 | hypothetical protein LOC146909 |
| 11. | 150271 | LOC150271 | hypothetical protein LOC150271 |
| 12. | 203 | AK1 | adenylate kinase 1 |
| 13. | 4050 | LTB | lymphotoxin beta (TNF superfamily, member 3) |
| 14. | 257019 | FRMD3 | FERM domain containing 3 |
| 15. | 8357 | HIST1H3H | histone 1, H3h |
| 16. | 23710 | GABARAPL1 | GABA(A) receptor-associated protein like 1 |
| 17. | 4171 | MCM2 | MCM2 minichromosome maintenance deficient 2, mitotin (*S. cerevisiae*) |
| 18. | 4176 | MCM7 | MCM7 minichromosome maintenance deficient 7 (*S. cerevisiae*) |
| 19. | 29089 | UBE2T | ubiquitin-conjugating enzyme E2T (putative) |
| 20. | 890 | CCNA2 | cyclin A2 |
| 21. | 51514 | DTL | denticleless homolog (*Drosophila*) |
| 22. | 440279 | UNC13C | unc-13 homolog C (*C. elegans*) |
| 23. | 11130 | ZWINT | ZW10 interactor |
| 24. | 9768 | KIAA0101 | KIAA0101 |
| 25. | 27338 | UBE2S | ubiquitin-conjugating enzyme E2S |
| 26. | 1846 | DUSP4 | dual specificity phosphatase 4 |
| 27. | 9833 | MELK | maternal embryonic leucine zipper kinase |
| 28. | 387103 | C6orf173 | chromosome 6 open reading frame 173 |
| 29. | 137392 | LOC137392 | similar to CG6405 gene product |
| 30. | 7374 | UNG | uracil-DNA glycosylase |
| 31. | 4915 | NTRK2 | neurotrophic tyrosine kinase, receptor, type 2 |
| 32. | 990 | CDC6 | CDC6 cell division cycle 6 homolog (*S. cerevisiae*) |
| 33. | 55165 | C10orf3 | chromosome 10 open reading frame 3 |
| 34. | 4001 | LMNB1 | lamin B1 |
| 35. | 51659 | Pfs2 | DNA replication complex GINS protein PSF2 |
| 36. | 11065 | UBE2C | ubiquitin-conjugating enzyme E2C |
| 37. | 4174 | MCM5 | MCM5 minichromosome maintenance deficient 5, cell division cycle 46 (*S. cerevisiae*) |
| 38. | 113130 | CDCA5 | cell division cycle associated 5 |
| 39. | 9535 | GMFG | glia maturation factor, gamma |
| 40. | 195828 | ZNF367 | zinc finger protein 367 |
| 41. | 55355 | DKFZp762E1312 | hypothetical protein DKFZp762E1312 |
| 42. | 9928 | KIF14 | kinesin family member 14 |
| 43. | 83879 | CDCA7 | cell division cycle associated 7 |
| 44. | 701 | BUB1B | BUB1 budding uninhibited by benzimidazoles 1 homolog beta (yeast) |
| 45. | 200734 | SPRED2 | sprouty-related, EVH1 domain containing 2 |
| 46. | 991 | CDC20 | CDC20 cell division cycle 20 homolog (*S. cerevisiae*) |
| 47. | 22974 | TPX2 | TPX2, microtubule-associated protein homolog (*Xenopus laevis*) |
| 48. | 3832 | KIF11 | kinesin family member 11 |
| 49. | 4288 | MKI67 | antigen identified by monoclonal antibody Ki-67 |
| 50. | 983 | CDC2 | cell division cycle 2, G1 to S and G2 to M |
| 51. | 28231 | SLCO4A1 | solute carrier organic anion transporter family, member 4A1 |
| 52. | 79801 | SHCBP1 | SHC SH2-domain binding protein 1 |
| 53. | 7804 | LRP8 | low density lipoprotein receptor-related protein 8, apolipoprotein e receptor |

TABLE IV-continued

| | ENTREZ GENE ID | GENE SYMBOL | GENE DESCRIPTION |
|---|---|---|---|
| 54. | 7298 | TYMS | thymidylate synthetase |
| 55. | 7083 | TK1 | thymidine kinase 1, soluble |
| 56. | 26147 | PHF19 | PHD finger protein 19 |
| 57. | 55839 | BM039 | uncharacterized bone marrow protein BM039 |
| 58. | 9232 | PTTG1 | pituitary tumor-transforming 1 |
| 59. | 10592 | SMC2L1 | SMC2 structural maintenance of chromosomes 2-like 1 (yeast) |
| 60. | 3398 | ID2 | inhibitor of DNA binding 2, dominant negative helix-loop-helix protein |
| 61. | 4085 | MAD2L1 | MAD2 mitotic arrest deficient-like 1 (yeast) |
| 62. | 1063 | CENPF | centromere protein F, 350/400ka (mitosin) |
| 63. | 3418 | IDH2 | isocitrate dehydrogenase 2 (NADP+), mitochondrial |
| 64. | 1163 | CKS1B | CDC28 protein kinase regulatory subunit 1B |
| 65. | 55215 | FLJ10719 | hypothetical protein FLJ10719 |
| 66. | 29127 | RACGAP1 | Rac GTPase activating protein 1 |
| 67. | 7153 | TOP2A | topoisomerase (DNA) II alpha 170 kDa |
| 68. | 122769 | PPIL5 | peptidylprolyl isomerase (cyclophilin)-like 5 |
| 69. | 79682 | MLF1IP | MLF1 interacting protein |
| 70. | 6790 | STK6 | serine/threonine kinase 6 |
| 71. | 3925 | STMN1 | stathmin 1/oncoprotein 18 |
| 72. | 11004 | KIF2C | kinesin family member 2C |
| 73. | 10276 | NET1 | neuroepithelial cell transforming gene 1 |
| 74. | 3015 | H2AFZ | H2A histone family, member Z |
| 75. | 891 | CCNB1 | cyclin B1 |
| 76. | 389835 | FAM72A | family with sequence similarity 72, member A |
| 77. | 5111 | PCNA | proliferating cell nuclear antigen |
| 78. | 9837 | PSF1 | DNA replication complex GINS protein PSF1 |
| 79. | 3148 | HMGB2 | high-mobility group box 2 |
| 80. | 7112 | TMPO | thymopoietin |
| 81. | 63901 | FLJ22794 | FLJ22794 protein |
| 82. | 51203 | NUSAP1 | nucleolar and spindle associated protein 1 |
| 83. | 29128 | UHRF1 | ubiquitin-like, containing PHD and RING finger domains, 1 |
| 84. | 79075 | DCC1 | defective in sister chromatid cohesion homolog 1 (*S. cerevisiae*) |
| 85. | 9319 | TRIP13 | thyroid hormone receptor interactor 13 |
| 86. | 1033 | CDKN3 | cyclin-dependent kinase inhibitor 3 (CDK2-associated dual specificity phosphatase) |
| 87. | 10189 | THOC4 | THO complex 4 |
| 88. | 9133 | CCNB2 | cyclin B2 |
| 89. | 55010 | FLJ20641 | hypothetical protein FLJ20641 |
| 90. | 83540 | CDCA1 | cell division cycle associated 1 |
| 91. | 1870 | E2F2 | E2F transcription factor 2 |
| 92. | 962 | CD48 | CD48 antigen (B-cell membrane protein) |
| 93. | 55789 | DEPDC1B | DEP domain containing 1B |
| 94. | 170954 | KIAA1949 | KIAA1949 |
| 95. | 332 | BIRC5 | baculoviral IAP repeat-containing 5 (survivin) |
| 96. | 445815 | PALM2-AKAP2 | PALM2-AKAP2 protein |
| 97. | 865 | CBFB | core-binding factor, beta subunit |
| 98. | 7913 | DEK | DEK oncogene (DNA binding) |
| 99. | 5983 | RFC3 | replication factor C (activator 1) 3, 38 kDa |
| 100. | 84515 | MCM8 | MCM8 minichromosome maintenance deficient 8 (*S. cerevisiae*) |
| 101. | 51053 | GMNN | geminin, DNA replication inhibitor |
| 102. | 1111 | CHEK1 | CHK1 checkpoint homolog (*S. pombe*) |
| 103. | 7443 | VRK1 | vaccinia related kinase 1 |
| 104. | 10376 | K-ALPHA-1 | tubulin, alpha, ubiquitous |
| 105. | 3014 | H2AFX | H2A histone family, member X |
| 106. | 9055 | PRC1 | protein regulator of cytokinesis 1 |
| 107. | 2237 | FEN1 | flap structure-specific endonuclease 1 |
| 108. | 81563 | C1orf21 | chromosome 1 open reading frame 21 |
| 109. | 51192 | CKLF | chemokine-like factor |
| 110. | 1062 | CENPE | centromere protein E, 312 kDa |
| 111. | 11339 | OIP5 | Opa interacting protein 5 |
| 112. | 10615 | SPAG5 | sperm associated antigen 5 |
| 113. | 55646 | LYAR | hypothetical protein FLJ20425 |
| 114. | 55706 | TMEM48 | transmembrane protein 48 |
| 115. | 1058 | CENPA | centromere protein A, 17 kDa |
| 116. | 3070 | HELLS | helicase, lymphoid-specific |
| 117. | 4173 | MCM4 | MCM4 minichromosome maintenance deficient 4 (*S. cerevisiae*) |
| 118. | 23421 | ITGB3BP | integrin beta 3 binding protein (beta3-endonexin) |
| 119. | 9530 | BAG4 | BCL2-associated athanogene 4 |
| 120. | 801 | CALM1 | calmodulin 1 (phosphorylase kinase, delta) |
| 121. | 54069 | C21orf45 | chromosome 21 open reading frame 45 |
| 122. | 283991 | MGC29814 | hypothetical protein MGC29814 |
| 123. | 63979 | FIGNL1 | fidgetin-like 1 |
| 124. | 64105 | FKSG14 | leucine zipper protein FKSG14 |

TABLE IV-continued

| | ENTREZ GENE ID | GENE SYMBOL | GENE DESCRIPTION |
|---|---|---|---|
| 125. | 4172 | MCM3 | MCM3 minichromosome maintenance deficient 3 (*S. cerevisiae*) |
| 126. | 24137 | KIF4A | kinesin family member 4A |
| 127. | 7398 | USP1 | ubiquitin specific protease 1 |
| 128. | 84930 | MASTL | microtubule associated serine/threonine kinase-like |
| 129. | 51512 | GTSE1 | G-2 and S-phase expressed 1 |
| 130. | 4678 | NASP | nuclear autoantigenic sperm protein (histone-binding) |
| 131. | 699 | BUB1 | BUB1 budding uninhibited by benzimidazoles 1 homolog (yeast) |
| 132. | 1719 | DHFR | dihydrofolate reductase |
| 133. | 494143 | LOC494143 | similar to RIKEN cDNA 2510006C20 gene |
| 134. | 55055 | FLJ10036 | Zwilch |
| 135. | 672 | BRCA1 | breast cancer 1, early onset |
| 136. | 64946 | CENPH | centromere protein H |
| 137. | 83461 | CDCA3 | cell division cycle associated 3 |
| 138. | 7465 | WEE1 | WEE1 homolog (*S. pombe*) |
| 139. | 5984 | RFC4 | replication factor C (activator 1) 4, 37 kDa |
| 140. | 64581 | CLEC7A | C-type lectin domain family 7, member A |
| 141. | 1230 | CCR1 | chemokine (C-C motif) receptor 1 |
| 142. | 4175 | MCM6 | MCM6 minichromosome maintenance deficient 6 (MIS5 homolog, *S. pombe*) (*S. cerevisiae*) |
| 143. | 55502 | HES6 | hairy and enhancer of split 6 (*Drosophila*) |
| 144. | 64151 | HCAP-G | chromosome condensation protein G |
| 145. | 11151 | CORO1A | coronin, actin binding protein, 1A |
| 146. | 203068 | TUBB | tubulin, beta polypeptide |
| 147. | 10926 | ASK | activator of S phase kinase |
| 148. | 11073 | TOPBP1 | topoisomerase (DNA) II binding protein 1 |
| 149. | 90417 | C15orf23 | chromosome 15 open reading frame 23 |
| 150. | 9493 | KIF23 | kinesin family member 23 |
| 151. | 387882 | LOC387882 | hypothetical protein |
| 152. | 23234 | DNAJC9 | DnaJ (Hsp40) homolog, subfamily C, member 9 |
| 153. | 2146 | EZH2 | enhancer of zeste homolog 2 (*Drosophila*) |
| 154. | 6627 | SNRPA1 | small nuclear ribonucleoprotein polypeptide A' |
| 155. | 5982 | RFC2 | replication factor C (activator 1) 2, 40 kDa |
| 156. | 51155 | HN1 | hematological and neurological expressed 1 |
| 157. | 10635 | RAD51AP1 | RAD51 associated protein 1 |
| 158. | 91057 | NY-REN-41 | NY-REN-41 antigen |
| 159. | 11168 | PSIP1 | PC4 and SFRS1 interacting protein 1 |
| 160. | 10403 | KNTC2 | kinetochore associated 2 |
| 161. | 4751 | NEK2 | NIMA (never in mitosis gene a)-related kinase 2 |
| 162. | 29028 | ATAD2 | ATPase family, AAA domain containing 2 |
| 163. | 26271 | FBXO5 | F-box protein 5 |
| 164. | 54892 | LUZP5 | leucine zipper protein 5 |
| 165. | 79723 | SUV39H2 | suppressor of variegation 3-9 homolog 2 (*Drosophila*) |
| 166. | 23590 | TPRT | trans-prenyltransferase |
| 167. | 2288 | FKBP4 | FK506 binding protein 4, 59 kDa |
| 168. | 23165 | NUP205 | nucleoporin 205 kDa |
| 169. | 6240 | RRM1 | ribonucleotide reductase M1 polypeptide |
| 170. | 81539 | SLC38A1 | solute carrier family 38, member 1 |
| 171. | 1894 | ECT2 | epithelial cell transforming sequence 2 oncogene |
| 172. | 55872 | PBK | PDZ binding kinase |
| 173. | 55635 | DEPDC1 | DEP domain containing 1 |
| 174. | 11013 | TMSL8 | thymosin-like 8 |
| 175. | 259266 | ASPM | asp (abnormal spindle)-like, microcephaly associated (*Drosophila*) |
| 176. | 10950 | BTG3 | BTG family, member 3 |
| 177. | 56992 | KIF15 | kinesin family member 15 |
| 178. | 29980 | DONSON | downstream neighbor of SON |
| 179. | 5757 | PTMA | prothymosin, alpha (gene sequence 28) |
| 180. | 5932 | RBBP8 | retinoblastoma binding protein 8 |
| 181. | 7903 | ST8SIA4 | ST8 alpha-N-acetyl-neuraminide alpha-2,8-sialyltransferase 4 |
| 182. | 348235 | FAM33A | family with sequence similarity 33, member A |
| 183. | 3182 | HNRPAB | heterogeneous nuclear ribonucleoprotein A/B |
| 184. | 3161 | HMMR | hyaluronan-mediated motility receptor (RHAMM) |
| 185. | 5985 | RFC5 | replication factor C (activator 1) 5, 36.5 kDa |
| 186. | 864 | RUNX3 | runt-related transcription factor 3 |
| 187. | 3930 | LBR | lamin B receptor |
| 188. | 1434 | CSE1L | CSE1 chromosome segregation 1-like (yeast) |
| 189. | 81610 | C20orf129 | chromosome 20 open reading frame 129 |
| 190. | 3146 | HMGB1 | high-mobility group box 1 |
| 191. | 55636 | CHD7 | chromodomain helicase DNA binding protein 7 |
| 192. | 54443 | ANLN | anillin, actin binding protein (scraps homolog, *Drosophila*) |

TABLE IV-continued

| | ENTREZ GENE ID | GENE SYMBOL | GENE DESCRIPTION |
|---|---|---|---|
| 193. | 5698 | PSMB9 | proteasome (prosome, macropain) subunit, beta type, 9 (large multifunctional protease 2) |
| 194. | 7277 | TUBA1 | tubulin, alpha 1 (testis specific) |
| 195. | 64282 | PAPD5 | PAP associated domain containing 5 |
| 196. | 201725 | LOC201725 | hypothetical protein LOC201725 |
| 197. | 7171 | TPM4 | tropomyosin 4 |
| 198. | 3838 | KPNA2 | karyopherin alpha 2 (RAG cohort 1, importin alpha 1) |
| 199. | 116832 | RPL39L | ribosomal protein L39-like |
| 200. | 4602 | MYB | v-myb myeloblastosis viral oncogene homolog (avian) |
| 201. | 54962 | FLJ20516 | timeless-interacting protein |
| 202. | 10541 | ANP32B | acidic (leucine-rich) nuclear phosphoprotein 32 family, member B |
| 203. | 9787 | DLG7 | discs, large homolog 7 (*Drosophila*) |
| 204. | 147138 | EVER2 | epidermodysplasia verruciformis 2 |
| 205. | 157313 | CDCA2 | cell division cycle associated 2 |
| 206. | 11340 | EXOSC8 | exosome component 8 |
| 207. | 2956 | MSH6 | mutS homolog 6 (*E. coli*) |
| 208. | 151246 | SGOL2 | shugoshin-like 2 (*S. pombe*) |
| 209. | 27346 | MAC30 | hypothetical protein MAC30 |
| 210. | 5873 | RAB27A | RAB27A, member RAS oncogene family |
| 211. | 79596 | C13orf7 | chromosome 13 open reading frame 7 |
| 212. | 10051 | SMC4L1 | SMC4 structural maintenance of chromosomes 4-like 1 (yeast) |
| 213. | 3336 | HSPE1 | heat shock 10 kDa protein 1 (chaperonin 10) |
| 214. | 6432 | SFRS7 | splicing factor, arginine/serine-rich 7, 35 kDa |
| 215. | 8819 | SAP30 | sin3-associated polypeptide, 30 kDa |
| 216. | 54801 | FAM29A | family with sequence similarity 29, member A |
| 217. | 1123 | CHN1 | chimerin (chimaerin) 1 |
| 218. | 694 | BTG1 | B-cell translocation gene 1, anti-proliferative |
| 219. | 153222 | LOC153222 | adult retina protein |
| 220. | 3669 | ISG20 | interferon stimulated exonuclease gene 20 kDa |
| 221. | 151556 | GPR155 | G protein-coupled receptor 155 |
| 222. | 6591 | SNAI2 | snail homolog 2 (*Drosophila*) |
| 223. | 5920 | RARRES3 | retinoic acid receptor responder (tazarotene induced) 3 |
| 224. | 400172 | LOC400172 | similar to KIAA1641 protein; melanoma-associated antigen; CLL-associated antigen KW-1 |
| 225. | 55281 | FLJ11000 | hypothetical protein FLJ11000 |
| 226. | 9783 | RIMS3 | regulating synaptic membrane exocytosis 3 |
| 227. | 6480 | ST6GAL1 | ST6 beta-galactosamide alpha-2,6-sialyltranferase 1 |
| 228. | 390 | RND3 | Rho family GTPase 3 |
| 229. | 10765 | JARID1B | Jumonji, AT rich interactive domain 1B (RBP2-like) |
| 230. | 154091 | SLC2A12 | solute carrier family 2 (facilitated glucose transporter), member 12 |
| 231. | 54981 | C9orf95 | chromosome 9 open reading frame 95 |
| 232. | 1663 | DDX11 | DEAD/H (Asp-Glu-Ala-Asp/His) box polypeptide 11 (CHL1-like helicase homolog, *S. cerevisiae*) |
| 233. | 54800 | DRE1 | DRE1 protein |
| 234. | 57515 | TDE2 | tumor differentially expressed 2 |
| 235. | 83719 | YPEL3 | yippee-like 3 (*Drosophila*) |
| 236. | 5269 | SERPINB6 | serine (or cysteine) proteinase inhibitor, clade B (ovalbumin), member 6 |
| 237. | 30061 | SLC40A1 | solute carrier family 40 (iron-regulated transporter), member 1 |
| 238. | 5660 | PSAP | prosaposin (variant Gaucher disease and variant metachromatic leukodystrophy) |
| 239. | 51646 | YPEL5 | yippee-like 5 (*Drosophila*) |
| 240. | 145788 | FLJ27352 | hypothetical LOC145788 |
| 241. | 81030 | ZBP1 | Z-DNA binding protein 1 |
| 242. | 57035 | C1orf63 | chromosome 1 open reading frame 63 |
| 243. | 9863 | MAGI2 | membrane associated guanylate kinase, WW and PDZ domain containing 2 |
| 244. | 9855 | FARP2 | FERM, RhoGEF and pleckstrin domain protein 2 |
| 245. | 57612 | KIAA1466 | KIAA1466 gene |
| 246. | 56243 | KIAA1217 | KIAA1217 |
| 247. | 8365 | HIST1H4H | histone 1, H4h |
| 248. | 440081 | DDX12 | DEAD/H (Asp-Glu-Ala-Asp/His) box polypeptide 12 (CHL1-like helicase homolog, *S. cerevisiae*) |
| 249. | 83937 | RASSF4 | Ras association (RalGDS/AF-6) domain family 4 |
| 250. | 56204 | FLJ10980 | hypothetical protein FLJ10980 |
| 251. | 22932 | POMZP3 | POM (POM121 homolog, rat) and ZP3 fusion |
| 252. | 10628 | TXNIP | thioredoxin interacting protein |
| 253. | 6720 | SREBF1 | sterol regulatory element binding transcription factor 1 |
| 254. | 1508 | CTSB | cathepsin B |
| 255. | 84513 | HTPAP | HTPAP protein |

TABLE IV-continued

| ENTREZ GENE ID | GENE SYMBOL | GENE DESCRIPTION |
|---|---|---|
| 256. 85352 | KIAA1644 | KIAA1644 protein |
| 257. 9388 | LIPG | lipase, endothelial |
| 258. 5163 | PDK1 | pyruvate dehydrogenase kinase, isoenzyme 1 |
| 259. 23446 | CDW92 | CDW92 antigen |
| 260. 10156 | RASA4 | RAS p21 protein activator 4 |
| 261. 23766 | GABARAPL3 | GABA(A) receptors associated protein like 3 |
| 262. 56904 | SH3GLB2 | SH3-domain GRB2-like endophilin B2 |
| 263. 6609 | SMPD1 | sphingomyelin phosphodiesterase 1, acid lysosomal (acid sphingomyelinase) |
| 264. 23259 | DDHD2 | DDHD domain containing 2 |
| 265. 23092 | ARHGAP26 | Rho GTPase activating protein 26 |
| 266. 27250 | PDCD4 | programmed cell death 4 (neoplastic transformation inhibitor) |
| 267. 3983 | ABLIM1 | actin binding LIM protein 1 |
| 268. 23461 | ABCA5 | ATP-binding cassette, sub-family A (ABC1), member 5 |
| 269. 4094 | MAF | v-maf musculoaponeurotic fibrosarcoma oncogene homolog (avian) |
| 270. 23646 | PLD3 | phospholipase D family, member 3 |
| 271. 51566 | ARMCX3 | armadillo repeat containing, X-linked 3 |
| 272. 58476 | TP53INP2 | tumor protein p53 inducible nuclear protein 2 |
| 273. 29994 | BAZ2B | bromodomain adjacent to zinc finger domain, 2B |
| 274. 283131 | TncRNA | trophoblast-derived noncoding RNA |
| 275. 4189 | DNAJB9 | DnaJ (Hsp40) homolog, subfamily B, member 9 |
| 276. 9123 | SLC16A3 | solute carrier family 16 (monocarboxylic acid transporters), member 3 |
| 277. 8473 | OGT | O-linked N-acetylglucosamine (GlcNAc) transferase (UDP-N-acetylglucosamine:polypeptide-N-acetylglucosaminyl transferase) |
| 278. 65018 | PINK1 | PTEN induced putative kinase 1 |
| 279. 23512 | SUZ12 | suppressor of zeste 12 homolog (Drosophila) |
| 280. 81611 | ANP32E | acidic (leucine-rich) nuclear phosphoprotein 32 family, member E |
| 281. 5880 | RAC2 | ras-related C3 botulinum toxin substrate 2 (rho family, small GTP binding protein Rac2) |
| 282. 6941 | TCF19 | transcription factor 19 (SC1) |
| 283. 8836 | GGH | gamma-glutamyl hydrolase (conjugase, folylpolygammaglutamyl hydrolase) |
| 284. 9830 | TRIM14 | tripartite motif-containing 14 |
| 285. 55026 | FLJ20716 | hypothetical protein FLJ20716 |
| 286. 84057 | GAJ | GAJ protein |
| 287. 6510 | SLC1A5 | solute carrier family 1 (neutral amino acid transporter), member 5 |
| 288. 84969 | C20orf100 | chromosome 20 open reading frame 100 |
| 289. 81620 | CDT1 | DNA replication factor |
| 290. 113115 | FAM54A | family with sequence similarity 54, member A |
| 291. 3159 | HMGA1 | high mobility group AT-hook 1 |
| 292. 3251 | HPRT1 | hypoxanthine phosphoribosyltransferase 1 (Lesch-Nyhan syndrome) |
| 293. 5214 | PFKP | phosphofructokinase, platelet |
| 294. 2171 | FABP5 | fatty acid binding protein 5 (psoriasis-associated) |
| 295. 57082 | CASC5 | cancer susceptibility candidate 5 |
| 296. 5889 | RAD51C | RAD51 homolog C (S. cerevisiae) |
| 297. 6628 | SNRPB | small nuclear ribonucleoprotein polypeptides B and B1 |
| 298. 134111 | FLJ25076 | similar to CG4502-PA |
| 299. 397 | ARHGDIB | Rho GDP dissociation inhibitor (GDI) beta |
| 300. 129401 | NUP35 | nucleoporin 35 kDa |
| 301. 6632 | SNRPD1 | small nuclear ribonucleoprotein D1 polypeptide 16 kDa |
| 302. 10212 | DDX39 | DEAD (Asp-Glu-Ala-Asp) box polypeptide 39 |
| 303. 6472 | SHMT2 | serine hydroxymethyltransferase 2 (mitochondrial) |
| 304. 55536 | CDCA7L | cell division cycle associated 7-like |
| 305. 64116 | SLC39A8 | solute carrier family 39 (zinc transporter), member 8 |
| 306. 79902 | PCNT1 | pericentrin 1 |
| 307. 7371 | UCK2 | uridine-cytidine kinase 2 |
| 308. 11332 | BACH | brain acyl-CoA hydrolase |
| 309. 3320 | HSPCA | heat shock 90 kDa protein 1, alpha |
| 310. 1019 | CDK4 | cyclin-dependent kinase 4 |
| 311. 10383 | TUBB2 | tubulin, beta, 2 |
| 312. 8243 | SMC1L1 | SMC1 structural maintenance of chromosomes 1-like (yeast) |
| 313. 1786 | DNMT1 | DNA (cytosine-5-)-methyltransferase 1 |
| 314. 22929 | SEPHS1 | selenophosphate synthetase 1 |
| 315. 10492 | SYNCRIP | synaptotagmin binding, cytoplasmic RNA interacting protein |

TABLE IV-continued

| | ENTREZ GENE ID | GENE SYMBOL | GENE DESCRIPTION |
|---|---|---|---|
| 316. | 26051 | PPP1R16B | protein phosphatase 1, regulatory (inhibitor) subunit 16B |
| 317. | 5168 | ENPP2 | ectonucleotide pyrophosphatase/phosphodiesterase 2 (autotaxin) |
| 318. | 51144 | HSD17B12 | hydroxysteroid (17-beta) dehydrogenase 12 |
| 319. | 9446 | GSTO1 | glutathione S-transferase omega 1 |
| 320. | 51002 | CGI-121 | CGI-121 protein |
| 321. | 51377 | UCHL5 | ubiquitin carboxyl-terminal hydrolase L5 |
| 322. | 10606 | PAICS | phosphoribosylaminoimidazole carboxylase, phosphoribosylaminoimidazole succinocarboxamide synthetase |
| 323. | 6929 | TCF3 | transcription factor 3 (E2A immunoglobulin enhancer binding factors E12/E47) |
| 324. | 262 | AMD1 | adenosylmethionine decarboxylase 1 |
| 325. | 3676 | ITGA4 | integrin, alpha 4 (antigen CD49D, alpha 4 subunit of VLA-4 receptor) |
| 326. | 39 | ACAT2 | acetyl-Coenzyme A acetyltransferase 2 (acetoacetyl Coenzyme A thiolase) |
| 327. | 23526 | HA-1 | minor histocompatibility antigen HA-1 |
| 328. | 79023 | NUP37 | nucleoporin 37 kDa |
| 329. | 6119 | RPA3 | replication protein A3, 14 kDa |
| 330. | 6657 | SOX2 | SRY (sex determining region Y)-box 2 |
| 331. | 27101 | CACYBP | calcyclin binding protein |
| 332. | 55752 | 11-Sep | septin 11 |
| 333. | 79017 | C7orf24 | chromosome 7 open reading frame 24 |
| 334. | 10808 | HSPH1 | heat shock 105 kDa/110 kDa protein 1 |
| 335. | 11051 | NUDT21 | nudix (nucleoside diphosphate linked moiety X)-type motif 21 |
| 336. | 5631 | PRPS1 | phosphoribosyl pyrophosphate synthetase 1 |
| 337. | 55352 | HSA272196 | hypothetical protein, clone 2746033 |
| 338. | 8727 | CTNNAL1 | catenin (cadherin-associated protein), alpha-like 1 |
| 339. | 26586 | CKAP2 | cytoskeleton associated protein 2 |
| 340. | 2271 | FH | fumarate hydratase |
| 341. | 23246 | BOP1 | block of proliferation 1 |
| 342. | 5696 | PSMB8 | proteasome (prosome, macropain) subunit, beta type, 8 (large multifunctional protease 7) |
| 343. | 25804 | LSM4 | LSM4 homolog, U6 small nuclear RNA associated (*S. cerevisiae*) |
| 344. | 5557 | PRIM1 | primase, polypeptide 1, 49 kDa |
| 345. | 4436 | MSH2 | mutS homolog 2, colon cancer, nonpolyposis type 1 (*E. coli*) |
| 346. | 5885 | RAD21 | RAD21 homolog (*S. pombe*) |
| 347. | 22948 | CCT5 | chaperonin containing TCP1, subunit 5 (epsilon) |
| 348. | 9126 | CSPG6 | chondroitin sulfate proteoglycan 6 (bamacan) |
| 349. | 9184 | BUB3 | BUB3 budding uninhibited by benzimidazoles 3 homolog (yeast) |
| 350. | 4869 | NPM1 | nucleophosmin (nucleolar phosphoprotein B23, numatrin) |
| 351. | 3150 | HMGN1 | high-mobility group nucleosome binding domain 1 |
| 352. | 10409 | BASP1 | brain abundant, membrane attached signal protein 1 |
| 353. | 4200 | ME2 | malic enzyme 2, NAD(+)-dependent, mitochondrial |
| 354. | 169270 | ZNF596 | zinc finger protein 596 |
| 355. | 3939 | LDHA | lactate dehydrogenase A |
| 356. | 961 | CD47 | CD47 antigen (Rh-related antigen, integrin-associated signal transducer) |
| 357. | 9368 | SLC9A3R1 | solute carrier family 9 (sodium/hydrogen exchanger), isoform 3 regulator 1 |
| 358. | 7086 | TKT | transketolase (Wernicke-Korsakoff syndrome) |
| 359. | 10801 | 9-Sep | septin 9 |
| 360. | 10785 | WDR4 | WD repeat domain 4 |
| 361. | 3033 | HADHSC | L-3-hydroxyacyl-Coenzyme A dehydrogenase, short chain |
| 362. | 8833 | GMPS | guanine monphosphate synthetase |
| 363. | 27316 | RBMX | RNA binding motif protein, X-linked |
| 364. | 5725 | PTBP1 | polypyrimidine tract binding protein 1 |
| 365. | 10128 | LRPPRC | leucine-rich PPR-motif containing |
| 366. | 84250 | ANKRD32 | ankyrin repeat domain 32 |
| 367. | 5358 | PLS3 | plastin 3 (T isoform) |
| 368. | 4673 | NAP1L1 | nucleosome assembly protein 1-like 1 |
| 369. | 3149 | HMGB3 | high-mobility group box 3 |
| 370. | 2289 | FKBP5 | FK506 binding protein 5 |
| 371. | 22856 | CHSY1 | carbohydrate (chondroitin) synthase 1 |
| 372. | 6566 | SLC16A1 | solute carrier family 16 (monocarboxylic acid transporters), member 1 |
| 373. | 54149 | C21orf91 | chromosome 21 open reading frame 91 |
| 374. | 54517 | FLJ20485 | hypothetical protein FLJ20485 |

TABLE IV-continued

| | ENTREZ GENE ID | GENE SYMBOL | GENE DESCRIPTION |
|---|---|---|---|
| 375. | 8514 | KCNAB2 | potassium voltage-gated channel, shaker-related subfamily, beta member 2 |
| 376. | 119 | ADD2 | adducin 2 (beta) |
| 377. | 1407 | CRY1 | cryptochrome 1 (photolyase-like) |
| 378. | 204 | AK2 | adenylate kinase 2 |
| 379. | 467 | ATF3 | activating transcription factor 3 |
| 380. | 64778 | FNDC3B | fibronectin type III domain containing 3B |
| 381. | 347733 | RP11-506K6.1 | tubulin, beta polypeptide paralog |
| 382. | 9604 | RNF14 | ring finger protein 14 |
| 383. | 7832 | BTG2 | BTG family, member 2 |
| 384. | 120196 | MGC34830 | hypothetical protein MGC34830 |
| 385. | 9910 | RABGAP1L | RAB GTPase activating protein 1-like |
| 386. | 55876 | GSDML | gasdermin-like |
| 387. | 1524 | CX3CR1 | chemokine (C—X3—C motif) receptor 1 |
| 388. | 23015 | GM88 | 88-kDa golgi protein |
| 389. | 1604 | DAF | decay accelerating factor for complement (CD55, Cromer blood group system) |
| 390. | 114793 | FMNL2 | formin-like 2 |
| 391. | 50640 | IPLA2(GAMMA) | intracellular membrane-associated calcium-independent phospholipase A2 gamma |
| 392. | 222166 | EIIs1 | hypothetical protein EIIs1 |
| 393. | 10140 | TOB1 | transducer of ERBB2, 1 |
| 394. | 1647 | GADD45A | growth arrest and DNA-damage-inducible, alpha |
| 395. | 25840 | DKFZP586A0522 | DKFZP586A0522 protein |
| 396. | 150759 | LOC150759 | hypothetical protein LOC150759 |
| 397. | 6448 | SGSH | N-sulfoglucosamine sulfohydrolase (sulfamidase) |
| 398. | 85236 | HIST1H2BK | histone 1, H2bk |
| 399. | 9728 | KIAA0256 | KIAA0256 gene product |
| 400. | 3727 | JUND | jun D proto-oncogene |
| 401. | 54741 | LEPROT | leptin receptor overlapping transcript |
| 402. | 5973 | RENBP | renin binding protein |
| 403. | 84897 | TBRG1 | transforming growth factor beta regulator 1 |
| 404. | 92370 | ACPL2 | acid phosphatase-like 2 |
| 405. | 23208 | SYT11 | synaptotagmin XI |
| 406. | 375593 | TRIM50B | tripartite motif-containing 50B |
| 407. | 94241 | TP53INP1 | tumor protein p53 inducible nuclear protein 1 |
| 408. | 1612 | DAPK1 | death-associated protein kinase 1 |
| 409. | 144203 | OVOS2 | ovostatin 2 |
| 410. | 3915 | LAMC1 | laminin, gamma 1 (formerly LAMB2) |
| 411. | 115701 | ALPK2 | alpha-kinase 2 |
| 412. | 1203 | CLN5 | ceroid-lipofuscinosis, neuronal 5 |
| 413. | 51363 | GALNAC4S-6ST | B cell RAG associated protein |
| 414. | 387263 | C6orf120 | chromosome 6 open reading frame 120 |
| 415. | 2824 | GPM6B | glycoprotein M6B |
| 416. | 8516 | ITGA8 | integrin, alpha 8 |
| 417. | 57730 | KIAA1641 | KIAA1641 |
| 418. | 10370 | CITED2 | Cbp/p300-interacting transactivator, with Glu/Asp-rich carboxy-terminal domain, 2 |
| 419. | 1611 | DAP | death-associated protein |
| 420. | 388677 | NOTCH2NL | Notch homolog 2 (Drosophila) N-terminal like |
| 421. | 132720 | FLJ39370 | hypothetical protein FLJ39370 |
| 422. | 29005 | PRO1073 | PRO1073 protein |
| 423. | 1030 | CDKN2B | cyclin-dependent kinase inhibitor 2B (p15, inhibits CDK4) |
| 424. | 23336 | DMN | desmuslin |
| 425. | 23643 | LY96 | lymphocyte antigen 96 |
| 426. | 4779 | NFE2L1 | nuclear factor (erythroid-derived 2)-like 1 |
| 427. | 7286 | TUFT1 | tuftelin 1 |
| 428. | 1200 | TPP1 | tripeptidyl peptidase I |
| 429. | 27344 | PCSK1N | proprotein convertase subtilisin/kexin type 1 inhibitor |
| 430. | 9473 | C1orf38 | chromosome 1 open reading frame 38 |
| 431. | 401152 | LOC401152 | HCV F-transactivated protein 1 |
| 432. | 5360 | PLTP | phospholipid transfer protein |
| 433. | 7846 | TUBA3 | tubulin, alpha 3 |
| 434. | 9240 | PNMA1 | paraneoplastic antigen MA1 |
| 435. | 81631 | MAP1LC3B | microtubule-associated protein 1 light chain 3 beta |
| 436. | 112770 | C1orf85 | chromosome 1 open reading frame 85 |
| 437. | 3998 | LMAN1 | lectin, mannose-binding, 1 |
| 438. | 8987 | GENX-3414 | genethonin 1 |
| 439. | 84218 | TBC1D3 | TBC1 domain family, member 3 |
| 440. | 51237 | PACAP | proapoptotic caspase adaptor protein |
| 441. | 55818 | JMJD1A | jumonji domain containing 1A |
| 442. | 11057 | ABHD2 | abhydrolase domain containing 2 |
| 443. | 2180 | ACSL1 | acyl-CoA synthetase long-chain family member 1 |
| 444. | 10525 | HYOU1 | hypoxia up-regulated 1 |
| 445. | 114915 | TIGA1 | TIGA1 |
| 446. | 55251 | C20orf36 | chromosome 20 open reading frame 36 |

TABLE IV-continued

| | ENTREZ GENE ID | GENE SYMBOL | GENE DESCRIPTION |
|---|---|---|---|
| 447. | 598 | BCL2L1 | BCL2-like 1 |
| 448. | 51111 | SUV420H1 | suppressor of variegation 4-20 homolog 1 (*Drosophila*) |
| 449. | 64065 | PERP | PERP, TP53 apoptosis effector |
| 450. | 2037 | EPB41L2 | erythrocyte membrane protein band 4.1-like 2 |
| 451. | 89796 | NAV1 | neuron navigator 1 |
| 452. | 9341 | VAMP3 | vesicle-associated membrane protein 3 (cellubrevin) |
| 453. | 1465 | CSRP1 | cysteine and glycine-rich protein 1 |
| 454. | 60492 | MDS025 | hypothetical protein MDS025 |
| 455. | 339448 | LOC339448 | hypothetical protein LOC339448 |
| 456. | 6513 | SLC2A1 | solute carrier family 2 (facilitated glucose transporter), member 1 |
| 457. | 3995 | FADS3 | fatty acid desaturase 3 |
| 458. | 155038 | GIMAP8 | GTPase, IMAP family member 8 |
| 459. | 90634 | CG018 | hypothetical gene CG018 |
| 460. | 55573 | H41 | hypothetical protein H41 |
| 461. | 7514 | XPO1 | exportin 1 (CRM1 homolog, yeast) |
| 462. | 196527 | TMEM16F | transmembrane protein 16F |
| 463. | 5471 | PPAT | phosphoribosyl pyrophosphate amidotransferase |
| 464. | 22823 | MTF2 | metal response element binding transcription factor 2 |
| 465. | 10856 | RUVBL2 | RuvB-like 2 (*E. coli*) |
| 466. | 6713 | SQLE | squalene epoxidase |
| 467. | 8407 | TAGLN2 | transgelin 2 |
| 468. | 26135 | PAI-RBP1 | PAI-1 mRNA binding protein |
| 469. | 84247 | LDOC1L | leucine zipper, down-regulated in cancer 1-like |
| 470. | 9201 | DCAMKL1 | doublecortin and CaM kinase-like 1 |
| 471. | 388403 | YPEL2 | yippee-like 2 (*Drosophila*) |
| 472. | 255631 | COL24A1 | collagen, type XXIV, alpha 1 |
| 473. | 8440 | NCK2 | NCK adaptor protein 2 |
| 474. | 81790 | RNF170 | ring finger protein 170 |
| 475. | 9706 | ULK2 | unc-51-like kinase 2 (*C. elegans*) |
| 476. | 4092 | SMAD7 | SMAD, mothers against DPP homolog 7 (*Drosophila*) |
| 477. | 51184 | MGC14560 | protein x 0004 |
| 478. | 7334 | UBE2N | ubiquitin-conjugating enzyme E2N (UBC13 homolog, yeast) |
| 479. | 84955 | NUDCD1 | NudC domain containing 1 |
| 480. | 5684 | PSMA3 | proteasome (prosome, macropain) subunit, alpha type, 3 |
| 481. | 51465 | UBE2J1 | ubiquitin-conjugating enzyme E2, J1 (UBC6 homolog, yeast) |
| 482. | 286319 | TUSC1 | tumor suppressor candidate 1 |
| 483. | 26207 | PITPNC1 | phosphatidylinositol transfer protein, cytoplasmic 1 |
| 484. | 51303 | FKBP11 | FK506 binding protein 11, 19 kDa |
| 485. | 9139 | CBFA2T2 | core-binding factor, runt domain, alpha subunit 2; translocated to, 2 |
| 486. | 57714 | KIAA1618 | KIAA1618 |
| 487. | 94240 | EPSTI1 | epithelial stromal interaction 1 (breast) |
| 488. | 659 | BMPR2 | bone morphogenetic protein receptor, type II (serine/threonine kinase) |
| 489. | 934 | CD24 | CD24 antigen (small cell lung carcinoma cluster 4 antigen) |
| 490. | 9532 | BAG2 | BCL2-associated anthanogene 2 |
| 491. | 23331 | KIAA1043 | KIAA1043 protein |
| 492. | 10675 | CSPG5 | chondroitin sulfate proteoglycan 5 (neuroglycan C) |
| 493. | 1102 | RCBTB2 | regulator of chromosome condensation (RCC1) and BTB (POZ) domain containing protein 2 |
| 494. | 2119 | ETV5 | ets variant gene 5 (ets-related molecule) |
| 495. | 255488 | IBRDC2 | IBR domain containing 2 |
| 496. | 55076 | TMEM45A | transmembrane protein 45A |
| 497. | 8364 | HIST1H4C | histone 1, H4c |
| 498. | 3725 | JUN | v-jun sarcoma virus 17 oncogene homolog (avian) |
| 499. | 384 | ARG2 | arginase, type II |
| 500. | 10129 | 13CDNA73 | hypothetical protein CG003 |
| 501. | 1960 | EGR3 | early growth response 3 |
| 502. | 27122 | DKK3 | dickkopf homolog 3 (*Xenopus laevis*) |
| 503. | 11178 | LZTS1 | leucine zipper, putative tumor suppressor 1 |
| 504. | 143888 | KDELC2 | KDEL (Lys-Asp-Glu-Leu) containing 2 |
| 505. | 1601 | DAB2 | disabled homolog 2, mitogen-responsive phosphoprotein (*Drosophila*) |
| 506. | 6542 | SLC7A2 | solute carrier family 7 (cationic amino acid transporter, y+ system), member 2 |
| 507. | 477 | ATP1A2 | ATPase, Na+/K+ transporting, alpha 2 (+) polypeptide |
| 508. | 90161 | HS6ST2 | heparan sulfate 6-O-sulfotransferase 2 |
| 509. | 81031 | SLC2A10 | solute carrier family 2 (facilitated glucose transporter), member 10 |

TABLE IV-continued

| | ENTREZ GENE ID | GENE SYMBOL | GENE DESCRIPTION |
|---|---|---|---|
| 510. | 56675 | NRIP3 | nuclear receptor interacting protein 3 |
| 511. | 1958 | EGR1 | early growth response 1 |
| 512. | 3714 | JAG2 | jagged 2 |
| 513. | 3897 | L1CAM | L1 cell adhesion molecule |
| 514. | 1488 | CTBP2 | C-terminal binding protein 2 |
| 515. | 145173 | B3GTL | beta 3-glycosyltransferase-like |
| 516. | 112399 | EGLN3 | egl nine homolog 3 (C. elegans) |
| 517. | 22871 | NLGN1 | neuroligin 1 |
| 518. | 8804 | CREG1 | cellular repressor of E1A-stimulated genes 1 |
| 519. | 401081 | FLJ22763 | hypothetical gene supported by AK026416 |
| 520. | 25924 | MYRIP | myosin VIIA and Rab interacting protein |
| 521. | 91694 | FLJ23749 | hypothetical protein FLJ23749 |
| 522. | 56155 | TEX14 | testis expressed sequence 14 |
| 523. | 1349 | COX7B | cytochrome c oxidase subunit VIIb |
| 524. | 3695 | ITGB7 | integrin, beta 7 |
| 525. | 1164 | CKS2 | CDC28 protein kinase regulatory subunit 2 |
| 526. | 56919 | DHX33 | DEAH (Asp-Glu-Ala-His) box polypeptide 33 |
| 527. | 3276 | HRMT1L2 | HMT1 hnRNP methyltransferase-like 2 (S. cerevisiae) |
| 528. | 116151 | C20orf108 | chromosome 20 open reading frame 108 |
| 529. | 25758 | G2 | G2 protein |
| 530. | 25861 | DFNB31 | deafness, autosomal recessive 31 |
| 531. | 9666 | DZIP3 | zinc finger DAZ interacting protein 3 |
| 532. | 1486 | CTBS | chitobiase, di-N-acetyl- |
| 533. | 3123 | HLA-DRB1 | major histocompatibility complex, class II, DR beta 1 |
| 534. | 317649 | EIF4E3 | eukaryotic translation initiation factor 4E member |
| 535. | 50854 | C6orf48 | chromosome 6 open reading frame 48 |
| 536. | 401024 | FLJ44048 | FLJ44048 protein |
| 537. | 114327 | EFHC1 | EF-hand domain (C-terminal) containing 1 |
| 538. | 8334 | HIST1H2AC | histone 1, H2ac |
| 539. | 284214 | LOC284214 | hypothetical protein LOC284214 |
| 540. | 10379 | ISGF3G | interferon-stimulated transcription factor 3, gamma 48 kDa |
| 541. | 113177 | C19orf36 | chromosome 19 open reading frame 36 |
| 542. | 56951 | C5orf15 | chromosome 5 open reading frame 15 |
| 543. | 285362 | SUMF1 | sulfatase modifying factor 1 |
| 544. | 3490 | IGFBP7 | insulin-like growth factor binding protein 7 |
| 545. | 1186 | CLCN7 | chloride channel 7 |
| 546. | 582 | BBS1 | Bardet-Biedl syndrome 1 |
| 547. | 339456 | LOC339456 | hypothetical protein LOC339456 |
| 548. | 26115 | DKFZP564D166 | putative ankyrin-repeat containing protein |
| 549. | 9895 | KIAA0329 | KIAA0329 |
| 550. | 1040 | CDS1 | CDP-diacylglycerol synthase (phosphatidate cytidylyltransferase) 1 |
| 551. | 51496 | HSPC129 | hypothetical protein HSPC129 |
| 552. | 1039 | CDR2 | cerebellar degeneration-related protein 2, 62 kDa |
| 553. | 130589 | GALM | galactose mutarotase (aldose 1-epimerase) |
| 554. | 3937 | LCP2 | lymphocyte cytosolic protein 2 (SH2 domain containing leukocyte protein of 76 kDa) |
| 555. | 3535 | IGL@ | immunoglobulin lambda locus |
| 556. | 1396 | CRIP1 | cysteine-rich protein 1 (intestinal) |
| 557. | 4291 | MLF1 | myeloid leukemia factor 1 |
| 558. | 9972 | NUP153 | nucleoporin 153 kDa |
| 559. | 10459 | MAD2L2 | MAD2 mitotic arrest deficient-like 2 (yeast) |
| 560. | 483 | ATP1B3 | ATPase, Na+/K+ transporting, beta 3 polypeptide |
| 561. | 8165 | AKAP1 | A kinase (PRKA) anchor protein 1 |
| 562. | 29097 | CNIH4 | cornichon homolog 4 (Drosophila) |
| 563. | 7037 | TFRC | transferrin receptor (p90, CD71) |
| 564. | 509 | ATP5C1 | ATP synthase, H+ transporting, mitochondrial F1 complex, gamma polypeptide 1 |
| 565. | 10682 | EBP | emopamil binding protein (sterol isomerase) |
| 566. | 56172 | ANKH | ankylosis, progressive homolog (mouse) |
| 567. | 100 | ADA | adenosine deaminase |
| 568. | 2821 | GPI | glucose phosphate isomerase |
| 569. | 54927 | CHCHD3 | coiled-coil-helix-coiled-coil-helix domain containing 3 |
| 570. | 58478 | MASA | E-1 enzyme |
| 571. | 292 | SLC25A5 | solute carrier family 25 (mitochondrial carrier; adenine nucleotide translocator), member 5 |
| 572. | 51096 | WDR50 | WD repeat domain 50 |
| 573. | 79053 | ALG8 | asparagine-linked glycosylation 8 homolog (yeast, alpha-1,3-glucosyltransferase) |
| 574. | 84300 | C6orf125 | chromosome 6 open reading frame 125 |
| 575. | 253461 | ZBTB38 | zinc finger and BTB domain containing 38 |
| 576. | 29080 | HSPC128 | HSPC128 protein |
| 577. | 1622 | DBI | diazepam binding inhibitor (GABA receptor modulator, acyl-Coenzyme A binding protein) |
| 578. | 2029 | ENSA | endosulfine alpha |
| 579. | 6404 | SELPLG | selectin P ligand |

TABLE IV-continued

| | ENTREZ GENE ID | GENE SYMBOL | GENE DESCRIPTION |
|---|---|---|---|
| 580. | 7295 | TXN | thioredoxin |
| 581. | 10539 | TXNL2 | thioredoxin-like 2 |
| 582. | 3422 | IDI1 | isopentenyl-diphosphate delta isomerase |
| 583. | 1964 | EIF1AX | eukaryotic translation initiation factor 1A, X-linked |
| 584. | 11191 | PTENP1 | phosphatase and tensin homolog (mutated in multiple advanced cancers 1), pseudogene 1 |
| 585. | 80853 | KIAA1718 | KIAA1718 protein |
| 586. | 7096 | TLR1 | toll-like receptor 1 |
| 587. | 440270 | LOC440270 | golgin-67 |
| 588. | 8879 | SGPL1 | sphingosine-1-phosphate lyase 1 |
| 589. | 493812 | HCG11 | HLA complex group 11 |
| 590. | 257103 | C21orf86 | chromosome 21 open reading frame 86 |
| 591. | 55615 | PRR5 | proline rich protein 5 |
| 592. | 7905 | C5orf18 | chromosome 5 open reading frame 18 |
| 593. | 64062 | C13orf10 | chromosome 13 open reading frame 10 |
| 594. | 10133 | OPTN | optineurin |
| 595. | 10116 | FEM1B | fem-1 homolog b (*C. elegans*) |
| 596. | 79027 | ZNF655 | zinc finger protein 655 |
| 597. | 79717 | FLJ11838 | hypothetical protein FLJ11838 |
| 598. | 10397 | NDRG1 | N-myc downstream regulated gene 1 |
| 599. | 3338 | DNAJC4 | DnaJ (Hsp40) homolog, subfamily C, member 4 |

TABLE V

| | ENTREZ GENE ID | GENE SYMBOL | GENE DESCRIPTION |
|---|---|---|---|
| 1. | 934 | CD24 | CD24 antigen (small cell lung carcinoma cluster 4 antigen) |
| 2. | 9532 | BAG2 | BCL2-associated athanogene 2 |
| 3. | 23331 | KIAA1043 | KIAA1043 protein |
| 4. | 10675 | CSPG5 | chondroitin sulfate proteoglycan 5 (neuroglycan C) |
| 5. | 1102 | RCBTB2 | regulator of chromosome condensation (RCC1) and BTB (POZ) domain containing protein 2 |
| 6. | 2119 | ETV5 | ets variant gene 5 (ets-related molecule) |
| 7. | 255488 | IBRDC2 | IBR domain containing 2 |
| 8. | 55076 | TMEM45A | transmembrane protein 45A |
| 9. | 8364 | HIST1H4C | histone 1, H4c |
| 10. | 3725 | JUN | v-jun sarcoma virus 17 oncogene homolog (avian) |
| 11. | 384 | ARG2 | arginase, type II |
| 12. | 10129 | 13CDNA73 | hypothetical protein CG003 |
| 13. | 401081 | FLJ22763 | hypothetical gene supported by AK026416 |
| 14. | 25924 | MYRIP | myosin VIIA and Rab interacting protein |
| 15. | 91694 | FLJ23749 | hypothetical protein FLJ23749 |
| 16. | 56155 | TEX14 | testis expressed sequence 14 |
| 17. | 1349 | COX7B | cytochrome c oxidase subunit VIIb |
| 18. | 1164 | CKS2 | CDC28 protein kinase regulatory subunit 2 |
| 19. | 56919 | DHX33 | DEAH (Asp-Glu-Ala-His) box polypeptide 33 |
| 20. | 3276 | HRMT1L2 | HMT1 hnRNP methyltransferase-like 2 (*S. cerevisiae*) |
| 21. | 3695 | ITGB7 | integrin, beta 7 |
| 22. | 51496 | HSPC129 | hypothetical protein HSPC129 |
| 23. | 1039 | CDR2 | cerebellar degeneration-related protein 2, 62 kDa |
| 24. | 130589 | GALM | galactose mutarotase (aldose 1-epimerase) |
| 25. | 3937 | LCP2 | lymphocyte cytosolic protein 2 (SH2 domain containing leukocyte protein of 76 kDa) |
| 26. | 3535 | IGL@ | immunoglobulin lambda locus |
| 27. | 1396 | CRIP1 | cysteine-rich protein 1 (intestinal) |
| 28. | 4291 | MLF1 | myeloid leukemia factor 1 |
| 29. | 9972 | NUP153 | nucleoporin 153 kDa |
| 30. | 10459 | MAD2L2 | MAD2 mitotic arrest deficient-like 2 (yeast) |
| 31. | 483 | ATP1B3 | ATPase, Na+/K+ transporting, beta 3 polypeptide |
| 32. | 8165 | AKAP1 | A kinase (PRKA) anchor protein 1 |
| 33. | 29097 | CNIH4 | cornichon homolog 4 (*Drosophila*) |
| 34. | 7037 | TFRC | transferrin receptor (p90, CD71) |
| 35. | 509 | ATP5C1 | ATP synthase, H+ transporting, mitochondrial F1 complex, gamma polypeptide 1 |
| 36. | 10682 | EBP | emopamil binding protein (sterol isomerase) |
| 37. | 56172 | ANKH | ankylosis, progressive homolog (mouse) |
| 38. | 100 | ADA | adenosine deaminase |
| 39. | 2821 | GPI | glucose phosphate isomerase |
| 40. | 54927 | CHCHD3 | coiled-coil-helix-coiled-coil-helix domain containing 3 |
| 41. | 58478 | MASA | E-1 enzyme |
| 42. | 292 | SLC25A5 | solute carrier family 25 (mitochondrial carrier; adenine nucleotide translocator), member 5 |

TABLE V-continued

| | ENTREZ GENE ID | GENE SYMBOL | GENE DESCRIPTION |
|---|---|---|---|
| 43. | 51096 | WDR50 | WD repeat domain 50 |
| 44. | 79053 | ALG8 | asparagine-linked glycosylation 8 homolog (yeast, alpha-1,3-glucosyltransferase) |
| 45. | 84300 | C6orf125 | chromosome 6 open reading frame 125 |
| 46. | 253461 | ZBTB38 | zinc finger and BTB domain containing 38 |
| 47. | 29080 | HSPC128 | HSPC128 protein |
| 48. | 1622 | DBI | diazepam binding inhibitor (GABA receptor modulator, acyl-Coenzyme A binding protein) |
| 49. | 2029 | ENSA | endosulfine alpha |
| 50. | 6404 | SELPLG | selectin P ligand |
| 51. | 7295 | TXN | thioredoxin |
| 52. | 10539 | TXNL2 | thioredoxin-like 2 |
| 53. | 3422 | IDI1 | isopentenyl-diphosphate delta isomerase |
| 54. | 1964 | EIF1AX | eukaryotic translation initiation factor 1A, X-linked |
| 55. | 11191 | PTENP1 | phosphatase and tensin homolog (mutated in multiple advanced cancers 1), pseudogene 1 |
| 56. | 1960 | EGR3 | early growth response 3 |
| 57. | 3338 | DNAJC4 | DnaJ (Hsp40) homolog, subfamily C, member 4 |
| 58. | 10397 | NDRG1 | N-myc downstream regulated gene 1 |
| 59. | 79717 | FLJ11838 | hypothetical protein FLJ11838 |
| 60. | 79027 | ZNF655 | zinc finger protein 655 |
| 61. | 10116 | FEM1B | fem-1 homolog b (*C. elegans*) |
| 62. | 10133 | OPTN | optineurin |
| 63. | 64062 | C13orf10 | chromosome 13 open reading frame 10 |
| 64. | 7905 | C5orf18 | chromosome 5 open reading frame 18 |
| 65. | 55615 | PRR5 | proline rich protein 5 |
| 66. | 257103 | C21orf86 | chromosome 21 open reading frame 86 |
| 67. | 493812 | HCG11 | HLA complex group 11 |
| 68. | 8879 | SGPL1 | sphingosine-1-phosphate lyase 1 |
| 69. | 440270 | LOC440270 | golgin-67 |
| 70. | 7096 | TLR1 | toll-like receptor 1 |
| 71. | 80853 | KIAA1718 | KIAA1718 protein |
| 72. | 1040 | CDS1 | CDP-diacylglycerol synthase (phosphatidate cytidylyltransferase) 1 |
| 73. | 9895 | KIAA0329 | KIAA0329 |
| 74. | 26115 | DKFZP564D166 | putative ankyrin-repeat containing protein |
| 75. | 339456 | LOC339456 | hypothetical protein LOC339456 |
| 76. | 582 | BBS1 | Bardet-Biedl syndrome 1 |
| 77. | 1186 | CLCN7 | chloride channel 7 |
| 78. | 3490 | IGFBP7 | insulin-like growth factor binding protein 7 |
| 79. | 285362 | SUMF1 | sulfatase modifying factor 1 |
| 80. | 56951 | C5orf15 | chromosome 5 open reading frame 15 |
| 81. | 113177 | C19orf36 | chromosome 19 open reading frame 36 |
| 82. | 10379 | ISGF3G | interferon-stimulated transcription factor 3, gamma 48 kDa |
| 83. | 284214 | LOC284214 | hypothetical protein LOC284214 |
| 84. | 8334 | HIST1H2AC | histone 1, H2ac |
| 85. | 114327 | EFHC1 | EF-hand domain (C-terminal) containing 1 |
| 86. | 401024 | FLJ44048 | FLJ44048 protein |
| 87. | 50854 | C6orf48 | chromosome 6 open reading frame 48 |
| 88. | 317649 | EIF4E3 | eukaryotic translation initiation factor 4E member 3 |
| 89. | 3123 | HLA-DRB1 | major histocompatibility complex, class II, DR beta 1 |
| 90. | 1486 | CTBS | chitobiase, di-N-acetyl- |
| 91. | 9666 | DZIP3 | zinc finger DAZ interacting protein 3 |
| 92. | 25861 | DFNB31 | deafness, autosomal recessive 31 |
| 93. | 25758 | G2 | G2 protein |
| 94. | 116151 | C20orf108 | chromosome 20 open reading frame 108 |
| 95. | 8804 | CREG1 | cellular repressor of E1A-stimulated genes 1 |
| 96. | 22871 | NLGN1 | neuroligin 1 |
| 97. | 112399 | EGLN3 | egl nine homolog 3 (*C. elegans*) |
| 98. | 145173 | B3GTL | beta 3-glycosyltransferase-like |
| 99. | 1488 | CTBP2 | C-terminal binding protein 2 |
| 100. | 3897 | L1CAM | L1 cell adhesion molecule |
| 101. | 3714 | JAG2 | jagged 2 |
| 102. | 1958 | EGR1 | early growth response 1 |
| 103. | 56675 | NRIP3 | nuclear receptor interacting protein 3 |
| 104. | 81031 | SLC2A10 | solute carrier family 2 (facilitated glucose transporter), member 10 |
| 105. | 90161 | HS6ST2 | heparan sulfate 6-O-sulfotransferase 2 |
| 106. | 477 | ATP1A2 | ATPase, Na+/K+ transporting, alpha 2 (+) polypeptide |
| 107. | 6542 | SLC7A2 | solute carrier family 7 (cationic amino acid transporter, y+ system), member 2 |
| 108. | 1601 | DAB2 | disabled homolog 2, mitogen-responsive phosphoprotein (*Drosophila*) |

TABLE V-continued

| | ENTREZ GENE ID | GENE SYMBOL | GENE DESCRIPTION |
|---|---|---|---|
| 109. | 143888 | KDELC2 | KDEL (Lys-Asp-Glu-Leu) containing 2 |
| 110. | 11178 | LZTS1 | leucine zipper, putative tumor suppressor 1 |
| 111. | 27122 | DKK3 | dickkopf homolog 3 (*Xenopus laevis*) |

The gene expression of the biomarkers of Table I or any of its subsets, Tables II through V, may be up- or down-regulated in response to the inhibition of FGFR3. In some instances, the detection of the presence of gene expression of one of the biomarkers may be sufficient to identify the patient for treatment or provide indication of a favorable response to treatment. In other instances, one may prefer the guidance provided by a higher level of alteration of gene expression or a stronger correlation with a particular inhibitory compound.

Further, in some instances, one may find identifying the most suitable patients for treatment for a particular cell proliferative disorder may best be accomplished by detecting an alteration in level of gene expression of two or more biomarkers or by a specific combination of biomarkers or even direction of alteration of gene expression. For example, a particular two of the biomarkers identified in Table I may be most correlated with a given condition and, thus, guide a certain treatment. Alternatively, a ratio of the relative levels of gene expression of two particular biomarkers may be indicative of the suitability of a given treatment for a patient. It is also contemplated that a particular condition may have a signature such as the up-regulation of one or more particular biomarker or biomarkers and/or the down-regulation of one or more other particular biomarker or biomarkers.

The alteration in the level of gene expression may be compared to a baseline level. A baseline level may be established in several ways. For example, in a method of monitoring response of a patient to treatment, a sample may be obtained from the patient and tested for measurement of gene expression prior to introduction of an FGFR3 inhibitor to the patient. Thus, the profile of gene expression levels, if any, of biomarkers in a treatment-naïve individual may serve as a baseline for that individual and later tests performed on samples obtained once treatment has begun may be compared to the individual's baseline. Alternatively, a baseline may be established through creation of a guide that consolidates information on gene expression levels taken from a pool of healthy or treatment-naïve individuals or even from an appropriate cell culture. Further, information on baseline levels of gene expression of particular biomarkers may be gathered from published sources or a gene database.

In one aspect, a sample is isolated from the patient after receipt of an amount of inhibitor of FGFR3, whether a therapeutically effective amount or a sub-therapeutically effective amount, which may be adequate for some purposes. Cell or tissue samples used for this invention encompass body fluid, solid tissue samples, tissue cultures or cells derived therefrom and the progeny thereof, and sections or smears prepared from any of these sources, or any other samples that may contain genetic information. Measurement of the expression of the biomarkers is described in further detail below.

Inhibitors of FGFR3

Some examples of small molecule inhibitors of FGFR3 include CHIR-258 (Chiron Corporation), SU-5402 (Pfizer, Inc.), and PD-173074 (Pfizer, Inc.).

The chemical structure and chemical name of CHIR-258 are shown below.

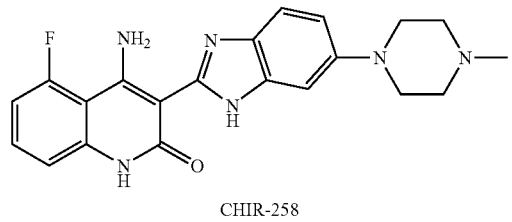

CHIR-258

4-Amino-5-fluoro-3-[6-(4-methylpiperazin-1-yl)-1H-benzimidazol-2-yl]quinolin-2(1H)-one is a small molecule inhibitor of VEGF-RTK, PDGF-RTK and other receptor tyrosine kinases such as fibroblast growth factor receptor (FGF-RTK). This compound has been described in a patent and several patent applications, the entire disclosures of which are incorporated herein by reference and for all purposes: U.S. Pat. No. 6,605,617, U.S. Ser. No. 10/644,055, U.S. Provisional Application Nos. 60/405,729, 60/428,210, and 60/484,048.

Related compounds are disclosed in patents and applications incorporated herein by reference, as noted. A plethora of substituted quinolinone compounds including quinolinone benzimidazolyl compounds and 4-amino substituted quinolinone benzimidazolyl compounds such as 4-amino-5-fluoro-3-[5-(4-methylpiperazin-1-yl)-1H-benzimidazol-2-yl] quinolin-2(1H)-one have recently been disclosed in references such as WO 02/22598, WO 2004/043389, WO 2005/047244, U.S. 2004/0220196, U.S. 2005/0137399, WO 2005/046590, and WO 2005/046589. Such compounds are disclosed as inhibiting VEGF-RTKs. Such compounds are also disclosed in published United States patent applications U.S. 2002/0107392 and U.S. 2003/0028018 and U.S. Pat. Nos. 6,605,617, 6,774,237, 6,762,194, and 6,800,760. Other such compounds are disclosed along with new uses of such compounds in inhibiting serine/threonine kinases and tyrosine kinases are disclosed in WO 2004/018419, and U.S. 2004/0092535, filed on Aug. 19, 2003, and claiming priority to each of the following provisional applications: U.S. Provisional Application No. 60/405,729 filed on Aug. 23, 2002; U.S. Provisional Application No. 60/426,107 filed on Nov. 13, 2002; U.S. Provisional Application No. 60/426,226 filed on Nov. 13, 2002; U.S. Provisional Application No. 60/426,282 filed on Nov. 13, 2002; U.S. Provisional Application No. 60/428,210 filed on Nov. 21, 2002; U.S. Provisional Application No. 60/460,327 filed on Apr. 3, 2003; U.S. Provisional Application No. filed on Apr. 3, 2003; U.S. Provisional Application No. 60/460,493 filed on Apr. 3, 2003; U.S. Provisional Application No. 60/478,916 filed on Jun. 16, 2003; and U.S. Provisional Application No. 60/484,048 filed on Jul. 1, 2003. Additional disclosure related to quinolinone compounds and uses thereof is set forth in U.S. Provisional Application No. 60/680,722, filed May 13, 2005; U.S. Provisional Application No. 60/681,893, filed May 17, 2005; U.S. Provisional Application No. 60/546,395, filed Feb. 20, 2004; U.S. Provisional Application No. 60/547,103, filed Feb. 23, 2004; U.S. Provisional Application No. 60/554,771, filed Mar. 19, 2004; U.S.

Provisional Application No. 60/647,568, filed Jan. 27, 2005; U.S. Provisional Application No. 60/669,245, filed Apr. 6, 2005; U.S. Provisional Application No. 60/538,594, filed Jan. 23, 2004; U.S. Provisional Application No. 60/683,999; filed May 23, 3005; U.S. patent application Ser. No. 11/061,386, filed Feb. 18, 2005; U.S. patent application Ser. No. 11/041,191, filed Jan. 21, 2005; and PCT Application No. PCT/US2005/05316, filed Feb. 18, 2005. Heterocyclic compounds related to benzimidazolyl quinolinones have recently been disclosed in WO 02/18383, U.S. 2002/0103230, and U.S. Pat. No. 6,756,383. Each of the references in this paragraph is hereby incorporated by reference in its entirety and for all purposes as if fully set forth herein.

The SU-5402 compound is 3-[3-(2-Carboxyethyl)-4-methylpyrrol-2-methylidenyl]-2-indolinone and has the following formula.

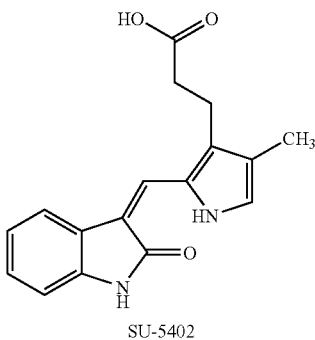

SU-5402

The PD-173074 compound has the compound structure and chemical name shown below.

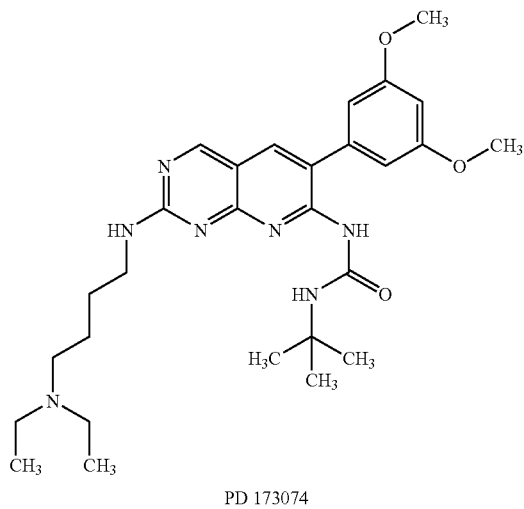

PD 173074

1-tert-butyl-3-[6-(3,5-dimethoxyphenyl)-2-(4-diethylaminobutylamino)-pyrido[2,3-d]pyrimidin-7-yl]-urea.

Measurement of Gene Expression

As noted previously, the measurement of gene expression is performed on a sample, preferably a biological sample, obtained from the patient. For example, the patient may undergo a blood draw or tissue biopsy and the measurement may be made on the resulting sample. Depending upon the technique utilized, the test may be performed on an isolated fraction of the sample or in situ.

Detection of the presence of gene expression of the biomarker of interest and/or detection of the level of alteration in the gene expression compared to baseline may be made utilizing standard techniques.

Detection can be by any appropriate method, including for example, detecting the quantity of mRNA transcribed from the gene or the quantity of cDNA produced from the reverse transcription of the mRNA transcribed from the gene or the quantity of the polypeptide or protein encoded by the gene. These methods can be performed on a sample by sample basis or modified for high throughput analysis. Additionally, databases containing quantitative full or partial transcripts or protein sequences isolated from a cell sample can be searched and analyzed for the presence and amount of transcript or expressed gene product.

In assaying for an alteration in mRNA level, nucleic acid contained in the aforementioned samples is first extracted according to standard methods in the art. For instance, mRNA can be isolated using various lytic enzymes or chemical solutions according to the procedures set forth in Sambrook et al. (1989), supra or extracted by nucleic-acid-binding resins following the accompanying instructions provided by manufactures. The mRNA of the biomarker contained in the extracted nucleic acid sample is then detected by hybridization (e.g. Northern blot analysis) and/or amplification procedures according to methods widely known in the art or based on the methods exemplified herein.

Nucleic acid molecules having at least 10 nucleotides and exhibiting sequence complementarity or homology to the biomarkers described herein find utility as hybridization probes. It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated.

In certain embodiments, it will be advantageous to employ probes or primers in combination with an appropriate means, such as a label, for detecting hybridization and therefore complementary sequences. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples.

Hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. See, for example, (Sambrook, et al., (1989), supra).

Briefly, multiple RNAs are isolated from cell or tissue samples as described above. Optionally, the gene transcripts can be converted to cDNA. A sampling of the biomarker transcript(s) is/are subjected to sequence-specific analysis and quantified. These gene transcript sequence abundances are compared to the baseline.

Alternatively any one of gene copy number, transcription, or translation of a biomarker can be determined using an amplification method such as PCR. General procedures for PCR are taught in MacPherson et al., PCR: A PRACTICAL APPROACH, (IRL Press at Oxford University Press (1991)). However, PCR conditions used for each application reaction are empirically determined. A number of parameters influence the success of a reaction. Among them are annealing temperature and time, extension time, $Mg^{2+}$ ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination.

In one aspect, the biomarkers are detected and quantitated by hybridization to a probe that specifically hybridizes to the appropriate probe for that biomarker. The probes also can be attached to a solid support for use in high throughput screening assays using methods known in the art. PCT WO 97/10365 and U.S. Pat. Nos. 5,405,783, 5,412,087 and 5,445,934, for example, disclose the construction of high density oligonucleotide chips which can contain one or more of the sequences disclosed herein. Using the methods disclosed in U.S. Pat. Nos. 5,405,783, 5,412,087 and 5,445,934 the probes of this invention are synthesized on a derivatized glass surface. Photoprotected nucleoside phosphoramidites are coupled to the glass surface, selectively deprotected by photolysis through a photolithographic mask, and reacted with a second protected nucleoside phosphoramidite. The coupling/deprotection process is repeated until the desired probe is complete.

In one aspect, the expression level of the biomarker is determined through exposure of a nucleic acid sample to the probe-modified chip. Extracted nucleic acid is labeled, for example, with a fluorescent tag, preferably during an amplification step. Hybridization of the labeled sample is performed at an appropriate stringency level. The degree of probe-nucleic acid hybridization is quantitatively measured using a detection device, such as a confocal microscope. See U.S. Pat. Nos. 5,578,832 and 5,631,734.

In an alternative embodiment, the method is performed by the detecting and comparing of two or more biomarkers that have been pre-determined to be predictive of a therapeutic response. In a yet further embodiment, a plurality of biomarkers, e.g., see Tables I through V, supra, are used in the method of this invention. In these embodiments, the biomarkers or probes that specifically hybridize and recognize the biomarker of interest are arranged on a high density oligonucleotide probe array that provides an effective means of monitoring expression of a multiplicity of genes.

In another preferred embodiment, the methods of this invention are used to monitor expression of the genes which specifically hybridize to the probes of this invention in response to defined stimuli, such as a drug or biologic.

In one embodiment, the hybridized nucleic acids are detected by detecting one or more labels attached to the sample nucleic acids. The labels may be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g. fluorescein-labeled UTP and/or CTP) incorporates a label in to the transcribed nucleic acids.

Alternatively, a label may be added directly to the original nucleic acid sample (e.g., mRNA, polya, mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

As described in more detail in WO 97/10365, the label may be added to the target (sample) nucleic acid(s) prior to, or after the hybridization. These are detectable labels that are directly attached to or incorporated into the target (sample) nucleic acid prior to hybridization. In contrast, "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. Fore a detailed review of methods of labeling nucleic acids and detecting labeled hybridized nucleic acids see LABORATORY TECHNIQUES IN BIOCHEMISTRY AND MOLECULAR BIOLOGY, Vol. 24: Hybridization with Nucleic Acid Probes, P. Tijssen, ed. Elsevier, N.Y. (1993).

The nucleic acid sample also may be modified prior to hybridization to the high density probe array in order to reduce sample complexity thereby decreasing background signal and improving sensitivity of the measurement using the methods disclosed in WO 97/10365.

Results from the chip assay are typically analyzed using a computer software program. See, for example, EP 0717 113 A2 and WO 95/20681. The hybridization data is read into the program, which calculates the expression level of the targeted gene(s). The figures may be compared against existing data sets of gene expression levels for diseased and healthy individuals. A correlation between the obtained data and that of a set of a predetermined baseline identifies patients likely to be responsive to the therapy.

Also within the scope of this application is a data base useful for the identification of patients likely to respond to a predetermined therapy, e.g., anti-FGFR3 therapy, wherein the database contains a combination of base line gene expression data against which the patient sample can be compared using bioinformatic techniques known in the art.

The pre-determined baseline information is stored in a digital storage medium such that a data processing system for standardized representation of the genes that identify patients that are responsive to therapy. The data processing system is useful to analyze gene expression between two samples. A suitable sample is isolated from the patient and then the genotype or phenotype of the cell or sample is determined using methods known in the art. In one aspect, the nucleic acids of the biomarkers if present in the sample are sequenced and transcribed to code. The sequences (in code form) from the sample are compared with the sequence(s) present in the database using homology search techniques. Greater than 90%, or alternatively, greater than 95% or alternatively, greater than or equal to 97% sequence identity between the test sequence and at least one sequence identified by the biomarkers identified in Tables I through V is a positive indication that the polynucleotide from a biomarker has been isolated from the patient sample.

Expression level of the biomarker can also be determined by examining the protein product. Determining the protein level involves (a) providing a biological sample containing expression product of the biomarker; and (b) measuring the amount of any immunospecific binding that occurs between an antibody that selectively recognizes and binds to the expression product of the biomarker in the sample, in which the amount of immunospecific binding indicates the level of the biomarker expression. This information is then compared to a pre-determined base line and analyzed to identify those patients suitable for therapy.

A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunoflourescent assays, and PAGE-SDS.

Antibodies that specifically recognize and bind to the protein products of the expression products of the biomarkers are required for immunoassays. These may be purchased from commercial vendors or generated and screened using methods well known in the art. See Harlow and Lane (1988) supra. and Sambrook et al. (1989) supra.

Treatment

Inhibition of activated FGFR3 has been shown to induce apoptosis (Trudel, et al., *Blood,* 105(7):2941-2948 (2005)) A patient may be beneficially treated by administration of an inhibitor of FGFR3, particularly a tyrosine kinase small molecule inhibitor (SMI) of FGFR3. Thus, treatment according to the invention may constitute administration of one or more small molecule FGFR3 inhibitors, such as those disclosed herein.

Alternatively, the small molecule inhibitors may be used in combination with other treatments. For instance, inhibitors that are not small molecules, e.g. biologicals, polynucleotides, gene therapy, etc. may be used for the ongoing treatment, in some cases, whereas the small molecule FGFR3 inhibitor may be used primarily as an initial aid in identifying candidates.

In another alternative, one inhibitor may be used prior to a gene expression level measurement step and another may be used subsequently.

The methods of the invention are useful for treatment of cellular proliferative disease and particularly neoplastic disease.

One disease model in which the genetic profiling methods taught herein are especially useful is multiple myeloma. A subset of approximately 15-20% of multiple myeloma patients have a chromosomal translocation denoted the t(4; 14) translocation that is associated with the ectopic expression of the receptor tyrosine kinase fibroblast growth factor receptor 3 (FGFR3). The t(4; 14) abnormality is typically diagnosed via a cytogenetic test, such as a fluorescence in situ hybridization (FISH) analysis, performed on a bone marrow aspirate taken from the patient. The t(4; 14) multiple myeloma patient has a poor prognosis, but the methods taught herein offer new hope in that they may be employed to great advantage to identify such patients for treatment with an FGFR3 inhibitor, monitor response to treatment in such patients, as well as to aid in the development of new and/or optimized FGFR3 inhibitors.

Therapeutic agents utilized according to this invention, include, but are not limited to small molecules. They may be polynucleotides, peptides, antibodies, antigen presenting cells and include immune effector cells that specifically recognize and lyse cells expressing the gene of interest. One can determine if a subject or patient will be beneficially treated by the use of agents by screening one or more of the agents against tumor cells isolated from the subject or patient using methods known in the art.

Various delivery systems are known and can be used to administer a therapeutic agent in accordance with the methods of the invention, e.g., encapsulation in liposomes, microparticles, microcapsules, expression by recombinant cells, receptor-mediated endocytosis (See e.g., Wu and Wu (1987) J. Biol. Chem. 262:4429-4432), construction of a therapeutic nucleic acid as part of a retroviral or other vector, etc. Methods of delivery include but are not limited to intra-arterial, intra-muscular, intravenous, intranasal and oral routes. In a specific embodiment, it may be desirable to administer pharmaceutical compositions locally to the area in need of treatment; this may be achieved by, for example, and not by way of limitation, local infusion during surgery, by injection or by means of a catheter.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents may be empirically adjusted.

Pharmaceutical compositions utilized according to the methods of the invention can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to the key active ingredients, the pharmaceutical compositions can also contain other pharmaceutically active compounds or a plurality of compositions of the invention.

More particularly, an agent administered according to the invention may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient and the disease being treated.

Ideally, the agent should be administered to achieve peak concentrations of the active compound at sites of disease. This may be achieved, for example, by the intravenous injection of the agent, optionally in saline or orally administered, for example, as a tablet, capsule or syrup containing the active ingredient. Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

While it is possible for the agent to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both and then, if necessary, shaping the product.

Formulations suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the agent through the skin or other affected areas. Examples of such dermal penetration enhancers include dimethylsulfoxide and related analogues.

The oily phase of the emulsions of a composition used according to this invention may be constituted from known ingredients in a known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the agent, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops or by aerosol administration by nebulizer, include aqueous or oily solutions of the agent.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents, thickening agents and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

Experimental Example

Transcriptional activity was assessed by measuring levels of messenger RNA (mRNA) in cells derived from human multiple myeloma tumors using Affymetrix HG-U133-Plus-2 GeneChips.

Expression of mRNA in cells treated with the small molecule inhibitors SU-5402, PD-173074 (both Pfizer Inc.) and CHIR-258 (Chiron Corp.), with FGF ligand, or with FGFR3 silencing RNA (siRNA) was quantitatively compared to expression in untreated cells (or cells treated with a scrambled siRNA control in the latter case). Specific differences and similarities to the other FGFR3 inhibitors were compared with CHIR-258.

The following multiple myeloma cell lines were used:
KMS11: Ras WT, FGFR3Y373C mutant; sensitive to CHIR-258 treatment
KMS18: Ras WT, FGFR3G384D mutant; sensitive to CHIR-258 treatment
H929: N13 Ras mutant, FGFR3 wild-type (WT); resistant to CHIR-258 treatment
U266: Ras WT, FGFR3 negative; resistant to CHIR-258 treatment
UTMC2: Ras WT, FGFR3WT; resistant to CHIR-258 treatment Bioinformatics analysis was performed on the raw data to provide the results.

Changes in gene expression level in response to the various FGFR3 inhibitors tested and deemed to be of statistical significance were utilized to generate Table I disclosed herein, and its various subsets. Within the parameters of this experiment, the biomarkers of Table I generally correlate with alterations in expression level of one-and-a-half-fold or greater, whereas the biomarkers of Table II generally correlate with alterations in expression level of two-fold or greater, and the biomarkers of Table III generally correlate with alterations in expression level of four-fold or greater. Table IV was generated with data showing alterations in gene expression in response to FGFR3 inhibition in the relevant cell lines of the experiment by the preferred compound, CHIR-258. Table V was generated with data showing alterations in gene expression in response to FGFR3 inhibition in the relevant cell lines of the experiment by the preferred compound, CHIR-258, but not to any significant extent by the other small molecule inhibitors tested.

What is claimed is:

1. A method of identifying a patient for treatment of a cell proliferative disorder with an inhibitor of FGFR3, the method comprising:
    testing a sample obtained from the patient after administration of the inhibitor to measure gene expression of at least one biomarker which is CCL3,
    wherein detection of an alteration in level of expression compared to a baseline gene expression measurement of the at least one biomarker is indicative of the candidacy of the patient for the treatment, and
    wherein the baseline gene expression measurement is the gene expression measured in the patient prior to administration of the inhibitor.

2. A method of identifying a patient for treatment of a cell proliferative disorder with an inhibitor of FGFR3, the method comprising:
    testing a sample obtained from a patient to measure gene expression of at least one biomarker which is CCL3,
    wherein detection of the presence of gene expression of the at least one biomarker is indicative of the candidacy of the patient for the treatment.

3. A method of monitoring response of a patient in need thereof to treatment for a cell proliferative disorder, the method comprising:
    administering an amount of an inhibitor of FGFR3 to the patient,
    testing a sample obtained from the patient after the administration of the inhibitor to measure gene expression of at least one biomarker which is CCL3,
    wherein detection of an alteration in level of expression of the at least one biomarker as compared to a baseline gene expression measurement is indicative of a response of the patient to the treatment, and
    wherein the baseline gene expression measurement is the gene expression measured in the patient prior to administration of the inhibitor.

4. A method of monitoring response of a patient to treatment by an inhibitor of FGFR3 for a cell proliferative disorder, the method comprising:
    testing a sample obtained from the patient after administration of the inhibitor of FGFR3 to measure gene expression of at least one biomarker which is CCL3,
    wherein detection of an alteration in level of expression of the at least one biomarker compared to a baseline gene expression measurement is indicative of a response of the patient to the treatment, and
    wherein the baseline gene expression measurement is the gene expression measured in the patient prior to administration of the inhibitor.

5. A method of utilizing a biomarker in treatment of a cell proliferative disorder in a patient, the method comprising:
    testing a sample obtained from the patient after administration of an inhibitor of FGFR3 to measure gene expression of at least one biomarker which is CCL3,
    wherein the patient is subsequently administered the same or a different inhibitor of FGFR3 provided alteration of the level of expression of the at least one biomarker is detected upon administration of the initial inhibitor.

6. A method of adjusting a dosage amount of an inhibitor of FGFR3 for treatment of a cell proliferative disorder in a patient, the method comprising:

monitoring gene expression of at least one biomarker which is CCL3 after the administration of an initial amount of the inhibitor, and adjusting the amount for subsequent administration of the inhibitor to the patient based upon the level of alteration of the expression of the biomarker or biomarkers that has occurred upon administration of the initial amount.

7. A method of utilizing a biomarker to identify an FGFR3 inhibitory compound for potential treatment of multiple myeloma or to guide a decision to progress an FGFR3 inhibitory compound to further development for treatment of multiple myeloma, the method comprising:

contacting the compound with a KMS18 or KMS11 cell culture, and testing a portion of the cell culture to measure gene expression of at least one biomarker which is CCL3, wherein detection of an alteration in expression of the at least one biomarker compared to baseline gene expression measurement is indicative of an identification of the compound for treatment or a favorable decision to progress the compound for further development, and wherein the baseline gene expression measurement is gene expression measured in cell culture prior to the contacting.

8. A method of selecting an appropriate inhibitor of FGFR3 to administer to a patient in need of treatment with said inhibitor, the method comprising:

testing a sample obtained from the patient after administration of an initial inhibitor of FGFR3 to measure gene expression of at least one biomarker which is CCL3, wherein the patient is subsequently administered the initial inhibitor of FGFR3 provided alteration of the level of expression of the at least one biomarker is detected upon administration of the initial inhibitor.

9. A method of utilizing CCL3 to identify an FGFR3 inhibitory compound for potential treatment of a cell proliferative disorder, the method comprising:

contacting the compound with a cell line or tissue associated with the disorder, and testing a portion of the cell culture or tissue after the contacting to measure gene expression of at least one biomarker which is CCL3 that has been altered compared to a baseline gene expression measurement, wherein detection of an alteration in expression of the at least one biomarker is indicative of an identification of the compound for treatment, and wherein the baseline gene expression measurement is the gene expression measured from the cell or tissue prior to the contacting.

10. The method of claim 1, wherein the measurement of gene expression is made by detecting the quantity of RNA transcribed by the biomarker.

11. The method of claim 1, wherein the measurement of gene expression is made by detecting the quantity of DNA produced from reverse transcription of an RNA transcribed by the biomarker.

12. The method of claim 1, wherein the measurement of gene expression is made by detecting a polypeptide or protein encoded by the biomarker.

13. The method of claim 1, wherein the at least one biomarker is operably linked to a gene chip.

14. The method of claim 1, wherein the at least one biomarker is represented in computer readable format.

15. The method of claim 1, wherein the testing comprises contacting the sample with a gene chip comprising CCL3.

16. The method of claim 1, wherein the detecting step comprises comparing the gene expression level of the biomarker with a gene database.

17. The method of claim 1, wherein the treatment comprises administration of a therapeutically effective amount of the same or a different inhibitor of FGFR3 to the patient.

18. The method of claim 1, wherein the treatment is for a neoplastic disease.

19. The method of claim 1, wherein the treatment is for multiple myeloma.

20. The method of claim 1, wherein the treatment is for t(4; 14) multiple myeloma.

21. The method of claim 1, wherein the inhibitor is selected from the group consisting of CHIR-258, SU-5402, and PD-173074.

22. The method of claim 1, wherein the inhibitor is CHIR-258.

23. The method of claim 1, wherein the at least one biomarker further comprises a biomarker selected from the group consisting of LOC150271, CD48, DUSP4, and ITGB7.

24. The method of claim 1, further comprising establishing a baseline gene expression measurement level for the patient prior to administering the FGFR3 inhibitor.

25. The method of claim 1, wherein the biomarker is not any or all of CCL3, DUSP6, ANXA9, CR2, AL531683, ZNF589, AW274468, FRMD3, LTB, and WDR42A.

26. The method of claim 3, wherein the administration is repeated before the step of testing a sample obtained from the patient.

27. The method of claim 3, wherein the inhibitor of FGFR3 is administered in a therapeutically effective amount.

28. The method of claim 5, wherein the initial inhibitor and the subsequently administered inhibitor are each selected from the group consisting of CHIR-258, SU-5402, and PD-173074.

29. The method of claim 5, wherein the initial inhibitor is CHIR-258.

30. The method of claim 5, wherein the subsequently administered inhibitor is CHIR-258.

31. The method of claim 6, wherein the monitoring comprises contacting the sample with a gene chip comprising CCL3 and comparing the gene expression level of CCL3 with a gene database.

32. The method of any one of claims 1-5 or 6-9, wherein the at least one biomarker further comprises one or more biomarkers selected Table I.

TABLE I

| ENTREZ GENE ID | GENE SYMBOL | GENE DESCRIPTION |
| --- | --- | --- |
| 200734 | SPRED2 | sprouty-related, EVH1 domain containing 2 |
| 117854 | TRIM6 | tripartite motif-containing 6 |
| 1846 | DUSP4 | dual specificity phosphatase 4 |
| 894 | CCND2 | cyclin D2 |
| 6241 | RRM2 | ribonucleotide reductase M2 polypeptide |
| 4821 | NKX2-2 | NK2 transcription factor related, locus 2 (*Drosophila*) |

TABLE I-continued

| ENTREZ GENE ID | GENE SYMBOL | GENE DESCRIPTION |
|---|---|---|
| 3037 | HAS2 | hyaluronan synthase 2 |
| 990 | CDC6 | CDC6 cell division cycle 6 homolog (S. cerevisiae) |
| 57405 | SPBC25 | spindle pole body component 25 homolog (S. cerevisiae) |
| 934 | CD24 | CD24 antigen (small cell lung carcinoma cluster 4 antigen) |
| 55165 | C10orf3 | chromosome 10 open reading frame 3 |
| 55388 | MCM10 | MCM10 minichromosome maintenance deficient 10 (S. cerevisiae) |
| 79019 | C22orf18 | chromosome 22 open reading frame 18 |
| 9768 | KIAA0101 | KIAA0101 |
| 51659 | Pfs2 | DNA replication complex GINS protein PSF2 |
| 4605 | MYBL2 | v-myb myeloblastosis viral oncogene homolog (avian)-like 2 |
| 161742 | SPRED1 | sprouty-related, EVH1 domain containing 1 |
| 4175 | MCM6 | MCM6 minichromosome maintenance deficient 6 (MIS5 homolog, S. pombe) (S. cerevisiae) |
| 11130 | ZWINT | ZW10 interactor |
| 26298 | EHF | ets homologous factor |
| 7117 | TMSL3 | thymosin-like 3 |
| 890 | CCNA2 | cyclin A2 |
| 79075 | DCC1 | defective in sister chromatid cohesion homolog 1 (S. cerevisiae) |
| 83879 | CDCA7 | cell division cycle associated 7 |
| 22873 | DZIP1 | DAZ interacting protein 1 |
| 51514 | DTL | denticleless homolog (Drosophila) |
| 55789 | DEPDC1B | DEP domain containing 1B |
| 55355 | DKFZp762E1312 | hypothetical protein DKFZp762E1312 |
| 10052 | GJA7 | gap junction protein, alpha 7, 45kDa (connexin 45) |
| 146909 | LOC146909 | hypothetical protein LOC146909 |
| 113130 | CDCA5 | cell division cycle associated 5 |
| 1017 | CDK2 | cyclin-dependent kinase 2 |
| 4176 | MCM7 | MCM7 minichromosome maintenance deficient 7 (S. cerevisiae) |
| 81610 | C20orf129 | chromosome 20 open reading frame 129 |
| 9833 | MELK | maternal embryonic leucine zipper kinase |
| 29128 | UHRF1 | ubiquitin-like, containing PHD and RING finger domains, 1 |
| 4171 | MCM2 | MCM2 minichromosome maintenance deficient 2, mitotin (S. cerevisiae) |
| 79801 | SHCBP1 | SHC SH2-domain binding protein 1 |
| 28231 | SLCO4A1 | solute carrier organic anion transporter family, member 4A1 |
| 113115 | FAM54A | family with sequence similarity 54, member A |
| 22974 | TPX2 | TPX2, microtubule-associated protein homolog (Xenopus laevis) |
| 9232 | PTTG1 | pituitary tumor-transforming 1 |
| 137392 | LOC137392 | similar to CG6405 gene product |
| 195828 | ZNF367 | zinc finger protein 367 |
| 4288 | MKI67 | antigen identified by monoclonal antibody Ki-67 |
| 701 | BUB1B | BUB1 budding uninhibited by benzimidazoles 1 homolog beta (yeast) |
| 9928 | KIF14 | kinesin family member 14 |
| 3832 | KIF11 | kinesin family member 11 |
| 11065 | UBE2C | ubiquitin-conjugating enzyme E2C |
| 9837 | PSF1 | DNA replication complex GINS protein PSF1 |
| 387103 | C6orf173 | chromosome 6 open reading frame 173 |
| 1870 | E2F2 | E2F transcription factor 2 |
| 79733 | E2F8 | E2F transcription factor 8 |
| 991 | CDC20 | CDC20 cell division cycle 20 homolog (S. cerevisiae) |
| 3014 | H2AFX | H2A histone family, member X |
| 10112 | KIF20A | kinesin family member 20A |
| 993 | CDC25A | cell division cycle 25A |
| 24137 | KIF4A | kinesin family member 4A |
| 80144 | FRAS1 | Fraser syndrome 1 |
| 55010 | FLJ20641 | hypothetical protein FLJ20641 |
| 9319 | TRIP13 | thyroid hormone receptor interactor 13 |
| 9355 | LHX2 | LIM homeobox 2 |
| 7153 | TOP2A | topoisomerase (DNA) II alpha 170kDa |
| 4174 | MCM5 | MCM5 minichromosome maintenance deficient 5, cell division cycle 46 (S. cerevisiae) |
| 55215 | FLJ10719 | hypothetical protein FLJ10719 |
| 11013 | TMSL8 | thymosin-like 8 |
| 5983 | RFC3 | replication factor C (activator 1) 3, 38kDa |
| 1063 | CENPF | centromere protein F, 350/400ka (mitosin) |
| 3683 | ITGAL | integrin, alpha L (antigen CD11A (p180), lymphocyte function-associated antigen 1; alpha polypeptide) |
| 2237 | FEN1 | flap structure-specific endonuclease 1 |
| 27338 | UBE2S | ubiquitin-conjugating enzyme E2S |
| 4001 | LMNB1 | lamin B1 |
| 29089 | UBE2T | ubiquitin-conjugating enzyme E2T (putative) |
| 55839 | BM039 | uncharacterized bone marrow protein BM039 |
| 2115 | ETV1 | ets variant gene 1 |
| 440279 | UNC13C | unc-13 homolog C (C. elegans) |
| 962 | CD48 | CD48 antigen (B-cell membrane protein) |
| 54910 | SEMA4C | sema domain, immunoglobulin domain (Ig), transmembrane domain (TM) and short cytoplasmic domain, (semaphorin) 4C |
| 1902 | EDG2 | endothelial differentiation, lysophosphatidic acid G-protein-coupled receptor, 2 |
| 64946 | CENPH | centromere protein H |
| 157570 | ESCO2 | establishment of cohesion 1 homolog 2 (S. cerevisiae) |
| 389835 | FAM72A | family with sequence similarity 72, member A |

TABLE I-continued

| ENTREZ GENE ID | GENE SYMBOL | GENE DESCRIPTION |
|---|---|---|
| 144455 | E2F7 | E2F transcription factor 7 |
| 51512 | GTSE1 | G-2 and S-phase expressed 1 |
| 7298 | TYMS | thymidylate synthetase |
| 7374 | UNG | uracil-DNA glycosylase |
| 5578 | PRKCA | protein kinase C, alpha |
| 672 | BRCA1 | breast cancer 1, early onset |
| 84952 | CGNL1 | cingulin-like 1 |
| 10252 | SPRY1 | sprouty homolog 1, antagonist of FGF signaling (*Drosophila*) |
| 79682 | MLF1IP | MLF1 interacting protein |
| 8851 | CDK5R1 | cyclin-dependent kinase 5, regulatory subunit 1 (p35) |
| 10635 | RAD51AP1 | RAD51 associated protein 1 |
| 22998 | KIAA1102 | KIAA1102 protein |
| 148203 | LOC148203 | hypothetical protein LOC148203 |
| 7465 | WEE1 | WEE1 homolog (*S. pombe*) |
| 83540 | CDCA1 | cell division cycle associated 1 |
| 3070 | HELLS | helicase, lymphoid-specific |
| 891 | CCNB1 | cyclin B1 |
| 6790 | STK6 | serine/threonine kinase 6 |
| 56992 | KIF15 | kinesin family member 15 |
| 7112 | TMPO | thymopoietin |
| 63901 | FLJ22794 | FLJ22794 protein |
| 9493 | KIF23 | kinesin family member 23 |
| 9133 | CCNB2 | cyclin B2 |
| 4173 | MCM4 | MCM4 minichromosome maintenance deficient 4 (*S. cerevisiae*) |
| 7083 | TK1 | thymidine kinase 1, soluble |
| 983 | CDC2 | cell division cycle 2, G1 to S and G2 to M |
| 11339 | OIP5 | Opa interacting protein 5 |
| 51203 | NUSAP1 | nucleolar and spindle associated protein 1 |
| 5111 | PCNA | proliferating cell nuclear antigen |
| 11004 | KIF2C | kinesin family member 2C |
| 54443 | ANLN | anillin, actin binding protein (scraps homolog, *Drosophila*) |
| 83461 | CDCA3 | cell division cycle associated 3 |
| 4085 | MAD2L1 | MAD2 mitotic arrest deficient-like 1 (yeast) |
| 9201 | DCAMKL1 | doublecortin and CaM kinase-like 1 |
| 1111 | CHEK1 | CHK1 checkpoint homolog (*S. pombe*) |
| 9055 | PRC1 | protein regulator of cytokinesis 1 |
| 7804 | LRP8 | low density lipoprotein receptor-related protein 8, apolipoprotein e receptor |
| 4915 | NTRK2 | neurotrophic tyrosine kinase, receptor, type 2 |
| 28951 | TRIB2 | tribbles homolog 2 (*Drosophila*) |
| 4281 | MID1 | midline 1 (Opitz/BBB syndrome) |
| 3148 | HMGB2 | high-mobility group box 2 |
| 3161 | HMMR | hyaluronan-mediated motility receptor (RHAMM) |
| 10276 | NET1 | neuroepithelial cell transforming gene 1 |
| 29028 | ATAD2 | ATPase family, AAA domain containing 2 |
| 1062 | CENPE | centromere protein E, 312kDa |
| 1491 | CTH | cystathionase (cystathionine gamma-lyase) |
| 10615 | SPAG5 | sperm associated antigen 5 |
| 64581 | CLEC7A | C-type lectin domain family 7, member A |
| 10592 | SMC2L1 | SMC2 structural maintenance of chromosomes 2-like 1 (yeast) |
| 332 | BIRC5 | baculoviral IAP repeat-containing 5 (survivin) |
| 4172 | MCM3 | MCM3 minichromosome maintenance deficient 3 (*S. cerevisiae*) |
| 64105 | FKSG14 | leucine zipper protein FKSG14 |
| 64151 | HCAP-G | chromosome condensation protein G |
| 1163 | CKS1B | CDC28 protein kinase regulatory subunit 1B |
| 122769 | PPIL5 | peptidylprolyl isomerase (cyclophilin)-like 5 |
| 3398 | ID2 | inhibitor of DNA binding 2, dominant negative helix-loop-helix protein |
| 22822 | PHLDA1 | pleckstrin homology-like domain, family A, member 1 |
| 1718 | DHCR24 | 24-dehydrocholesterol reductase |
| 145482 | ZADH1 | zinc binding alcohol dehydrogenase, domain containing 1 |
| 1847 | DUSP5 | dual specificity phosphatase 5 |
| 26271 | FBXO5 | F-box protein 5 |
| 9212 | AURKB | aurora kinase B |
| 29968 | PSAT1 | phosphoserine aminotransferase 1 |
| 26147 | PHF19 | PHD finger protein 19 |
| 55635 | DEPDC1 | DEP domain containing 1 |
| 10403 | KNTC2 | kinetochore associated 2 |
| 64081 | MAWBP | MAWD binding protein |
| 84858 | ZNF503 | zinc finger protein 503 |
| 55723 | ASF1B | ASF1 anti-silencing function 1 homolog B (*S. cerevisiae*) |
| 7272 | TTK | TTK protein kinase |
| 9535 | GMFG | glia maturation factor, gamma |
| 1058 | CENPA | centromere protein A, 17kDa |
| 84515 | MCM8 | MCM8 minichromosome maintenance deficient 8 (*S. cerevisiae*) |
| 54069 | C21orf45 | chromosome 21 open reading frame 45 |
| 5984 | RFC4 | replication factor C (activator 1) 4, 37kDa |
| 389831 | LOC389831 | hypothetical gene supported by AL713796 |
| 157313 | CDCA2 | cell division cycle associated 2 |
| 29127 | RACGAP1 | Rac GTPase activating protein 1 |

TABLE I-continued

| ENTREZ GENE ID | GENE SYMBOL | GENE DESCRIPTION |
|---|---|---|
| 55872 | PBK | PDZ binding kinase |
| 4678 | NASP | nuclear autoantigenic sperm protein (histone-binding) |
| 7171 | TPM4 | tropomyosin 4 |
| 7443 | VRK1 | vaccinia related kinase 1 |
| 699 | BUB1 | BUB1 budding uninhibited by benzimidazoles 1 homolog (yeast) |
| 3925 | STMN1 | stathmin 1/oncoprotein 18 |
| 865 | CBFB | core-binding factor, beta subunit |
| 399664 | RKHD1 | ring finger and KH domain containing 1 |
| 11168 | PSIP1 | PC4 and SFRS1 interacting protein 1 |
| 84057 | GAJ | GAJ protein |
| 57082 | CASC5 | cancer susceptibility candidate 5 |
| 23286 | KIBRA | KIBRA protein |
| 285513 | LOC285513 | hypothetical protein LOC285513 |
| 259266 | ASPM | asp (abnormal spindle)-like, microcephaly associated (*Drosophila*) |
| 150468 | FLJ40629 | hypothetical protein FLJ40629 |
| 6659 | SOX4 | SRY (sex determining region Y)-box 4 |
| 51053 | GMNN | geminin, DNA replication inhibitor |
| 3159 | HMGA1 | high mobility group AT-hook 1 |
| 81620 | CDT1 | DNA replication factor |
| 11332 | BACH | brain acyl-CoA hydrolase |
| 4751 | NEK2 | NIMA (never in mitosis gene a)-related kinase 2 |
| 1033 | CDKN3 | cyclin-dependent kinase inhibitor 3 (CDK2-associated dual specificity phosphatase) |
| 8864 | PER2 | period homolog 2 (*Drosophila*) |
| 3418 | IDH2 | isocitrate dehydrogenase 2 (NADP+), mitochondrial |
| 63979 | FIGNL1 | fidgetin-like 1 |
| 55646 | LYAR | hypothetical protein FLJ20425 |
| 91614 | LOC91614 | novel 58.3 KDA protein |
| 8630 | HSD17B6 | hydroxysteroid (17-beta) dehydrogenase 6 |
| 1038 | CDR1 | cerebellar degeneration-related protein 1, 34kDa |
| 6941 | TCF19 | transcription factor 19 (SC1) |
| 256435S | T6GALNAC3 | ST6 (alpha-N-acetyl-neuraminyl-2,3-beta-galactosyl-1,3)-N-acetylgalactosaminide alpha-2,6-sialyltransferase 3 |
| 54892 | LUZP5 | leucine zipper protein 5 |
| 4603 | MYBL1 | v-myb myeloblastosis viral oncogene homolog (avian)-like 1 |
| 1719 | DHFR | dihydrofolate reductase |
| 170954 | KIAA1949 | KIAA1949 |
| 7903 | ST8SIA4 | ST8 alpha-N-acetyl-neuraminide alpha-2,8-sialyltransferase 4 |
| 9787 | DLG7 | discs, large homolog 7 (*Drosophila*) |
| 56935 | FN5 | FN5 protein |
| 3015 | H2AFZ | H2A histone family, member Z |
| 10189 | THOC4 | THO complex 4 |
| 494143 | LOC494143 | similar to RIKEN cDNA 2510006C20 gene |
| 6240 | RRM1 | ribonucleotide reductase M1 polypeptide |
| 1894 | ECT2 | epithelial cell transforming sequence 2 oncogene |
| 7913 | DEK | DEK oncogene (DNA binding) |
| 2146 | EZH2 | enhancer of zeste homolog 2 (*Drosophila*) |
| 55055 | FLJ10036 | Zwilch |
| 11073 | TOPBP1 | topoisomerase (DNA) II binding protein 1 |
| 55502 | HES6 | hairy and enhancer of split 6 (*Drosophila*) |
| 55247 | NEIL3 | nei endonuclease VIII-like 3 (*E. coli*) |
| 54885 | FLJ20298 | FLJ20298 protein |
| 83641 | C10orf45 | chromosome 10 open reading frame 45 |
| 64919 | BCL11B | B-cell CLL/lymphoma 11B (zinc finger protein) |
| 26095 | PTPN20 | protein tyrosine phosphatase, non-receptor type 20 |
| 23590 | TPRT | trans-prenyltransferase |
| 387882 | LOC387882 | hypothetical protein |
| 51232 | CRIM1 | cysteine-rich motor neuron 1 |
| 801 | CALM1 | calmodulin 1 (phosphorylase kinase, delta) |
| 55964 | SEPT3 | septin 3 |
| 493861 | EID3 | E1A-like inhibitor of differentiation 3 |
| 29980 | DONSON | downstream neighbor of SON |
| 147138 | EVER2 | epidermodysplasia verruciformis 2 |
| 80150 | ASRGL1 | asparaginase like 1 |
| 5985 | RFC5 | replication factor C (activator 1) 5, 36.5kDa |
| 51155 | HN1 | hematological and neurological expressed 1 |
| 7004 | TEAD4 | TEA domain family member 4 |
| 4325 | MMP16 | matrix metalloproteinase 16 (membrane-inserted) |
| 203068 | TUBB | tubulin, beta polypeptide |
| 4602 | MYB | v-myb myeloblastosis viral oncogene homolog (avian) |
| 55706 | TMEM48 | transmembrane protein 48 |
| 348235 | FAM33A | family with sequence similarity 33, member A |
| 8871 | SYNJ2 | synaptojanin 2 |
| 81563 | C1orf21 | chromosome 1 open reading frame 21 |
| 51192 | CKLF | chemokine-like factor |
| 2326 | FMO1 | flavin containing monooxygenase 1 |
| 91057 | NY-REN-41 | NY-REN-41 antigen |
| 10376 | K-ALPHA-1 | tubulin, alpha, ubiquitous |
| 23234 | DNAJC9 | DnaJ (Hsp40) homolog, subfamily C, member 9 |

TABLE I-continued

| ENTREZ GENE ID | GENE SYMBOL | GENE DESCRIPTION |
|---|---|---|
| 5982 | RFC2 | replication factor C (activator 1) 2, 40kDa |
| 51063 | FAM26B | family with sequence similarity 26, member B |
| 9953 | HS3ST3B1 | heparan sulfate (glucosamine) 3-O-sulfotransferase 3B1 |
| 79723 | SUV39H2 | suppressor of variegation 3-9 homolog 2 (*Drosophila*) |
| 79596 | C13orf7 | chromosome 13 open reading frame 7 |
| 23165 | NUP205 | nucleoporin 205kDa |
| 9530 | BAG4 | BCL2-associated athanogene 4 |
| 3146 | HMGB1 | high-mobility group box 1 |
| 445815 | PALM2-AKAP2 | PALM2-AKAP2 protein |
| 5557 | PRIM1 | primase, polypeptide 1, 49kDa |
| 2983 | GUCY1B3 | guanylate cyclase 1, soluble, beta 3 |
| 51776 | ZAK | sterile alpha motif and leucine zipper containing kinase AZK |
| 10926 | ASK | activator of S phase kinase |
| 8833 | GMPS | guanine monphosphate synthetase |
| 84930 | MASTL | microtubule associated serine/threonine kinase-like |
| 90417 | C15orf23 | chromosome 15 open reading frame 23 |
| 8530 | CST7 | cystatin F (leukocystatin) |
| 9532 | BAG2 | BCL2-associated athanogene 2 |
| 23310 | hCAP-D3 | KIAA0056 protein |
| 283991 | MGC29814 | hypothetical protein MGC29814 |
| 91607 | FLJ34922 | hypothetical protein FLJ34922 |
| 7398 | USP1 | ubiquitin specific protease 1 |
| 2669 | GEM | GTP binding protein overexpressed in skeletal muscle |
| 151246 | SGOL2 | shugoshin-like 2 (*S. pombe*) |
| 23421 | ITGB3BP | integrin beta 3 binding protein (beta3-endonexin) |
| 84969 | C20orf100 | chromosome 20 open reading frame 100 |
| 201725 | LOC201725 | hypothetical protein LOC201725 |
| 5361 | PLXNA1 | plexin A1 |
| 3708 | ITPR1 | inositol 1,4,5-triphosphate receptor, type 1 |
| 55740 | ENAH | enabled homolog (*Drosophila*) |
| 126731 | C1orf96 | chromosome 1 open reading frame 96 |
| 57037 | ANKMY2 | ankyrin repeat and MYND domain containing 2 |
| 23331 | KIAA1043 | KIAA1043 protein |
| 3930 | LBR | lamin B receptor |
| 3838 | KPNA2 | karyopherin alpha 2 (RAG cohort 1, importin alpha 1) |
| 1230 | CCR1 | chemokine (C-C motif) receptor 1 |
| 2200 | FBN1 | fibrillin 1 (Marfan syndrome) |
| 6867 | TACC1 | transforming, acidic coiled-coil containing protein 1 |
| 27115 | PDE7B | phosphodiesterase 7B |
| 11151 | CORO1A | coronin, actin binding protein, 1A |
| 6385 | SDC4 | syndecan 4 (amphiglycan, ryudocan) |
| 3182 | HNRPAB | heterogeneous nuclear ribonucleoprotein A/B |
| 5757 | PTMA | prothymosin, alpha (gene sequence 28) |
| 83990 | BRIP1 | BRCA1 interacting protein C-terminal helicase 1 |
| 9830 | TRIM14 | tripartite motif-containing 14 |
| 57761 | TRIB3 | tribbles homolog 3 (*Drosophila*) |
| 2026 | ENO2 | enolase 2 (gamma, neuronal) |
| 8727 | CTNNAL1 | catenin (cadherin-associated protein), alpha-like 1 |
| 5880 | RAC2 | ras-related C3 botulinum toxin substrate 2 (rho family, small GTP binding protein Rac2) |
| 864 | RUNX3 | runt-related transcription factor 3 |
| 10950 | BTG3 | BTG family, member 3 |
| 81539 | SLC38A1 | solute carrier family 38, member 1 |
| 26051 | PPP1R16B | protein phosphatase 1, regulatory (inhibitor) subunit 16B |
| 5793 | PTPRG | protein tyrosine phosphatase, receptor type, G |
| 2767 | GNA11 | guanine nucleotide binding protein (G protein), alpha 11 (Gq class) |
| 55013 | FLJ20647 | hypothetical protein FLJ20647 |
| 4885 | NPTX2 | neuronal pentraxin II |
| 79710 | MORC4 | MORC family CW-type zinc finger 4 |
| 490 | ATP2B1 | ATPase, Ca++ transporting, plasma membrane 1 |
| 2956 | MSH6 | mutS homolog 6 (*E. coli*) |
| 6611 | SMS | spermine synthase |
| 6627 | SNRPA1 | small nuclear ribonucleoprotein polypeptide A' |
| 1434 | CSE1L | CSE1 chromosome segregation 1-like (yeast) |
| 7371 | UCK2 | uridine-cytidine kinase 2 |
| 7277 | TUBA1 | tubulin, alpha 1 (testis specific) |
| 1786 | DNMT1 | DNA (cytosine-5-)-methyltransferase 1 |
| 54801 | FAM29A | family with sequence similarity 29, member A |
| 54908 | FLJ20364 | hypothetical protein FLJ20364 |
| 119467 | MGC32871 | hypothetical protein MGC32871 |
| 90390 | THRAP6 | thyroid hormone receptor associated protein 6 |
| 60468 | BACH2 | BTB and CNC homology 1, basic leucine zipper transcription factor 2 |
| 6510 | SLC1A5 | solute carrier family 1 (neutral amino acid transporter), member 5 |
| 6628 | SNRPB | small nuclear ribonucleoprotein polypeptides B and B1 |
| 205 | AK3L1 | adenylate kinase 3-like 1 |
| 116832 | RPL39L | ribosomal protein L39-like |
| 79902 | PCNT1 | pericentrin 1 |
| 54962 | FLJ20516 | timeless-interacting protein |
| 23279 | NUP160 | nucleoporin 160kDa |

TABLE I-continued

| ENTREZ GENE ID | GENE SYMBOL | GENE DESCRIPTION |
|---|---|---|
| 23046 | KIF21B | kinesin family member 21B |
| 2288 | FKBP4 | FK506 binding protein 4, 59kDa |
| 5698 | PSMB9 | proteasome (prosome, macropain) subunit, beta type, 9 (large multifunctional protease 2) |
| 10160 | FARP1 | FERM, RhoGEF (ARHGEF) and pleckstrin domain protein 1 (chondrocyte-derived) |
| 8502 | PKP4 | plakophilin 4 |
| 10675 | CSPG5 | chondroitin sulfate proteoglycan 5 (neuroglycan C) |
| 29899 | GPSM2 | G-protein signalling modulator 2 (AGS3-like, *C. elegans*) |
| 10602 | CDC42EP3 | CDC42 effector protein (Rho GTPase binding) 3 |
| 8243 | SMC1L1 | SMC1 structural maintenance of chromosomes 1-like 1 (yeast) |
| 6347 | CCL2 | chemokine (C-C motif) ligand 2 |
| 5932 | RBBP8 | retinoblastoma binding protein 8 |
| 6877 | TAF5 | TAF5 RNA polymerase II, TATA box binding protein (TBP)-associated factor, 100kDa |
| 10801 | SEPT9 | septin 9 |
| 55536 | CDCA7L | cell division cycle associated 7-like |
| 11340 | EXOSC8 | exosome component 8 |
| 5873 | RAB27A | RAB27A, member RAS oncogene family |
| 53354 | PANK1 | pantothenate kinase 1 |
| 2534 | FYN | FYN oncogene related to SRC, FGR, YES |
| 55166 | C6orf139 | chromosome 6 open reading frame 139 |
| 27346 | MAC30 | hypothetical protein MAC30 |
| 79037 | MGC2463 | hypothetical protein MGC2463 |
| 116496 | C1orf24 | chromosome 1 open reading frame 24 |
| 84314 | MGC10744 | hypothetical protein MGC10744 |
| 23531 | MMD | monocyte to macrophage differentiation-associated |
| 6558 | SLC12A2 | solute carrier family 12 (sodium/potassium/chloride transporters), member 2 |
| 64282 | PAPD5 | PAP associated domain containing 5 |
| 55636 | CHD7 | chromodomain helicase DNA binding protein 7 |
| 55026 | FLJ20716 | hypothetical protein FLJ20716 |
| 22929 | SEPHS1 | selenophosphate synthetase 1 |
| 10541 | ANP32B | acidic (leucine-rich) nuclear phosphoprotein 32 family, member B |
| 79621 | FLJ11712 | hypothetical protein FLJ11712 |
| 6432 | SFRS7 | splicing factor, arginine/serine-rich 7, 35kDa |
| 5214 | PFKP | phosphofructokinase, platelet |
| 26031 | OSBPL3 | oxysterol binding protein-like 3 |
| 1102 | RCBTB2 | regulator of chromosome condensation (RCC1) and BTB (POZ) domain containing protein 2 |
| 6929 | TCF3 | transcription factor 3 (E2A immunoglobulin enhancer binding factors E12/E47) |
| 6632 | SNRPD1 | small nuclear ribonucleoprotein D1 polypeptide 16kDa |
| 2047 | EPHB1 | EPH receptor B1 |
| 5168 | ENPP2 | ectonucleotide pyrophosphatase/phosphodiesterase 2 (autotaxin) |
| 55257 | C20orf20 | chromosome 20 open reading frame 20 |
| 81611 | ANP32E | acidic (leucine-rich) nuclear phosphoprotein 32 family, member E |
| 23246 | BOP1 | block of proliferation 1 |
| 23526 | HA-1 | minor histocompatibility antigen HA-1 |
| 84250 | ANKRD32 | ankyrin repeat domain 32 |
| 6999 | TDO2 | tryptophan 2,3-dioxygenase |
| 8317 | CDC7 | CDC7 cell division cycle 7 (*S. cerevisiae*) |
| 55752 | SEPT11 | septin 11 |
| 39 | ACAT2 | acetyl-Coenzyme A acetyltransferase 2 (acetoacetyl Coenzyme A thiolase) |
| 54830 | FLJ20130 | hypothetical protein FLJ20130 |
| 83732 | RIOK1 | RIO kinase 1 (yeast) |
| 10808 | HSPH1 | heat shock 105kDa/110kDa protein 1 |
| 489 | ATP2A3 | ATPase, Ca++ transporting, ubiquitous |
| 3251 | HPRT1 | hypoxanthine phosphoribosyltransferase 1 (Lesch-Nyhan syndrome) |
| 10051 | SMC4L1 | SMC4 structural maintenance of chromosomes 4-like 1 (yeast) |
| 55816 | DOK5 | docking protein 5 |
| 3676 | ITGA4 | integrin, alpha 4 (antigen CD49D, alpha 4 subunit of VLA-4 receptor) |
| 8819 | SAP30 | sin3-associated polypeptide, 30kDa |
| 4436 | MSH2 | mutS homolog 2, colon cancer, nonpolyposis type 1 (*E. coli*) |
| 10212 | DDX39 | DEAD (Asp-Glu-Ala-Asp) box polypeptide 39 |
| 5889 | RAD51C | RAD51 homolog C (S. cerevisiae) |
| 134111 | FLJ25076 | similar to CG4502-PA |
| 51377 | UCHL5 | ubiquitin carboxyl-terminal hydrolase L5 |
| 6657 | SOX2 | SRY (sex determining region Y)-box 2 |
| 241 | ALOX5AP | arachidonate 5-lipoxygenase-activating protein |
| 79888 | FLJ12443 | hypothetical protein FLJ12443 |
| 1368 | CPM | carboxypeptidase M |
| 397 | ARHGDIB | Rho GDP dissociation inhibitor (GDI) beta |
| 3336 | HSPE1 | heat shock 10kDa protein 1 (chaperonin 10) |
| 2104 | ESRRG | estrogen-related receptor gamma |
| 2171 | FABP5 | fatty acid binding protein 5 (psoriasis-associated) |
| 6574 | SLC20A1 | solute carrier family 20 (phosphate transporter), member 1 |
| 2743 | GLRB | glycine receptor, beta |
| 1019 | CDK4 | cyclin-dependent kinase 4 |
| 9295 | SFRS11 | splicing factor, arginine/serine-rich 11 |
| 56952 | PRTFDC1 | phosphoribosyl transferase domain containing 1 |
| 6472 | SHMT2 | serine hydroxymethyltransferase 2 (mitochondrial) |
| 23512 | SUZ12 | suppressor of zeste 12 homolog (*Drosophila*) |

TABLE I-continued

| ENTREZ GENE ID | GENE SYMBOL | GENE DESCRIPTION |
|---|---|---|
| 586 | BCAT1 | branched chain aminotransferase 1, cytosolic |
| 8836 | GGH | gamma-glutamyl hydrolase (conjugase, folylpolygammaglutamyl hydrolase) |
| 10383 | TUBB2 | tubulin, beta, 2 |
| 54101 | RIPK4 | receptor-interacting serine-threonine kinase 4 |
| 130271 | PLEKHH2 | pleckstrin homology domain containing, family H (with MyTH4 domain) member 2 |
| 129401 | NUP35 | nucleoporin 35kDa |
| 10128 | LRPPRC | leucine-rich PPR-motif containing |
| 51703 | ACSL5 | acyl-CoA synthetase long-chain family member 5 |
| 9448 | MAP4K4 | mitogen-activated protein kinase kinase kinase kinase 4 |
| 79017 | C7orf24 | chromosome 7 open reading frame 24 |
| 262 | AMD1 | adenosylmethionine decarboxylase 1 |
| 960 | CD44 | CD44 antigen (homing function and Indian blood group system) |
| 81930 | KIF18A | kinesin family member 18A |
| 64116 | SLC39A8 | solute carrier family 39 (zinc transporter), member 8 |
| 26586 | CKAP2 | cytoskeleton associated protein 2 |
| 51144 | HSD17B12 | hydroxysteroid (17-beta) dehydrogenase 12 |
| 51002 | CGI-121 | CGI-121 protein |
| 9126 | CSPG6 | chondroitin sulfate proteoglycan 6 (bamacan) |
| 79154 | MGC4172 | short-chain dehydrogenase/reductase |
| 11096 | ADAMTS5 | a disintegrin-like and metalloprotease (reprolysin type) with thrombospondin type 1 motif, 5 (aggrecanase-2) |
| 84803 | MGC11324 | hypothetical protein MGC11324 |
| 4082 | MARCKS | myristoylated alanine-rich protein kinase C substrate |
| 4086 | SMAD1 | SMAD, mothers against DPP homolog 1 (*Drosophila*) |
| 9446 | GSTO1 | glutathione S-transferase omega 1 |
| 23636 | NUP62 | nucleoporin 62kDa |
| 81839 | VANGL1 | vang-like 1 (van gogh, *Drosophila*) |
| 3149 | HMGB3 | high-mobility group box 3 |
| 79023 | NUP37 | nucleoporin 37kDa |
| 10606 | PAICS | phosphoribosylaminoimidazole carboxylase, phosphoribosylaminoimidazole succinocarboxamide synthetase |
| 10492 | SYNCRIP | synaptotagmin binding, cytoplasmic RNA interacting protein |
| 3320 | HSPCA | heat shock 90kDa protein 1, alpha |
| 6119 | RPA3 | replication protein A3, 14kDa |
| 55352 | HSA272196 | hypothetical protein, clone 2746033 |
| 9759 | HDAC4 | histone deacetylase 4 |
| 5725 | PTBP1 | polypyrimidine tract binding protein 1 |
| 2119 | ETV5 | ets variant gene 5 (ets-related molecule) |
| 10019 | LNK | lymphocyte adaptor protein |
| 9734 | HDAC9 | histone deacetylase 9 |
| 5885 | RAD21 | RAD21 homolog (*S. pombe*) |
| 79930 | DOK3 | docking protein 3 |
| 22837 | COBLL1 | COBL-like 1 |
| 339448 | LOC339448 | hypothetical protein LOC339448 |
| 11051 | NUDT21 | nudix (nucleoside diphosphate linked moiety X)-type motif 21 |
| 9735 | KNTC1 | kinetochore associated 1 |
| 4148 | MATN3 | matrilin 3 |
| 4200 | ME2 | malic enzyme 2, NAD(+)-dependent, mitochondrial |
| 26084 | SGEF | Src homology 3 domain-containing guanine nucleotide exchange factor |
| 27101 | CACYBP | calcyclin binding protein |
| 23012 | STK38L | serine/threonine kinase 38 like |
| 54566 | EPB41L4B | erythrocyte membrane protein band 4.1 like 4B |
| 6566 | SLC16A1 | solute carrier family 16 (monocarboxylic acid transporters), member 1 |
| 54947 | FLJ20481 | hypothetical protein FLJ20481 |
| 255488 | IBRDC2 | IBR domain containing 2 |
| 2289 | FKBP5 | FK506 binding protein 5 |
| 5036 | PA2G4 | proliferation-associated 2G4, 38kDa |
| 4869 | NPM1 | nucleophosmin (nucleolar phosphoprotein B23, numatrin) |
| 10384 | BTN3A3 | butyrophilin, subfamily 3, member A3 |
| 10785 | WDR4 | WD repeat domain 4 |
| 3099 | HK2 | hexokinase 2 |
| 56121 | PCDHB15 | protocadherin beta 15 |
| 10155 | TRIM28 | tripartite motif-containing 28 |
| 6340 | SCNN1G | sodium channel, nonvoltage-gated 1, gamma |
| 25804 | LSM4 | LSM4 homolog, U6 small nuclear RNA associated (*S. cerevisiae*) |
| 3939 | LDHA | lactate dehydrogenase A |
| 57552 | AADACL1 | arylacetamide deacetylase-like 1 |
| 9184 | BUB3 | BUB3 budding uninhibited by benzimidazoles 3 homolog (yeast) |
| 657 | BMPR1A | bone morphogenetic protein receptor, type IA |
| 5631 | PRPS1 | phosphoribosyl pyrophosphate synthetase 1 |
| 204 | AK2 | adenylate kinase 2 |
| 55270 | NUDT15 | nudix (nucleoside diphosphate linked moiety X)-type motif 15 |
| 10265 | IRX5 | iroquois homeobox protein 5 |
| 4640 | MYO1A | myosin IA |
| 79180 | EFHD2 | EF hand domain family, member D2 |
| 4076 | M11S1 | membrane component, chromosome 11, surface marker 1 |
| 55276 | PGM2 | phosphoglucomutase 2 |

TABLE I-continued

| ENTREZ GENE ID | GENE SYMBOL | GENE DESCRIPTION |
|---|---|---|
| 83857 | ARG99 | ARG99 protein |
| 116448 | OLIG1 | oligodendrocyte transcription factor 1 |
| 5696 | PSMB8 | proteasome (prosome, macropain) subunit, beta type, 8 (large multifunctional protease 7) |
| 1407 | CRY1 | cryptochrome 1 (photolyase-like) |
| 11177 | BAZ1A | bromodomain adjacent to zinc finger domain, 1A |
| 51015 | ISOC1 | isochorismatase domain containing 1 |
| 1789 | DNMT3B | DNA (cytosine-5-)-methyltransferase 3 beta |
| 22948 | CCT5 | chaperonin containing TCP1, subunit 5 (epsilon) |
| 158563 | LOC158563 | hypothetical protein LOC158563 |
| 89891 | WDR34 | WD repeat domain 34 |
| 119 | ADD2 | adducin 2 (beta) |
| 5358 | PLS3 | plastin 3 (T isoform) |
| 7086 | TKT | transketolase (Wernicke-Korsakoff syndrome) |
| 51174 | TUBD1 | tubulin, delta 1 |
| 23255 | KIAA0802 | KIAA0802 |
| 54149 | C21orf91 | chromosome 21 open reading frame 91 |
| 2271 | FH | fumarate hydratase |
| 55076 | TMEM45A | transmembrane protein 45A |
| 10436 | C2F | C2f protein |
| 8553 | BHLHB2 | basic helix-loop-helix domain containing, class B, 2 |
| 10409 | BASP1 | brain abundant, membrane attached signal protein 1 |
| 22856 | CHSY1 | carbohydrate (chondroitin) synthase 1 |
| 84451 | KIAA1804 | mixed lineage kinase 4 |
| 3150 | HMGN1 | high-mobility group nucleosome binding domain 1 |
| 961 | CD47 | CD47 antigen (Rh-related antigen, integrin-associated signal transducer) |
| 79038 | ZFYVE21 | zinc finger, FYVE domain containing 21 |
| 7291 | TWIST1 | twist homolog 1 (acrocephalosyndactyly 3; Saethre-Chotzen syndrome) (Drosophila) |
| 9738 | CP110 | CP110 protein |
| 10625 | IVNS1ABP | influenza virus NS1A binding protein |
| 9368 | SLC9A3R1 | solute carrier family 9 (sodium/hydrogen exchanger), isoform 3 regulator 1 |
| 3613 | IMPA2 | inositol(myo)-1(or 4)-monophosphatase 2 |
| 8514 | KCNAB2 | potassium voltage-gated channel, shaker-related subfamily, beta member 2 |
| 4957 | ODF2 | outer dense fiber of sperm tails 2 |
| 4673 | NAP1L1 | nucleosome assembly protein 1-like 1 |
| 26018 | LRIG1 | leucine-rich repeats and immunoglobulin-like domains 1 |
| 3033 | HADHSC | L-3-hydroxyacyl-Coenzyme A dehydrogenase, short chain |
| 139886 | LOC139886 | hypothetical protein LOC139886 |
| 10360 | NPM3 | nucleophosmin/nucleoplasmin, 3 |
| 200894 | ARL2L1 | ADP-ribosylation factor-like 2-like 1 |
| 8364 | HIST1H4C | histone 1, H4c |
| 378708 | APITD1 | apoptosis-inducing, TAF9-like domain 1 |
| 169270 | ZNF596 | zinc finger protein 596 |
| 6917 | TCEA1 | transcription elongation factor A (SII), 1 |
| 7091 | TLE4 | transducin-like enhancer of split 4 (E(sp1) homolog, *Drosophila*) |
| 3725 | JUN | v-jun sarcoma virus 17 oncogene homolog (avian) |
| 1736 | DKC1 | dyskeratosis congenita 1, dyskerin |
| 8566 | PDXK | pyridoxal (pyridoxine, vitamin B6) kinase |
| 51176 | LEF1 | lymphoid enhancer-binding factor 1 |
| 87 | ACTN1 | actinin, alpha 1 |
| 10838 | ZNF275 | zinc finger protein 275 |
| 54517 | FLJ20485 | hypothetical protein FLJ20485 |
| 5150 | PDE7A | phosphodiesterase 7A |
| 384 | ARG2 | arginase, type II |
| 27316 | RBMX | RNA binding motif protein, X-linked |
| 389206 | CCDC4 | coiled-coil domain containing 4 |
| 51312 | SLC25A37 | solute carrier family 25, member 37 |
| 9112 | MTA1 | metastasis associated 1 |
| 6711 | SPTBN1 | spectrin, beta, non-erythrocytic 1 |
| 10129 | 13CDNA73 | hypothetical protein CG003 |
| 80014 | BOMB | BH3-only member B protein |
| 27131 | SNX5 | sorting nexin 5 |
| 23089 | PEG10 | paternally expressed 10 |
| 5270 | SERPINE2 | serine (or cysteine) proteinase inhibitor, clade E (nexin, plasminogen activator inhibitor type 1), member 2 |
| 6764 | ST5 | suppression of tumorigenicity 5 |
| 7791 | ZYX | zyxin |
| 22995 | Cep152 | KIAA0912 protein |
| 4137 | MAPT | microtubule-associated protein tau |
| 5411 | PNN | pinin, desmosome associated protein |
| 3087 | HHEX | hematopoietically expressed homeobox |
| 23171 | GPD1L | glycerol-3-phosphate dehydrogenase 1-like |
| 56905 | DKFZP434H132 | DKFZP434H132 protein |
| 3189 | HNRPH3 | heterogeneous nuclear ribonucleoprotein H3 (2H9) |
| 9099 | USP2 | ubiquitin specific protease 2 |
| 10098 | TSPAN5 | tetraspanin 5 |
| 401505 | C9orf105 | chromosome 9 open reading frame 105 |

TABLE I-continued

| ENTREZ GENE ID | GENE SYMBOL | GENE DESCRIPTION |
|---|---|---|
| 51444 | RNF138 | ring finger protein 138 |
| 11118 | BTN3A2 | butyrophilin, subfamily 3, member A2 |
| 8089 | YEATS4 | YEATS domain containing 4 |
| 84108 | PCGF6 | polycomb group ring finger 6 |
| 7514 | XPO1 | exportin 1 (CRM1 homolog, yeast) |
| 9818 | NUPL1 | nucleoporin like 1 |
| 10923 | PC4 | activated RNA polymerase II transcription cofactor 4 |
| 6526 | SLC5A3 | solute carrier family 5 (inositol transporters), member 3 |
| 26010 | DNAPTP6 | DNA polymerase-transactivated protein 6 |
| 5307 | PITX1 | paired-like homeodomain transcription factor 1 |
| 2643 | GCH1 | GTP cyclohydrolase 1 (dopa-responsive dystonia) |
| 1503 | CTPS | CTP synthase |
| 5777 | PTPN6 | protein tyrosine phosphatase, non-receptor type 6 |
| 23122 | CLASP2 | cytoplasmic linker associated protein 2 |
| 5588 | PRKCQ | protein kinase C, theta |
| 64770 | CCDC14 | coiled-coil domain containing 14 |
| 6426 | SFRS1 | splicing factor, arginine/serine-rich 1 (splicing factor 2, alternate splicing factor) |
| 81831 | NETO2 | neuropilin (NRP) and tolloid (TLL)-like 2 |
| 56888 | KCMF1 | potassium channel modulatory factor 1 |
| 9221 | NOLC1 | nucleolar and coiled-body phosphoprotein 1 |
| 79366 | NSBP1 | nucleosomal binding protein 1 |
| 51729 | WBP11 | WW domain binding protein 11 |
| 84444 | DOT1L | DOT1-like, histone H3 methyltransferase (*S. cerevisiae*) |
| 80218 | MAK3 | Mak3 homolog (*S. cerevisiae*) |
| 84319 | MGC4308 | hypothetical protein MGC4308 |
| 112479 | MGC16943 | similar to RIKEN cDNA 4933424N09 gene |
| 64396 | GMCL1L | germ cell-less homolog 1 (*Drosophila*)-like |
| 5905 | RANGAP1 | Ran GTPase activating protein 1 |
| 2177 | FANCD2 | Fanconi anemia, complementation group D2 |
| 55632 | KIAA1333 | KIAA1333 |
| 3695 | ITGB7 | integrin, beta 7 |
| 9793 | CKAP5 | cytoskeleton associated protein 5 |
| 5318 | PKP2 | plakophilin 2 |
| 6652 | SORD | sorbitol dehydrogenase |
| 80709 | AKNA | AT-hook transcription factor |
| 55120 | FANCL | Fanconi anemia, complementation group L |
| 92667 | C20orf72 | chromosome 20 open reading frame 72 |
| 3654 | IRAK1 | interleukin-1 receptor-associated kinase 1 |
| 55975 | KLHL7 | kelch-like 7 (*Drosophila*) |
| 6397 | SEC14L1 | SEC14-like 1 (*S. cerevisiae*) |
| 29117 | BRD7 | bromodomain containing 7 |
| 6732 | SRPK1 | SFRS protein kinase 1 |
| 401081 | FLJ22763 | hypothetical gene supported by AK026416 |
| 8520 | HAT1 | histone acetyltransferase 1 |
| 3119 | HLA-DQB1 | major histocompatibility complex, class II, DQ beta 1 |
| 7283 | TUBG1 | tubulin, gamma 1 |
| 4809 | NHP2L1 | NHP2 non-histone chromosome protein 2-like 1 (*S. cerevisiae*) |
| 2778 | GNAS | GNAS complex locus |
| 5359 | PLSCR1 | phospholipid scramblase 1 |
| 196294 | FLJ25059 | hypothetical protein FLJ25059 |
| 3181 | HNRPA2B1 | heterogeneous nuclear ribonucleoprotein A2/B1 |
| 1794 | DOCK2 | dedicator of cytokinesis 2 |
| 55148 | C14orf130 | chromosome 14 open reading frame 130 |
| 25924 | MYRIP | myosin VIIA and Rab interacting protein |
| 7533 | YWHAH | tyrosine 3-monooxygenase/tryptophan 5-monooxygenase activation protein, eta polypeptide |
| 64968 | MRPS6 | mitochondrial ribosomal protein S6 |
| 4830 | NME1 | non-metastatic cells 1, protein (NM23A) expressed in |
| 165055 | FLJ32745 | hypothetical protein FLJ32745 |
| 151827 | LRRC34 | leucine rich repeat containing 34 |
| 93081 | LOC93081 | hypothetical protein BC015148 |
| 196527 | TMEM16F | transmembrane protein 16F |
| 1827 | DSCR1 | Down syndrome critical region gene 1 |
| 203562 | TMEM31 | transmembrane protein 31 |
| 11335 | CBX3 | chromobox homolog 3 (HP1 gamma homolog, *Drosophila*) |
| 3662 | IRF4 | interferon regulatory factor 4 |
| 8624 | DSCR2 | Down syndrome critical region gene 2 |
| 4092 | SMAD7 | SMAD, mothers against DPP homolog 7 (*Drosophila*) |
| 6934 | TCF7L2 | transcription factor 7-like 2 (T-cell specific, HMG-box) |
| 26112 | DKFZP434C171 | DKFZP434C171 protein |
| 3329 | HSPD1 | heat shock 60kDa protein 1 (chaperonin) |
| 5577 | PRKAR2B | protein kinase, cAMP-dependent, regulatory, type II, beta |
| 3202 | HOXA5 | homeo box A5 |
| 79442 | LRRC2 | leucine rich repeat containing 2 |
| 9631 | NUP155 | nucleoporin 155kDa |
| 55366 | LGR4 | leucine-rich repeat-containing G protein-coupled receptor 4 |
| 23350 | SR140 | U2-associated SR140 protein |
| 6434 | SFRS10 | splicing factor, arginine/serine-rich 10 (transformer 2 homolog, *Drosophila*) |

TABLE I-continued

| ENTREZ GENE ID | GENE SYMBOL | GENE DESCRIPTION |
|---|---|---|
| 7975 | MAFK | v-maf musculoaponeurotic fibrosarcoma oncogene homolog K (avian) |
| 3187 | HNRPH1 | heterogeneous nuclear ribonucleoprotein H1 (H) |
| 94239 | H2AFV | H2A histone family, member V |
| 54913 | RPP25 | ribonuclease P 25kDa subunit |
| 9521 | EEF1E1 | eukaryotic translation elongation factor 1 epsilon 1 |
| 5471 | PPAT | phosphoribosyl pyrophosphate amidotransferase |
| 340252 | ZNF680 | zinc finger protein 680 |
| 1021 | CDK6 | cyclin-dependent kinase 6 |
| 10560 | SLC19A2 | solute carrier family 19 (thiamine transporter), member 2 |
| 4201 | MEA1 | male-enhanced antigen 1 |
| 440145 | LOC440145 | similar to RIKEN cDNA 2410129H14 |
| 3843 | RANBP5 | RAN binding protein 5 |
| 3298 | HSF2 | heat shock transcription factor 2 |
| 387914 | TMEM46 | transmembrane protein 46 |
| 27347 | STK39 | serine threonine kinase 39 (STE20/SPS1 homolog, yeast) |
| 6256 | RXRA | retinoid X receptor, alpha |
| 6637 | SNRPG | small nuclear ribonucleoprotein polypeptide G |
| 22800 | RRAS2 | related RAS viral (r-ras) oncogene homolog 2 |
| 91694 | FLJ23749 | hypothetical protein FLJ23749 |
| 22823 | MTF2 | metal response element binding transcription factor 2 |
| 51184 | MGC14560 | protein x 0004 |
| 10856 | RUVBL2 | RuvB-like 2 (E. coli) |
| 7188 | TRAF5 | TNF receptor-associated factor 5 |
| 5272 | SERPINB9 | serine (or cysteine) proteinase inhibitor, clade B (ovalbumin), member 9 |
| 11169 | WDHD1 | WD repeat and HMG-box DNA binding protein 1 |
| 5606 | MAP2K3 | mitogen-activated protein kinase kinase 3 |
| 4783 | NFIL3 | nuclear factor, interleukin 3 regulated |
| 51691 | LSM8 | LSM8 homolog, U6 small nuclear RNA associated (S. cerevisiae) |
| 1528 | CYB5 | cytochrome b-5 |
| 79899 | FLJ14213 | hypothetical protein FLJ14213 |
| 7334 | UBE2N | ubiquitin-conjugating enzyme E2N (UBC13 homolog, yeast) |
| 2730 | GCLM | glutamate-cysteine ligase, modifier subunit |
| 23157 | SEPT6 | septin 6 |
| 56155 | TEX14 | testis expressed sequence 14 |
| 23658 | LSM5 | LSM5 homolog, U6 small nuclear RNA associated (S. cerevisiae) |
| 1400 | CRMP1 | collapsin response mediator protein 1 |
| 5684 | PSMA3 | proteasome (prosome, macropain) subunit, alpha type, 3 |
| 6713 | SQLE | squalene epoxidase |
| 84955 | NUDCD1 | NudC domain containing 1 |
| 64318 | C10orf117 | chromosome 10 open reading frame 117 |
| 10196 | HRMT1L3 | HMT1 hnRNP methyltransferase-like 3 (S. cerevisiae) |
| 29841 | GRHL1 | grainyhead-like 1 (Drosophila) |
| 10055 | SAE1 | SUMO-1 activating enzyme subunit 1 |
| 9214 | FAIM3 | Fas apoptotic inhibitory molecule 3 |
| 57406 | ABHD6 | abhydrolase domain containing 6 |
| 25914 | RTTN | rotatin |
| 23244 | SCC-112 | SCC-112 protein |
| 3183 | HNRPC | heterogeneous nuclear ribonucleoprotein C (C1/C2) |
| 55117 | SLC6A15 | solute carrier family 6, member 15 |
| 6950 | TCP1 | t-complex 1 |
| 4660 | PPP1R12B | protein phosphatase 1, regulatory (inhibitor) subunit 12B |
| 134429 | STARD4 | START domain containing 4, sterol regulated |
| 157503 | LOC157503 | hypothetical protein LOC157503 |
| 253832 | ZDHHC20 | zinc finger, DHHC-type containing 20 |
| 375061 | MGC15887 | hypothetical gene supported by BC009447 |
| 84986 | ARHGAP19 | Rho GTPase activating protein 19 |
| 8407 | TAGLN2 | transgelin 2 |
| 285704 | RGMB | RGM domain family, member B |
| 5050 | PAFAH1B3 | platelet-activating factor acetylhydrolase, isoform Ib, gamma subunit 29kDa |
| 4208 | MEF2C | MADS box transcription enhancer factor 2, polypeptide C (myocyte enhancer factor 2C) |
| 55614 | C20orf23 | chromosome 20 open reading frame 23 |
| 388796 | LOC388796 | hypothetical LOC388796 |
| 85463 | ZC3H12C | zinc finger CCCH-type containing 12C |
| 51465 | UBE2J1 | ubiquitin-conjugating enzyme E2, J1 (UBC6 homolog, yeast) |
| 9994 | CASP8AP2 | CASP8 associated protein 2 |
| 26135 | PAI-RBP1 | PAI-1 mRNA binding protein |
| 5634 | PRPS2 | phosphoribosyl pyrophosphate synthetase 2 |
| 286319 | TUSC1 | tumor suppressor candidate 1 |
| 6470 | SHMT1 | serine hydroxymethyltransferase 1 (soluble) |
| 9397 | NMT2 | N-myristoyltransferase 2 |
| 10762 | NUP50 | nucleoporin 50kDa |
| 201161 | PRR6 | proline rich 6 |
| 5019 | OXCT1 | 3-oxoacid CoA transferase 1 |
| 159 | ADSS | adenylosuccinate synthase |
| 23587 | DERP6 | S-phase 2 protein |
| 10151 | HNRPA3P1 | heterogeneous nuclear ribonucleoprotein A3 pseudogene 1 |
| 8564 | KMO | kynurenine 3-monooxygenase (kynurenine 3-hydroxylase) |

TABLE I-continued

| ENTREZ GENE ID | GENE SYMBOL | GENE DESCRIPTION |
|---|---|---|
| 1349 | COX7B | cytochrome c oxidase subunit VIIb |
| 283824 | LOC283824 | hypothetical protein LOC283824 |
| 1123 | CHN1 | chimerin (chimaerin) 1 |
| 57522 | SRGAP1 | SLIT-ROBO Rho GTPase activating protein 1 |
| 253782 | LASS6 | LAG1 longevity assurance homolog 6 (S. cerevisiae) |
| 57685 | KIAA1573 | KIAA1573 protein |
| 79695 | GALNT12 | UDP-N-acetyl-alpha-D-galactosamine: polypeptide N-acetylgalactosaminyl-transferase 12 (GalNAc-T12) |
| 90861 | C16orf34 | chromosome 16 open reading frame 34 |
| 26207 | PITPNC1 | phosphatidylinositol transfer protein, cytoplasmic 1 |
| 1164 | CKS2 | CDC28 protein kinase regulatory subunit 2 |
| 396 | ARHGDIA | Rho GDP dissociation inhibitor (GDI) alpha |
| 57530 | CGN | cingulin |
| 1633 | DCK | deoxycytidine kinase |
| 9208 | LRRFIP1 | leucine rich repeat (in FLII) interacting protein 1 |
| 6453 | ITSN1 | intersectin 1 (SH3 domain protein) |
| 24147 | FJX1 | four jointed box 1 (Drosophila) |
| 9882 | TBC1D4 | TBC1 domain family, member 4 |
| 169200 | DKFZp762C1112 | hypothetical protein DKFZp762C1112 |
| 9331 | B4GALT6 | UDP-Gal:betaGlcNAc beta 1,4-galactosyltransferase, polypeptide 6 |
| 55183 | RIF1 | RAP1 interacting factor homolog (yeast) |
| 221362 | LOC221362 | hypothetical protein LOC221362 |
| 8458 | TTF2 | transcription termination factor, RNA polymerase II |
| 1047 | CLGN | calmegin |
| 56919 | DHX33 | DEAH (Asp-Glu-Ala-His) box polypeptide 33 |
| 93949 | CXorf10 | chromosome X open reading frame 10 |
| 5569 | PKIA | protein kinase (cAMP-dependent, catalytic) inhibitor alpha |
| 6891 | TAP2 | transporter 2, ATP-binding cassette, sub-family B (MDR/TAP) |
| 1960 | EGR3 | early growth response 3 |
| 11252 | PACSIN2 | protein kinase C and casein kinase substrate in neurons 2 |
| 51762 | RAB8B | RAB8B, member RAS oncogene family |
| 81575 | DKFZP434F0318 | hypothetical protein DKFZp434F0318 |
| 56906 | THAP10 | THAP domain containing 10 |
| 55110 | FLJ10292 | mago-nashi homolog |
| 5267 | SERPINA4 | serine (or cysteine) proteinase inhibitor, clade A (alpha-1 antiproteinase, antitrypsin), member 4 |
| 1844 | DUSP2 | dual specificity phosphatase 2 |
| 9612 | NCOR2 | nuclear receptor co-repressor 2 |
| 3276 | HRMT1L2 | HMT1 hnRNP methyltransferase-like 2 (S. cerevisiae) |
| 257415 | MGC40405 | hypothetical protein MGC40405 |
| 79720 | FLJ12750 | hypothetical protein FLJ12750 |
| 160897 | ITR | intimal thickness-related receptor |
| 4522 | MTHFD1 | methylenetetrahydrofolate dehydrogenase (NADP+ dependent) 1, methenyltetra-hydrofolate cyclohydrolase, formyltetrahydrofolate synthetase |
| 4668 | NAGA | N-acetylgalactosaminidase, alpha- |
| 84890 | C10orf22 | chromosome 10 open reading frame 22 |
| 5198 | PFAS | phosphoribosylformylglycinamidine synthase (FGAR amidotransferase) |
| 55544 | RNPC1 | RNA-binding region (RNP1, RRM) containing 1 |
| 2618 | GART | phosphoribosylglycinamide formyltransferase, phosphoribosylglycinamide synthetase, phosphoribosylaminoimidazole synthetase |
| 9261 | MAPKAPK2 | mitogen-activated protein kinase-activated protein kinase 2 |
| 285761 | DCBLD1 | discoidin, CUB and LCCL domain containing 1 |
| 23225 | NUP210 | nucleoporin 210kDa |
| 9792 | SERTAD2 | SERTA domain containing 2 |
| 56938 | ARNTL2 | aryl hydrocarbon receptor nuclear translocator-like 2 |
| 23254 | KIAA1026 | kazrin |
| 4628 | MYH10 | myosin, heavy polypeptide 10, non-muscle |
| 23176 | SEPT8 | septin 8 |
| 1432 | MAPK14 | mitogen-activated protein kinase 14 |
| 84549 | RBM13 | RNA binding motif protein 13 |
| 84133 | ZNRF3 | zinc and ring finger 3 |
| 6502 | SKP2 | S-phase kinase-associated protein 2 (p45) |
| 59274 | MESDC1 | mesoderm development candidate 1 |
| 51496 | HSPC129 | hypothetical protein HSPC129 |
| 55151 | TMEM38B | transmembrane protein 38B |
| 57609 | KIAA1463 | KIAA1463 protein |
| 1039 | CDR2 | cerebellar degeneration-related protein 2, 62kDa |
| 143098 | MPP7 | membrane protein, palmitoylated 7 (MAGUK p55 subfamily member 7) |
| 130589 | GALM | galactose mutarotase (aldose 1-epimerase) lymphocyte cytosolic |
| 3937 | LCP2 | protein 2 (SH2 domain containing leukocyte protein of 76kDa) |
| 5420 | PODXL | podocalyxin-like |
| 6509 | SLC1A4 | solute carrier family 1 (glutamate/neutral amino acid transporter), member 4 |
| 64397 | ZFP106 | zinc finger protein 106 homolog (mouse) |
| 4860 | NP | nucleoside phosphorylase |
| 3535 | IGL@ | immunoglobulin lambda locus |
| 1396 | CRIP1 | cysteine-rich protein 1 (intestinal) |
| 1660 | DHX9 | DEAH (Asp-Glu-Ala-His) box polypeptide 9 |
| 4291 | MLF1 | myeloid leukemia factor 1 |

TABLE I-continued

| ENTREZ GENE ID | GENE SYMBOL | GENE DESCRIPTION |
|---|---|---|
| 26973 | CHORDC1 | cysteine and histidine-rich domain (CHORD)-containing, zinc binding protein 1 |
| 81037 | CRR9 | cisplatin resistance related protein CRR9p |
| 10574 | CCT7 | chaperonin containing TCP1, subunit 7 (eta) |
| 79892 | C10orf119 | chromosome 10 open reading frame 119 |
| 9972 | NUP153 | nucleoporin 153kDa |
| 10459 | MAD2L2 | MAD2 mitotic arrest deficient-like 2 (yeast) |
| 483 | ATP1B3 | ATPase, Na+/K+ transporting, beta 3 polypeptide |
| 7552 | ZNF6 | zinc finger protein 6 (CMPX1) |
| 8165 | AKAP1 | A kinase (PRKA) anchor protein 1 |
| 29097 | CNIH4 | cornichon homolog 4 (*Drosophila*) |
| 11198 | SUPT16H | suppressor of Ty 16 homolog (*S. cerevisiae*) |
| 2184 | FAH | fumarylacetoacetate hydrolase (fumarylacetoacetase) |
| 7037 | TFRC | transferrin receptor (p90, CD71) |
| 6461 | SHB | Src homology 2 domain containing adaptor protein B |
| 509 | ATP5C1 | ATP synthase, H+ transporting, mitochondrial F1complex, gamma polypeptide 1 |
| 5591 | PRKDC | protein kinase, DNA-activated, catalytic polypeptide |
| 10682 | EBP | emopamil binding protein (sterol isomerase) |
| 9188 | DDX21 | DEAD (Asp-Glu-Ala-Asp) box polypeptide 21 |
| 3837 | KPNB1 | karyopherin (importin) beta 1 |
| 3191 | HNRPL | heterogeneous nuclear ribonucleoprotein L |
| 10236 | HNRPR | heterogeneous nuclear ribonucleoprotein R |
| 6907 | TBL1X | transducin (beta)-like 1X-linked |
| 56172 | ANKH | ankylosis, progressive homolog (mouse) |
| 23367 | LARP1 | La ribonucleoprotein domain family, member 1 |
| 5778 | PTPN7 | protein tyrosine phosphatase, non-receptor type 7 |
| 100 | ADA | adenosine deaminase |
| 2821 | GPI | glucose phosphate isomerase |
| 9697 | TRAM2 | translocation associated membrane protein 2 |
| 54927 | CHCHD3 | coiled-coil-helix-coiled-coil-helix domain containing 3 |
| 58478 | MASA | E-1 enzyme |
| 6322 | SCML1 | sex comb on midleg-like 1 (*Drosophila*) |
| 292 | SLC25A5 | solute carrier family 25 (mitochondrial carrier; adenine nucleotide translocator), member 5 |
| 10857 | PGRMC1 | progesterone receptor membrane component 1 |
| 55342 | STRBP | spermatid perinuclear RNA binding protein |
| 7150 | TOP1 | topoisomerase (DNA) I |
| 874 | CBR3 | carbonyl reductase 3 |
| 51096 | WDR50 | WD repeat domain 50 |
| 253558 | LYCAT | lysocardiolipin acyltransferase |
| 79053 | ALG8 | asparagine-linked glycosylation 8 homolog (yeast, alpha-1,3-glucosyltransferase) |
| 84300 | C6orf125 | chromosome 6 open reading frame 125 |
| 8975 | USP13 | ubiquitin specific protease 13 (isopeptidase T-3) |
| 220988 | HNRPA3 | heterogeneous nuclear ribonucleoprotein A3 |
| 5315 | PKM2 | pyruvate kinase, muscle |
| 7411 | VBP1 | von Hippel-Lindau binding protein 1 |
| 1665 | DHX15 | DEAH (Asp-Glu-Ala-His) box polypeptide 15 |
| 10963 | STIP1 | stress-induced-phosphoprotein 1 (Hsp70/Hsp90-organizing protein) |
| 253461 | ZBTB38 | zinc finger and BTB domain containing 38 |
| 29080 | HSPC128 | HSPC128 protein |
| 84275 | MGC4399 | mitochondrial carrier protein |
| 1622 | DBI | diazepam binding inhibitor (GABA receptor modulator, acyl-Coenzyme A binding protein) |
| 4953 | ODC1 | ornithine decarboxylase 1 |
| 2029 | ENSA | endosulfine alpha |
| 6404 | SELPLG | selectin P ligand |
| 81034 | MFTC | mitochondrial folate transporter/carrier |
| 81542 | TXNDC | thioredoxin domain containing |
| 25816 | TNFAIP8 | tumor necrosis factor, alpha-induced protein 8 |
| 51582 | AZIN1 | antizyme inhibitor 1 |
| 27436 | EML4 | echinoderm microtubule associated protein like 4 |
| 55720 | FLJ10534 | hypothetical protein FLJ10534 |
| 7295 | TXN | thioredoxin |
| 10539 | TXNL2 | thioredoxin-like 2 |
| 86 | ACTL6A | actin-like 6A |
| 6731 | SRP72 | signal recognition particle 72kDa |
| 23314 | SATB2 | SATB family member 2 |
| 2273 | FHL1 | four and a half LIM domains 1 |
| 3422 | IDI1 | isopentenyl-diphosphate delta isomerase |
| 10935 | PRDX3 | peroxiredoxin 3 |
| 2958 | GTF2A2 | general transcription factor IIA, 2, 12kDa |
| 4144 | MAT2A | methionine adenosyltransferase II, alpha |
| 1964 | EIF1AX | eukaryotic translation initiation factor 1A, X-linked |
| 60 | ACTB | actin, beta |
| 11191 | PTENP1 | phosphatase and tensin homolog (mutated in multiple advanced cancers 1), pseudogene 1 |
| 90843 | TCEAL8 | transcription elongation factor A (SII)-like 8 |
| 57181 | SLC39A10 | solute carrier family 39 (zinc transporter), member 10 |
| 11147 | HHLA3 | HERV-H LTR-associating 3 |

TABLE I-continued

| ENTREZ GENE ID | GENE SYMBOL | GENE DESCRIPTION |
|---|---|---|
| 10553 | HTATIP2 | HIV-1 Tat interactive protein 2, 30kDa |
| 3338 | DNAJC4 | DnaJ (Hsp40) homolog, subfamily C, member 4 |
| 84888 | SPPL2A | signal peptide peptidase-like 2A |
| 1955 | EGFL5 | EGF-like-domain, multiple 5 |
| 329 | BIRC2 | baculoviral IAP repeat-containing 2 |
| 29927 | SEC61A1 | Sec61 alpha 1 subunit (*S. cerevisiae*) |
| 9559 | VPS26 | vacuolar protein sorting 26 (yeast) |
| 23270 | TSPYL4 | TSPY-like 4 |
| 6309 | SC5DL | sterol-C5-desaturase (ERG3 delta-5-desaturase homolog, fungal)-like |
| 10397 | NDRG1 | N-myc downstream regulated gene 1 |
| 27032 | ATP2C1 | ATPase, Ca++ transporting, type 2C, member 1 |
| 11112 | HIBADH | 3-hydroxyisobutyrate dehydrogenase |
| 1476 | CSTB | cystatin B (stefin B) |
| 9620 | CELSR1 | cadherin, EGF LAG seven-pass G-type receptor 1 (flamingo homolog, *Drosophila*) |
| 56650 | C3orf4 | chromosome 3 open reading frame 4 |
| 29922 | NME7 | non-metastatic cells 7, protein expressed in (nucleoside-diphosphate kinase) |
| 8887 | TAXI BP1 | Tax1 (human T-cell leukemia virus type I) binding protein 1 |
| 5445 | PON2 | paraoxonase 2 |
| 81889 | FAHD1 | fumarylacetoacetate hydrolase domain containing 1 |
| 694 | BTG1 | B-cell translocation gene 1, anti-proliferative |
| 29058 | C20orf30 | chromosome 20 open reading frame 30 |
| 2752 | GLUL | glutamate-ammonia ligase (glutamine synthase) |
| 79717 | FLJ11838 | hypothetical protein FLJ11838 |
| 170622 | COMMD6 | COMM domain containing 6 |
| 5792 | PTPRF | protein tyrosine phosphatase, receptor type, F |
| 64393 | WIG1 | p53 target zinc finger protein |
| 549 | AUH | AU RNA binding protein/enoyl-Coenzyme A hydratase |
| 51282 | SCAND1 | SCAN domain containing 1 |
| 79027 | ZNF655 | zinc finger protein 655 |
| 6451 | SH3BGRL | SH3 domain binding glutamic acid-rich protein like |
| 1347 | COX7A2 | cytochrome c oxidase subunit VIIa polypeptide 2 (liver) |
| 550643 | L00550643 | hypothetical protein L00550643 |
| 6926 | TBX3 | T-box 3 (ulnar mammary syndrome) |
| 51614 | SDBCAG84 | serologically defined breast cancer antigen 84 |
| 9520 | NPEPPS | aminopeptidase puromycin sensitive |
| 51065 | RPS27L | ribosomal protein S27-like |
| 10116 | FEM1B | fem-1 homolog b (*C. elegans*) |
| 10521 | DDX17 | DEAD (Asp-Glu-Ala-Asp) box polypeptide 17 |
| 81557 | MAGED4 | melanoma antigen family D, 4 |
| 10133 | OPTN | optineurin |
| 54504 | CPVL | carboxypeptidase, vitellogenic-like |
| 64062 | C13orf10 | chromosome 13 open reading frame 10 |
| 401115 | LOC401115 | hypothetical gene supported by BC038466; BC062790 |
| 6892 | TAPBP | TAP binding protein (tapasin) |
| 8087 | FXR1 | fragile X mental retardation, autosomal homolog 1 |
| 7905 | C5orf18 | chromosome 5 open reading frame 18 |
| 3916 | LAMP1 | lysosomal-associated membrane protein 1 |
| 22982 | KIAA0934 | KIAA0934 |
| 55615 | PRR5 | proline rich protein 5 |
| 5651 | PRSS7 | protease, serine, 7 (enterokinase) |
| 10449 | ACAA2 | acetyl-Coenzyme A acyltransferase 2 (mitochondrial 3-oxoacyl-Coenzyme A thiolase) |
| 8934 | RAB7L1 | RAB7, member RAS oncogene family-like 1 |
| 10114 | HIPK3 | homeodomain interacting protein kinase 3 |
| 57560 | WDR56 | WD repeat domain 56 |
| 51205 | ACP6 | acid phosphatase 6, lysophosphatidic |
| 6238 | RRBP1 | ribosome binding protein 1 homolog 180kDa (dog) |
| 151011 | SEPT10 | septin 10 |
| 22920 | KIFAP3 | kinesin-associated protein 3 |
| 3958 | LGALS3 | lectin, galactoside-binding, soluble, 3 (galectin 3) |
| 84186 | ZCCHC7 | zinc finger, CCHC domain containing 7 |
| 9452 | ITM2A | integral membrane protein 2A |
| 10159 | ATP6AP2 | ATPase, H+ transporting, lysosomal accessory protein 2 |
| 23641 | LDOC1 | leucine zipper, down-regulated in cancer 1 |
| 967 | CD63 | CD63 antigen (melanoma 1 antigen) |
| 2517 | FUCA1 | fucosidase, alpha-L- 1, tissue |
| 23219 | FBXO28 | F-box protein 28 |
| 79982 | DNAJB14 | DnaJ (Hsp40) homolog, subfamily B, member 14 |
| 7328 | UBE2H | ubiquitin-conjugating enzyme E2H (UBC8 homolog, yeast) |
| 23355 | KIAA0804 | KIAA0804 |
| 257103 | C21orf86 | chromosome 21 open reading frame 86 |
| 6307 | SC4MOL | sterol-C4-methyl oxidase-like |
| 23376 | KIAA0776 | KIAA0776 |
| 57700 | KIAA1600 | KIAA1600 |
| 85461 | TANG | TPR domain, ankyrin-repeat and coiled-coil-containing |
| 4247 | MGAT2 | mannosyl (alpha-1,6-)-glycoprotein beta-1,2-N-acetylglucosaminyltransferase |
| 3383 | ICAM1 | intercellular adhesion molecule 1 (CD54), human rhinovirus receptor |
| 493812 | HCG11 | HLA complex group 11 |

TABLE I-continued

| ENTREZ GENE ID | GENE SYMBOL | GENE DESCRIPTION |
|---|---|---|
| 5921 | RASA1 | RAS p21 protein activator (GTPase activating protein) 1 |
| 23563 | CHST5 | carbohydrate (N-acetylglucosamine 6-O) sulfotransferase 5 |
| 51100 | SH3GLB1 | SH3-domain GRB2-like endophilin B1 |
| 339988 | LOC339988 | hypothetical protein LOC339988 |
| 79080 | MGC2574 | hypothetical protein MGC2574 |
| 55761 | TTC17 | tetratricopeptide repeat domain 17 |
| 144871 | LOC144871 | hypothetical protein LOC144871 |
| 4194 | MDM4 | Mdm4, transformed 3T3 cell double minute 4, p53 binding protein (mouse) |
| 51030 | FAM18B | family with sequence similarity 18, member B |
| 1650 | DDOST | dolichyl-diphosphooligosaccharide-protein glycosyltransferase |
| 147463 | ANKRD29 | ankyrin repeat domain 29 |
| 3757 | KCNH2 | potassium voltage-gated channel, subfamily H (eag-related), member 2 |
| 116442 | RAB39B | RAB39B, member RAS oncogene family |
| 10972 | TMP21 | transmembrane trafficking protein |
| 57798 | GATAD1 | GATA zinc finger domain containing 1 |
| 1314 | COPA | coatomer protein complex, subunit alpha |
| 2581 | GALC | galactosylceramidase (Krabbe disease) |
| 91452 | ACBD5 | acyl-Coenzyme A binding domain containing 5 |
| 8879 | SGPL1 | sphingosine-1-phosphate lyase 1 |
| 4897 | NRCAM | neuronal cell adhesion molecule |
| 23209 | MLC1 | megalencephalic leukoencephalopathy with subcortical cysts 1 |
| 440270 | LOC440270 | golgin-67 |
| 5034 | P4HB | procollagen-proline, 2-oxoglutarate 4-dioxygenase (proline 4-hydroxylase), beta polypeptide (protein disulfide isomerase-associated 1) |
| 148646 | FLJ32096 | hypothetical protein FLJ32096 |
| 399917 | LOC399917 | similar to polymerase |
| 7096 | TLR1 | toll-like receptor 1 |
| 80853 | KIAA1718 | KIAA1718 protein |
| 378938 | MALAT1 | metastasis associated lung adenocarcinoma transcript 1 (non-coding RNA) |
| 1266 | CNN3 | calponin 3, acidic |
| 58486 | LOC58486 | transposon-derived Buster1 transposase-like protein gene |
| 1040 | CDS1 | CDP-diacylglycerol synthase (phosphatidate cytidylyltransferase) 1 |
| 9895 | KIAA0329 | KIAA0329 |
| 1509 | CTSD | cathepsin D (lysosomal aspartyl protease) |
| 26115 | DKFZP564D166 | putative ankyrin-repeat containing protein |
| 57162 | PELI1 | pellino homolog 1 (Drosophila) |
| 57599 | WDR48 | WD repeat domain 48 |
| 285464 | FLJ34443 | hypothetical protein FLJ34443 |
| 55857 | C20orf19 | chromosome 20 open reading frame 19 |
| 339456 | LOC339456 | hypothetical protein LOC339456 |
| 51569 | UFM1 | ubiquitin-fold modifier 1 |
| 582 | BBS1 | Bardet-Biedl syndrome 1 |
| 4637 | MYL6 | myosin, light polypeptide 6, alkali, smooth muscle and non-muscle |
| 1186 | CLCN7 | chloride channel 7 |
| 3490 | IGFBP7 | insulin-like growth factor binding protein 7 |
| 5095 | PCCA | propionyl Coenzyme A carboxylase, alpha polypeptide |
| 10966 | RAB40B | RAB40B, member RAS oncogene family |
| 285362 | SUMF1 | sulfatase modifying factor 1 |
| 56122 | PCDHB14 | protocadherin beta 14 |
| 57534 | MIB1 | mindbomb homolog 1 (Drosophila) |
| 56951 | C5orf15 | chromosome 5 open reading frame 15 |
| 113177 | C19orf36 | chromosome 19 open reading frame 36 |
| 10379 | ISGF3G | interferon-stimulated transcription factor 3, gamma 48kDa |
| 64224 | FLJ22313 | hypothetical protein FLJ22313 |
| 65084 | FLJ22104 | hypothetical protein FLJ22104 |
| 10537 | UBD | ubiquitin D |
| 8548 | BLZF1 | basic leucine zipper nuclear factor 1 (JEM-1) |
| 284214 | LOC284214 | hypothetical protein LOC284214 |
| 8334 | HIST1H2AC | histone 1, H2ac |
| 80210 | FLJ12584 | melanoma/melanocyte specific protein KU-MEL-1 |
| 1182 | CLCN3 | chloride channel 3 |
| 26751 | SH3YL1 | SH3 domain containing, Ysc84-like 1 (S. cerevisiae) |
| 114327 | EFHC1 | EF-hand domain (C-terminal) containing 1 |
| 7351 | UCP2 | uncoupling protein 2 (mitochondrial, proton carrier) |
| 10724 | MGEA5 | meningioma expressed antigen 5 (hyaluronidase) |
| 9652 | KIAA0372 | KIAA0372 |
| 200958 | MUC20 | mucin 20 |
| 161527 | LOC161527 | hypothetical protein LOC161527 |
| 10314 | LANCL1 | LanC lantibiotic synthetase component C-like 1 (bacterial) |
| 2923 | PDIA3 | protein disulfide isomerase family A, member 3 |
| 84247 | LDOC1L | leucine zipper, down-regulated in cancer 1-like |
| 3006 | HIST1H1C | histone 1, H1c |
| 9562 | MINPP1 | multiple inositol polyphosphate histidine phosphatase, 1 |
| 115024 | MGC20781 | hypothetical protein MGC20781 |
| 65982 | FLJ12895 | hypothetical protein FLJ12895 |
| 5268 | SERPINB5 | serine (or cysteine) proteinase inhibitor, clade B (ovalbumin), member 5 |
| 94240 | EPSTI1 | epithelial stromal interaction 1 (breast) |
| 2621 | GAS6 | growth arrest-specific 6 |

TABLE I-continued

| ENTREZ GENE ID | GENE SYMBOL | GENE DESCRIPTION |
|---|---|---|
| 401024 | FLJ44048 | FLJ44048 protein |
| 57142 | RTN4 | reticulon 4 |
| 50854 | C6orf48 | chromosome 6 open reading frame 48 |
| 317649 | EIF4E3 | eukaryotic translation initiation factor 4E member 3 |
| 4179 | MCP | membrane cofactor protein (CD46, trophoblast-lymphocyte cross-reactive antigen) |
| 54884 | RetSat | all-trans-13,14-dihydroretinol saturase |
| 10154 | PLXNC1 | plexin C1 |
| 2630 | GBAP | glucosidase, beta; acid, pseudogene |
| 7077 | TIMP2 | tissue inhibitor of metalloproteinase 2 |
| 23741 | CRI1 | CREBBP/EP300 inhibitor 1 |
| 949 | SCARB1 | scavenger receptor class B, member 1 |
| 1519 | CTSO | cathepsin O |
| 51136 | LOC51136 | PTD016 protein |
| 3428 | IFI16 | interferon, gamma-inducible protein 16 |
| 9516 | LITAF | lipopolysaccharide-induced TNF factor |
| 3123 | HLA-DRB1 | major histocompatibility complex, class II, DR beta 1 |
| 1389 | CREBL2 | cAMP responsive element binding protein-like 2 |
| 5027 | P2RX7 | purinergic receptor P2X, ligand-gated ion channel, 7 |
| 6782 | STCH | stress 70 protein chaperone, microsome-associated, 60kDa |
| 5645 | PRSS2 | protease, serine, 2 (trypsin 2) |
| 84282 | RNF135 | ring finger protein 135 |
| 9852 | EPM2AIP1 | EPM2A (laforin) interacting protein 1 |
| 84333 | PCGF5 | polycomb group ring finger 5 |
| 23475 | QPRT | quinolinate phosphoribosyltransferase (nicotinate-nucleotide pyrophosphorylase (carboxylating)) |
| 11142 | PKIG | protein kinase (cAMP-dependent, catalytic) inhibitor gamma |
| 54832 | VPS13C | vacuolar protein sorting 13C (yeast) |
| 1486 | CTBS | chitobiase, di-N-acetyl- |
| 4601 | MXI1 | MAX interactor 1 |
| 1365 | CLDN3 | claudin 3 |
| 81622 | UNC93B1 | unc-93 homolog B1 (*C. elegans*) |
| 54664 | FLJ11273 | hypothetical protein FLJ11273 |
| 9993 | DGCR2 | DiGeorge syndrome critical region gene 2 |
| 57179 | KIAA1191 | KIAA1191 protein |
| 55958 | KLHL9 | kelch-like 9 (*Drosophila*) |
| 81671 | TMEM49 | transmembrane protein 49 |
| 9666 | DZIP3 | zinc finger DAZ interacting protein 3 |
| 10509 | SEMA4B | sema domain, immunoglobulin domain (Ig), transmembrane domain (TM) and short cytoplasmic domain, (semaphorin) 4B |
| 3782 | KCNN3 | potassium intermediate/small conductance calcium-activated channel, subfamily N, member 3 |
| 4644 | MYO5A | myosin VA (heavy polypeptide 12, myoxin) |
| 55179 | FAIM | Fas apoptotic inhibitory molecule |
| 9687 | GREB1 | GREB1 protein |
| 25861 | DFNB31 | deafness, autosomal recessive 31 |
| 9197 | SLC33A1 | solute carrier family 33 (acetyl-CoA transporter), member 1 |
| 10549 | PRDX4 | peroxiredoxin 4 |
| 27090 | ST6GALNAC4 | ST6 (alpha-N-acetyl-neuraminyl-2,3-beta-galactosyl-1,3)-N-acetylgalactosaminide alpha-2,6-sialyltransferase 4 |
| 3988 | LIPA | lipase A, lysosomal acid, cholesterol esterase (Wolman disease) |
| 10577 | NPC2 | Niemann-Pick disease, type C2 |
| 441951 | HSUP1 | similar to RPE-spondin |
| 26275 | HIBCH | 3-hydroxyisobutyryl-Coenzyme A hydrolase |
| 401397 | LOC401397 | hypothetical LOC401397 |
| 81555 | YIPF5 | Yip1 domain family, member 5 |
| 19 | ABCA1 | ATP-binding cassette, sub-family A (ABC1), member 1 |
| 2896 | GRN | granulin |
| 1312 | COMT | catechol-O-methyltransferase |
| 127018 | LYPLAL1 | lysophospholipase-like 1 |
| 5911 | RAP2A | RAP2A, member of RAS oncogene family |
| 3017 | HIST1H2BD | histone 1, H2bd |
| 9139 | CBFA2T2 | core-binding factor, runt domain, alpha subunit 2; translocated to, 2 |
| 50848 | F11R | F11 receptor |
| 3728 | JUP | junction plakoglobin |
| 8615 | VDP | vesicle docking protein p115 |
| 79090 | MGC2650 | hypothetical protein MGC2650 |
| 51303 | FKBP11 | FK506 binding protein 11, 19kDa |
| 64747 | MFSD1 | major facilitator superfamily domain containing 1 |
| 23471 | TRAM1 | translocation associated membrane protein 1 |
| 1832 | DSP | desmoplakin |
| 125144 | MGC40157 | hypothetical protein MGC40157 |
| 10150 | MBNL2 | muscleblind-like 2 (*Drosophila*) |
| 3082 | HGF | hepatocyte growth factor (hepapoietin A; scatter factor) |
| 7750 | ZNF198 | zinc finger protein 198 |
| 2908 | NR3C1 | nuclear receptor subfamily 3, group C, member 1 (glucocorticoid receptor) |
| 25758 | G2 | G2 protein |
| 10653 | SPINT2 | serine protease inhibitor, Kunitz type, 2 |
| 116151 | C20orf108 | chromosome 20 open reading frame 108 |

TABLE I-continued

| ENTREZ GENE ID | GENE SYMBOL | GENE DESCRIPTION |
|---|---|---|
| 8933 | CXX1 | CAAX box 1 |
| 475 | ATOX1 | ATX1 antioxidant protein 1 homolog (yeast) |
| 23406 | COTL1 | coactosin-like 1 (*Dictyostelium*) |
| 57561 | ARRDC3 | arrestin domain containing 3 |
| 55205 | ZNF532 | zinc finger protein 532 |
| 25796 | PGLS | 6-phosphogluconolactonase |
| 283846 | DKFZp547E087 | P1-3-kinase-related kinase SMG-1-like |
| 57185 | DJ462O23.2 | hypothetical protein dJ462O23.2 |
| 54431 | DNAJC10 | DnaJ (Hsp40) homolog, subfamily C, member 10 |
| 5800 | PTPRO | protein tyrosine phosphatase, receptor type, O |
| 1465 | CSRP1 | cysteine and glycine-rich protein 1 |
| 950 | SCARB2 | scavenger receptor class B, member 2 |
| 51019 | CGI-116 | CGI-116 protein |
| 5476 | PPGB | protective protein for beta-galactosidase (galactosialidosis) |
| 54145 | H2BFS | H2B histone family, member S |
| 65981 | C1QDC1 | C1q domain containing 1 |
| 81502 | HM13 | histocompatibility (minor) 13 |
| 3572 | IL6ST | interleukin 6 signal transducer (gp130, oncostatin M receptor) |
| 1299 | COL9A3 | collagen, type IX, alpha 3 |
| 1386 | ATF2 | activating transcription factor 2 |
| 4134 | MAP4 | microtubule-associated protein 4 |
| 3981 | LIG4 | ligase IV, DNA, ATP-dependent |
| 57714 | KIAA1618 | KIAA1618 |
| 80315 | CPEB4 | cytoplasmic polyadenylation element binding protein 4 |
| 107 | ADCY1 | adenylate cyclase 1 (brain) |
| 8804 | CREG1 | cellular repressor of E1A-stimulated genes 1 |
| 84181 | CHD6 | chromodomain helicase DNA binding protein 6 |
| 22871 | NLGN1 | neuroligin 1 |
| 659 | BMPR2 | bone morphogenetic protein receptor, type II (serine/threonine kinase) |
| 79158 | MGC4170 | MGC4170 protein |
| 112399 | EGLN3 | egl nine homolog 3 (*C. elegans*) |
| 10550 | ARL6IP5 | ADP-ribosylation-like factor 6 interacting protein 5 |
| 55573 | H41 | hypothetical protein H41 |
| 51706 | NQO3A2 | NAD(P)H:quinone oxidoreductase type 3, polypeptide A2 |
| 79738 | FLJ23560 | hypothetical protein FLJ23560 |
| 6672 | SP100 | nuclear antigen Sp100 |
| 145173 | B3GTL | beta 3-glycosyltransferase-like |
| 3275 | HRMT1L1 | HMT1 hnRNP methyltransferase-like 1 (*S. cerevisiae*) |
| 54059 | C21orf57 | chromosome 21 open reading frame 57 |
| 571 | BACH1 | BTB and CNC homology 1, basic leucine zipper transcription factor 1 |
| 6990 | TCTE1L | t-complex-associated-testis-expressed 1-like |
| 9341 | VAMP3 | vesicle-associated membrane protein 3 (cellubrevin) |
| 2180 | ACSL1 | acyl-CoA synthetase long-chain family member 1 |
| 2799 | GNS | glucosamine (N-acetyl)-6-sulfatase (Sanfilippo disease IIID) |
| 9236 | CCPG1 | cell cycle progression 1 |
| 51111 | SUV420H1 | suppressor of variegation 4-20 homolog 1 (*Drosophila*) |
| 598 | BCL2L1 | BCL2-like 1 |
| 57674 | C17orf27 | chromosome 17 open reading frame 27 |
| 1488 | CTBP2 | C-terminal binding protein 2 |
| 80267 | C1orf22 | chromosome 1 open reading frame 22 |
| 90701 | SEC11L3 | SEC11-like 3 (*S. cerevisiae*) |
| 84218 | TBC1D3 | TBC1 domain family, member 3 |
| 7844 | RNF103 | ring finger protein 103 |
| 8440 | NCK2 | NCK adaptor protein 2 |
| 25934 | NIPSNAP3A | nipsnap homolog 3A (*C. elegans*) |
| 3897 | L1CAM | L1 cell adhesion molecule |
| 114915 | TIGA1 | TIGA1 |
| 754 | PTTG1IP | pituitary tumor-transforming 1 interacting protein |
| 10525 | HYOU1 | hypoxia up-regulated 1 |
| 966 | CD59 | CD59 antigen p18-20 (antigen identified by monoclonal antibodies 16.3A5, EJ16, EJ30, EL32 and G344) |
| 25976 | TIPARP | TCDD-inducible poly(ADP-ribose) polymerase |
| 3714 | JAG2 | jagged 2 |
| 8780 | RIOK3 | RIO kinase 3 (yeast) |
| 55827 | IQWD1 | IQ motif and WD repeats 1 |
| 55830 | GLT8D1 | glycosyltransferase 8 domain containing 1 |
| 4779 | NFE2L1 | nuclear factor (erythroid-derived 2)-like 1 |
| 7286 | TUFT1 | tuftelin 1 |
| 1028 | CDKN1C | cyclin-dependent kinase inhibitor 1C (p57, Kip2) |
| 60492 | MDS025 | hypothetical protein MDS025 |
| 27319 | BHLHB5 | basic helix-loop-helix domain containing, class B, 5 |
| 1958 | EGR1 | early growth response 1 |
| 89796 | NAV1 | neuron navigator 1 |
| 9240 | PNMA1 | paraneoplastic antigen MA1 |
| 6773 | STAT2 | signal transducer and activator of transcription 2, 113kDa |
| 7494 | XBP1 | X-box binding protein 1 |
| 11057 | ABHD2 | abhydrolase domain containing 2 |
| 9451 | EIF2AK3 | eukaryotic translation initiation factor 2-alpha kinase 3 |

TABLE I-continued

| ENTREZ GENE ID | GENE SYMBOL | GENE DESCRIPTION |
|---|---|---|
| 8878 | SQSTM1 | sequestosome 1 |
| 302 | ANXA2 | annexin A2 |
| 2590 | GALNT2 | UDP-N-acetyl-alpha-D-galactosamine: polypeptide N-acetylgalactosaminyltransferase 2 (GalNAc-T2) |
| 1200 | TPP1 | tripeptidyl peptidase I |
| 5973 | RENBP | renin binding protein |
| 7259 | TSPYL1 | TSPY-like 1 |
| 112770 | C1orf85 | chromosome 1 open reading frame 85 |
| 93953 | ACRC | acidic repeat containing |
| 90634 | CG018 | hypothetical gene CG018 |
| 1030 | CDKN2B | cyclin-dependent kinase inhibitor 2B (p15, inhibits CDK4) |
| 158158 | RASEF | RAS and EF hand domain containing |
| 2824 | GPM6B | glycoprotein M6B |
| 9706 | ULK2 | unc-51-like kinase 2 (*C. elegans*) |
| 92370 | ACPL2 | acid phosphatase-like 2 |
| 1203 | CLN5 | ceroid-lipofuscinosis, neuronal 5 |
| 8337 | HIST2H2AA | histone 2, H2aa |
| 3998 | LMAN1 | lectin, mannose-binding, 1 |
| 56675 | NRIP3 | nuclear receptor interacting protein 3 |
| 4864 | NPC1 | Niemann-Pick disease, type C1 |
| 3358 | HTR2C | 5-hydroxytryptamine (serotonin) receptor 2C |
| 304 | ANXA2P2 | annexin A2 pseudogene 2 |
| 81790 | RNF170 | ring finger protein 170 |
| 2537 | G1P3 | interferon, alpha-inducible protein (clone IFI-6-16) |
| 55251 | C20orf36 | chromosome 20 open reading frame 36 |
| 27344 | PCSK1N | proprotein convertase subtilisin/kexin type 1 inhibitor |
| 10057 | ABCC5 | ATP-binding cassette, sub-family C (CFTR/MRP), member 5 |
| 81031 | SLC2A10 | solute carrier family 2 (facilitated glucose transporter), member 10 |
| 467 | ATF3 | activating transcription factor 3 |
| 94103 | ORMDL3 | ORM1-like 3 (*S. cerevisiae*) |
| 375593 | TRIM50B | tripartite motif-containing 50B |
| 23015 | GM88 | 88-kDa golgi protein |
| 55818 | JMJD1A | jumonji domain containing 1A |
| 5274 | SERPINI1 | serine (or cysteine) proteinase inhibitor, clade I (neuroserpin), member 1 |
| 23336 | DMN | desmuslin |
| 255631 | COL24A1 | collagen, type XXIV, alpha 1 |
| 3995 | FADS3 | fatty acid desaturase 3 |
| 5797 | PTPRM | protein tyrosine phosphatase, receptor type, M |
| 55876 | GSDML | gasdermin-like |
| 999 | CDH1 | cadherin 1, type 1, E-cadherin (epithelial) |
| 84897 | TBRG1 | transforming growth factor beta regulator 1 |
| 51363 | GALNAC4S-6ST | B cell RAG associated protein |
| 9961 | MVP | major vault protein |
| 2982 | GUCY1A3 | guanylate cyclase 1, soluble, alpha 3 |
| 706 | BZRP | benzodiazapine receptor (peripheral) |
| 144203 | OVOS2 | ovostatin 2 |
| 8516 | ITGA8 | integrin, alpha 8 |
| 2037 | EPB41L2 | erythrocyte membrane protein band 4.1-like 2 |
| 1524 | CX3CR1 | chemokine (C-X3-C motif) receptor 1 |
| 222166 | Ells1 | hypothetical protein Ells1 |
| 339803 | LOC339803 | hypothetical protein LOC339803 |
| 5360 | PLTP | phospholipid transfer protein |
| 1612 | DAPK1 | death-associated protein kinase 1 |
| 90161 | HS6ST2 | heparan sulfate 6-O-sulfotransferase 2 |
| 115701 | ALPK2 | alpha-kinase 2 |
| 50640 | IPLA2(GAMMA) | intracellular membrane-associated calcium-independent phospholipase A2 gamma |
| 8473 | OGT | O-linked N-acetylglucosamine (GlcNAc) transferase (UDP-N-acetylglucosamine: polypeptide-N-acetylglucosaminyl transferase) |
| 252839 | TMEM9 | transmembrane protein 9 |
| 150759 | LOC150759 | hypothetical protein LOC150759 |
| 401152 | LOC401152 | HCV F-transactivated protein 1 |
| 64065 | PERP | PERP, TP53 apoptosis effector |
| 114793 | FMNL2 | formin-like 2 |
| 477 | ATP1A2 | ATPase, Na+/K+ transporting, alpha 2 (+) polypeptide |
| 59338 | PLEKHA1 | pleckstrin homology domain containing, family A (phosphoinositide binding specific) member 1 |
| 3727 | JUND | jun D proto-oncogene |
| 85236 | HIST1H2BK | histone 1, H2bk |
| 6513 | SLC2A1 | solute carrier family 2 (facilitated glucose transporter), member 1 |
| 155038 | GIMAP8 | GTPase, IMAP family member 8 |
| 3055 | HCK | hemopoietic cell kinase |
| 6542 | SLC7A2 | solute carrier family 7 (cationic amino acid transporter, y+ system), member 2 |
| 8996 | NOL3 | nucleolar protein 3 (apoptosis repressor with CARD domain) |
| 9728 | KIAA0256 | KIAA0256 gene product |
| 51237 | PACAP | proapoptotic caspase adaptor protein |
| 8987 | GENX-3414 | genethonin 1 |
| 132720 | FLJ39370 | hypothetical protein FLJ39370 |
| 1601 | DAB2 | disabled homolog 2, mitogen-responsive phosphoprotein (*Drosophila*) |

TABLE I-continued

| ENTREZ GENE ID | GENE SYMBOL | GENE DESCRIPTION |
|---|---|---|
| 54741 | LEPROT | leptin receptor overlapping transcript |
| 81631 | MAP1LC3B | microtubule-associated protein 1 light chain 3 beta |
| 9473 | C1orf38 | chromosome 1 open reading frame 38 |
| 94241 | TP53INP1 | tumor protein p53 inducible nuclear protein 1 |
| 5816 | PVALB | parvalbumin |
| 115294 | LOC115294 | similar to hypothetical protein FLJ10883 |
| 23461 | ABCA5 | ATP-binding cassette, sub-family A (ABC1), member 5 |
| 10370 | CITED2 | Cbp/p300-interacting transactivator, with Glu/Asp-rich carboxy-terminal domain, 2 |
| 9604 | RNF14 | ring finger protein 14 |
| 387263 | C6orf120 | chromosome 6 open reading frame 120 |
| 9120 | SLC16A6 | solute carrier family 16 (monocarboxylic acid transporters), member 6 |
| 3915 | LAMC1 | laminin, gamma 1 (formerly LAMB2) |
| 23092 | ARHGAP26 | Rho GTPase activating protein 26 |
| 64778 | FNDC3B | fibronectin type III domain containing 3B |
| 10140 | TOB1 | transducer of ERBB2, 1 |
| 23208 | SYT11 | synaptotag min XI |
| 57730 | KIAA1641 | KIAA1641 |
| 120196 | MGC34830 | hypothetical protein MGC34830 |
| 7832 | BTG2 | BTG family, member 2 |
| 23259 | DDHD2 | DDHD domain containing 2 |
| 84981 | MGC14376 | hypothetical protein MGC14376 |
| 6448 | SGSH | N-sulfoglucosamine sulfohydrolase (sulfamidase) |
| 9910 | RABGAP1L | RAB GTPase activating protein 1-like |
| 1611 | DAP | death-associated protein |
| 126823 | KARCA1 | kelch/ankyrin repeat containing cyclin Al interacting protein |
| 388403 | YPEL2 | yippee-like 2 (*Drosophila*) |
| 6720 | SREBF1 | sterol regulatory element binding transcription factor 1 |
| 58476 | TP53INP2 | tumor protein p53 inducible nuclear protein 2 |
| 8605 | PLA2G4C | phospholipase A2, group IVC (cytosolic, calcium-independent) |
| 3983 | ABLIM1 | actin binding LIM protein 1 |
| 4189 | DNAJB9 | DnaJ (Hsp40) homolog, subfamily B, member 9 |
| 1604 | DAF | decay accelerating factor for complement (CD55, Cromer blood group system) |
| 29994 | BAZ2B | bromodomain adjacent to zinc finger domain, 2B |
| 10156 | RASA4 | RAS p21 protein activator 4 |
| 9123 | SLC16A3 | solute carrier family 16 (monocarboxylic acid transporters), member 3 |
| 7846 | TUBA3 | tubulin, alpha 3 |
| 3956 | LGALS1 | lectin, galactoside-binding, soluble, 1 (galectin 1) |
| 1647 | GADD45A | growth arrest and DNA-damage-inducible, alpha |
| 6609 | SMPD1 | sphingomyelin phosphodiesterase 1, acid lysosomal (acid sphingomyelinase) |
| 56904 | SH3GLB2 | SH3-domain GRB2-like endophilin B2 |
| 440081 | DDX12 | DEAD/H (Asp-Glu-Ala-Asp/His) box polypeptide 12 (CHL1-like helicase homolog, *S. cerevisiae*) |
| 5163 | PDK1 | pyruvate dehydrogenase kinase, isoenzyme 1 |
| 25840 | DKFZP586A0522 | DKFZP586A0522 protein |
| 51566 | ARMCX3 | armadillo repeat containing, X-linked 3 |
| 9388 | LIPG | lipase, endothelial |
| 27250 | PDCD4 | programmed cell death 4 (neoplastic transformation inhibitor) |
| 6302 | SAS | sarcoma amplified sequence |
| 83937 | RASSF4 | Ras association (RalGDS/AF-6) domain family 4 |
| 388677 | NOTCH2NL | Notch homolog 2 (*Drosophila*) N-terminal like |
| 23646 | PLD3 | phospholipase D family, member 3 |
| 23643 | LY96 | lymphocyte antigen 96 |
| 9855 | FARP2 | FERM, RhoGEF and pleckstrin domain protein 2 |
| 65018 | PINK1 | PTEN induced putative kinase 1 |
| 57035 | C1orf63 | chromosome 1 open reading frame 63 |
| 85352 | KIAA1644 | KIAA1644 protein |
| 283131 | TncRNA | trophoblast-derived noncoding RNA |
| 143888 | KDELC2 | KDEL (Lys-Asp-Glu-Leu) containing 2 |
| 56204 | FLJ10980 | hypothetical protein FLJ10980 |
| 23446 | CDW92 | CDW92 antigen |
| 23766 | GABARAPL3 | GABA(A) receptors associated protein like 3 |
| 1508 | CTSB | cathepsin B |
| 4094 | MAF | v-maf musculoaponeurotic fibrosarcoma oncogene homolog (avian) |
| 22932 | POMZP3 | POM (POM121 homolog, rat) and ZP3 fusion |
| 56243 | KIAA1217 | KIAA1217 |
| 1663 | DDX11 | DEAD/H (Asp-Glu-Ala-Asp/His) box polypeptide 11 (CHL1-like helicase homolog, *S. cerevisiae*) |
| 1414 | CRYBB1 | crystallin, beta B1 |
| 154091 | SLC2A12 | solute carrier family 2 (facilitated glucose transporter), member 12 |
| 4121 | MAN1A1 | mannosidase, alpha, class 1A, member 1 |
| 11178 | LZTS1 | leucine zipper, putative tumor suppressor 1 |
| 10628 | TXNIP | thioredoxin interacting protein |
| 83719 | YPEL3 | yippee-like 3 (*Drosophila*) |
| 9863 | MAGI2 | membrane associated guanylate kinase, WW and PDZ domain containing 2 |
| 5660 | PSAP | prosaposin (variant Gaucher disease and variant metachromatic leukodystrophy) |
| 145788 | FLJ27352 | hypothetical LOC145788 |
| 84513 | HTPAP | HTPAP protein |
| 57612 | KIAA1466 | KIAA1466 gene |

TABLE I-continued

| ENTREZ GENE ID | GENE SYMBOL | GENE DESCRIPTION |
|---|---|---|
| 57515 | TDE2 | tumor differentially expressed 2 |
| 29005 | PRO1073 | PRO1073 protein |
| 51646 | YPEL5 | yippee-like 5 (*Drosophila*) |
| 5269 | SERPINB6 | serine (or cysteine) proteinase inhibitor, clade B (ovalbumin), member 6 |
| 30061 | SLC40A1 | solute carrier family 40 (iron-regulated transporter), member 1 |
| 81030 | ZBP1 | Z-DNA binding protein 1 |
| 347733 | RP11-506K6.1 | tubulin, beta polypeptide paralog |
| 390 | RND3 | Rho family GTPase 3 |
| 10765 | JARID1B | Jumonji, AT rich interactive domain 1B (RBP2-like) |
| 9783 | RIMS3 | regulating synaptic membrane exocytosis 3 |
| 27122 | DKK3 | dickkopf homolog 3 (Xenopus laevis) |
| 151556 | GPR155 | G protein-coupled receptor 155 |
| 8365 | HIST1H4H | histone 1, H4h |
| 6480 | ST6GAL1 | ST6 beta-galactosamide alpha-2,6-sialyltranferase 1 |
| 6591 | SNAI2 | snail homolog 2 (*Drosophila*) |
| 54800 | DRE1 | DRE1 protein |
| 3669 | ISG20 | interferon stimulated exonuclease gene 20kDa |
| 23710 | GABARAPL1 | GABA(A) receptor-associated protein like 1 |
| 400172 | LOC400172 | similar to KIAA1641 protein; melanoma-associated antigen; CLL-associated antigen KW-1 |
| 153222 | LOC153222 | adult retina protein |
| 54981 | C9orf95 | chromosome 9 open reading frame 95 |
| 5641 | LGMN | legumain |
| 257019 | FRMD3 | FERM domain containing 3 |
| 8357 | HIST1H3H | histone 1, H3h |
| 55281 | FLJ11000 | hypothetical protein FLJ11000 |
| 4050 | LTB | lymphotoxin beta (TNF superfamily, member 3) |
| 203 | AK1 | adenylate kinase 1 |
| 5920 | RARRES3 | retinoic acid receptor responder (tazarotene induced) 3 |
| 284801 | LOC284801 | hypothetical protein LOC284801 |
| 150271 | LOC150271 | hypothetical protein LOC150271. |

33. A method of identifying a patient for treatment of a cell proliferative disorder with an inhibitor of FGFR3, the method comprising:

testing a sample obtained from the patient after administration of the inhibitor to measure gene expression of at least one biomarker selected from the group consisting of CCL3, DUSP6, ANXA9, CR2, AL531683, ZNF589, AW274468, FRMD3, LTB, and WDR42A, wherein at least one selected biomarker is CCL3, wherein detection of an alteration in level of expression compared to a baseline gene expression measurement of the at least one biomarker is indicative of the candidacy of the patient for treatment, wherein the baseline gene expression measurement is the gene expression measured in the patient prior to administration of the inhibitor.

34. A method of monitoring response of a patient to treatment by an inhibitor of FGFR3 for a cell proliferative disorder, the method comprising:

testing a sample obtained from the patient after administration of the inhibitor of FGFR3 to measure gene expression of at least one biomarker selected from the group consisting of CCL3, DUSP6, ANXA9, CR2, AL531683, ZNF589, AW274468, FRMD3, LTB, and WDR42A, wherein at least one selected biomarker is CCL3, wherein detection of an alteration in level of expression of the at least one biomarker compared to a baseline gene expression measurement is indicative of a response of the patient to the treatment, and wherein the baseline gene expression measurement is the gene expression measured in the patient prior to administration of the inhibitor.

* * * * *